(12) United States Patent
Loessner et al.

(10) Patent No.: US 10,435,669 B2
(45) Date of Patent: Oct. 8, 2019

(54) **BACTERIOPHAGE FOR BIOCONTROL OF *SALMONELLA* AND IN THE MANUFACTURING OR PROCESSING OF FOODS**

(71) Applicant: Micreos B.V., Wageningen (NL)

(72) Inventors: Martin Johannes Loessner, Ebmatingen (CH); Steven Hagens, Bennekom (NL); Albert Johannes Hendrikus Slijkhuis, Nijmegen (NL); Jochen Achim Klumpp, Gockhausen (CH); Roger Marti, Zurich (CH)

(73) Assignee: MICREOS B.V., Wageningen (NL)

( * ) Notice: Subject to any disclaimer, the term of this patent is extended or adjusted under 35 U.S.C. 154(b) by 383 days.

(21) Appl. No.: 14/399,383

(22) PCT Filed: May 7, 2013

(86) PCT No.: PCT/NL2013/050342
§ 371 (c)(1),
(2) Date: Nov. 6, 2014

(87) PCT Pub. No.: WO2013/169102
PCT Pub. Date: Nov. 14, 2013

(65) Prior Publication Data
US 2015/0125424 A1 May 7, 2015

Related U.S. Application Data

(60) Provisional application No. 61/643,420, filed on May 7, 2012.

(30) Foreign Application Priority Data

May 7, 2012 (EP) .................................. 12166986

(51) Int. Cl.
| | | |
|---|---|---|
| *C12N 7/00* | (2006.01) | |
| *A23K 30/00* | (2016.01) | |
| *A61K 45/06* | (2006.01) | |
| *A23L 3/3463* | (2006.01) | |
| *A61K 35/76* | (2015.01) | |
| *A01N 63/00* | (2006.01) | |

(52) U.S. Cl.
CPC ............... *C12N 7/00* (2013.01); *A01N 63/00* (2013.01); *A23K 30/00* (2016.05); *A23L 3/34635* (2013.01); *A61K 35/76* (2013.01); *A61K 45/06* (2013.01); *A23V 2002/00* (2013.01); *C12N 2795/10121* (2013.01); *C12N 2795/10122* (2013.01); *C12N 2795/10131* (2013.01); *C12N 2795/10132* (2013.01)

(58) Field of Classification Search
CPC ............ C12N 7/00; C12N 2795/10132; C12N 2795/10131; C12N 2795/10122; C12N 2795/10121; A23K 30/00; A61K 45/06; A61K 35/76; A23L 3/34635; A01N 63/00; A23V 2002/00
USPC ....................................... 435/235.1; 424/93.6
See application file for complete search history.

(56) References Cited

FOREIGN PATENT DOCUMENTS

WO 2012036580 A2 3/2012

OTHER PUBLICATIONS

Leiman et al. (2010) Virol. J, vol. 7:355, 1-28.*
Chibani-Chennoufi, Sandra et al. Comparative Genomics of the T4-Like *Escherichia coli* Phage JS98: Implications for the Evolution of T4 Phages; Journal of Bacteriology; vol. 186, No. 24; XP-002680315, 8276-8286 (Dec. 2004).
Denou, Emmanuel et al. "T4 phages against *Escherichia coli* diarrhea: Potential and problems"; Virology; vol. 388, No. 1, XP-002680316; 21-30 (May 2009).
Petrov, Vasiliy M. et al. "Genomes of the T4-related bacteriophages as windows on microbial genome evolution"; Virology Journal; vol. 7, No. 1, XP-021080222; pp. 1-19 (Oct. 2010).
Lopez-Cuevas, Osvaldo et al. "Characterization of bacteriophages with a lytic effect on various *Salmonella* serotypes and *Escherichia coli* 0157:H7"; Canadian Journal of Microbiology; vol. 57, No. 12, XP-002680317, 1 page, Database Biosis [Online] Biosciences Information Service, Philadelphia, PA; Database Accession No. PREV201200141228 abstract (Dec. 2011).
Monson, Rite et al. "The Pseudomonas aeruginosa generalized transducing phage phi PA3 is a new member of the phi KZ-like group of 'jumbo' phages, and infects model laboratory strains and clinical isolates from cystic fibrosis patients"; Microbiology; vol. 157, Part 3, XP-002680318, 1 page, Database Biosis [Online] Biosciences Information Service, Philadelphia, PA; Database Accession No. PREV201100250160 abstract (Mar. 2011).
Zuber, Sophie et al. "Decreasing Enterobacter sakazakii (*Cronobacter* spp.) food contamination level with bacteriophages: prospects and problems"; Microbial Biotechnology; vol. 1, No. 6, XP-002680319, 1 page, Database Biosis [Online] Biosciences Information Service, Philadelphia, PA; Database Accession No. PREV201100317043 abstract (Nov. 2008).

(Continued)

*Primary Examiner* — Anne Marie S Wehbe
(74) *Attorney, Agent, or Firm* — Volpe and Koenig, P.C.

(57) ABSTRACT

The invention relates to the field of microbiology, specifically to a bacteriophage, polypeptide and a corresponding polynucleotide, a nucleic acid molecule and/or vector and/or cell comprising such polynucleotide, a composition comprising said bacteriophage, polypeptide, polynucleotide, construct, vector and/or cell, preferably for preventing, treating or diagnosing contamination with and/or a condition in an individual related to *Salmonella*. The invention further relates to an antimicrobial composition for medical use or for use as a food additive or as a disinfectant, or for detecting bacteria, preferably in a diagnostic application, wherein said antimicrobial composition comprises a bacteriophage, polypeptide, corresponding polynucleotide, construct and/or vector and/or cell comprising such polypeptide and/or composition according to the present invention.

7 Claims, 8 Drawing Sheets
Specification includes a Sequence Listing.

(56) References Cited

OTHER PUBLICATIONS

Shin, Hakdong et al. "Prevalence of Bacillus cereus bacteriophages in fermented foods and characterization of phage JBP901"; Research in Microbiology; vol. 162, No. 8, XP-002680320, 1 page, Database Biosis [Online] Biosciences Information Service, Philadelphia, PA; Database Accession No. PREV201100719471 abstract (Oct. 2011).
International Search Report, International Patent Application No. PCT/NL2013/050342 dated Jul. 3, 2013, 7 pages.
O'Flaherty et al. (2005) The Recombinant Phage Lysin LysK has a Broad Spectrum of Lytic Activity Against Clinically Relevant Staphylococci Including Methillin-Resistant *Staphylococcus aureus*, Journal of Bacteriology, V. 18, No. 20, pp. 7161-7164.

\* cited by examiner

SEQUENCE LISTING

<160> NUMBER OF SEQ ID NOS: 17

<210> SEQ ID NO 1
<211> LENGTH: 160221
<212> TYPE: DNA
<213> ORGANISM: Unknown
<220> FEATURE:
<223> OTHER INFORMATION: Salmonella bacteriophage S16

<400> SEQUENCE: 1

| | | | | | |
|---|---|---|---|---|---|
| aattacctct | tagatggcgc | cctggagcgc | cgcaatttc | atgatgtcag | tgtagtattc | 60 |
| ttctcgagaa | atgtagtatt | cttcaagcat | ataccaaatc | actgggtatt | ttttagcaaa | 120 |
| ttcgtcagaa | gctttattaa | aatcagactt | tgacgataag | atgagtttat | tataaatctt | 180 |
| ataacataaa | gcaattttt | cagcggcttc | tgactgattt | actgttgtgt | taatagagcg | 240 |
| gtaatttaat | gcttccgcta | tacggttaag | aactaaagac | ttttcccagt | tatcaccgga | 300 |
| gataaaattc | ttcagcaacg | gattaagcgc | ttttatatta | atcatagcgt | tgaagcgtct | 360 |
| gatattaaac | aaatgtggat | gaattaaatc | atcaagtacg | tcgtcaatca | aatctgcgta | 420 |
| actatcagct | aaaacatcaa | aaactgaagt | tagagaatta | ttgtctttga | catatttcat | 480 |
| tgcgctagga | cgaatagtat | aaaattcttt | tatatctgcc | gctttacatg | cttgtctaat | 540 |
| attttcaatg | ctgtaactcg | tagagcattc | tgttcttaat | tcaacaatgt | cttctcgatt | 600 |
| aattccaact | gctaaaacctt | ccaattcacg | aacttcattt | gcagttaaaa | acaaattagt | 660 |
| cgattcccaa | tgaagttctg | aatccaattt | ccatagatga | acattcggag | atttggacg | 720 |
| tttaaccgca | tctgaattat | ctggcttatt | gatttcagca | tctttggcac | gggcttgttc | 780 |
| catatcagaa | gctttaaaaa | taactacttc | atcgccttca | aacaacttct | tggcaagttc | 840 |
| tacaacttct | aaatggtctt | cattattcgg | gtcaattaaa | ataacttgac | agcctttatg | 900 |
| aatattaagg | taactcatcc | cacgaatagt | gcttgctctg | cggtttggct | tatcgtcaat | 960 |
| cataaaaaca | atctttttct | gattaacatg | aattaagcca | gatgccgaat | atcgattacg | 1020 |
| cgtgctccat | gaattactaa | ttttgcggcg | ttcagccata | tcgccgacaa | agtaagtata | 1080 |
| catattagat | gaatacattt | tattttcgag | agcacgttgg | tcgaaataat | caagccattc | 1140 |
| gcggcaagtt | ttgccttgaa | tttttgattg | gctattacca | ataatagcaa | gagacctgct | 1200 |
| ggaaaatttc | tttaactcac | ggaccagttc | tcgcttattg | gttatacttt | caagatgttt | 1260 |
| gatatcgtct | cttagatttg | tttcttcgat | tttattaatt | ttattgcgaa | tagcttcgat | 1320 |
| agtttcttca | ttgtaagaaa | gctcttcacg | gctaggagta | atatcaagtt | cacctaattc | 1380 |
| aaaattaaca | taaccgtgc | tatacttgtt | attcagccat | tcgcatttga | taccaggaac | 1440 |
| ttcttgaacc | ttaatcggat | aaacaattcg | tccataaatt | gcatacaaat | tcgaatcagt | 1500 |
| atcaaaataa | gagcgttgtt | tattaaacca | ttgcttttct | ggagtgaact | cttcgaaata | 1560 |
| atcaatattg | atattagcac | cttcaatttc | tggttcaaca | ccagcaaatg | tgcgcaaagt | 1620 |
| acgacggact | tcatgatgcc | acttatcaat | atcgtcagtt | tttacaggga | cagtaatttc | 1680 |
| aataccagtg | tattcatctt | cttccattgc | tgtgtcaaac | agcggaataa | tttctggacc | 1740 |
| agtatttttc | attatagcgg | tgtaaccgcg | cttacggcct | ttatgacaag | aaacgactgt | 1800 |
| aaaagttttt | gtatagctaa | atggagattt | tgagccaaga | cccattgccc | cgatgaaatc | 1860 |
| atttgagtcg | gctttagttg | aagcaaaata | agtattatac | aagcctggag | catcatcagt | 1920 |
| tccacgaatt | tgttcatcgc | tcatacctgg | gccaaaatcg | cgaattacga | agcgcgggtc | 1980 |
| tatacgagta | ggaactttaa | tagtgaacgg | acgagtttgg | ccattcagtt | tatgagcatc | 2040 |

```
aagacagtta gtagataatt cacgaacgat agcgtaaatt ttattggtat ataacttgtc    2100
tgaaagaacc atgaacgctt tcatgttgtt ctcaatgcca aacttacttg ccttctgatt    2160
ggctgaacca aaaatctgct cttcttcttg tttaataatc atcttttttct ctcattcact    2220 taaattaatc ttggttacgc ttaatcaatt ctgcaacttc tagaagttct tctgccgttg    2280
cggtgttgtt ttgtatttta aaccgtattt ccttaaagcg ttctttaaaa tcttcagctt    2340
cactcatgtc aaaaaatctt tgaatgatgc ggtactcttt atatacagcg tcatcaaata    2400
ataccataca aacgttaaag cttttcattt cctacctctc tgaggatggc tgcaaactgg    2460
ctcatagtgt gtttttcacg tacagagtaa accagcctca aagcggtttg ttgtaggttc    2520
accggaatga tctggttgtt ttcaactaat acagcaatat gttctatcat attagagaat    2580
ttatttaacc agatttcatc tggtgtattc tctgttttat tcagaaacat atctttacta    2640
tctctaattg ttgctgctac gttgtataaa ttaacataac ttccgttaag catttcata    2700 gctgtaatca ccatactaaa aagggactcc cgaaggagtc cctgttatta ccatgtggct    2760
tttgacacca tacctgtaac tttcttcaaa gagttgtccg gctgacgaac acgaatagta    2820
gccatatcac cagggagagg aagagcatct ccccacatat aaccgaaact tccatctaca    2880
agcgttaccc agatttgtga cataaactct cctatacggg cggaataccc gtattattta    2940
ttcactcatc cagaccttgc gaggagcagc atcattaccc ataaccattt caaaaagttc    3000
tttccaattt ggaggtaatg aaactacatc atacaccggc ttctggataa ctcgttcata    3060
ctcatcttct tctaaagaac caagtcccct gatataacga agtttccatc ctgtgagttt    3120 atcttttca gcttcatact cagcggcatt gtaataccat ttttgctcag agcccttgga    3180
cataataatc accgggggtt taacaaaacg aatacgacct tcttcgaaca acttcggcca    3240
attagcaaaa aatgctaaca gacttggata aattgaccct gtgccaaata tctctattgt    3300
gaggtatatc aatgattagc ccgaaggcta accatcaaca tcagcatcgg tcatgatggc    3360
gatgttttta taattcaaag aagaagttga tgtacggcgt acgattgtct gggctttata    3420
tgacttcata tcgatttcag tttctttaac tttagcaaat ttcatttaaa acctcataaa    3480 attttttcatc aggagtccaa ccgttttttaa actgattgaa cgcgattttg aacagtttcg    3540
ttttgatagt tatattatta accgttttcc atttagcaat tccggttttc ttataactaa    3600
ctgggtcata aacgttagca taccaatcat aaagggacgg aatcaactta actgcgtctg    3660
gattggtttt agatttgtta taccaaggtt tagatttttc aagggcggct gctacttttg    3720
tagcgtttaa cgtgttacca actccgcata aaccaaggtc ctttattaaa gggtcgtccg    3780
ttcttagtct ataggttgtg ttatctttat ccttgtaaac tccgtatcct ttcacacctt    3840 caaatttttct tccgtaattt acgccaaccc aatcttcttc agtgtattcg cctttcgtca    3900
gtaatcgaca ttctccagtt tctttatttc taagtaaaat tttgtcacgc atgaactcag    3960
cagaccaatc tgaaatcata ttaacataat ttttcctggc tatttcataa agtttagaac    4020
gaaatattgt tccagaattc attatccggt tcaaagcata agacatttct tgttttttat    4080
gaattttaaa caataaccag tgcgcaataa aatgttcgcg atatgtcaat tttaccaaat    4140
tatctgaagt atctaatcca cccatgcttc ttggaagtat atgatgaatt tctccttttaa    4200 ccggcggaac cctggtttta ccccgggaaa ttagtttttc atatatcaaa ctataattca    4260
tactaagtct tttacttttt tccagacgcc atcaataaaa atttcgtcat tgatattaac    4320
tacaatatct tcaccggcaa catttacagt ataccattgt tcgccggctt caacttccgt    4380
```

-continued

```
gaatgggtct tcaccaatga ctaacccagt aattgcacaa atatcaaaga tttctttgtt    4440
tttcaaagca tcacctgcag acattcccca ggtgttcatc actttaccac gtaatggata    4500
accgccatga agggcacggt cacgagtatt aattagataa ccaatagcag aatcaccttc    4560
tgttaagaac aaagttgttt ctactttatc attaccatat tcaccagctt tgatgtgttt    4620
atgaacttta gctttggccg ccttttttcgc tgctttggtt tctgctgcct tctcagccgc    4680
cagtttacgt gctaacgcag cttcaataat cggcattaaa atagcatcag atttcataat    4740
ctgattagaa attttctttg catcgagatt taagtgagat ttaatttcgc cccatggact    4800
tgtaagacgc tctttggttt gcgagtcaaa gcgcaagtta ctcatatctc gaataaacat    4860
caacacagta aaacactctt taatacgagc tttgtttact tcaattttgt gtttacgttt    4920
aatagccgga attaattcat tagcaatttc gtcaataaca taatcaatat gcgaaccgcc    4980
attctttgta tgaatgttgt taacataagt catttgacga aaaccatctg gagaattacc    5040
tatcgccaaa gaataatttt cttcatcaat aatgatagca tttttatcat actgcttaga    5100 atatttttg aaattactat caacttttt attgttaaat ttaaattcaa tttttggata    5160
aacgactgcc aatgtctgca aacggtccag cataatatca aaataaacat catcaaaatt    5220
gttcatttcg aaatggctaa aatctggaat aaattctacc ttagttcctt tataagagga    5280
ttttttggat ttccaagaaa cattgtcaga attattgcta caagaaactg ttaattcatt    5340
ttctccatca gatgttgtac cttttaaacat aacagagaaa atattagtca atgaagaacc    5400
aacaccgttt tgcccgccag ttttacgctc ttcatcagct ccaaagtttc cgcctgcctt    5460 agtttttcgtc cacgctgcta ctgggccagg aatttcttca ccctcaggag tagtaaccat    5520
agcctgtgga attccacggc cattatcttc tacggtcact ttgcttgtgg aagaatcgat    5580
attgactgaa attttattag caaatttaaa acttgtacgg atagcttcat caacagagtt    5640
atcgataatt tcatcaataa gtttgagaac gccagctacg tattgtaccc gcttaaattc    5700
gccaaaaaca aaacgctcat gaaattcgtt agatacactt ccgatgtaca ttccaggacg    5760
cttaagaacg tgttccttgt cagagagcat ttgaattta tttcaatca tgttattatc    5820 ccagtttgaa tttgtctgat aattatatca tcaatttaat ttagcaatta attcatcacg    5880
atatttcatg agatgatgaa gcgccggagc cccatatata ggagaacaca aacttgaatt    5940 aggttttta caaaatatgg tgtgaatagc ttgctcttca ctttcgtatg aaaacgtcaa    6000
agtttggcta taccgatcat cataataggc agcataatta ttttcttcaa ttacgataaa    6060
ttcttgaaca actttataat atttttgtaa caagatgtac cgtccgttat ccaatttagt    6120
cgggaacaat gcgaatttat attttccaat cgctcgttca actaatctaa gcttgcgggc    6180
ggcattcttt tgaattgaag attttccaaa tatcataata ttttctcac tcagccgtta    6240 agaataatcg cgattttttgt atccgttgta atgaacagcg ggcgcagcgg tttctcggaa    6300 cattttcct tcacaattca gaaatgaaca ttcaattggt tcatcacgtt ctgagacctt    6360
gcgcatcttt tctaccttttt caccgcaggc ttcgcacgtg taatcataaa ttggcattat    6420
agtaatcctt ttaacatttc aatagccgct ttgacttgat ttttattagt aattgctaaa    6480
gtgatatgag gaatttcatt ttcttctgaa gcttcatatt cgtcatcatt agccgccgaa    6540
ttaagtgttt ccaacttaaa atatttagct tcgtcaggca agataaagaa atattcatta    6600
ctagttttaa taccagaata ttctggtatt ttgtcaatta tatcttgcgc gccgcataga    6660
gcctggctta atgttataat tgcttcagcg gagccacacc aattaacgct taaaactta    6720 aaaaatccgc catttttatt aatgaaatta ataattgatt tgttgtgtct atgagctttg    6780
```

```
acaaatccgt cgtaatcttt aatagaatac cattgacctt taacgaaatg tgttaaattc      6840
tgtgtagtca ttagatagtt tccttccaat aagaagttcc gttttcattg atgtaacgaa      6900
ctaccgcata gattgcacgg ctgttttcgt aaacgtaggc gtatgtatga tgttctagat      6960
gtccttgaac ttcttttgc acaatagtca actctgggtt gaacaagata tcttcaaact       7020
gctcttgtgt taaaatgcgg ttcatttatt ttcctcgttt gttttgatag ggttatagta      7080
tcataaccct caaggaaagt aaacagttta aactttcacg ctcagaaaac ggcttgaacg      7140
gattactgct gggataacta aatccaaatc tttagtagcc attaaagcgt attcaccctg      7200
ataaaccacg ttcgcaactt cttcgccgtc aatatcataa accaaggtaa ctaatccaca      7260
cttacggtca caaatgtgac agtctccctg accgccggaa tgctcgattg ctgcatctgc      7320
gtttcgaatt cgtacaatat cgccaatttc aataacacaa cgctgagaag cttctttcgt      7380
ataagtgtcg ttttcagaca catagtagtc ttttacataa attgtgttat tagttttaac      7440
atcgcgcaga cgtatccgt cacgctttga atgacctaga acaataccaa cacgaccagc      7500 attttacca ctaattacac gaagttcagt acctttagca aacatattat cacctttcaa      7560
ttttcagatt tgagaaatta ttttatatta aatatttaa agcgttatcc acgaccttt        7620 ggaagtgaaa gagagtcaat ttcagcaccg accggagctt cttctaagcc aagcgcatat     7680
cgttgagcat acttcagcat cagaatatct ttagcacaat catggatact atcatgagcg     7740
atgaacccgt caagtacacc attacgcaat ggagttgttg ttaaatttct agtcatcagc     7800
agagcttcta ttgctgtacg gatatctcgc tggttccaga atttacatgg ttccaaatta    7860
aatgtgtcaa tatctttatc ttcaattcct ttccggagtt caccttcacg taggatatca    7920
acaagaatag gaaagtcaaa tgactgtccg cggcaccatc cgaatgagtt ccatgcatct    7980
actccgttat ctttcaggaa tttaagaagt ttataaagtc cttcgacgtg gtcaatgtca    8040
tcatcagacg gtgcaaggtt agctctagct tcagctgact gcttttccca ccaagctaaa    8100
gtacttgcac cgaataaccg aaatggacgc tgagaccgga ggtcaaactt tagttttcatt   8160 cccctagaaa ctagttcgtc gaacgtttcg ataacttccg gattagggtc aaaaactacc    8220
accgcacagt caataactgc tgatcgagaa acgttaccga atgtctccca atcaataata    8280
aaatctttta cgcccggcat agatattcct taaattcatt aatctgttta gatattttat     8340
cattaattga tataagcggt acttgtcctt ggaaccaagc gatactcata gcttcgtcgc    8400
gaatctcgtt tagttgaagc aataacgtag attgatgacc gcgccaccaa gcatcttcgg    8460
gtttgttaat ttcaatagca ttaatcaact tatcaaaatc atcaatatca agagtaaaca    8520
tatttgttcc ttatacaaag aaaacatcat ggcggccacg agttgcaccc acataaagaa     8580
gttctagctt aaacttatta tcgctgctta cgtgaataca cggagtataa atgaaactac    8640
tatctacaga ataccctga gctttatgga acgttgaaca aggtaaagct ttaaccttat     8700
gaaattttcg tttagcatcc cagaattctg accaaggagc tttaccgcct ttattccagt   8760
ttttataagt atctgccgtc tttgccaaga aaaactgaaa tttgttcatt tcttgttcgt    8820
cagatattac attaattttc tcacgagcat attcttcatc gtcataagtt tctacatcta   8880
aaacccagtg acgaattaga tgttcaccag atactccctt tgctcccaag aatgaagatg    8940
tgtaatctgc acttagaata cgaacatatt gaccattagt aaataatgtt tcatggaatt    9000 ttttttccctc aaatacaagt tccctcatta aaggttcttg cataacaata acttctccta   9060
ctacgaacgc ttcttccgtt tgatataaac gtctacgaat gatagagttt aatttatcaa    9120
```

```
ccgacttatt tgtgaatgcg agcattcggt tttcaaacaa atcttccggt gatttgacga    9180
tactaaaata ttgcatcata aaatctttaa gtgccgttgt acttgtaaat ccatgcacac    9240
catgaccatc aacagttttt tcgtaaatcc atgaaccgtt tcttatatca gtagcaacat    9300
caataatcgg agcgttactg cgcattactt cagtaagatt taattgttta aaatctttat    9360
gaataaagaa aggagatata tgagcttctg tttctccagg gtcaaccgga cgaatttgag    9420
cgacatctcc aatagcgact atagtacacc atttaggaat tgaagccatt agtattttaa    9480
ataatttgcg gtcccacatt gaagcttcgt cacatattag cactcggcat gatgctaaat    9540
ctggcacttc ttttttgttca aacaacatac tttcttcata tgttgtgggg ttaattttta    9600
aaattttatg aatagtatta gcttccatgc cggacaattt ggttaatact tttttggctg    9660
catgtgtagg agccgtcaaa ataataccag tttcgccagt agaaactaaa tgctccatga    9720
taaattttgt taacgtagtt ttaccagtac ccgctggacc gttgatagta acatggtttt    9780
tcttttcttt tatagctcta atagtttcat caaatgctag tttctggcca gaagtcaact    9840
gctcaaatgt aatcatacca ctgatccct tttaacactt aatgtgttca taatttgtct    9900
gttcattcta ctttcaattt cagaaagctt tttaaacttc atttcaactt tatcgaacca    9960
gaaacgacgt ttcttaattg tagtttctac tttaccgaca ttcaatatat gagtaagata   10020
agtttttagc tgctcatagt gcttcacagc atcatcaaat ttttcataga ttgtagcctt   10080
tccagattcg aagtacggga gttcaaaccc gtctttatct ttgtagacta acatgtatcc   10140
atagtgcatc acatttttgcc tcggataagt tgtaacaatg ttgcagaaag tggaagacct   10200
tttttcagct tcgctttatc caaacgagat aaatttggga aacgagtaag accttgaata   10260
ataatatcat aatctttcac ggtgatttct gctttgctat tcttttttgga tgcagcgcct   10320 gaagttacag cttcagaaga cgggtatttt tcaaatattc tctttaatgt tttaattccg   10380
cctttgatgc gagtttctag agaatcgcga gtgtctttct gtattccggc ttgcttaaga   10440
tgactgcggc gggcctgcac gtttgcccaa atgcgtttag cttcttcacg gcggacaccg   10500
gaaattttag accaatcagg ctctttgttc caatcatgag tttctaatac aaagtcagaa   10560
tgattgaggt caacagcagg ttctacaact ttgtttttag agtcaacggc ggaaacgatg   10620
cgcgcagcta gttcttcttg cttttttaatg aggtcatcaa tttcgaagtt ggcgcgcagt   10680
ttattgtact tcattttaac aggaataacg ttgccttcta catatccttt gttgttatca   10740
aaccgctcga gagtcatttg gtcaggccca agttccttct tgaacttttc tcctgaatat   10800
gcacaagtat cttgctccat gatgttcatc aagtacttca aagaaagatt aaattcttta   10860
cttctagaag aagcactttt gtatgtatga accaaacgtt gagcgataac aatttcacga   10920
ggcatggcca taacgatatt ccttatttgc tttttatgcg aatgtggtat aatggtttca   10980
aggattattc taatacactc tatccggaaa gtaaacggtt agaatgaata aaaatccaaa   11040
tgatatacag tatatgacgg agataaaggg tcatactgta actcttcaat ctccactatc   11100
tcaaattgtg ttccaatagg gaacatccat tcatcttctc cattgaccat ttcaagttta   11160
tccagtcttt catcaaaaat aaaatctggg tctatgctgt gcataaattc tgtgtctggc   11220
gcagccagaa gcatattcag tgcgtgctct tgatagttaa aagcaaatgg gcaattacgt   11280
aatgacaaaa tagtatgagt accatacaca ctccctccag cgaattgtct tgctgtggaa   11340
aaatctgatg taaacgacgt aactcggtca tcagcaataa ttcttcctac agccatattt   11400
ttcaaccaag cttcggtacg ttttgacact cctctgtaga gttcaactgg aacgtcagaa   11460
ctaatatgct tacgtataat tttgtccagt tctacatgca aagttttgtc aatttttatca   11520
```

```
ttcatacact gccaaagtat gctctgttca aaatcactga acatcttaat ttttcttca      11580 tacaatccat agagattgtt atcaactatg ttacaaacga tttcattaag ctgagaattt     11640
gtgtataaca taatagcctc cgtagtttac agaagctatc ataacacatt ttgactggga     11700
tgtaaacggt tattctgtcc acggagccca aggaggaggg tctaaccaga tagaagagag     11760
ttcttctacg aaagtgtcgt tgagttttac accatgccgt aaggcaagaa caaaaagctc     11820
ttgtttgatt tcagcacgtc ggttgccaaa tgcttctgaa ttttttgact ggtcttcttc     11880
aaataaatca aataaatccg acattacata cctctgatgt atttgacagc agttacggac     11940
atagtttttt cttcaaatcc attacgacga attccagtat cattaaaatg atgccaaatg     12000
aatttttcca attcaacgat gtgttcagga gtatttacaa taaatttttt gaagattttt     12060
ttgccatatc catctgtacg acacaaaggt tcgctaaaat tgaattccgg aaaaatgtat     12120
ttctgactaa gcaaagtttc taccatacca aacggtgaat tttcgcattt gtcgatatta     12180
caatcatgaa tgatttctaa caatgcattt tcgggaattc gcattttcat aaactgcttt     12240
tctagattat tataatgctc gtttgaaaaa ggtgcaggtt caccatactg agttagaaca     12300
acttcaaact tttctcgagt ttcttctact cgtcgattag ttcttttata gaatttcact     12360
acaaatgact ttgttttcat atttttcatg atattctctt attttatgac ttatcgccgt     12420
aaatgttagt taaaagcttt ttagcttcta ttgaaatacg tttagcttct tgttcattgc     12480
gccaatttct agcgtattct tccgcttcat gttgaagttc ttgctcaact ttagcaaccc     12540
attcatcatc taaatgagta ggtgtttcaa accattttt gaattcttcg taccatcgtt      12600
taatcataac caggatgtcc caaagcgaat aacagatttt tcacctacaa agtgaaagtg     12660
agcctcatat acgacacgta aagcagtacc ttcctcacgg tagcaatgaa taaagatgtc     12720
tactaaatca tacagatttg ggctatttgc gataaacaaa tgttcatgaa ttaagcgatt     12780
tgcaataaga ctattgatac caccaacttc ttcaactggc ttcatccagt tagatgtttt     12840
cataatatta tcctcatttg ataaaagaat tatatcatat cgtttaaaag caaaaaaggg     12900
actcccgaag gagtccctgc aatcaatcac ctggtactac tggcggtacg cctttaaaca     12960
tatcagcgtt tttggcaatc caagcgtctc tttggtcctc ttcaaaaacg gtagaatacg     13020 ccgcttttc ggaagggaag agttgataat gagaaccagc aatttgatgc acgtcggagt      13080
aaagcttaaa agctacagaa acttccatac cttttacttc accgtcggca tttgtatggt     13140
caaacgtttt tacgttaaca taactcatgt aattctcctt tgttgattac atgagtattt     13200
attaatagtt atttaaagcc tctactatat ctgctatgat atcttcagaa tcgccaataa     13260
gttctcgaag agatttgtac ttatcttctg gacttagagg atttaagccc aatatttta     13320 ttaaagcatt tcaatatca gaatatgaaa tcattagtat cctcggtttt gccgctcaaa      13380
gttttcagca ttttcagat agtaaagttt aaagatttct tcagccgaca tgcctaatcc      13440
ttggaacata ttcaacacaa agtgaagaat atcaatcatt tcaaatttaa tttctaattg     13500
gtcttttgaa gacatttcag aaataagacg attgcgtaat tctgcatgtt gtgctttcca     13560
cggtttccag acagaagaag cagccttctc gccattagac ataccgccca gagaagtcaa     13620
cagctcacgg aattcgtcat cgatataatc tttctgatta cgtagccaat caacaacttc     13680
accagcttta gctaagtcat ctggattgcg gttatagtca ggtttatcat ttgctagacg     13740
cacttgcaat gattttgca tgtcaagcat cacttgaagc gggtcaatac cagcattcac      13800
agcatcataa tacgcatttt ctgcttttc attgccagag atgagttgag aacattcatt      13860
```

-continued

```
aaaatgggcc attatatttc ctgtcaaagt attaaatagt ttaggaggat ttatgtctga   13920
aaaaattaaa accccagaaa ataaaaatct gaagtctcaa ttcgttgaga acaaaggtaa   13980
attaatctta gttggagtta ttacagctgt aataacagca tggaactata ttatcatccc   14040
tttcgcatta gcatatgggt ttactttacc tccaattcca ttggataaag ttattcattt   14100
cattatgctc ggaggatttt aaactccaat ctttgagtaa ttcttaaggc gaagttgagc   14160
catcaaaccc gaagatatat tttcggaaat atatttttcg atgtcttcaa ctttcgcccc   14220 ttcattttt atcatatcat taatgtcttt ttctttccat tgagatttat cccaaaacac   14280
aactctttcg ccagcgtcta tcaaacgctt cattcgcttg attgtgtctt cttttcttgg   14340
ttcatggtcc ataatccata ctctatcttc tttaaatgga accaaatcca aatcaatagc   14400
gccaccggtg atggcaatag cattgcccaa gaacaatgag tctatcgggc cttctaatac   14460
aaaaatattt tgaccggtct ttgctgtgtc taatccgtat attttttgttg catgttcgtt   14520 tcgtttaatt gttatgtatt tttgagggg gtctttacgc aatgctcttc cttgaaaact   14580
ttcaataata cctttctcat taaagattgg aattactaaa cgaggctcat tacgttctgt   14640
tttataagtt ccgggattaa cggaattcac caaagctggc cattccatcg taaaatacaa   14700
acggttccaa cgcgatttg gaatacaacg atgtttaacg tattttataa taggatgctc   14760
ttctgacaaa ctatctaagc ggctgcaatg aactaattta attccttctg gttctttaat   14820
ttcaactttt ttcacctctg gttttgtatc aggcttaaaa gtcattttgt cctttctgag   14880
ttctaaaata aactcacggt ataaatcagg ttcatattcc tttaaataca ccccaattgg   14940
ttttccataa tcacagttat aacacttcaa aaatacatca tcgcccgtgc ataagcccca   15000
aaaacgagct tttaatgcgt ctttctgtga gtcgccacag actgggcagc ggcagtttaa   15060
cttgaattgg gatacgttgt ttacttgacg aaagcgaggt aagtgagata atgcgcgaaa   15120
tgcaaactca ttgtgaaccc aagacatata ttctcctaag tggccttatt tctaaggcca   15180
ttatattaca atttcttaag attaacttta atgcgcttac gttttgaggg gatttgttct   15240
ggacccttgt tggttattgc tccggttgtg gtaccagagg cgatattctg gacacttcca   15300
ccggaatcac cggctaccat gtcctcgaac atagggagag catcaaatat ctcttttctgt   15360 tcggattcgg ttatattgta tctagaagcg attgaagacc aagctgacat catagaagct   15420
attccattta aaccgggaac agttgacatc attcgcttca ttgaacgaac agccgcgtga   15480
aacggagtat acgctgcctt ttcttcaggg gttgatggtc gtttaagcac gctgcctttt   15540
tcgtcaatga ttttttgcttc atatgcgttc cattcagtga atggttttg cattagacga   15600 ataaacttat atgcataaac agcatctata ccgttttta tagtgctcat aaacacctcc   15660
tacgatattt aatcaataac aaaaacggct ttatttccgt ttgcgtctgt tacttcataa   15720
gtatcttcgt catagagagg tataaaccat tctacatcag tatctgacat aacagaaata   15780 atatttctg aaattttgt catttcgtat tcttcaaata aacgaaacac atcgatattt   15840
gtacttgtgc aagttgcagt agacatttag cctctcattt aaagtccaat ccattccagc   15900
acttcaggaa ctgatttatt ttcacaataa agattagtgc cagcaactac caaatcattc   15960
tggtcgacat cttcaatgag catcttttga ttcgcattag ctccagcaag aaggtcttta   16020
attagcttag gttttaccgt atcccaatca ccttcgacaa atttaaggca ttgaatagaa   16080
ttataatcag ctactcccgg agttgcatgg gctggaactg ctgaacatga tgctactacc   16140
aatacgagac ttgcaattaa cttttttcatt attactctcc agtttgttga taagtaata   16200 gtatcacatc cttccatgga tgtaaacggt caactcaaac ttttcattgc ttcttcaaaa   16260
```

```
gttaatttttt taacggaaag ataccgcgcc gagctaattt tcttaccatt gctaaggacg    16320
accagtgtcc cgtagtccca tcctgataaa tctattgagt tccatatatc aacacatact    16380
tgtagtgact catccgctac tatgaacttc tcgtgaccat ctcggtcacg attggcaatt    16440
aaaacataaa tcaaaattta agttcctctg caagtgcgtc cagcttagct cgggctgatg    16500
tctggtctgt gcgttgttgt ctattagcct cggcttttcg ttgctgagct ccggatgttt    16560
cagtaactgg agttggctga gttccacctt cctgtgcaat ttcaacccag cgctgatttc    16620
ctttcttaac gcctaccgca aacttattcc aaatatttttt atcgccataa cgagatttaa    16680
tctgcttgat gagttgttgt cccatctgag caagttcttc tgtctcaatc acagcaagca    16740
tgaagtccgc cgttgccggt aagccagctg attctgcaat gtcggacata ttcatatcag    16800
aagcatccca tgcaccacga ccaacctgag ccgcagacca gactacagtt tctgattcta    16860
ctgccaatgc acggagttct tcggcaattg cttttcactaa agtgtaactg ttttcagtat    16920
aaacacgaat acgacaagaa ccacatattc ctagatagtc aatcataatg atatcaggaa    16980
caaaattctt tttaagtttt aactcattta gtaaagctct aaatgtgttc gcattagctc    17040
cgccggtagg atattgttta atgattaaac gaccaagagt attttatct cgccattttt    17100 ccatcttacc tttgtattct gcatatgaca cattgccatc atcaatatca tccaaagata    17160
catcaagcag gttagcatca atacgtttag cgcagacctc ctcggccatc tccatggaga    17220
tataaagaac attcttacca gtttgaagat aatcagctgc taaagaacac aatccaagag    17280
acttaccaac gttaacacca gccatgagaa tgttgagagt gccagtttct gccccgccct    17340
tagtgatacg gttcaaaata ttcatcaaga atggaacttt acgagccttg ttctgatacg    17400
ctaaccaacg agcttcataa tcttccatcc aatcatgacc gacataagag tcaaaactaa    17460
tagaaagagc ttgacgcata atgtctggaa ttgctccaac atccggtaat ttttatttc    17520 ttttttctgg cggtagttca gcgttcgttt gaatttcaat gattttgat gttgcgttat    17580 acatcgcatg agactgtaca tatttctcag tctcttttac caaccatgct tggtcttctg    17640
gcgtatctgc taatttatca attaattttt tagcttgttc agcttcagat tcgcctagag    17700
ttgaattgtc taatgcaata ttcaaagcat tgattgaagg gacagattga tattcgttga    17760 tatgttttttg taataagtta aacacatttt tagccgggcc atgttcaaaa tattctgaat    17820
ccatatatgg ccaaactttt gcgaaatatc cttgattaaa aataagatgc gataatattg    17880
tttctaccac ggtaacctca ttaaaataat ttgaaacgtt ttttattacg ctcagctaac    17940
gcttgctcaa tttgaatttt aacacatttt tcaacatgcg gagctagttc tgcttttcta    18000
tcttcggata atgtagaaaa atctacagaa atttcgtttc cattgtgatt tattgatgtg    18060
acataaacta tatgtgaaga accatcttct aatgttagca aaatttcttg tactatatta    18120
gccattgcct ttttgacaat atctaatgat ttttggtaaa ctctttctgt cctctcaaat    18180 tcccctcct gagaggggggc ttcttcgacg acttcaagat ttaaatctaa ttcgcttaaa    18240
tcataatcgt cttgtttcat tattcgtcca tcatagagtc aaggtcatct tcaattgctg    18300
ccggagacgg agcatgagaa ccttcgggag ctttgaaaac ctcagttttt gaattaatca    18360
atgcatcaac ttcagcatca acaaccgcat tactatcaat tgcgcccagt tgatatttac    18420
gtttaattgc atcacggaat ggttgatgct tgaacatcgg tccccagaaa tctacgcacg    18480
atgtagctgc tgcgcgccat gattttttctt cacgaaccat ttcaccggtt tcaatgtcca    18540
aatattcgcg agcataccaa ccatttttgt gtttaactac aaacccgagc tccaatgcca    18600
```

```
tttcaagcaa accagaatac gggtcaatac caccgtcaaa tttaacatca ataaagaact   18660
tagatttctc tttaactgta cgagattttt ctgcgtttaa aacaaactga taaccttgca   18720
aatcagtacc gtctttaatc tgacgtttac caataataaa cacggtatcc gcagaataca   18780
tcggaccagt accaccggtc attaccgttt tactgaacat ttcaatagtt tcaattgtat   18840
ggttaactgc aacacatgga atgttcttaa tactgaagta tggagtaacg atacggaaca   18900
gagatttcaa tgctttcgca cgggtcatat ctgcgaccga ttttcgttc aacgcatctt   18960 cagtttcttt cttggaagcc aggttaccaa ttgagtcgat gaatacaata accttttcac   19020
cacgctcaat ttcttctagc tgatttacca tatcaatctt aagttgttca acagactgaa   19080
caggagtatg aataacacgg tcagggtcaa cgcccataga tttcagataa gccggagtaa   19140
taccgaattc actatcatag aacagacaaa ttgcatcagg atgttttgtc atataagcac   19200
tgaccattgt cagagacata ttcgatttaa agtgctttga cggaccagca aagattgtta   19260
aaccagactg cataccacca tctaatgccc cactgattgc aatgttcagc atcggaattt   19320
tagtacggat aacgtctttt tcgttgaaga attttgactt agttagttcc gcggtcattt   19380
tagaagtgga tgctttaatc agacgagatt ttaaatcaga cattcatttt ttccataagt   19440
ctccattata ttttctcat aggtttaaag atagagtaa ttatatcaaa acaaatttaa   19500
agcgatttaa cttttattac gcacttaatt ggtgagttga ccattgattt tcgaggttta   19560
gacattttaa cctcaggcac atcctcagtt ctttaatcc aacttttgta tggacagtat   19620 ttttcttct tggtcatgat atttccggtt taaattttg aaagaaggta cactagaagt   19680
ataccttcgc gaaaattttt aaacttacag gtcaatagcc ttgcggaact cttcttgcca   19740
aattggtttt tcatcaagat atttttgaag aattttgtgc tgatatttca aagtttcaac   19800
acggaactct tcatcttctt taatcttgtt gattttatct actaattctt gacgattact   19860
cacataaaag aaatcattac cttccatgat attcatgtca gggtcaaacg tgctatcgaa   19920
gaatgccact gcagtagatg ctagagcttc ccatacacga ggagtgattt ggttgttatc   19980
gtaggtttta tcacctaata caatagtagc atacgcggtt gagttgcgtt gaaccatttc   20040
acgagagtct actttaccgg ggaataccgg cggagttgtc caaggaaatt ctgggttctt   20100
gaactgttct gctttcactg aaccaaagaa ttcaacatcc aatccagtat caaataggta   20160
ttcaatcatt ttagcttcac ggttaccaga acggaaagtg ccgccataaa tcaggtctcg   20220
cattttgatg ccatctgcgg caatcttaaa gacactatga tacatttat gacggtccaa   20280 agcaaaatga acgaattcta gtttatcgga taaacatcca actaaacgat cagaatgaat   20340
tttcttgcat tgctctagat ttcttccttg agatacaata cgcattggag atgttacaat   20400
gaattgttct tctttatatt tactggacca tttcttttta gacatccttc gccaagcttg   20460
ctcaaacgga agacgaatat cggtgaacaa ataataaatt tttgatttat acttattcat   20520
gaacatataa gcttctttgt tcatcttatt ttcttcgccg ccatagaagt tcagagcagc   20580
attaacgacc aataagcggt catacacatt cgggtctttt actgaatcga aagaaattcc   20640
atactgtgta ttttcattg aaataaggtc aacatcaaga cccatatctt ttaaacattc   20700
ggacaaataa attgtttctg aagcaggggt tgttttaaac ccctggatgt tattgcccat   20760
attaataata gcaattttca tagtgtcggt tcaatctcgc taaatttatg aaaagcatct   20820
gacttctgct ttttagcaac acacatacga agtactttca aaggttcatc agtaccaaac   20880
atagttttgg ttgggtcacc ttctgatttc caccgagctt gagttgggaa gtcagcatga   20940
attttttcca gcgctctgtt ctgtttagca gcattacgca tagatgatac accgcctgga   21000
```

```
gcttgtcctt tacctgattt aacgagatat ttaaaaatcg ccaaatgagg ataacccata   21060
ttaatgagtt taagaaacgc gtatgtatct tcggataggt ctactatacc atatccaatg   21120
tcatcggcag aaagtttgct taaatcataa aaagtatttg taaacccgta agagttctca   21180
cggaaatgac cccatttaga gtcaatcttg aatattggca agcgagcgtg accatgataa   21240
aagccgcagt ccatcgctgt ttcaacataa agacaaagat tattaaattc atcccaggtc   21300
attccaacat catggagaat gcgccggtca tcttttttcgc gaatttccgt tgtatgaata   21360
gtagtatcat catccaacat ccagatgcgt tgtccttgat acatttcggt aattaaacga   21420
cgagtaccag caatcccatt tacatcatcc gggatagtta ctattttagc aattgtgcta   21480
tatcgagttt cgtattcttc tttttgagat tcgcgaacta caagatgagc gacataacct   21540
ttagggaaca tgtctagggc agtaactgcc ccgacacgat tataacttgg aattacaaat   21600
tgaatcattt ccataaccct ttgtaatctt tctttgatat atgagtttca ccagtatggt   21660
aaaaatggtc aactagatag aagtgacgag aataaacatg caaactacct acgttccaaa   21720
taatgtcacc aactacgtat tttttatcgc ggccacagtt aagtgtttgt actaataatt   21780
ctaacacatg ttttttgccaa gcatagtcat ttctaaaacc gaagactaca tcattgcttc   21840
tcatactcac aacagcatga acttgctcat cgcgaattaa atattgaacc gtgtttgtac   21900
acatgaaatc actcataccg tcacggttat aatcagtctg catacttgga cgagtataaa   21960
tcataattcc gcggcgagaa tctggattga cactcagttc agccacacaa cttgcaaatt   22020
ggttataatt atctttattc caaattgccc atccgtagtt tgagttaatc tcgccgtttt   22080
tggatgaaat ctggtcccaa attgctggag ttttcctgg aatgtcttta acgaataaac   22140
tttgagactt ataccattct aattcgcggg ctacatattc atcattaact gaaccaaaaa   22200
taagttcttc atctgcaata aaagatgcgc cgataatttc aatagttttt acgccagttt   22260
tgtcaataac aaactcttca ttttcgagag ctacagcaaa ttcctgacga atgtcttgta   22320
ctgtcaaagg tgtgataatc attttgcctc tttaattacg ataatttgtt gaggttggtt   22380 atttttcgc tcggcgacga atgcccaaat taaagcaacc aaccatccaa tgaaagtcca   22440
accaaaaata agatttaaaa agaaaattcc aacattagat tttgtcccac gaagaagagc   22500
aataatccac ggaagaaaat acgctaaaaa cgctaagaac aatgaaccaa accaagtgc   22560 cgctgtaccc aatacgatag tttccattat aatttcctct attttatcaa atgatttatt   22620
tagcgttttt agccatacat ttattaaaag cttcactttt tccgcctgaa cgataatgaa   22680
taactgccag acgagttta ttatttggat ttttgaagta ttgttcacga agaacttctt   22740
catgagcttc tacaacaaat tcacacattc tgatagcttt ttccttttta tcgagtgcag   22800
cttgacgttc atcgccttca gctactgatt tttaattgc agcttcaagc ggactattcg   22860
cgcgccgttc ttcaatttct ttaatagcgt taagagtttc ctgcgagact tgagaagttg   22920
cacgagtata aaccattcca gaagctggct tataaaccaa attaccttca cttccataat   22980
gtggttgcga ataaggttga atagaacaac ctgctaaagt agttgctgct agaacaatca   23040
atgatttcaa attaaatttc atttattttt cctcatttgt tttgatgaga ataatagtaac   23100 acatccttcc atggatgtaa acggttagaa gtcaaacata tcttctaatg atgctttctc   23160
ttcgtagtcc ataccagcag cctcacacat gccagtcaaa ggtttgacaa aagacttctg   23220
aaagagcgta gtgtaatcca tccaagccaa tacttctgaa cgaatttcct gtggcaactc   23280
agtaccggat ggccaagcaa tacacttatc accaaacggg tttccttcac gcaaaggaac   23340
```

```
aatcattact ttattccccct caagaattgg agtagcgctg aacccagcag tcgctcggtt    23400
gtaagtcaaa gcacctcgaa tgtggaacgg acacttaaat ccaggccatc cgttatcatc    23460
atacttggcg atgtcattac atgtcttaac ttctgcaatg attttgtaat caagaccacg    23520
gtattctttt tcaaactgtt tgtaatattc ttgtactgat ttttcacctt cttgaagcat    23580
acgacgaata ctttcttcca atgctgcctg caccgccttt ggagtagaag attgctgagt    23640
ttccataccc atgattttta gatgcggctc agtgtaacga gtatcttcca tgtcatatac    23700
gttcaatgca taacgtttct tagctttcca gaaaccgcca atacccttg  aaccaagagg    23760 aggacaagaa atagcctcac ggtccatatg cattaagtgt tctttattat tcatgtactc    23820
gcaaagctca cggtaagctt tgtcaatcat aggttccatt ttttcttac  caaattggtt    23880 catgaattca accaaatcat tggtattttt aaaacgctct aaacctactt tttcaattac    23940
tttatcaaca gaaacgtaaa ctgagtcagt gtcgcctgcc gctataaaat cttcatttgt    24000
tgtaccgcat actcggttaa gatactcgtt aatcttacga gcaatccact ggataccaac    24060
ctgaccgaac agagtgatag cagtcgcatt acgaaggtca aaatatcgga aataaatgtt    24120
accgagagca cctaaaagac tgttgatgag aattttacgg ttcaactggt ttgtattagc    24180
caaaatactc gcaagttcac aatcatgcag catcgctttc agagctgaca cacttaacct    24240
gtagagttca ttcttcactt catcgctaaa atctttataa cgctcaacct gaattttacc    24300
gccagttcca ccggatttg  aagcgataac agcattaata acttcgatgt tacggttttc    24360
ggcttgctgc ttttcttcc  aatctttacg ttggaaaaat accttcgcaa tctcaaccgg    24420
gataatacct tcacggtctt tgtgatacat ccaaccattt ggtgaacatg aatatgtgtc    24480
actaggacgc ggtgctgttc cattgatgta ttcatgaatt ggatgaagct taaactgacc    24540
agcgatagtt tctggactga tattcacttg acgaatgata cttggataaa gagacgtcaa    24600
gtcaaaactc atgatataat tacgagcaca tgcttttggt tcaaatacgt aagcacccgg    24660
gaagctctgc ttaacatgcg aacgtccttg cggaaccact cgcttatctt ctttgagact    24720
attgaaaata atagcatccc aggttttaat cgggctcatt acaccgccaa aaggcatttt    24780
agcgtaataa gacatactaa ttgctaggtc gatgaaccca cgaacttggt cgataccttg    24840
caccgattca acgtccatga tgttataact aatataacgt tgatggttcg tttcacgcaa    24900
tttgttaatc ggaccatcat aaggcagttt accttttttg gtctcatatt ttgcgacata    24960
atccaaagta taagacggtt ggttcgtgaa actgtacttt ttgtacaaat ccatgtaatc    25020
aagaatagtt acgccatcaa tgctaaatac ttctttatca ccatacatgt tagtgataat    25080
tttagatttc acgcgattga ttggtgaaaa acgcttcatc gaacgttcac ctagaacttg    25140
cttaacgcgg ttcatgatat acggaatatc aaaaccttca atgttccaac cggtgaaaat    25200
tgctggacgc ttttgttccc aaagacgaat atattccatc aatagttcgg cttcagtttc    25260
aaacggtaga taaacaaccc ggtcaagaat atcttgcgga acttcatcgc cgccgtctgc    25320
ttcgcaccga gctgctaact ttttatccca tttggatact gacccataca acgaatggag    25380
taaatcaaag acataaaatt tgtcatcaat ggaatcgtaa tgagtgatag catcaatttc    25440
atattctgct ttcatcgggt ctgggaattt atcgccagta acttcgatgt cacagttcgc    25500
tacacgaatg aattttcggt cataaacaat ttcggaacca tatgtgtcac tgatatatgc    25560
gagtttaaaa tcatccattc ccattgcttc aagaccgaca tcttccatgc gcttgaacca    25620
atcacgggca tccttcattg taggaaaatt aattggttcg cagtcctttc catagatgtc    25680
tttgaatttt gatggtttat caacatgacg gaacagagtc ggagaatatt cgacgcgccg    25740
```

```
agttttttct acgccatctt caatatatcg ttcaacaata tcattaccaa cagtttctac    25800
agatacataa aatttcataa ggttccttag ttttccagt ggtccgagtg attagacctt     25860
gggtgtatta tattctattc tttgaatagc agaaaaggcc cggaggcctt tcattgagt     25920 tacgcgccta tagtatattt cgcgataagt ttccaatcgt cttttttgctt aaatgtgatg   25980 acgcggaaat tattttgcat agcttgcaga gaacctctgt ctacgagttc gattaaaccc    26040
caatcttcca ggagttgagc aattgagtcg cggcggataa tatcttcatc atcaatagtg    26100
actggccgtc cgtccagttt aagcatctct ttaaaatgaa ctacataata aagaccctgc    26160
ttctgtaaga tatgacaact ttgatataat acacggtctc tgttattagc aatacccata    26220
cgagtaagag tttcttttac tttcaggaag tcttcaggtt gtttcagttt aatttcgatc    26280 attttttacca ttccaatgct tgttttttaa attgttttg ttctttaaca ttttggtca     26340 cgtctttcaa aaattcatct gtgaccaacc ctttggcttc ttttaatact acgcccaatt    26400
tacctttgcg ttctagggtt tctctataaa cctgagcgtc atttaaatta atagtataat    26460
atttcattaa taccctgaga ataagtatct cctgggtatc ctctattaac ttagcccact    26520
taccaaaacg gcggccttga ggaacagcag ctaccatata gttgaaatgt gcttcatctg    26580
acagttcaga accgataaga ttcattgtat aaactgctgt catgcattcc ggatgttgcg    26640
ataacgcatt ttcaaccatg aatttgttat attcttttg agcgatggaa cattgtttct     26700
tttcgttaat tgcgccgatt atttcaaaaa attcattttc tgctttctgt tgaaagtat     26760 cagccatttc ttgaactttg ttccaatctt tagaataccaa agctacctga tgctcattaa    26820
attggacgtc atcatcaaat aaactcatta tttccactca ttattaagtt cagctgttaa    26880
acgcaagaac atatacatca catgaagttc agtatttgag gcaactcctt tgtactggtt    26940
gttttcacca ataatttcgt acattgccat tataccaggt cctttaagca tagagtataa    27000
ttcttcggcg agtttaccta caaaccaaga gtaatcagta gaatattttg gagccaaagc    27060
cctaagctgt ttaacatctc gattttttag agcatcaatc acatctgaaa ttgaactaga    27120
gtctttagtt acaatactca gaattccagc atccagaacg cctttggacg aatacatatc    27180
aagttcgcca atagtcttac gaaaatctgg aaagttcttt ttaactaaag cagcaacaac    27240
ttttaaatcg gcgatttcaa tgttttcatt tttacatatt tcaaccatac gacgaatcat    27300
ctgtttcatc attgttgtac ggtcttcttc tgttgcttgg ccaaatttaa ttactcggca    27360
acgcgaacga agtggttcaa taatgccgtc aatattgttg gcagtaataa aacagaaca    27420 gttacttgaa tatgcttcta aaaatgaacg caaatgacgc tgagattcag caagtccaga    27480
acggtcaaat tcgtcaataa caataacttt ttgacgacct tcaatagaag cagaacttgc    27540
aaaattagtt aatggcccac ggacaaaatc aattttacaa tctgaaccat tcacaaacat    27600
catatcagca tttgtgtcat tacacaaagc ttttgctgta gttgttttac ctgtacctgg    27660
tgaagcagat accagaatca tatgagggat tttaccgctt ttaacaattt tattcattgt    27720
ttcgcggtcg gcggcgggaa ggatacattc ttcaattgta gaaggacgat accgttgttc    27780
aaggatgtgt tctttttcgt taattgtaat cataatttcc tcatattaat attcaaagca    27840
atggggccgt aaccccattt taaatcattt tatttacagc attaaaaatc atgagtagaa    27900
tcagcttcca tagctactac ataacttgca tgttcaccctt caaacttagc tgctgttttc    27960
ttaccatcag cccacagcat caatttgtat gaagcgggtt gcattttcat attagccatg    28020
ttaataacaa agttaaagtt attggtgccg tcatagtcac ccaaagtcaa agaatatttt    28080
```

```
acacgaacca aagcagaatc ttcaacttta ttataaccat tcagaataat tttaccatct    28140
ttgttagtga atgtgatggt atcaatctgc aaaccgcgag aaactcgcat cagctgctga    28200
aggtcttcac ctttaaaatc tacaataact gaagcgaccg ggaacggaat tggtttgctc    28260
ggaaaaacaa tggtgcttgg gtcagctgct ggccagaaaa tagttgaacg agcatctgcg    28320
attttcacat taccatcatc tgccatggaa atctctgcgt cttcattgac caaaccgaga    28380
atacccagaa aaccattcaa atcataaatt gctacttcaa aatcaattgt gtctgcgata    28440
gttgcttcag cataagttgt gccgtttaca gcacgtgtca tgataaagtt accctgctta    28500
agcatgatac cagagttaat agtagagaaa ttttttcagaa tattcagagt atctttagac    28560
agtttcatta ttttttccttt caattacacg tttaataaga tttattatat tacttaaaag    28620
tttttgcaag ttcttcgata acttcttcag ataccagcaa agcagcagaa atcaattgtt    28680
catcagcgtt aacacagaaa tcatcttcaa gacgctcgcc accaatacgg tccagaacaa    28740
atttagcgcc ggcagaaaca gattcattgt aatgcttccg catcagttca atccatttat    28800
catttacggt gcggtcaatt gactgataat atgcatggcg cgcttcagca atagggatac    28860
gtttgcggat aagttcagca ccttgttcac ccatagcaag tacccatgct cgacgaattt    28920
tgttttggtt attagggtta gagtcagtac gtacatttttt aggctggata tctttagtat    28980
caattgcaaa attcaagttc ataatatttc ctattcaatt aatcaaagta ttctattact    29040
gtccaagcgg tgttgcggtt agacattatt ttaacatatt cgtctttaaa agcatctctg    29100
agctgtattt cagtaactaa gtggtcttca cctgaaaaat tattagtcag tatatatctt    29160
ttaatttccg gtacgcccaa cagctgttgg ccatttttaa agtctgtcat ttttccatta    29220
ccgtgaatct gccaactttc ttcatctgaa gatgttgtcc ataatcctgc gggtcatggt    29280
ctttatggct tatgataaag atattactat cagtcattcc attgagaatt gttcctactc    29340
gcttaatacc ttcattatca aacgcgccat cataaacttc atcaagaaag agacagttaa    29400
ttttaacatt agaaactttt tcagcaatgt ctcgccacgt gaacagcaac gcaatatcaa    29460
tacgagcttt ttcgccttgg ctgaatgacg cataactgaa ttcttcgcgc ccgcgagatt    29520
taatagtttc ggtgaattct tcgttcaaag taaagacata atcagcttcc ataattttaa    29580
gatactgatt aatctgtttg ttgaacatcg gaatatattt gctaataata gctcccttga    29640
tacccgaatc tttcagcatt tcagttaaaa tgcctcgatg atattttttcc ataaccatat    29700 tggatttggt atcaactatt ttattcaatt cttcgttaag cgtttttaatc tcatctgcat    29760 gattgatgaa ttcttttgat gcttttttcaa tcgccgcttt tacttttttta gccttttcta    29820 ctgttgaaat taaagtttgc ttttttagatt ttatgtcttg agcaagttca cgttgcgttc    29880
taacgttgct ctcatattca tatactagtg tctctagatt ggctctatga ctttctaacg    29940
actctgattt atgtttacat tcattaatct tatcgttaat ctgagtgact agagatgacc    30000
cagagtctaa ttgttgcatg catgttgggc atgaacctcc agaatgatac aaagaaacaa    30060
ccttattata tgagtcaatt ttagacttaa tcaacagagt ttgattacca atttcagtaa    30120
acgcggaccg agggtcttca tcaagcacga tagatgttaa acgctcagtt gcttttttcaa    30180 tttcggattt aatagaacgt gcttcagtcg caagttcatc atacatggtc tgaaaacgag    30240
ctatattttc tcctgatagc ttttttctggc gttcaacgtt ctcttcataa attttaatct    30300
gttggataat tccgtctttc tttgcgtcca acacagagac ttgtgaatta atttctctta    30360
tatgagattt attcaattta tccatttcag ctaatgtaga aacttcgagc aagtcttcta    30420
ctaacttccg gcgagctgga gtactcaaac ccatgaacgg tgtataacca gctgtaccaa    30480
```

```
gcacaactac ttgcttaaag ctggaataag acattttgat aagttcttca aaatagcttt    30540
gaaaatcttt aacagaagct gcctcgtcca ggcgaactcc gtctcgagtt atttcaaaga    30600
tattcggctt ttgaccgcgc tttatataaa aatgcttacc gtcatactcc atccaaagct    30660
ctactaacat atctttttta ttaatagagt ttattagttg acctttctta atatcacgga    30720
acggtttgcc aaataaagca aatgtaatag cttccagcat ggtactcttg ccaccgccgt    30780
ttttgccggt gatgagagtt ttttgtacct tatcaagttg aatatcaatg ggcgaaccgc    30840
ccactgacat aatgttctgg tacttgatgc ggtttaactt aaatgttttc atgtgttatt    30900
ctcgcgaata taattgcggc aatattccag cataaaatct tcggatatat gcattacatc    30960
aaaatattct tgccatgata cacctaatga acactcagat gtaacaaaca ttatgccttt    31020
aaacccgccg tcttcgggcc agtattcaat attaccatac caaccattgc ctaaattaaa    31080
ttcatgaagt ttcacgagtt ttgaacctcg atataaagtt gattagcata ttttataact    31140
gcttccctgt catcatcgga taaatcaggt aaagagttaa tatattcttc cataagttca    31200
agtaagcttt taacttctac ttcagcttct tcatcaactt caagagaatt atcaatcttt    31260
gaaacggtac gaagctcatg aacaactttt tcgagttcgc tttcaaattt tggaaggtct    31320
ttatcaactt ctgtgataat gacacgaact gaaatatttt tgtaacgatt aatatcaaat    31380
ttacccttaa atggataaat tattttttga tgccagcatg tttcgttttc gataaaatca    31440
aaactgtcat ctcgagtgtc ctgtatccag aaacctcgcg ggtcattttc gtctcccgca    31500
gtaagtgtcc atggcgtgcc aatatatttg acattagctg cgctagagat agtatgaaag    31560
tgtccagaac gaacatgttt atatttttta aggaaatcag gttccaaccc gtgggatttt    31620
agtcctttgt aataataaaa accacttaat tcccaatgac caatacaaat atcggcatca    31680
gatgttttga tgtgattcat tatatcggac gcgttctctt cgcacatcca cggaatcata    31740
tcaatcaaac aaccatcaaa atctacagtt tcaggagtat catgaattat gatatggtca    31800
tatttaccta ataactcagt gattgcattc ggatgcattt tgttttata gtgaagatcg    31860 tggttaccta cgatggtgtg catcgtaata ccagcttcac ctaaagaagt tgctatctca    31920
cgagcaaatt ccatagtctt gtgagtgata gctttacgaa cgtcaaaaat atcaccatat    31980
tgaacccaca tagttatccc atgcttttttg gagtattcaa tcttttggcg tattccgtct    32040
cgttgaatat tctggagcca tgggtcatcg cccttaactc ctaaatgcca gtcacctgta    32100
tggagaattt tcatatttta acctgtacaa aaatgataat taattatacc atgtatataa    32160
aaagcaaatt agtacgcgca aatattttt gaaacgtttg actggttaat tttgtgaata    32220
aactcacatt tttcttctgg cgataattcg tgatttctga tgagtgccgc gcaaggatat    32280
tttggtggat aatctttctt taaaactaaa agtaactcat ctaaatatcc gcaactatca    32340
taagcatgcc gaagtttaac aatatcaaca tgcttaatgc gttcaaaatc tttagagctt    32400
tgtactgtac ttcgccaatg cacttcatta tctttagtcg ttggagaaat ataaactgca    32460
actcttagtt cagtgtcatt taatttaatt ttttccatta ttacctcaaa gaacaaaggg    32520
agcctcggct cccttaaatt ttacgatatg ttatagtatt ttcagctttt gctttatcgt    32580
gtaacagttt gaattgtgac atcattccag acatgctgtt atgtatttt gtataatcaa    32640 cagtcttctt tggagtttct gtcacgattt ttaccatttc caccaccgtt taacttgaaa    32700
agtatcagcc caaactaatg ttttttcatc tatagcaatc tctgaacttt tagttacacc    32760
atacggacca agaattttgt atgtgttttt agaagttttt agagccattg ttccattaac    32820
```

```
catagataga gtgaaacaag cattaacttt aagacgtttg aatttaacct ttactattgc    32880
catttacaat ttcccaaatc tgtcgacgag tggtttccca ctgtactttg acaagttcat    32940
ctgtataagg ttggcgtaaa atgtcccgag atttctcgat agcatatttg tacgccgcga    33000
agttattttc tagtactgct ctttgcgcat gctcatttaa acgttaagt tcttttgcat     33060 gcttttata aattttcgct gctttagcgt tagcttcttg acgtgttgct tcttccattc     33120
gagcgataat ttgttctact tcttctgggt tttcatcaat tttattgata ttatcaataa    33180
tctctggaga catttaatta ccttattttg gaaaataatc caatgaaaaa taaaatccgt    33240
cgggagatac aacatattga tgaggaactt cttttccatc aacaataaat gtaatatcgt    33300
gcggattagt tgggtcaata tgaatatcca tttcaagaac ttcccttaaa tacatttta     33360 gtatataagg aatagcttct aattctggaa tatcttcaag cattcctgcg aggtcaatct    33420
tcagcctcat ataaaaaatc caaattcgga gaatcgtcta cttcaacact cttttgtca    33480 gaccctggtg ctttgtaggt agattcttca taatgcgtca ttttatcgta gatgtcctga    33540
atgaacgttt catctgctaa cgcgaccata tcatcgtcac gactgtcata gacattgtga    33600
acaaaatagc tatatttctt tgccatctct ttgcgttctt ttttgatacg ctgaacgaaa    33660
gcattaaaac aagcctgagt tatgtatgca tgtgggtttt tgtatttctc ttcgtcaaag    33720
tttttgagac ctttaatagc agcctcaact ccatcagaaa tcatttcatc tttccatgat    33780
tgggtgtatc ctgaaaagtt aaaacgcttt gacaatccct cggaaataag cataatagct    33840
tttccaatag tgtcattctg acggacaagc gttccttctg gcgcttctct acattttgt     33900 ttccattcac atattgcgtt gtaaagctct tgttgttta catagtcagc cattaatacc     33960
tcatcgcctc aagtttatat atactttat tatatcatat ttgtgggaca agaggttatt     34020
tgctaattag aagaacgaag aatgcaatac atctgaaaaa gttgttcacc aatttcttta    34080
aattggtcaa ataaaagaaa ataagctgtg tatgaataca agtcattatc ttcccaaaaa    34140
tcgttgaaac tattaaacat ttcggtataa tcttttggt tgagttttga agcatgagaa      34200
tgccaatata ctccaggcat cacaccagtt tcaaatttaa ttcccatcat ataatcaaca    34260
ctaaaaatac caaaattctc ataattaat ttaagttctg ttcttttcat tgctcctcac     34320
atgtttcggc agttaacttc aaattatcag attttttagca gcttctaaag ctttatccat   34380
tgaactgaat gcatctaccg agtgataatc tttacctgtg tattcatata accaccaggc    34440
gtcaaagtct tcttcaataa cgtaaccaac accgttcttc gaagtacctt caatcatcag    34500
cctcccatct tcaacagaag catcaaatcc cgcgagttct aaatctgcaa caatttgttc    34560
tttattcatt cagatattcc tcaagctctt ttcttgttaa tccttcattc cacatagtag    34620
aaggattagg acagtcagtg ttgctagtac taataggata atatctcatt tctttaccga    34680
gagcatacag acatccaaat gcttcgtaat aattaacagc ttgttgagtt tcaatccgtt    34740
cgggcaatga aatagccttt gcgcctgtaa tagtgggttt caagtaaact gcaataagtg    34800
ctatgccttc gccgaattcg ctcatttcgc cgccttaaca attttgaggt caacaaatcc    34860
tttcttgcgc tgattttca ttttacgaat agtgcgttcg gaaatttcag gttttttatt      34920
tgttggaata ccaaaagcat ctagattaaa ttcatcaata atatagcaaa caatcaattc    34980
gcgaattcga gcttttccaa tcttctggtc gttctctttc atagttccat gaagagcagt    35040
ttcccattca tctaaaattt caggcgtgac aataacagat ttgaattcac catcaacttt    35100
catttcttca actttaggga aaacaaaaga gttcagaacg ttttgatag cttgcgacat      35160 gttattttcc tcattggtcg ttagatgttt gacatagaga ttttaaatta aaatccctat    35220
```

```
agcaaactca actcatctgt atgtttttag cattatgaac aattttgaaa ttatccttcg   35280
acataccaac ctttatcttg ccacgcttcg cctttatacc aacgagtcat atcataaccg   35340
ccattgtcgc gaaccgttcc attatcataa atgaaatact catctgatgt gaaatattca   35400
tgacgaatac acttgccggt aattttttgaa gtcatcacag cttcttggta agtcattatg   35460
cacctcttac agcatcaatc aattctcgta ccacagtatc caattcactt gtgtatacat   35520
ccggaaccag agctttaata caattactca ttcgtcccgg gtagtgttga gcatgattga   35580
gcgaaacatc tgtccgacaa cccttcgccc ggaaaacaac ttcttcgtca gagatttcaa   35640
ctgtgagtgg cactttatcg gtggatgaag tacgaataat catttcatac ttaatcatac   35700
tcgttttaga tacgataatc atctttaact ccatttgttt ggtatgaggt aatagtaaca   35760
cagtttttgg aggatgtaaa cggttgatat gaaagaaaag agggaccgct agggtccctc   35820
ggatttaaag tcaatatatt atattagaat gatacaagaa tgggatagag tatcactctt   35880
cgtccaggtt ataacctaag acgctaagtt gttctaatag gtgggatttg ttgcgtattc   35940
tttggttgtt caaaagacg ataggatatc gtagagctaa actcggataa ctacctacac   36000
gtttagccgc ttcagtaatt cggtctctgt catagacaaa tccaacttcg ttttcgtttg   36060
gaattattac atcgtaaaaa gcataaggga tattttcatc atccaaagtt ttacgaattg   36120
aatagcaggc cggacaccgg cctactgtct caggaattcc gtatatttct attttttgcag   36180
acatcttatt tcttcaataa gcgcttcaat ttgtttaagt ttatcttcaa ttgaagcttt   36240
ggaggttgat tcaattatgt atttctcgtc aacttcatat agaacatctt tgtcgtagaa   36300
gttgaataaa cagctttggt caaaatcgtc cgcgtcaaaa atacgcttat catgactaag   36360
aattctcatg acttcagcat gttcaccata cccatttaat tctagtactt taaatgcgcc   36420
gcctttgagc ttgtcataaa gttttttcatc accttttgcc cgtcgcgcag ataaccattt   36480
gcttacttct gccgggttat aagcgtacca ttgacctgct ttgaattcag taatcatatt   36540
aatattgtcc aaagaaaatg aaagcataaa gagcagggaa ctcttcacta aaacgctcaa   36600
tgtaactgta catgtacact tgaagttcat gaatccaagg atagtgaatc tgcatttaac   36660
cattcctcat tgtgttgttt ccatagccgc tggttatctg aaccacgcca tggcttatca   36720
gttgggttat cttgttcata tttaccatca ataataacat caatgtattt tagcaattca   36780
aggtgcttga tgtcttcaaa cttgtaacca gtccacatcc agatatcttt tttgggaaaa   36840
cgcgctttaa cccatttaac tagagcttca atatcttctc tgtttcctcg ataaagaggg   36900
tctcctccag taagagtaag tccttggatg tatggttttg aaagatgttc tgcgatttct   36960
tttactgtat tagtgttaaa tgtctcaccg ttgcaagggt tccaagtgct tttattatag   37020
catccttggc atttatgaat acaacccgta acgaaaagaa cgaccctgca accagggcca   37080
ttcacaaaat cgcatggata aattctatca tatttcaatg tgttttgtcc tatgcatgat   37140
ttctttattc ttacctaggt taaatcctcg atcagaagga ttaccgagat atccgcaagt   37200
ccttctaata gtattcatct tcttaggatt agtctcgcca caaacagtac attcaaatcc   37260
gttttcagtt ggtttcattt catgagttga cccgcaactc aaacatttat caactggcat   37320
attaacacca aaataatcca gttttttctac agcataatcc cagactgctt caagagcttg   37380
aatatttctc ttcatatcag gcaattcaac ataagatatg tgtccaccct ttgcaatgaa   37440
gtggtatttt gcttctcggt caattttttc gaatggagaa attttttctt caactgaaac   37500
atggaagcta ttagtatacc atcctttgtc ggttacacct ttgactattc catgttcggc   37560
```

```
tgcgtcaatt ttacagaaac gataacataa cgattctgcc ggggtactat aaaggctaaa   37620
agcatatcct gtttcttctg tccattcgcg tagataatca ttcatgtgtt taagcactaa   37680
ttcaccgatg cctttgtggg tcattagttc aagctcgtga attccgatat atccaagcga   37740
aatagaactt ctaccatttt taaacaactc aatgatttca tcatctggtt tcattcgaac   37800
gccaaaagct ccttcttgat acagaatcgg agctacagaa gcttttacac cttttaacga   37860
ttcaatacga agcagcaacg cgtctttaca aatcttcatt cggcagtcta gtagacgcat   37920
gaacatgttt aaatctgttt tgccgttgac ctgagaatcc aaagctatac gaggaagatt   37980
taatgtaaca acacctaaat tattgcgtcc gtcaagaata aatttaccat cggaatttta   38040
ccatgcgctc aaaaagcttc tacaccccat tggagataca ggaataggag aaccagtaat   38100
cttacgatta ttttttggcgc taataatatc gggatacatt cgcttagaag cgcattctaa   38160
agctagttgt ttgatatcat aatttgggtc ttcactatga agatttaaac cttcttcaac   38220
gaacataacc aatttaggaa aaattggagt aattccatga cgacctaatc ctcgaatacg   38280
atttttaaga atagcttgtt gaattagttt ttcttcccaa gatgtcccca taccaaatgt   38340
aatggtaacg aaaggtgttt ggccgttaga actgaaaaga gtattaactt catattcata   38400
tccttgaaaa gcatcgaata catctttttc tgttttttct tgagcgtata attcagcttc   38460
tggaatatga tatcggcgag cgtcttcgat atgtttgttg aaagttgctt ctacataagg   38520
agctagtact tggtcgacat tagcaaatgt agttccacca tattgatgag aagctacttg   38580
agctgtaatt tgagccatta cggcagttgc tacaccaatt gaatttgatg tttcaatttc   38640
agcattaccg agtttaaacc cattttgaag cattccggct aaatctacta agcaacagtt   38700
agtaaacgga agcgatggtg aataatccat gtcatgaaaa tggataattc ctttatcatg   38760
agcatctagt atagagactg gaatgacctt acgggcgaca tgcttagaaa caatgccggc   38820
cataaggtca cgttgggtgg gaaatacccg cgaatcttta ttcgcgtttt catttaaaag   38880
gtctgtatta gttctatcaa acagacccttt gatttcagtt tcaattgtca ttttaagcct   38940
ttctttaaat aatagacata atcttcaagc cattctattg tcaatagaat ttcttcgggg   39000 cttttttaaat tagcctttat ttcttttaaaa gaatttgtca ttatttttaga agtatgttca   39060 attttaatag tttctactaa atttaaagtc gaaagtctct caatgtaaga ctttttatct   39120
tcaatttgta atttaataat ctcgccagat ttaacaaatt tagaacagct tccacgatta   39180
gaaccaaaga attcttcgac ttcggaattt gacgcaaact ttttaccagt ttccacatgt   39240
tgaaacttcc atcgctgacg tcgaattgaa ggatgtagtg tccatcgatc tttatataa   39300 tcaagttttc catttaataa atttgtaata tgagacgatg aaatatcatt ttttcttgca   39360
aattcagctt gatttattac ttcgatttcg cacgaattta gttcatccca aattttaaat   39420
ttagaaacag aatgatacac tgataatttt tcttcctttg agcgaccaaa ttgccagcca   39480
gaatctaaat acttttgaac atcatcgggt ttaacatatt tggtttttg accaatttta   39540 tacatcatcg gccatgaaac atgctcattt cctttgtcaa aattcatcca tcgagcaata   39600
tcttcttctg ttaaatcatc gaagcagtta gggttaaaat gcccgccaat tgtttgtttt   39660
aaccacatag ggtctcgtaa tacgtcatta gcaagttgca tttccatttc agccattaaa   39720
gttttacccc aagttggata ccatccaaca attagatatt ctttaggctt tataccatttt   39780 tccaacatcg aattcaattc atttgatgaa gatgtataag tcttccaatc tgattcttca   39840 aatcctttt taggaccgcg tttaaacgtt gaagggcag ctttaattct tttccaaatc   39900
tttttagcgc ctacatactt tttaccgtct tcaaacgtga ttacataaac aaatccaata   39960
```

```
ttatttttaa tatctgtttc ttcaaaaaca gaccaatgac cataatctga cattataaat   40020 acatccttt  tactaatatt atgatgtatt tatacaataa gctaaaccat taatttatct   40080
aaattataga gccaatacgt ccttgcccat tcttacggt  ttcggatttg agctttagtc   40140
ggcttagtag agaaccacca agaaatttta tacccatcat cttcaataat ttcaaaaact   40200
ttattcacta aactcatatt aaattccatc actttttagt attcggagta tcaaataatg   40260
atatgctaca atccggattt ccagttatat gacaacttgt aaatagagcc cagcggctca   40320
aagcatgttt acctaaaatt tttctagacc tgttattaga ttcttcatta ctgagagtca   40380
tattaagtct tggaaaataa acagaagtta taccagttat ttctccggtg tcagtaaaac   40440
tcgtatagca tttggaaata acaatttcat cgccagggat aatacccata tctttgaaat   40500
agtctatcac atcaccaagc tcatgcttaa ctttaaaaac ttccggtttt actgtaagtt   40560
taagtccagt taaattcatt ataatttact caattaaaaa ttaaacaagc gattaattct   40620
tttataccga cgaattaatc gcggagtcaa cttagaaacg ctcaaaaccg tcgtaaatgt   40680
tccgtctttg ttagatataa cgaatttcca tatgcaagaa ccatctagct ttttgtcatg   40740
aataatttta gtattcatta aagccctcac aatctagcat ctcgttcatc gtgggttcat   40800
tataacatgg ttcttcatct gtgtaaactg gttcttctgg ttcgggctct acggtttccc   40860
accgagctgc ccaccatggt tttaaagcgt aacccattct gtgattgtcc tcatcacgac   40920
gcgttcttgt ttttcaacaa gcgaaacatc aggttcattg taataccaat ccgaatgata   40980
tgaacccgaa cgagtttcat ttacagcaac atgaacatca tgcttttgc  tgtagtaaac   41040 tacctgtcgg tattgatatt tgtggtcttg aacccagtct tcggcttcca cttttttcgag  41100 atattcagaa tcgtcaaaat cataatattc gttatacccca tcatggtctt ccatgatttc   41160
tttaagaata tcagtttgtc caggagtcat tattcaccct gtaaatgatt aagctgttcg   41220
tcatcaaccc aactctcaag tccagatggc aggtcgcatt caatctgcca aagtaactct   41280
tcaacttcgt ataaccgaaa gagctcttct tgtttaataa ctgcttcgtc gtcattcaat   41340
tcaatcgttt tcattgtagt gtccacataa acttaaaaag attttcttgg accactgcgt   41400
catcccaacc ccagacatta atatcttctg ctaattcagt tggaagaaca tcaagaaacct   41460 gttgagcagt cggagctgat atacaaattc ttttggcgca tcggctataa gcagctaaaa   41520
actcgtcata gttattaatc ataaagtttc accataacaat caccgtattt ccattttgac   41580 ataactttt  cacccgtaga gtaagttact tcaaccttag ctcgatgatt ttttatttga   41640
acaattcggc cggtttcaag accaccgtaa ccataataaa gcgcaattat atcattaacg   41700
aaaagctcct ttccgcgata atcacgcatg taatcttgac cttcaaccat gcgttctatc   41760
accgaaaata ctcgcgcaat ttatcaaaac caccaatata acttccatct ggagcaaata   41820
tttgcggtac ggtaagaccg atttgtgtat ctcttccaag acgagtcaaa agttcagcaa   41880
taatttcatc gtcaaataca ccttttttctg gcatgatatt gatgaattca tatggttgtt   41940
ttttaacatc cagaagacgt ttagcgttat cacagaatac gcatttatga atgttgctgt   42000
cgtaaccgaa tactttgaac attattttac ctctacaggg aatacttgag ctaattttgc   42060
ggcaatagct ttatcaataa tttcgctaaa actttcgttc aatcgagaaa caatcatttc   42120
ttcatattgt cgttcattaa tcttaattgc atcagcgata taattttcca ttcgtttagc   42180
tgctgcgtct accgagctca caagtgagtc caaaagttgt tcatgcgcta tacgttcagc   42240
ttcttctttc atcactcgtt tgagttcaac tgtacccta  acattccagc cattacgctc   42300
```

```
aaaaaacttc tcgagctctt tgcgaaccgc atcttctacg ttaggaatgt tagaaccctg   42360
aaaagcaatt tcagatttaa ctgcttcagc aattttattt ttggagtcct taacaacaag   42420
ttctttaaca atattgttaa tcacggattg ttgtaaagca actcgcattg cagagccttc   42480
agggaacaac tgacgaactg cgtgagtatc taattttaaa tcaatcattc tgtaataacc   42540
tcatagtatg cgtcgctcgc cgctagataa attctgtcag atatatttt atacggattt    42600 ttagtaaatt tttgatttgc tttatgttta aaataaatta catcaaaagc tgtagccgcg   42660
ttaatacagt tatgaataaa attaatatca gttttttcgc cggcgtcaat agtgtgttgt   42720
acaataattt cagcgtgtaa tttacgaagt tctttaaaaa gagacttcat ttcctctgat   42780
tcgcacattg cgtcagatga actaaaggga ttcataacta acctcaatat caaatttacc   42840
aatttcacga aaaattaaat tcaacaaatc ctcttcagta aaattggacg atgagcagca   42900
actagcgaat ggatgaagtt cattatattg tacaccatca ataactacat cgtatccctc   42960
ggctgaattc cagcaaccca gatcgcaatc tccactatca gcatacagct tagttacttc   43020
aattttcatt tagcaccttt gtaaatttgt gtttacattt acggcatttc attttaagaa   43080
ctttagtatg ccaattaatt aattgaactt gattggtttc gcattttggg caaggagtaa   43140
cttgtttcat ggaccgttca cgacggtccg ccatttctaa tacagtattc caatcaattt   43200
caaaatcttc ttcattttga actaaatctt cttttaattg gttccgcata atactgcatt   43260
agcctcttta agtttctgtg attgttcttt aagacgttta agtttaaat tagacttctt    43320 aattttatca cttaaatctt tttgcactga tacttctttt tcaatttcca ctttaattag   43380
gtcaataaag tgttgaattt gattagaaac atgagtttct accaatacgt cagttgtctc   43440
aaactgcatt gtcggagaaa atttattata aaccaccgga ttattagcgt caatgcgccg   43500
tgaataagtt ccactaatag tatctttcat atcttcagtc tctttcaatt tgatattaat   43560
tttaattctt gttttacgtt ttgaatcgcc ataattaata tcgacattaa catcttcaac   43620
ataattcata tgctttaaac cagcagcaaa ttgttcagct ataattctag aaacattatc   43680
agactgccca atcatcattt taattgaaaa ttgaatatca taatctctta aaggagacgt   43740
agttacttca gtttgaacat atctcaaccg gttgataaaa cactgagaat attcatgaat   43800
taaggtttta cggccaagtg taataatttg tttgtattca ctctttaaag cattaataaa   43860
tttgtattta aaaatttcag acttttcaca ataattttt cgttcactcg ttgaatttct    43920
ttcttcagtg aacatattca atgcacttaa ttccatgaat gagcgcaagc gcatcactga   43980
cgtgatatat gaagttattt tacaacgagt cacttcttga aaaaattcat catatgtttt   44040
attatacgtt ttaatagaat aaaaattata attgaatttg ttaaacagaa aattcaatgt   44100
tttagcatcc agacctttg aaacaaaagc atcaatatat tgctttgtcc gagtttatt     44160 ttcataacca aaatcaaaca ctggcttcat atattctttt aaatctgctg ctgttttaat   44220
ttcttcaaat ttcatttcaa ttatctccag aatccgtaaa cccattataa cactattaat   44280
tagtaagcat tttaacagca gatgggcgtt tataaaaggc gtgagtattg tcatcaactg   44340
ctttagtaaa agtagctttg aactcaattt cgccgcgata atttacatca actgctccgg   44400
gtaatgaacc ataaacagta gctccatttt caagacgcac catcattta gcagatactc    44460 cccaatagtc ttggtaaatt tttgttgaaa ctactctgcc ttttactact tgttttcctt   44520
caggtgcttc gcctttagtt gctttaagtt tatcgtagta agcattgaac cattcttcgg   44580
agtatttctg aattgcttca agaatacttt tatgggctct aatttctgcc atcaaaactg   44640
cagtattatc ttcaagttcc caatgcttat atggttcgcg gacttcaata gggcatccgt   44700
```

```
aaagcttgag ctcattaagc atatcagatg ttaaacgaag tttccaccag ccaaaatctc   44760
cagtgaattc cggcttatct aaaacatcga gctcagtaac atacggaagg taactccctc   44820
catgataagc ttcaacttcg ccaagttcat tttcccaaag ataaccgtca aacggagcat   44880
gtggacggtc gtcaattccc catgttggtg caaccaccct ttcaaatcct tcgcgactgt   44940
agagagtctt cgcccatcct gcattcaatt cctgagcgcg tttttcaact ttcgctcggc   45000
gagcagcacg tgctttgcga ttttcatcta agattgaatt gatgatatca gttaacattt   45060
tagtctccgt tagtagatta cgaaactatc atatactaaa cttaatgcgt tgtaaacggc   45120
tgaagtaaaa atttttaaag ttaaccagaa cggttaagag gaactttctt aggaaggatg   45180
attaatcata ttacgaggat ataaaaatgc cccagcgaag ccggggcgta cactagtggt   45240
aagatggtgc aacatcgtca ccttggaacc aggctgaatt ggaagatact ttattagcat   45300
attcccattt ttctgttaag tcatttagcc cagcttgcat ttttgcgtat gacgcttgct   45360
gatatcggtc cattgttatt aaagattttg tcattgtgga caaagttttt cgcctacctt   45420
cattgccata attgcgaata agcgctctat tatattccgg cactaaaaat gaaagcgagt   45480
gcccaatgtc agacaaatgc tcagccttta attttaatct tttaacggca atagttttc    45540 ttaactttc aatcattgtc aattatcctc ggtttgctaa tgcgtattca ttagcattaa    45600
tataatcctc agcaaaaacg atatcaccga tttttagttg aattacaaat agagagtcta   45660
aaaactcagg tggtttaatc tcgatagaca tttcttcttt aataatttct attaccgcgc   45720
ggtgtaattc atctttagtc atcatttacc tgcaattaaa acaccgacca taaaaataat   45780
ccagaacggg taaagaaaa ccattgacca ttctgcaact atttttgtca gtttctgttt    45840
agtagtacga cagctcgacg ctggcattcc aatacaccaa gcaaattttc taacaaataa   45900
aaaaccgata attaaataag caactacacc taatacaatt aaaatttcca taattacacc   45960
gccattataa acccaatgca tcccgttctg attcggttaa ttttgctaaa gcttgttcgc   46020
gtactcgttt aatgcgctct tctttgtctt tggcagtttc tcgttgaata tcaaaaccat   46080
ttttaacgat aaatgaaagc gtcttttccat ctgcaaatat aactgttaaa gcttcttttg   46140
acgtgtctga aacatgtccg tcactgccgt accaggattt accggcgaca ctctcacgcg   46200
ctttttcata cgagtcatag tatccataat gttgagttct gcggtcatct ggggatatcg   46260
tagcttccca gacctttttca attttactgc taataatagt tgtattatta atcattttta   46320
attcctcata tatggctttc acaatttacc cttaaagaat tctgcccggg aagcacgttt   46380
aggttcgcag ttccaatatt tatctttaca cggagtgcta caaaactat gttgccaact    46440 acgcttcgta ataacctttc ggcaataagg acaatacatt tttgtcccta ctttcactaa   46500
agtgttgtta tcgtaaattg gtttcattac attataacga gtatctaatt cttcctcttc   46560
aacgtaatcc caatcttcat ctaatccgta tcccattatc ctttgctcca attattaatt   46620
atttcaacat tgttacttct gagatttcac gccaattttt ctcgtctgtt gctacgaaat   46680
ccgccaaata caaggcagta cgtaaagata cattgcgaag acgatttacg ttattttca    46740 taaattcaag aacatctaca acttgtgaat tacgtaatcc gcgattttgc aacatccggg   46800
tattcataat aacttcttca acacggacca ttatttcttc atttgaatga acgcctaaat   46860
ctaaataaac tgaacgtgat accaaagcgg cgagatgtgg tgctaatttg cttccgcgtt   46920
ctaattcttt atcaatatca acgtttgtga taaaaactac tgttccctca tattcaaatt   46980
catttgggat gttttttct tccaagtaag aagaagcagt actccagcaa accttgcgtt    47040
```

```
tatcgcccga atccaaagca gctttaagaa gatttagaat atccatatca gaaaatacat    47100
ccacatcatc aataagcaga actgaattag cattgcgaga ttcccaaagg cggcagtaaa    47160
gaccaatccc ggaaatttta ccattgactg atttatattc aattctacca tcattgtgag    47220
cattttctaa tgctttatcc aaggtgtaag ttttaccaat acccgcagct cccgagatga    47280
taagtgaacg aatgttacca tttataatac cattcgtcat aaatcccata acgttaaagc    47340
gcttattaat gcgagctttc atatcatcta cgctttcgat aagttcaatc tttttagtag    47400
ttccgctgta gctgatatct gatttgtaaa cccaaacacc tttttcttta ccgtcaatca    47460
ttacgaatac tttaccatca ccctgggcgg catcttcggg tttcaaagtt tccgggaacc    47520 attccctac taattcgaac gtcccggaaa tttcttttcc gaagttaata cctttattga    47580
tagtgatggt tgtcatttta ttctccaagt taattttgtt ttaccattta tttggtatga    47640
agtaatagta tcatcatttc ataccgttgt aaacattatt ttttgaaatt tgcgttttta    47700
actgtaactt catcttctgg gttgaaaacg aactgcttaa ataatgtttc tgcttttgga    47760
ttgaaaatca tagtgaagaa agttaaagta ccaggttcaa cttcacgaac cccacaaata    47820
tcgtattcaa cgttatcaac aatgagtttg tttgagttca gtgcatcttt agctttgatt    47880
acagaagttt cgattttcag ggtaactttc attttattct ccaagttagt ttttgtttta    47940
ccatttattt ggtatgaggt aatagtatca cagttttttgg agcatgtaaa ccttttttga    48000 aattttctt caaaaacaac aaaacctccc gaaggaggtt atttggagta tttttctagc    48060
tgacgctcag cgaaccgttt agggagcatc aacaaccatt ttaagatatg ccagagaccc    48120
gttaagataa aaacaggtaa ccataatagt aatacaaaca ggtaagaaga agtgtcctca    48180
atcgtccctc gtttaacaag ggcatttgtt ataaccagc cgcatgttag ataaactaac    48240
gtaacaatga taggcataat ccaccaaagc tgagctaaaa gtaaagtaac cataattcac    48300
cggtagtaat ggttgtgatt ttcaagataa acctcttcca agaacttgtc ccagaatgtc    48360
atatcaattt tgttaggcat tccattttta gacgcagtca ttgccagtgc ttcaacttca    48420
tctacgatgt cttcaagact agcttggaca tctttgaatg ggattaatcc ttgcttaatt    48480
tctaagatga atggcgcagt acaaagagga tattttaagt cgcctgtttt gtaaatttcc    48540
tttaactgat atccagcacg gtacgcatga ctcagagctt tccaatcaat gccttcgtta    48600
gcttctgcct ttcgtgctcg ttcgccatat tcactatcaa gtttgtttaa agactgtttg    48660
agctcagtaa cagagagtgt agtctggtat ttgcgtccta agacggtata gaacgtctgt    48720
gggccagttt tctcgtggtt atggaatacc cattcacaga attcattctc tggaagacga    48780
tgtttaatat cttcaacctt agtgcgtcgg acccggacta tatcatcttc taggtaatca    48840
acccattttt caggaacatc attaataatt tctaaaaccc gacgaagagc agccaggcgc    48900
gaacctttta caccatattt ggcagcttgt ttcctgacat atccaagata agatttcata    48960
ttagtggtgt aaaaccgcca acggttgtct tggataaatt tccaaacatc aggaaggtcg    49020
gatttgacaa caagtcccgg aggagtatga agcatatcca acgcgacagt ttcacccgtt    49080
gcggccaaat gaaagaagta tttcaatgaa tacaattcat ggtccacgtc gtctttggtg    49140
tttttagttt aagtgttatt ggtgttaaaa tttgtgtggt tcatagcccg tccaagcaga    49200
atgtctcggg catttggaac aaaaatttct ttaaaatcga catcactctc aggcgtagat    49260
gtaccgtata aatgacttcc aaaatagctt tttacaactg ttttcatatt agccccaaaa    49320
taatccgtac gcgaaaagcg cgtcttcatc tttaaaatta atcatttcaa ttttacgagt    49380
attttcgttt tcaacaacta cagcagagca gctatcatta acataaacta ctttccaata    49440
```

```
tccagaactt gaaggtttag aaagcatatc accaacagcc acaggaacat taatgaattt    49500
tttcttattt acaactttac ataatgtata tttttgaggg tcaaaaacaa gttcttcgcc    49560
tttatattca acaatagaaa aatgttcaac tttgaaaaaa tctgagccgt tataatctaa    49620
aattccgtct ttaaagtcca cacgaacgat agcatccggg tctccaacta ctgtgccaaa    49680
tatataattc tggcgccctg cgtccggaaa ttctccaaaa caagttttac ctactacacg    49740
tatttcgtat tttttggttc cagcgaggtc aatcaaaata ttaagaatat cgccagtttc    49800
aattggcact agttccggtt caattactgt cttggatttt ttaaatgaaa ttttgctcat    49860 gttttttctca tagataaata tgtagacctt tagcaaactc aataagagct ttgccgtttt    49920
cacaagctgt attagcttgc tcttcacttt cattatattt cgagaccagt gaaagcatac    49980
caattttttg atgaactgaa taatgagtca catcaatcat acgatattct cgacggtctg    50040
gatgagattc gcgagataca ttcttaataa cacttgggtt atgcattggg tataagcacc    50100
aatcatttaa tccgcgaatc aaagccatgc tagtaacaac ttttttataa gggaagttag    50160
tgatataacc caagaccctg gtttcagggt ccttcattgc gaagctgata tctgaataag    50220
atgctaactt catttgttta acgatagaca aagataattt cttctttgtt gttacaattt    50280
cgatttccat cattttttcct gcataaattc aatatgtgga cagaattttt ctttgcgagc    50340
tttaataaaa gcgaagataa tattaggctg ttgttcagca taagcaccat ttctggcagc    50400
ttcccatttt ttatattctt tcctttcttt tcgatgttcg cggaaactgt aaattccatt    50460
accaatgcat ataagtatac caaaaacaac tgctagtata agccaaccaa taattaaccc    50520
aggaataaac gcctctactg aagaaagaat tacaccgcat tgggcaaaca accaaatagc    50580
taaatctgca ccaatacccc agctggcgaa acaaactacg aatatagcaa ataacaaaag    50640
gaaagcatgc caaacacctt tccaaaaata aggacataaa gaatatggag cgatttcaga    50700
accattcata gtaacaagtt tatagtgcca agagccttta ttgatttgca ttattcattt    50760
cctttcatag aaggcagtac aacgttcaaa tagtcacgaa gttttcagc ttcagctttc    50820 aacagaaaaa tttctacatc ttcgtcttca taatctttat gaattatgct aacaatctca    50880
tagttttgtc cttgacactt atgctcaata acatttaagt tgagaacact tatttcgcca    50940
aaagacgcat caattacatt agcttcgcga ccaacacctt taaaattcat cacagtcatt    51000
actatttcct attattaaca atacaattat aattaaaaga actatagata ttatagtctc    51060
aaacccataa agcgtaataa attctatcat ttatgcttat cctgttccct tttgattggt    51120
tttgttagca atataagaca ttttagcagc ataaacataa gaagaacttt tatgaataat    51180
ttgagctaaa tggggtagtg cttcagtatc ttttataaac ctttctagct gtgaacgaca    51240
tattccatct tccaacattt catcgtatat ggtatacatc aaaaacccgg tctggccctt    51300
gtactggcaa atttcaattc gttcattgcc gtcataacaa cgagtaacaa gcaaatcacc    51360
tacttcaagt tttggaaaac tcatcttaca ctcccagata ttaaagttca ttgtaaactt    51420
actttagcaa attcagcgat attattcatt gtccactgtt tcccaagcaa gagttactac    51480
aatgttttca atagattgca ctaagtgttg ttttgcacca gttgataaat catactgaca    51540
taacgaatta gctaattcaa ttaactttct tttagtctct tcatgagctg tttcgtcata    51600
tttcattgta aacttcccctt aaccaattca acgatgccat tcacaagatt gtaagtaaac    51660
aatggatgat tgtattgaac gaacagataa acagcaataa taacgttttt catatatcct    51720
ccatatgatg agataattat actatatctc atcatgaatg tacaatcaaa aattaaatga    51780
```

```
tttcaaaaac gcttttcat ctatcgggct attattttta gcgtattcag catctttgg    51840 gtcactaaat tcattatctt tcaattctgc gcagaaatga attgctccac caaaattagt   51900
aaaaactcgg ttcaaattat aaaccgtgct tcgctctgaa gtctcaacgc ccatatcagc   51960
caaagaagat tcagttacgt attctttaat accatcaaaa cttttatact ttcgaatatg   52020
tttaacaaac caagatttag aatacccaaa atctaccaag aatggatgac tcaaaacaat   52080
aagtttgtca atagactctt ctgagacttc agtttcggta cgatgaattc catagacatg   52140
atacagaact cggccaggga caaaatcttc gaatttagct ttcatgatat tttcctcatt   52200
tgttttgata agttaatagt atcacagttt ttagaggatg taaacggttg atatgaaaat   52260
gccctggact gatgccaggg cgataggatt actccaaggt aaggaggtac ttcagttggt   52320
aaaatgctcc aacaatctca tccaccgtgt tctgtatagc gcgaggaatt ttatcataaa   52380
ttgcgtcaga ttcagttaag atgagttcaa tcatttttat agtgtcgctt ggcaaagtct   52440
tttgttctgg aatgtccgga acgtaaggct tgccagaaaa gcctagccat tgttcaccaa   52500
acttatcaat caagtcaggt aattcatcaa atataaaatt gtatgcttta tgacgagcat   52560
agcttttagt ttcgaaatga gctgaatgaa aatatgaacg agaaaccatt aacaagccaa   52620
gatatctatt ggcttcgttt gatttgccgc ctttagcaaa atcttcaaat ttcatgttct   52680
tccttttcag taaatcgatt agtgtaatat tctttagcaa cctctacacc agcagcttcg   52740
cacgtgctag tacatggttg tctatcccat tttgacttaa caaatgagaa gaattgctca   52800
ctttcccgtt tattataaat tttatattga gtatacactt taagcgcacc ctcaaaatac   52860
tcatcaaatt taggattaaa cgtgtctgca tgtactggaa cacacataat tccaataagc   52920
gcagatagaa atagagctct taaggccata atcggcctcc ttattttgt ccagtgtttt    52980 gtttgtgctg taatacagcc ttaacttcac tgaggtattt ttccagctta cgtttacgtg   53040
tataatctgc tttcgaaccg tatagacgta attcttcttg aaggtgcgaa ataccatgcc   53100
caatctcacg acgaagttcg tccaattgtt ctacagtaag attacgaagt tgcttttcgt   53160
ttaaatgctg catatacacc tcattagtta gtaatagtat ttataaatgt agtactatta   53220
ttacatacca gttaattcac accagtgttt gcggcaaaga gatacatact tatcttcgcc   53280
acctaactct attgtattac cttctttcac agcgtttcca ttttcgtcta tacgagccac   53340
catggtagct tttcttccgc aatgacaaac gcctttcatt tctatcaatt tgtcagcaac   53400
cgccaaaaga gaagctgaac cagtaaataa tttacctcta aaatctgtgc gcaatccata   53460
tgccataact ggaacattat agatatccac gattttacat aactcatgaa cattagcttc   53520
agttaaaaat tgcgcttcat caacaaatac gcaatgaata tctcgttgag tttgagccca   53580
tttgaaaaat tcaaatatat ccatatcagg cgtgattaca ttagcttctt ggcgaagacc   53640
aatgcgtgac acaacttcag ttgccgaatc tctatcatca attcccggtt tgagaattaa   53700
tgtacccata ccacgttctt tatagttatg agcagctgta agaagagaag ctgatttccc   53760
ggcattcatg cttgcatagt aaaatacaa ttgagccatt ataagtcctt cactaaattt    53820
tccagatatt gttctagagc attttcagct tttgttaatt tatctgataa ttgataatat   53880
gtttcagcgt cgccataatc agaattaatc tcaaacgaca tatcttttc caaatcaatt    53940 atatcactaa tcatctgaag tatatcatgc ttttgttcct ttgtcatgtc gttatctcat   54000
ctaaatattt tttaaacgct gctttatcgt catctaaaat tttacgataa gtttcccaat   54060
catgaccagt aattaattca gcttcataat taatttgaga attcaaaatc tcttcgacta   54120
aataaagtat ttcttattt tgctcagtag taatcatact ggctctcctg gttcaatcca    54180
```

```
ttctggagta tattgaaaga atccttcacc aacgtgattc ttacacgttt tgttggagca    54240
atataaccac caatcccacg cattataagg tggagtattc atcagcccgt cattacataa    54300
agaaaatact acgggccatt tacaatcttt acaacggtgt ttttcttttta tatgagtttg   54360
catttttagcc atcccaatcc acaacaataa tatcaatgtc aggagtaaac atatcaataa   54420
tcaactcaat tttattccaa tcaccgcctg cgataccggc accaatgcga ggaatataaa    54480
tcacaggcct gaataattgt cttttagccc aacaatttaa gccctggaaa gcatagagta    54540
atgcaccata attgatgtta ggacctggct cgtattgggt ataaagatta aagcaaattt    54600
gaccacgttc gccagtcgct tgagtgtaat ttcccaattt atctgggtct gcatgctcag    54660
tttcgtaaac atcaatttcc aaaataggag gatatgcctt agctagttgt ccagctactc    54720
ctgcacccat tgtatggaaa caattacaac cgtgagctac attgtgacct tctaagaata    54780
tttttacaat atcgcctttg atatattttt taatcatttt ttcaccatat aagttgaata    54840
ttcgtcaaca tcattatata ctctaataaa aaatgtatcg cacgttttca ttatagtttt    54900
cgctgtgtta taactatcaa atgacgctat caaaaacgat tgctctattt ctcctttagc    54960
gcttttctcg cagcccctga tattaaaaga accaacgggt ataacgactt ggtcaccttt    55020
atcattataa ttataaaacg atataccaag aagctcttta attggaatat aaattaattc    55080
tacatttcgt ttaaaagaac cggaagtttc aatttgttta ccggttaatg ctaaaacctc    55140
ttcgggatag cctgggagtt tttcccaggc attcaacgca aatgtaacga ataataaaca    55200
tattaatttt ttcaattagt taatcctctc atgtattgct ctaataatct atttcggtaa    55260
tcaaaacaga tttcagtatt tggagcttta tcacacagat tattaagttg tttagtttta    55320
cgatttatta aaacgttcca ctccgatttt gatttagatg ctcttactcc gtcttcatac    55380
gccccgtcca attgcaagga caagatatca atacattctg cgtttgtaga acaaaatgat    55440
ttagcgattt taagcgattc ctccatatta tcaccagaag catttgctcc tgatataagc    55500
aaaagactaa gcacaagagc gatttttttgc attattctac ctcaattctc aatagtttat    55560
ttgactttag ataatatgct ttttctagga cttgactagc atatctgttt ccagatttcc    55620
agttgttccc ggcgttgtaa cttgcaatag cttttcgcat attaccatta tatctatttta   55680
accaataaga aagttcaata tatgaccatg acgctgaatt cgagcgttta ttcaacattt    55740
taattatttc agcatcagtc atttcccatc caatttgttt caatctagcc cgcattgttg    55800
gaagatagtt ttgaaacatt ccatatgctt ggtgaccaga ttttccttttg gttttcaacc   55860
cagcggaaga ttcttgccag accaaagctg ccataatata acctagccct ttattatcat    55920
agcggtttgc ttgtgtttta tatttgccat cctttgcaaa ttgctctcca aactgataag    55980
cataattcag atttttcgagt tggacattac tgaagttgtg ctcggaccca aaggccattg    56040
aacaaaaggc caatagacct acgcatagag cttttttcat gtttacctca tttaaaactt    56100
aaagataaat tacgtgtttg ctagtttttc cttcgtatct atttgtatta acaaagcca    56160
tccgacactg catagaataa ggagtagaga agttttacc aggagtaggt tttgaaacag    56220
tgaaaccaag ccaaagagtt ttgtcagtga tttcaaggcg aagaggtcga tactcaatat    56280
ttgggtctaa attttctttt gcatctggtc gttccgggag ctcaagaaat tcattaactt    56340
cgacaacatg atttgaaagc ttgtgaaaaa gttcaaaaac atagttctcg tcaatttctc    56400
gttgaatggc gcggtccaat aaatgctgag aatattttac atgaaaacct ggaactccag    56460
cggattcgca tgctgctttt atttcggaat taattttagc aaaattccgtt tcaaaagac   56520
```

```
gacgaagttt gttgcggcgg atgaatactt ctgcgttagt tgacatttat ttctcctctt    56580
tatgatataa gattataata acacatccag aggagaaagt aaacggtttg taggcttaat    56640
gtcttagttg tatttcactt cctcatttgt agcaatatca tattcaacta aacgaatagg    56700
ctcttccatc ccatacccac tcatagagat ataagtggat ggataaattg tttcttttcc    56760
gtcccaagta ccgccggacc atgcttccat aaagtcttgt tcgccggaat taactagcca    56820
atcaacaaat gatttaaggg ccatttccga cccttcaata acgattttag ccatgatgct    56880
tacaccttat aatgataaat cttattgcat tcctatcaca aaaaattgcg gtcgcgcagt    56940
ttgattgttt ttataacaat caactcgaca acaatactgc atggtttcca tatgaacatc    57000
gtaaagctta tccatatcag gagcttttac aggttcatca attatataca agattcttga    57060
aagcgataga cctcggaatt tgtatccttt attgcctata aaactacgca cagaatcagt    57120
gaacaagcga atcggatat catcattaga ataacgcgaa aattccttt taatgtgatt    57180 tgcggaaagt tcagcgtatg ccgatttatt ggataaaaca ataaccgttc cactatcata    57240
cagccaattg gcggcgaagt tagttacagc gattgattta ccagattggc gcccaccgtc    57300
tagtcgaaga gtgcaatatt cttttaagcag ggtttctaat ggcggaaccc agccattttt    57360
gcaaatttca tctactctag catcagaatg atgtgtaaaa gcattcatca gggatagata    57420
tggtgcagtt aaaaatgttc tcatttgttt ctcttaagtt tgtggcccgt tacgtcggcg    57480
catgattggt ccttctaccg ctatgtaaac ctattaccgc acttgggctc gaccttatta    57540
caggttggaa aaggttcatc actcagagga cacgacgttc atgaggagag gctgcgttac    57600
cctttattag gcaggaaatg tttaagcttt accgcctgaa acaattccaa aattatcaaa    57660
atcgtcttca acatcagaag ggtctacctt tttaccaggt acaacataag caatttcgcg    57720
gcgtttagca tgagtaacaa tttctttacc taagccgtta aagaaagaat agccatttcg    57780
ttttagagac ccaaagtctt ctgcgtcgcc agtaaatgca cgaactttaa atgcgccttt    57840
tggagctttt actgactcgt taataaattc ttcgtaagtt ttcatttaat ttccagtatt    57900
aaccaaatag ttagtaacgt tctgtagaat aattataaca tcatctacag aacgtgtaaa    57960
catttaaatt atttgattga tttgacgtat cgggtaacac ctttgtcatt gacaaatgca    58020
atcttaccgc ggctgttata cattgtcaca gtacgctgat agccataagt ctgtttaccc    58080
gcctgataac caatcaaagc gaagttatct tcaccaggct tgttcagttt agctttgata    58140
cgttcatggc cataagccat taaacttctc tgatcacctg tgttcaatgc tttgcgaaca    58200
ctttcatcgt caacagagga aacaaaatcc tcaaatgaac tgaacttggc gtggctcttg    58260
ttgtaaagtt tgccttcaac tacataatta tagcccataa catccatatc aacttcagta    58320
ccatcttcaa gtactacagt gattttctga cctttcttgt atttcagcag accatcagta    58380
gattcgttaa tgataatctg agaaattacg cgggcttcat tgataaaatc ttcataagtt    58440
ttcatatgct ttccaagttc ctgttttcaaa agttttaata acgcggcggg cgcgattagt    58500
tgtttgtctg taccatttag attgagctaa atttacagca gctctatccc aatctttagc    58560
ttttagtaaa gccatagaat ttttaaaacc cgctacacca gctacaccca tttgaaaaac    58620
catgttaatc agagcagcca gacgaggttc atcaccaata aaagaattat atacggggcg    58680
taatacagaa ttagaaagaa ttcctgaaat agcttttca acgtctgtat taaaaatttt    58740
ttcagcttcc gctttagtaa tttaccggga tgtagcccgg ccaacaagac ggtccaactc    58800
gctaatagct accgatttat tagggttttt agtcaaaaga tgacctatac cgacggtcca    58860
aaaaccttca gtatctttat aaatttcaag ttttaagcct tcgtcgatgc gaagcatgtc    58920
```

```
aaaaatgttc ataatacctc ctttaataga ggtatttatt attcccgact ttttacaaaa    58980
aggtctgcca tgaattcttc caggcgagtt tctacggacg atgcaacacc ggatgatgta    59040
gaaacaagat aaccgctcat aggactgaaa ctttctaaat tgctttccat ttcgtatttg    59100
atttgttctt cggactcgtt atcgctaaat gaatagagat aattatatcc ctttgaattt    59160
acgtaaattg ctacactcat catatcaccc atgaatagcg catcattaac acaccagaag    59220
ctgctaatgg ctcaacagaa taaatccacg tttttgtata ttttcgacat aagtctacta    59280
actcacctat gtcatgaacc acaacggatg ttaaaggcag agttatatga cccgtattag    59340
ttaatactat cgctttcggg tcatcaataa ctaagtgctc aatcttctcg tcttctaaat    59400
aatttacaag ttcttcgagt ttattcgtat accatccaaa ttatatagta cgtccttcga    59460
cgattttagc gaaagaccaa ttttagtaa tgaattcaat tattaaattc aattctttag    59520
cttcgacaat atcagttacg tggttttcgt gatttccagt attcagaaca gcacgaaaac    59580
gatcgaattt accaaaatca ttagttactt tatcgatagt tacagtgtta aatttagcca    59640
tgattttatt ctccaagtta attttgtttt accatttatt tggtatgaag taataataac    59700
acatccgtcc atggatgtaa acggttgaag taaaaatttt taaagttaac cagaacggtt    59760
gagagattgg atacagaaag gataatagat tataaatcta tacaaataaa aatgccctag    59820
agttaaacta gggcgtgaga gattaaatct tatagaacct gaacggattt atatggaaag    59880
caagcattgc tctaggtatc ggacgggata acaagctttt aagtttccac ccgcaataaa    59940
ctcgtaggta aaattgaatt tttccaattc ttagataagg aacagcagca aaaactcccc    60000
aagcgtcatc gttccacata aacagccatc catgatgagc tttatccgga gaacccgatt    60060
ctacattagg gtttccacga taatgaaact ctgaagtagc ggggcggcca aggacataat    60120
atgcaaagtt ataagcttta tttcgccaca gccatgctac gcgttgaaag tatttaccta    60180
aaactggaat tttcgaccag cgctcaatat gtccacggtc tccatcaata ggattgtcgt    60240
atgtttccat ccaacggaat cctttaggta agtgaccagt cttttcagaa tagaatggaa    60300
caataaatgg agccaataca acagctaaaa ccatagaaat gaaatctagt ggaacaagaa    60360
aaatccatga agcgtatttt agaaatttag tcataatcta ctctaattaa aatatttatt    60420
gaagcgaatt tcgaattcta gtcaattgag cgcaaaattc ccgctccgta agaatagttt    60480
ccgtttcttt atttttaccc attgaatgag ttaatgtagc gttacgggtt gctaaaagag    60540
ctcttttgaa cccgtcgttt tgggacagtg catcatatgc tcttgtgatt aaattttgat    60600
aagcctctga cgaccgatga ataggaacac cacgccagta caatgtctga gttggccacc    60660
atcgtttctt tttaccttgg aatttagctt gtcttccaac taaagtgcaa acatgctctt    60720
gcatttcaac cgaagaaaat ttgagggatt gtaaaaatcc ctccattgaa gcacatttaa    60780
ctccgtcaat ttcaaatgaa tgtggagcaa agttgcttaa tgaagacgac ggataacccg    60840
accctgaacc aatatccatt taatcaacct tataaacaaa tatggaggga tttatccctc    60900
catcatatta atactgacta cgcatttag ctttaatggc tttaagttgc ggagaatcat    60960
tgccgtatgc tttccaaacg accatttcag caccgttgtt ttccatggag tgaacgataa    61020
ttttaccgtt cttaccttt tctacaccag cttgatagcg ttggaaatcg ctgttagtaa    61080
ttttcttaaa gtctttgata tcaccttcaa tctcatatga gaaattgaag ccgctccact    61140
tactttcatt gataaattct tggtaagttt tcattgttat ctgcctagtt aataaaaata    61200
tatttattat agcataaaga gttgaaataa ggatttgaac cttatatagt tgcacagacg    61260
```

| | |
|---|---|
| tatctgcctt cgaattcctc actaagttta agcaactatt caattaaatt ggtcgagaca | 61320 |
| gaaggattct aaccttcaac ctacggttta gaagaccgtt gctctatact attaagctat | 61380 |
| gcctcggaaa tagttttgcg tctatatact tctccgtcgt aatatttatc gacaagacgc | 61440 |
| tttacttgac tgtgtgatat ttttaatatt ttagagacat cagaaaccca cccaaattta | 61500 |
| gttttatcca cgtctttat taagtttaat tgagacgtag ataattctag acctctaatc | 61560 |
| ttggctttag cactaccagc ttttcctagt ttaacaccgg ccaaataaag ttgttccttg | 61620 |
| gttcgagtat caactctttt tccatttgta tggaggtctt tattattttg gctattagta | 61680 |
| gcgcaataaa cattttcaat agaataaggt ccagaatcac cgatgcgaca catacaatat | 61740 |
| tgttgagctt tattaccgcg tttttctaat tttccagttg aaatccacca attaagccag | 61800 |
| gactcatatg taaataacca ttctatgttt ctagccttcg cctttcttct ttgattttca | 61860 |
| tatttaactt tcatgtttat tgctttcact cggctatcca attttaagaa gagtgagagt | 61920 |
| cttagtcttg tacggagtaa cctttttatac attggcagct atcgcgcgat tcgcacttcc | 61980 |
| gataaatgga gttaccgtta cactctaatt tggctgggaa tactgggctc gaaccagtgc | 62040 |
| atcccggaat caaaatccgg tgccttacca acttggctaa ttcccaatta tttggtggcc | 62100 |
| cttgctggtt tcgatccagc tacctatcag ttatgagctg acagtctcc cattgagcta | 62160 |
| aagggccgta attctattat gaaaggctct atgttaagaa cctttggtaa tagagggtac | 62220 |
| ttattaataa taacactaat ttcttaaagc aaattaaaac gtatgcagat atattttacg | 62280 |
| aatatgtttc aattttaacg gattttcaaa aatattgtag tcctttcggc catcttcagt | 62340 |
| tagtaaaaag aactcaaaat tgacagtgtt aaactcacgc tcatttccta ccatttaac | 62400 |
| gacagaagag ctccggtcaa tgtcaatata ttcaacttca aaatatgata aaattccgtg | 62460 |
| ttcttcaatt aatgatttgg cagccacctg gtcagttgcg tatccgtttt cagtattatt | 62520 |
| tacagctgtg tagagaatca tcaccacact cctttgtcaa taatagtgtg agtgttggca | 62580 |
| ttcacaattt gccaccattt ggcatggtag aaactgtgtt taggcttttt ctgattttct | 62640 |
| tcgataagtt cacgaagctc atcttcagaa aaagcagtag caattaaatc attgtatccg | 62700 |
| cccgcgggat aataattatc accgccaaat aacaagaaat tgactttagt catatttacc | 62760 |
| ttttaaacat ctgatgagtc atgtagacaa taaccgctaa ccataaaaat acactattaa | 62820 |
| tcgacgttaa gacaaggcct gctataattc cagcaaaagc aaaatcccac tcagtgaatt | 62880 |
| ctttcttgtc aaaattatag ttttttctaa aatatttctg aatttcttta agcttttca | 62940 |
| ttagaaattt tgtccataac aaatgatact acgccgagaa ccgctacggc aatgaaagca | 63000 |
| ctcatagttt cagctttaga taaaattgct aaagaccctg ccatgataga aaaaccaaag | 63060 |
| ccaccaagac ataatactgc agatatatta cgaataagtt cacaacgttt cattttattt | 63120 |
| tcctcatttg ttttgatagg gttatagtat cataaccctc aaggaaagta aacggttaaa | 63180 |
| tcgcgccgtc gtcttttgca atattaagaa tagtatcata caattcctca gcttccttcc | 63240 |
| ggcgggccga gattttagtg tactcttcat attgctcaat cttagaaagc atagatttta | 63300 |
| cagatgaata atggttttc aacttttga tttcagaaat agtaaaacgt ttatctaggc | 63360 |
| cttcgttcaa ataagtcgat tcgttaacaa attcttaaaa agatttcata atagttccat | 63420 |
| gtttgttgat agagttatag tatcataacc tgcaagaaat gtaaaatgtt tacatttac | 63480 |
| ttccacgaat gacaccatag gttgcgaaat catcagtgat atcttagca gaatttctac | 63540 |
| ctgttcaat atatgcaata tcagattttt tcgaaaaga agtgatttg ttataattag | 63600 |
| agtctaaaaa ggtgtaacca ttacgcatta gattttcaaa atcttcagca tcgccacgtc | 63660 |

```
ctttaaaatc tacccatttg taagtgtttt tcttactaag acccataggc catgattttt   63720
cggtaagaaa agcttcgtta ataaattctt gataagtttt cattttaaat cttctgtcca   63780
attaatttta agtggttctt tatactccct gtcaagtata acagggactt ggactatgcc   63840
cgaaaattgg gcaggtccta cgttgtagct cagtgtgatg tgtggagaat aatcatcaaa   63900
atcatgagta gctccgaggg cgcgggcgta attgtgacga aatttaagat agtcagagtc   63960
cagaactaaa accaatgttc tgccatcttg cgtgtcccag acttggagtt ctccagaatt   64020
tgctacttca aaacttccag tagaaaccac ataaggcaca ttaacccgag aatagcaaat   64080
agtgctatgt attttatgtc ttggaactgg attaggaacc ttcaattctc gctgaaggtt   64140
ctcaatttca tctaatgtgc tatcgctaaa ttttgctgca acgtagagtc cagaactaaa   64200
gtcctggaat tcatcattc atcatccggc gttgcggtta actcatcaat ttttcaaga    64260
atagcttcaa aggtcacttg gccttcaaca acttctagac cgattttttc tacaatttta   64320
cttaccaaat cgcttagcga ctgaaccgtg ttagtagttt cagcaaattg ctcattcaaa   64380
tcaaaaagac gagctttaag aacagttaca gtagcttcaa gctgtttaat tttatcagtc   64440
atttttaaaac cttttttaatt tttgcataaa gttcttctaa agaaccgtca ttagtaataa   64500
ctgtatcgcc ttgtttaata ggcaagccag cttctgttat atgagtgtca acttttgaat   64560
tgactgagct aggacgaact acatgaatta ccgtagcacc catcgcccta gccgcgtcca   64620
attcatggtc ttgacgagtg tctggtacta taaaataatc gagatttttt ccaaaattat   64680
ctaaatagac cagagaaaac catttaaccc aatacatacg gtcgaagtga ttgaccatga   64740
tgtctgtccc aagggtctgc atgagacgac gaactgacca ttcatcttca atactattta   64800
tagtgtcttt aattattgaa agagaacgat ggtcgatata tccgttataa aaataagcat   64860
ttttaataga taacgtacca cttagccatg acatggcaga ctcaatgatg tttataactt   64920
gcacctttga aattttcaaa tcaacttcac ggtcataatc aattccttcc caatcacttc   64980
gatttaaaac tggaaacaat ttaccgaggt cttttgacat aatagcaact tgataagcat   65040
agcaaagagc atctttaatt ggtccagcta attggtgctt aattgcgcca taattttcca   65100
ttatgtaatc agcggttgtg tcctttccac ttcgtttttt accaatcaaa aaattaatt    65160
tcattatttc ctcatagatg gatgcattcc aatgcgttga ttagcagcct cggccatatt   65220
ttgccgtgtt gtaataattc taccatcttt ttctatttgc aaatacttat acggcatgat   65280
ggcttgacat gttacagctg ggtcagtatc ttctgtgtag ttgtattcca cttcgcctaa   65340
gtcgcttatc caacatccat agtaatgaat agacaaaaca attctagttt tgctattgtc   65400
taaaatatga acactgacgt gttcaggcat actgccgtcg cgccatgcga agttatctcc   65460
agtttgatag ttgtttatgc ctatcatcca ttgatacatc tgcagccaag agtccagttc   65520
ttcatccacc aaaaatctga taaccagtgg gtcgaattcg aacgttgaac caggaaggtt   65580
cgctcgtcca agaccatag tgccagaggg aatatcagta acaggaattc ttataccagg    65640
tatattagct gattgcgcgt taagcgtaaa accttttgtc aagccaacat ccggaatgtc   65700
tacaacaaag ttagttatgt tggtttgatt gtatatctgt tgtgtgttca atctgctttt   65760
ctccagatgt tgttataatg aatttgtcct tccggttaat caataatca accagaagaa    65820
caagaaagta aatagaatta tgatttccat acagcgtttg cgctgaaacg tttacccttta   65880
ctttggaaat tctgaagagg taacataact acatttgccc aatcagcagg tttaatttca    65940
atcaaactcc cctttatatg accaggtaaa tatgctttaa tcattttatc tgcaccttga    66000
```

```
aatcctttca cttgactcca gttcactttc aatttcgttt tgtttgttat agttggagtg   66060
ttagaatact gctttagcag ctcttcaaga aattgttgcc gagcctttgg cggaatatag   66120
tgtaagttca atccatacat taatgtagaa ttgccttgtt tacccattcc taaataaatt   66180
attaatggaa atctatccca atatggaaga gtatctttat gcttagcatc atacatataa   66240
gcatataatt ttccaggttg aggttttgtt acttgatggc ctctgatgtt cttttttgata  66300 gtctcggaga accatttagc agatttatta ttgactgccg ctccttcatt tctaatttta   66360
tcgcgaagcg aagacctgaa actattaatc attatcagtt gtctttcttg ctttgacaac   66420
ttattagcag gttttccttc aagtttagca atcttttctg cgaactttat cttagaagaa   66480
taccttgaca tagccttagt gaaagtagca taaggtattt ctttggactc agcaaattct   66540
tttgagctca tcccttttgga tttagcttta ttaaattcaa gccctatttc aacccatttc  66600
ttttcatttc ttgaaactgg tttaggacga gtagtagaac ttgcagcctc gccaatgatt   66660
tcaaaaatag ccattatcct ttccacccta gtcttcgaag accatcttct gttaataatc   66720
tgaactgtat attattttt tctgctactt gtaacgcagc tttccactta tcagtattta    66780
ctgaatatgt ataaattgaa tcgatgtatc ttttctttgc tgctgtagtt aatttagcag   66840
gtttaggagg agggactgtt tcttttttgg gttttacttc aaagaaaaac tcttggcctg   66900
tatcaaattt cacccaaaaa tccatgaaat atcggcgttt tttgccgtcg gcattgctaa   66960
agtatggaat taccacttct tctgaattcc acttcactac ttgaggattt gtatcgcacc   67020
atctcataaa aaactgttcc catgaagagc gataagttat tttacggatg tctcctctat   67080 attttgatg gttcgttgga gtgaaccttc ctgaatatgc cattattatc tcctctaata   67140
aatactaata ttatttatat gtgggagagg ttccatgatt tttcttttt tcgacccaat    67200 tgattataag gcaaaaactg tcgataaaaa ttccaaaact attaaatga ctgacatctt    67260 tcgcaattac aaatcttact ttaaacgtgt tgcggcgggt tatcgtctaa gaacttatta   67320
cattcaagga agtccaagac ccgaagaact agcttatcaa atttacgaa actctcagtt    67380 atattgggtt cttttatttt gtaatgataa ttatgacccg tattacggct ggataatttc   67440
acaagatgct tcttatcttg cagcaatgca gcgttatgaa aaagcgggag gagaacaagt   67500
actttatcac gtagatgaaa atggcgagcg ctattataat ctaatagaag accctaataa   67560
ccctggtact tggtatgata aaggcgacct agaaatgaaa tatcctcaat acaatggagc   67620
tctcgctgca gttgatatct atgaagctgc tatcattgat aatgaaaaaa gacgagaaat   67680
aaaaattatt tctcctaatg atatcgattc gtttattaac gacttaatta gagagatgga   67740
gattgcttaa tggatatgat taataacaac gtcgaatggt ttgtcggcgt tgtagaagat   67800
agaatggacc cgttaaaaca aggacgagtt cgtgtgagag ttataggtct tcatccattc   67860
cagaaagttc aaggccctgt atcgggaatg ccaacagaag accttccatg gatgagtgtt   67920
ttacaaccta taacatccgc atctatgtca ggaataggcg gttctgtcac tggacccgtc   67980
gaaggaactc atgtttatgg tcattggttg gacaaatatc gtactaatgg tttagtgatg   68040
ggcacatacg gagtaaatgc cagagttaga ccaaacacta cagagggttt ctctgatcca   68100
actggccaat atccgcgtta cttaggtaat gatactaacc ttttgaacca aggcggcgaa   68160
gcgggatttg agtcaatccc taacgttatt caagataata accttgatac agctattaat   68220
cccgacgaca cagattttatc aaatattcca gaagataata atccaaatta tactatagaa   68280
gctatgcttc gccgcgacga aggtcttcgt ttgaaagtat actgggacac tgaaggatac   68340
ccgactatcg gtattgggca tcttatcatg agacaaagag tccgtgatat gactcaaatt   68400
```

```
aataaagtgc tttcaaatca agttggaaga gaagttaaag gaaatcccgg ttctatatca    68460
atggatgaag catccgcatt atttgctaaa gacctagctg atatgcaaag agatataaaa    68520
accaactcaa aagtcggtcc agtttatgtc aaaatgaata aatcgagaca aatggctctt    68580
gaaaatatga gttttcaaat gggagttggt ggtgtagcta atttcactaa tatgcttaaa    68640
gccatggatg aaggccgttg gaaagatgca tataacgaat ctcgaaactc tttatggttt    68700
cagcagacta aaggacgagc ttctagagta tctatgatta ttcttactgg taatatggaa    68760
tcgtacggtg ttcctgttaa tccggttcaa ggaaaatctg ttggtgctca attagctact    68820
gttaaagctt cagttaatcc aagcgaccct cctataccaa gtgacagcag aattcttttt    68880
aaagagcctg tatcatcata taaggacaa taccccttatg tccatacaat ggaaactgaa    68940
tctggtcaca ttcaagaatt tgatgatact ccggggttatg aaagatatcg tcttgttcac    69000
ccaacaggga catatgaaga agtagctcct gatggaagaa gaactagaaa aacagtaaat    69060
gatttatacg atattgctaa tggtgatgga aattatttag tttccggtga taaaaggta    69120 aacgttggtg cagatgaaac atactataac atggccaaca gattacatca aattgacgga    69180
aataatattt tgtttatccg tggagatgaa acaaaaactg tcgaaggaga tggaacactt    69240
tacgttaaag gaaatataaa gatagtcgtt gacggaaatg ctgatatctt ggttaaagga    69300
gatgctaaaa ctcaggttga aggaaatcac gattatacag taaacggaaa cgtaaaatgg    69360
actgtaaatg gtagtgttaa tatgacagtt gctgggaatt ggtcagaaac tatgagctca    69420
atgtcttcta tagctcaggg ccaatatact attgatggca gtcgtgtgga cattggttta    69480
taaatattaa ttattgacta actggaaatt atatggccca gatacttccc gttaatacat    69540
ccctcggcga tattcaagaa ggcggggctg ttgatttgac tttcactgct cagcttgatg    69600
ctactgatac attaaagtca ataaatataa tagattatca gccaacttct ggtataatag    69660
ttgaaggttc cagatactac ggaaattata atagcgtatt ttcatttgga gctgatgcat    69720
taaaatatcg tgaaggcgat gaattaaaaa ccgcagcaac ttgggaggat ttacctcctc    69780
ccaaaactgc agatttatat atgtggagag cccctagttc actccagaga acttttacgt    69840
atacggttga atgtatatat gaatatcagt cggaagagtc ttctggcggt tctggtgaat    69900
caggaggtac aactcctcca ccggtcgaac gaagaataac aaaaacatat actcaattag    69960 tttacgaaa ttggagtcgt tggggaaata aacttcgtga atatgtgtat gcggggaact    70020
aatggcaggt ttaagttta atcaatgtat aacatctggt catgatgcat ttcctcctac    70080
cgtaattaat tcaactcagc caaaagtgtt tactggcgga attccggtat tagttgatgg    70140
agaccaaatc actcctcata cacgcatcgt aaaaccatat gacacgcacg gtggagcagt    70200
ccagccaaga acatctaaag tttatgtgac tggaaagaaa gctgttcaaa tggctgaccc    70260
tatttcatgc ggcgatacag tcgcgcaatc ttcttataag gttttcataa aataatggca    70320
gacccaatta actatcaatt aacgcgcacc gtaaacgcta ttccggacat ttttgtagga    70380
ggaacattcg gtgaaatcaa gagagattta cttgattggc ttcgcgggca aaacgagttt    70440
ctagattatg attttgaagg ttctcgtttta aacgtattat tagaccttt agcttataat    70500 acactttaca ttcagcaatt tggtaatagc gcagtctacg aatcatttat gagaactgca    70560
aacttgagaa gttccgtagt tcaagctgct caggacaatg gatatttacc ttcttcaaag    70620
tcagcggcgc aaattgaaat aatgcttgaa tgtactcatg ctttaaattg gaacactata    70680
agtattcctc gtggtacaag attttttggcg tacgcgttag aaacttctgt taacccatat    70740
```

| | |
|---|---|
| tcatttgtaa caacagaaga agtcacagca gttcgtgatg ctaataataa gtattttcca | 70800 |
| cgaattaaat tagttcaagg ccgaattgtt cgtactgaat tacgatatga taaaatgaag | 70860 |
| cctatcatta ttcgtgattc caatattgac cgtaatgaag ttaaattatc ggttaatgga | 70920 |
| gttgaatgga ctaactggac ccgccgctct atggttcacg caggttctac atctacaatt | 70980 |
| tattatatgc gtgaaactgt agacgggcat actgaaattt tcttcggaga aggtgaacag | 71040 |
| agtgtgtcag ttgcgggtgg ggctcttgaa gccaattata ttggcggatt aaaaccggta | 71100 |
| caagactcta ccatcgttat agaatatatt cgcactgaag gagctgctgc aaatggggcg | 71160 |
| acagaattca gttatgctga tactttaaat tatataacag ttcaaagaat atatgaaaac | 71220 |
| cctgatgact ccaaagatta tgttggagct gacggcggcg gcgaccatga agatatagaa | 71280 |
| cgtatccgtg aacttggcac gataaagaga gaaactcaac aacgttgcgt aactgcaacc | 71340 |
| gactatgaca cctttgtttc agagcgtttt ggctctatcg ttcaagcagt ccaaacattt | 71400 |
| actgatatgt ataaacctgg ttatgcattt attgctatca gcctaaaatc cggtttgtac | 71460 |
| ttaacttcag tacaacgaga agatattcag aactatttga agcaatataa cttagcacct | 71520 |
| attactccat ctgttatatc tccgaactat ttgttttttga gacataatat taaagtatct | 71580 |
| tatgcgctga ataaattaca agaaacggac caatggctca gaggcaaagt cttagaccag | 71640 |
| attgatagat attatattga cgaagttgaa attttttaatg cgtcatttgc taaatctaag | 71700 |
| atgttaacct atattgacga tgcagaccat agtattattg gttcgtctgc gacaattcaa | 71760 |
| atggttcgcg aagttcaaaa cttctttaaa acaccggaat ctggtattaa atattataat | 71820 |
| caaatgatta acaggtcatt agagtcaaac tctttcactt ttcacggtga agattctgat | 71880 |
| tatatggtta gaatagttgg ttcagacccc gaccaaaatg gaattggtaa agttataatt | 71940 |
| ggcccgttta agacggcga tgttaaagaa aaccaagata tccagcctta catgggaacc | 72000 |
| gattttaata agcttaatgc agaaaatcgt gataagtact atgtaattgg ggaaattaat | 72060 |
| tacccaggag ataaacttat ttggaatatt tcggcaatag acttaacgtc tgaacaattt | 72120 |
| gaggttcaaa ctatcgagct ttattctaca ccaaaggaag ataacatttt cacaagagat | 72180 |
| ggttcattaa tagttttttga gaatgatttg cgtcctcaat acacaaccat tgaattggag | 72240 |
| cctatagcac aatgacagta aaagcaccat cagtaacgag tctcagaatt gttaaattgt | 72300 |
| cagcaaacca tgttcatatt aaatgggatg atgttggtgc taacttttac tattttgttg | 72360 |
| aactcgcaaa caccgcaca tcagaagggg tctctttaga cccctctaga tatcaatgga | 72420 |
| gaaatctagg atacacgtca gaaaacgaat ttttcgaaag tggatttatt cgaccgaacg | 72480 |
| attattatgt tatgcgtgtg tcagttgcag ctcaagggtt tgaacgctct aattgggtac | 72540 |
| aaactgaaga atttcaaaca tttttaacaa acgcatatac gtttcagtct atgctcgaaa | 72600 |
| tgactttggc taataaattc atcagagaaa aatttactaa taacaatcaa agttatgtag | 72660 |
| atttcaaccg tgatacagtt atggcggctt aatggatga gtcatttcaa tttagcccta | 72720 |
| attatgaaat agtatcgtca atttctgacc atatattatt tgaagaagaa tatcatgaaa | 72780 |
| tacaaagtag catttctgcg gtatgtaaag acataaaccg agtaatgcta atggaatctg | 72840 |
| aaggaatttt atatctgttt gaaagatttc agcctgtagt aaaagtttct aacaacaaag | 72900 |
| gtcaaacttg gcaagcagtt aaattactaa acgaccgtgt tggtaatcca gtttcccgta | 72960 |
| ctgtgtatta tcaaagtgaa tatacaactt atttgcttgg atacgataga attttttatg | 73020 |
| gacgtaaaag taatgatata agatggtctt cagatgaagt tcgttttttct tctcaggacg | 73080 |
| ttactttcgc taaaattggc gaccaactta aacttggatt tgatgttgaa atatttggaa | 73140 |

```
catatgcatc tttgccggca gacgtttcca gaattgctga agctataaca actactgatg   73200
atttcatata tgttgtagcc agagataaag ttcgttttgc taaaacgcgc aatgcgccta   73260
ttgaccaaga cacattatca cctacattcg gtgaaaaatt atttgagcca gaagtactaa   73320
caataactgg taatccaaaa gcagtgtgct ataaaatgga agctgttaat ggtaaagttt   73380
ttgctcttat tactggcgaa gttaaagaag acaggatgga cccgactgtt ccagaaaacg   73440
taatagattc tcaatcaaaa ggaatttaca ttcttcagtc cgataataca tttaagcgtg   73500
tatttggtaa tacagaagaa gaacggcgtc ggatagagca tggttatact tctatgtcta   73560
ccaacggaac agaagtattc atttcttcta gcaattttaa attttaaat gaccaaattg    73620 tgcaagaccc agacacagcg ttaaaacatg atttgttagg agccgttaaa tatgaatttc   73680
cgcgcgaatg gctttctgat aagcattatc atatgatgtc ttttagagct gacgaaaaat   73740
ctggttatga acaatttgtt cccggcgcta tgaattatta tgctgaacca ttttttagct   73800
ggtctagaaa atctggtact cgctgctgga ttaataattc tgatagaatt gtggttgttt   73860
attcaaatat tactcataca aaaataattg acactcatgg ttccggttct ccagaacgag   73920
ttttgcatga attctgggat aaaggcactt gtactgtaac tgctccaaat gttgaattca   73980
acggatttac taaatacgct tctggtattc tcttttataa atcttccggt gaaataattt   74040
catattacga attcaattat cgtgttcgag atgaaactaa aataatttgg aaaccgtctg   74100
aaatattcct taaagcttat ttgcaaaatc aagagcgaga aacggaatgg aagccagaag   74160
aacgagacgg aatacaagac ccagatttaa gaccgttgat tagaactatg atgcctgaca   74220
gctatttgct agaggacaca aatttgaaa aattctgtga cgcatatatt caatacttat    74280
ctgatggata tggaactcaa tataacaatc tattgaattt gataagaaac caatatccac   74340 gagaaaaga ctcatgggaa tatctttggt ctgaagtata caaaagaaac atttatctta    74400
acaaagataa gcgggatgcg gtatcaagat ttttcgaagc tagacgttca gattttatt    74460 caacaaaagg tattgaagct tcttataagt ttttgtttaa actcttatat aacgaagacg   74520
ttgaaataga aatagagtct aactctggaa ccgaatatga catagttatt ggatctgatt   74580
ctattaatga agacttagtt ggtcaaacca tttatactcc aactggacgt tgtaatgtta   74640
cttatattga aggtcttat tcaaaaggaa aacttcagtg gaacgtaaca attcacaact    74700
tattaggacg cttaattcaa ggccaagaag taaaggctga acgctatcca ggctttaatg   74760
gaatgatagt tagaggtgtt cgtggtaagg aattagtaga aaatactatt gattacatca   74820
accgcaaccg ttcttattat gttatgaaaa tacgttcaaa tcttccaaca tcaagatatc   74880
gtaatgatgt gttaagattt gttcatcccg ttggatttgg ctttattggt attacgttat   74940
tgactatgtt cataaacgtg ggtttaacta tgaaacatgt ccaaactata atcaataaat   75000
acaaaaacta caaatgggat gctggtatac cgactttta tccagatcga gtagcatcat    75060
tagattcaag tggaaatgta gaaaagacc cagtcacagg tgaagtaatt tatcttcctg    75120
gaccaatgtc tggtattgca tatcctgtcc cggctgacta tgactctgag aatgataatt   75180 ctatttttcca aggtcaaact cctactgagc gtcggaaatc aatgagtccg ttattcgatc   75240
aatctgccgt aacttttct caattcagag acttagttga gcagcgtttg attgataaaa    75300
caggtctgcc tcgcgaacct aataatccaa cacaggttaa aatagatgaa tgattcaagc   75360
gtaatttatc gtgcgattgt tacttcaaag tttcgcactg aaaaaatgca gaattttat    75420 gattcgatag gagattcggc aaataaaaat tcactttata taactttcgg tcgttctact   75480
```

```
ccttgggctg ataatgagaa tgaggtgggg tttgccccac cttatccagt tgacgatact   75540
cagggcgtag ttgatatgtg gactaacatg atgggttctg taaaagttat gccatcaatg   75600
ttagacgcta ttgttccaag aaaagattgg ggtgatataa gatatccaaa cccacgtaac   75660
tttcaaattg gagaaattgt tgtagttaat agtgctccat ataatgcaac tgaggttggt   75720
gctggttggt tagtttatcg tgtgcttgat attccagatt ctggaacttg ctctatacaa   75780
gatataaaca acaaagatga gtgtattaaa ttaggtggta aatggacctc ttctatacca   75840
agcgctaatc ctcctcgtgg aagaggtgat gcagaaaaag ggactttgac tatagacaca   75900
aacgatggat atttatggga gtatttgtat gaaattccac cagatgtgtc aattaacaga   75960
tgcacaaatg aatatattgt cgttccttgg cccgatgaaa tagctgaaga cccaatcaga   76020
tggggattgc agaataatct ttcttggcaa caagatgatt atgggttaat ttatagagta   76080
aaagcttaca ctatgagatt taaagcgtac tttgactcag tttattttcc cgaggccgct   76140
cttcccggca atgatggttt taggcagatt tcagttatag tcaatccgct tgaaaagaaa   76200
gataaaccta atgaccctaa tgttaaggct gaagattgt actacaagcc tcatgatttg    76260
gaacgtcatt caggcgagat gatttacatg gaaaatagag ctcctattat tatggcaatg   76320
gaccaaactg aagaaataaa tatcattttt gaattctagc agggactcct tcgggagtcc   76380
cttttttatt gcataaatat aaatataaag aatagacgga tatcacttga ggaatagata   76440
tgtataatca agaaccaaaa caattaatcg acgtcggtga aatcggtaac gcctctactg   76500
gtgatatctt attcgacggc ggtttaaaac ttaattctaa tatgaacgca atttataatt   76560
cgttcggtga ccaacgcaaa atgtctttag atagtggaca aggaactact ggtcaagtta   76620
tccatgccac aggttattac caaaaatcag aaaatccggc tgtagatttt caaactccgg   76680
tgcaaaacgg ctctatgcat gacattgata catcagctgg tccagtcgtt gttagattag   76740
accaaggtgt ccgtggagaa ggtgtgtttt ttattaactc aagcggctct atttcagtcc   76800
agaacccgtt gacaatagaa cctaaagaca attttgtcgg catctctgga ccgcttgtag   76860
tgacttctcc atttagtgaa attaaagtat ggtgtatttc tgatgatggc ggacggtcag   76920
tatggaacta ttcaatcaga aacatgtttg gggattatca tgacccggtc caaggaactt   76980
ggcaaatacc agtcgcgggg gtagttgatt ttcctctttt tcataaaaat gaatatatag   77040
cttcaaaact tttagttact tctaggtcta atgacggtaa aagaataaag tcttccgaaa   77100
taaatatatt aatagatgta gtaactaata cagtgatatc tactgaatac gctgttatgc   77160
gagtaggagc gttaacagaa gaggacgata tcgtaactta ttctttagt ataagcggaa    77220 caggaatgat aacgatgact gctaacggcg catcaggatt aagagtagct gttaaatcta   77280
tcacaactca gaaaatcggg gcagcacaat gaaacaagat ttaaaaattg gagctgtggt   77340
tgatgacggc tctggagact acctgcgtaa aggtggcgaa aaaattaata ataacttcaa   77400
tgagttgtat tatcaactag gcgatggtga tttcccgcat gcagcaggcg cgtggaaaac   77460
tttcaaatca gctgataact caattctgac agccgacttt gggcgttctt atgttttaga   77520
tacaaccgct ggcagaatga catttgaatt accaaaggga aatactccag attataacca   77580
tgttattcga gttagagatg tatttggtac ttggcagaca aatccggtta ccattactcc   77640
agcggcggga gatactctga agggtaatcc aaacccaatc gaatttaatg ttccactgac   77700
tgatttagaa cttgtttatt gccctcctgg acgctgggaa tatgtagaaa ataaacaaat   77760
taacaaaatc agtaattcag atttagcttc tgtaattcgt aaagaatttt tagtagaaac   77820
tcaagaccaa gttgattttt tagacgtttt tgacgggtac gattataata aagctaatac   77880
```

-continued

```
ccaggtctat catcgtggta acattcttta ttatggaaaa gaatttagcg aaaatagtga     77940
ttacggctct cctggagcta cacccgatga agtagttgct ttaaatggta aagatattcg     78000
tttacgtcaa aaatgcaata ttggtgatac agtaatagtt gtttcttacg ttgatggtat     78060
tagtcaatgg cgtagttctt ataataaacg ccaaattatg ttactggatt cttctaaaac     78120
aaatcaagtt tcagttcccg gttcaacatt cgtaggcgat ttgaaaaata ctgatacatt     78180
cacagtagaa atgtttggat tgactttaca tgacccgata aatcctaatt cgttggaagt     78240
tgaatttaac ggcataagtc aagtgttagt gggaacaacc ggtttgcctg aagtctattg     78300
tcaaggagct gacgcagata cttatgagtc ttgcgttgct cttggaggaa cttggacttc     78360
atctaatatg gattattcag tcaattttga tacagataac cgtattgttt ctatcacaac     78420
agaccgagaa atggaacacg gcgatattat taccataaaa tggtataata acaatattgg     78480
aactaccaca agcatggaag atattattca agagactgat tctctttata tctctcaagg     78540
cggtccaatt catttaactg gcaagtttc aataaccgat tatgataatc ctcgtattcc     78600
gaatactgaa cctgtagcac aacagatgt tttggtcaca agtccgtatg ctttatttga     78660
tttaatttat ccagttggaa ctatctacga aaacgctgtt aatccaaata atccagctac     78720
ttatatgggt attggtcgat gggtattgtg gggtcaagga ctagttactg ttggttggaa     78780
ttcagatgta aatgacccaa gatttgctat gaataacaac gatttagata tttctggaca     78840
gccatctcac actgccggtg gaactactgg agaaatttct gttagtatat caaatgaaaa     78900
ccttcctact actcaaaccg atgagaaagt gctaatagca gacaacaacg gtccaattgt     78960
cgtaggtggt tgtcaaattg acccagatga tacaggtcca gtttatacta aataccgcga     79020
agactacgcg aagactaatg aaagtcatgt caatgttaaa tcacttgaca atgttcaacc     79080
gtcaattacc gtatatcgct ggttaaggat tgcataatga gcgtaatgag tactaaagcg     79140
ggtgttaaat cccgctattc tgataatatt cagtttatac cttcgcctaa taataacgat     79200
gtaatgagta agcagccata tggtagctta acaatttctg agtattcaaa aggcattgaa     79260
ttccctaacg tacaatcagc aattaatgat gttagaaatt ttaccattcg tcctataaat     79320
tctatagaaa ttaacacaga cggcgtttct ccagaaggaa tttctcaaac cgacacctgg     79380
acattcgctg gtacagttgt taaaccggat ggagctactg gcgatgctat tatttctgtg     79440
ttcggttttc cggtgacagt aactgttgga gatactgccg aagaagttac cgcaaaagct     79500
aaattagttt ggaagatgc agttcttaaa aattttatta ttaacacagt ttcgcaaggg     79560
ttgactgggg ctgaacttac agtttcttat attgataacc aaactcatgt tcttaaaccg     79620
gaaacacgtt ttggcattac agtaagttca actatcgtat ctccagctaa accgggttat     79680
ggagcttgga cacgtatagg aacaaaaacc gaaacattag aaggttcagc ggacccggta     79740
ttgttgcact actttaagag attagcataa tgcaaaacaa cactctaaaa cacatatcag     79800
atgaatccaa atatgtaaca tttgacccaa ctaaagtgg ttttaatgaa aatataacta     79860
atgtgcagga tgctttatct gctattagcg ttgatggtat ttcaggagtt ccacaagcta     79920
cagaaaccgt cgcaggtaaa gctagaattg caactcaatt ggaagtcgat gctggtgttt     79980
ctgcggatac atttataaca ccagcaacgt tatcatatag gatgcaacgt ccagaagcga     80040
gtacaactgt acttggtgta actcaatatg caactgatga agaggctata gctggaactg     80100
ctacaaaccg cactattgtt gcgtcatcgt tgaaggctac tatagacaat gtttttacag     80160
ttagaacatc aactgaaact tccaatggtg ttttaaaaat atcatctacg ccagctgctc     80220
```

| | |
|---|---|
| aagctggcgt agatgacacc acagcaatga caccattaaa aaccaaacaa gctatagctg | 80280 |
| cagcaactgc tcttattcca gcttggggac ctgctactga atcagagcaa ggtgtagttc | 80340 |
| gtttggcaac attgtctcaa ttaagagacc ctaatataag agacggttat tcagtgtctc | 80400 |
| catttacgtt gaatcagtgg caatctactg agtcaaattt aggtgctatt aagcttgcaa | 80460 |
| catcaggtca tatggatgga ggttctgacc atacaactgc tgtaactcca tatcgttttg | 80520 |
| cttccactag agcgacaacg ggaagagcag ggacaactat tttgtccaat gatttgaatg | 80580 |
| gagatggttc taaagcatta tcagctaact cagcagttct tccaagtaat agggcagcgg | 80640 |
| tatcagctgg agtatatgaa catgatactg ccgctgataa caagtacatg acacgaaata | 80700 |
| atcttaaagc ttatttacct gttggtacta tgacacttgc tgcttataat tacgacaccg | 80760 |
| gtaattgctt gaaatgtaat ggtcgttggt taaataagca tcaatggcct gaattatttg | 80820 |
| ctgtcattgg atttacttat ggcggagatt ggggagataa ctttgctatt cctgatatgc | 80880 |
| gcggcttagt tccacgcgga tttgatgatg gcgtggtct tgacccaggg cgaggttttg | 80940 |
| gcagttatca agaagatacg atgcagcaaa taactgctgg atggacaatg gatgaccaag | 81000 |
| cagtaacttc aaactatcct ccttcgggag catgtgaagc tagagattat ggctctgtca | 81060 |
| actatgacgc aagttctgat gatagaaaat ggcgcggatt tagaatgtat ttcgactcag | 81120 |
| ctagacaaac tcgagtttct catgaaactc gccagaagaa ccttgcactt aactatgtaa | 81180 |
| ttgtagctcg ataaagagga aattatgaa ttaaagccat taccgtttgt taatggcctt | 81240 |
| ccagaagaag gccaacagcg tataaattgg attaaaaatg gggaggaatt aggcgcggca | 81300 |
| agtactaaat ttggtactga cggtgaacta atcgtggtc ccaatcaagt acagtctaac | 81360 |
| gtggtcgtaa tagatgaaaa cgttagaaaa cttgcagaag cttcgactga aatgtcagct | 81420 |
| caaatatcaa ccatcaatag cgtgttagaa gtttctggta atactgaagc tctttctcaa | 81480 |
| attggtaaaa atacaacaga tattggttta ttaaagcaat ctactactac aatacaagat | 81540 |
| ggagtgcttg aactagacac tcgagtgtca tttatcgaag aagatgttgg agttttaat | 81600 |
| ccttctcttg atacgcttca acgcccaatt cgcgatgatt tgtattggat taaaaagaa | 81660 |
| atggggcaat atccgggcca ggatataaat ggacaagctg taaccggaaa tgaagcgacc | 81720 |
| gggatgaaac gccgaattat taataactct tcagcaatta ataataacaa tgagcgttta | 81780 |
| tctaaactcg agaaatcttt ttctgactca gatgtaggtt ctttaacatc tgaagttaca | 81840 |
| agcattaggg cagaattagg gccgaaacct actggaacta ttgaccctat atattctcgt | 81900 |
| ttaacaaaaa tgaatggtag tattggcggt cttgctatta acatggaaga cgtcatggat | 81960 |
| tccataggat ataactccgg tgtaacaagc attattggat tagtaaatac aaacacttcc | 82020 |
| gatattgtta gtataaatgg aaaattatct aactcaacga cgggagttat accaagatta | 82080 |
| gatattgttg aagctaaaat cggagacgat gcttctacaa attcaatcaa tggaagaata | 82140 |
| aaaacaaaca ctaattcaat taacaattta atcaaattg ttggggctga tacttcttcc | 82200 |
| ggattgaggg gacaagtagc ttggataaat caaacagtag gtattgttcc tagtggttct | 82260 |
| tctccatctc cgacttctgt gatttataga gtagaccatt tagaaactca acaagatgct | 82320 |
| actaatagtt caattcaaga tttacaaatt gaaattggta ataacactga gggacttaaa | 82380 |
| ggtcaagtaa ttcgtttaaa tactactatt aatggtactt cttctggcgg gacagtagaa | 82440 |
| caaaaaggat tgcttcctac ggtcaaagag cacgaagaaa gtatcaataa aataaaccta | 82500 |
| gatatgcaaa atcttattcc agaagccccg atggacggaa aggcttatgt gcgtagagat | 82560 |
| ggtgcatggg ttgatattac aactttaact ccataatata aagggccgaa aggcccttga | 82620 |

```
ggtacttatg tctattcacg ctccacaaaa ccctaaagaa ttaaaagacg ctattttaac   82680
tagacttggc gctccaattt taaatgttga actcacagaa gacatgattt ataattgcat   82740
tcaaagagcg cttgaattat tcggagagta tcattatgat ggtttaaata aaggctatca   82800
tatgttttat atcggtgatg atgaagaact ttataagcat ggagtatttg atttaagagg   82860
ctcaaatatt tttgctgtaa ctaagatagt tcgcactaat gttggctcta ttacttctat   82920
ggacggcaac gcgacttatc catggtttac tgattttta ttaggaatgg ctggtataaa    82980
tggcggaatg ggaagttctt gtaacaaatt ttacggccct aacgcttttg gtgcagactt   83040
ggggtatttt acccagttaa tgacttatat gactatgatg caagacatgt tgtctccact   83100
gccggattat tggtacaatg gagctaatga gcaattaaag gtcatgggta atttccagaa   83160
acacgatatt attatcatag aagttttac actagcttat tcgggagttg ataaaactgt    83220
tggaaacaaa gctggatatg gatatgcagg taaagccgac caatggtcta tttctgacca   83280
atgggataat atggacaggt ctttgccaca acggcgtgct ggagaagacg caaacgttaa   83340
gcagggcgca tataataatc gttgggtgaa agattatgcg actaccttag cgaaagaact   83400
tctaggtcag gttttagcta acaccaagg aatgcaatta cccggtggag tcactctaaa    83460
cggagagaga ttgttagacg aagctgaaag agaaaaagaa agattgcgag aagaattata   83520
tttactcgat cctccttttg ggattttgat tggttaattg agaggaatta aaaatgatga   83580
ataataattt attcgcaaag ttagaaaata aaaacggata tgaaaaaaca aatgttgcta   83640
atattctcaa tccgtatgta aattttaacg ggcataaaaa cacccaatca ttggcagaca   83700
ctcttgtagc tgaatcaatt caaatgcgcg gcgtggaatg ctattatatt ccaagagaat   83760
atgttaaacc tgaccagtta tttggagaag acttacaaaa taaatttact aaagcttgga   83820
tgtttgcggc ttatgttaac tcatttgaag gatatgaagg agctaactca tttttttagta  83880 aattcggtat gcaagtttcc gacgaaataa ctttatccat aaatcctgga ttatttaagc   83940
atcaaaccaa tggaactgag ccaaaggaag gagatttaat ttatttcaaa atggataata   84000
gtttgtttga aataaattgg gttgaacctt acgacccgtt ctaccaagtt ggaactaact   84060
caattcgtaa ataacagca ggtaaattta tttactcagg cgaagaactt aatccagaat    84120
tgcagaaaaa tcctggtatt gaaattccag aatttagtga attggattta tctccggtta   84180
aaaatcttga cggtcttgct gatattggag aaattcaata cgaggaagtc gaccagatta   84240
ataaagaagc ttctgaattt gttaaagaat atgtagtaat aaacggacgc ggcattaatg   84300
acccgcagaa cactagccca tttgatgatg gttttatgtc ataaatataa ttataaacat   84360
actaggccct tagtggcctt tggagaaaaa attgttcgga cattttata actcgtcttt    84420 cagacggtac attttgctta tgggtgattt attctctaat attcaagtag caagaacccg   84480
cgaagacact ggaactagat acataaaagt ccctgttact tatgcatcaa agaacatttt   84540
tatgatgaaa cttaacaaat ggacttcagt taactctcaa caagatgttg ctaaggttga   84600
aacaattctt ccacgaatta atttacatct cgttgatgtt atgtataacg gaacatataa   84660
aactaatata tctaatagga ctgctcttca acaagctgat cctaaaccaa ctactatttc   84720
tcaatttaat ccaactccat ataaaatgat ttttgaattg gaattttta cgcggtatga    84780 agatgatatg tatcaaattg ttgagcagat acttccatat tttcaacctc atttcaacac   84840
tacaatgacc gaacaattcg gtgatgagat tgaattcgaa cgagatatta gaattgtttt   84900
tcaatctata tcagtagatg aacaaattga cggagacaac atcagtagac gtagacttga   84960
```

```
atggtctatt atgtttgaag ttcaaggttg gatgtatccg ccgcagcgtg atattaaagg    85020
cgaaatcaga acagtttatt tggattttca tgctaatacc cgtgaattag ttccagaagg    85080
aattttcgaa tccgttgact cagaagttga accacgggat gtcaatgttc aggattggaa    85140
cggagactct aaacaaactt attcttctaa tatacctatt cctactccgc ctgcccctcc    85200
agggccaaga attgtaaaag aagatgatta gtgaggaaaa atgagcgaac aattagatat    85260
taccaaactc ttagatatcg gggaaatccc tggtattgat ggggaagaaa ttccggtata    85320
tgaaaaatta gaattagtag aagtaaaaag taatccaaat gaccgtaaac cagacttaga    85380
agatgattac acggtcgttc gtaaaaatat gcatttttcaa caacagatgt tgatggacgc    85440
cgcaaaaata tttttagaga ctgctaaaaa cgcggatagt ccaagacaca tggaagtatt    85500
tgctacttta atgggtcaga tgacgactac taataaagaa attctaaaac ttcacaaaga    85560
gatgaaagaa attactgccg aaaacgttgg aacacaaggt ggcaatcaaa ctaataacat    85620
tgaaaacgca acgttctata tgagttctcc tactgacctg atggacgaat taggagattc    85680
atatgaatct caagagcgtc aggagaaatt agtaaatgga acagactcaa ccgtataacg    85740
ttctgaatga cgctcatccg ctgaatgatg ccaataaaat tgtaattaaa cacccaggtc    85800
agctagaaag aatggttgac caaggaatta attggattaa atcgcagtgg gacgataagt    85860
ggtatccaga aaaatttgat gattatttaa gaataaacaa aattgtaaag attaaattac    85920
agggtgaaga cccagataat tttcagactt ttaaaaataa aaacgtaaaa cgttctaggt    85980
atatgggtct tccaaaccta aaacgctcta atatcaaagt taattacacc aaggagatga    86040
ttcttgagtg gaaaaaatgc cgcgatgata ttgtttattt tgctgaaaca tattgtgcta    86100
tcacacacat tgactacggt acgataaaag ttcagttacg agattatcag cgtgatatgc    86160
ttagaattat gcataaaaaa cgtatgcacg tttgtaactt gtctcgccag cttggtaaaa    86220
caactgtagt agctattttt cttgcgcact ttgcctgttt taataaagac aaagctattg    86280
gtattttggc gcataaaggt tcaatgtctg ctgaagtact ggaccgtaca aaacaagcta    86340
ttgagttatt accagatttt ctccagcctg gtattgttga atggaacaaa ggttctattg    86400
aattagacaa tgggtcatct ataggagctt acgcgtcgtc tccggatgct gtgcgtggta    86460
actcattcgc gatgatttac atcgacgaat gcgcatttat tcctaacttc atagacgcat    86520
ggcttgctat tcaaccagta atttcatccg gtcgacggtc taaaattatt atcacaacga    86580
ctcctaatgg attgaaccat ttctatgata tttgggatgc agcaataact ggtaaatccg    86640
ggtttgagcc atatactgct atatggaact cggttaaaga acgcctatac gatgataacg    86700
acgtgttcga tgacggttgg caatggagct cacagacgat ttctgcttca tcgcttgaac    86760
agtttaaaca ggaacactgc gctgaattcc acggaacttc aggtactctt atttctggta    86820
tgaaacttgc taatatggaa tggacggaag taactccaga ttcttatgga tttagcaaat    86880
ttaaagaacc agaagaaggt cataaatata tagcaacatt agatagtgca gaaggccgcg    86940
gacaagatta tcacgcattg catataattg atataacaaa tccaatatgg gaacaagttg    87000
gagtgcttca cagtaattct atttctcatc ttattcttcc ggatatcatt atgagatatc    87060
ttattgagta caatgaggct ccaatttata ttgaattgaa ctctaccggt gtttcggttg    87120
caaaatctct ttatatggat ttagaatatg agggagttat ttgtgattca atgcaagact    87180
taggcatgaa acaaactaga agaactaagc ccgtaggttg ttcggcatta aaagatttaa    87240
tagaaaaaga taagctaatt ttgcaccaca agcaactatc caagaattcc gcactttcct    87300
cagagaaagg ggtttcatgg gcagctgaag acggatacca tgatgacttg gtgatgagcc    87360
```

```
ttgttatttt tgcttggtta tccacacaaa ctaaattcac tgaatatgct gaaaaagatg   87420
atatgcgtct agcttctgaa gttttcagtc gtgaattaga agatatgaat gacgattacg   87480
caccagtagt tttcttggat gcagtggccg gggccgagta caacccaact gaacacggtc   87540
tgtcgtttgt ataaatatac taaagcacac atctagagga tttattcatg gctttactct   87600
cgccgggcgt tgagctcaaa gaaactagtg tacaaagcac tattgttaat aatgctacag   87660
gccgtgccgc tatcgctggt aaatttcaat ggggtcctgc atttcaggta attcaggtaa   87720
ccaatgaagt tgaactcgtc gatttatttg gtactcctaa tagcgaaact gctgattatt   87780
ttatgtcagc tatgaacttc ttgcaatacg gtaatgattt acgtgtagca cgtgcagtta   87840
atcgtgacgt ggcgaaaaac tcttctccta ttgcagaaaa tattgaaacc acaatttccg   87900
cggctggttc taactataca gttggcgatg ttatccgtgt acgtcataat atggatgtaa   87960
ttgaaactgc tggtaaagtt actcgtgtag atgctgacgg taaaattctg ggagtgtata   88020
ttcctactgg taaaattatc gcttatgcga aaagtactaa ccaatatcca gacctaggtc   88080
caaactggac tgcagaaata gcttcaagtt cttctggcgt atctggtact attactcttg   88140
gaaaaattat cactgattct ggtattttgt taactgaacc tgaaaatgct tatgaagcta   88200
ttcgtaatac cactttccag aacaatttga aaaaatatgg tatgccgggt gtagttgctc   88260
tttatccagg tgaaatcggc tctcaacttg aaattgaaat tgtttcaaaa gctacgtatg   88320
aaaagggcgc ggcatctgaa cttcaatttt atccaacggg cggaactcga gttactaccg   88380
cacgggcagt atttggttat ggtccacaaa ctgatgacca atacgcgatt attgttcgcc   88440
gtgatggagc aattgtagag tcagctgttc tttcaactaa agaaggcgaa aaagacattt   88500
acggaaataa catctatatg gatgattatt ttgccaaagg ttctagtaac tatattttg    88560 gaacagcaat aggctggcct aaaggttttt ctggcatcat caaattgaac ggcggcattt   88620
ctgcgaactc agctgttacc gcaggcgatg taatgcaagc atgggattta tttgctgacc   88680
gcgaagcatt gcacgttaac ttacttattg ctggcgcgtc tgcaggcgaa agtttagaat   88740
ttgcttctac tgtgcagaaa cacgtagttt ctattgccga cgaacgccaa gattgtcttg   88800
ctttaatttc tcctccgcgt gaaattatcg taaatattcc gttaactcgt gctattgata   88860
acttggttaa ctggcgtaca gcatcggcag cttataccga cgataacatg aacatcagtt   88920
caacttacgc atttattgat ggtaactata aatatcaata tgataagtac aatgatgtta   88980
accgttgggt gccactttct gctgatatgg cgggtctgtg cgctcgtact gataatgtta   89040
gtcaaccttg gatgtctcca gctggttata accgtggtca aattctgaac gtaattaaac   89100
tagctgttga agctcgtcaa ccgcaacgtg accgtttgta tcaagaagca attaacccgg   89160
ttactggcac aggtggtgat ggttttgttc tgtttggcga taaaactgct accaaagttc   89220
caactccatt tgaccgtgtt aacgttcgtc gtttgtttaa tatgctgaaa acgaatatcg   89280
gtaattcatc gaaatatcgt ctgtttgaga ttaacgataa ctttactcgt tcttcttttcc  89340 gcatggaaac tagccagtat ctgcagggaa ttaaagctct tggtggtatg tatgagtatc   89400
gcgtagtttg tgatactact aataacaccc catcggtcat cgatcgtaat gagtttgttg   89460 caagcttta tgtgaagccc gcgagatcga taaattatat taccctcaac ttcgttgcaa    89520
ctgcgactgg tgcggatttc gacgaattga tcggaccgca ataatatctc actgggcctt   89580
cgggcccttt ggattaaaag tgattatctc taaaactgtt aagataaaaa tcgttcctca   89640
gaacttcaag tacttctcta atcttggata taaactatct ccgcttggag cagttaaaca   89700
```

```
tggatttgaa tattattcta tcgatgttag tgtagagcat ctaaaacctg gatcaaatat   89760
tgatgtagaa tgtgtatgtg ataaatgcag tgagcattat actcaaagat tttgtagaaa   89820
tactgatgta tgttatgaat gtagaagtgg aaaatttaag ctcggcaata aaattggaac   89880
taagaacaaa ggaaaaatct tggtttctat gcacggcgaa aatcatcctc gttggaatcc   89940
aaacaaatca gactacaata agtacgcttc tgaagttcgt cgcataacca atagaaataa   90000
atcgatttat tcaaagtggg aaaatttcga taaaatcgga ttatgtgtg tagaaggagc     90060 ttatcagtta gatcacaagg tttctatcaa atacggattt tatcatcata taccagcaga   90120
aattataggg tgtattgaca atttagagat aatcacttgg gaatccaata gagataagtc   90180
cggtaaatct agtatcgatt tatgggattt acttaagtga tcatagaatt aacttaggga   90240
ccttctaacg agggtccata aatatataca gatcacacaa tttaattcgt ctcgatggtt   90300
ctggtgaatc tggagctata taaataaaca catagaggtt attatgtttc ttgatgacat   90360
gactcgtgca tttgagtctg gcgacttagc tcgtcctaac ttgtttgaag tagaaattcc   90420
gtaccttggc agaaacttta gctttaaatg taaagctgct ccaatgcccg ctggtatcgt   90480
agaaaaagta ccagttggtt atatgaaccg taaaatcaac ttagctggtg accgtacatt   90540
tgatgattgg actgtgacta tctataacga tgatgctcat actactcgtc aagctatcgt   90600
tgactggcag gctatctgtc atggtcaagg caacgaaatt actggcggta ctccggctga   90660
atataagaaa actgcggttg ttcgtcaata ccatcgtgat ggtaagacag taactaaaga   90720
agtaacaatc accgggctgt ggccaactaa cgttggtgaa gtacaaatgg attgggattc   90780
gaataacgag atagaaacgt ttgaagtaac gtttgcgatg gactggtggt tgtaataaat   90840
atattcaaac ctcaacttca ttgtttgaat atgttgcact tatcttacaa tttatacggg   90900
gaataaactt ccccgtcatt ttttagatgc tgcaaaactg ttataaataa gtatatgctt   90960
attacccttt cacggagact ctaatgaatt tcaatatttt aagtcttttt gctccttggg   91020
cgaaagaaga cgaacaaaat tataaagaac aaattaaaaa tgacttagag tctattactg   91080
ctccaaaact ggatgacggt gcgcatgaga ttgagtcttc agccaatgaa gcttcttata   91140
acggcctgtt ccaaaaaatg ctaggaagtc atgaacctgg catgaaaaat accagggagc   91200
ttatcaatac ataccgtaat ttgatgaata attacgaagt tgataacgct gtacaagaaa   91260
tagtaatgga ttctatcgta tacgaagacg gtcatgaagt tgttgctatt gagcttgata   91320
caacggattt tagtcaacgt ataaaagacc ggattattga agaatttaac gaagttttaa   91380
attgtcttaa ttttcaaaga aaaggcgctg atcattttag gcgttggtat atcgattcca   91440
gaattttctt tcacaaaata ataaatccaa aaaacgtcaa agaaggaatt caggagctcc   91500
gtcgtttaga cccacgaaat gttcaatata tcagagaagt tgtaactgat atggaacaag   91560
gagtaaaaat tgtaaaggg tataaagaat attttatata cgacaccggc aatgagtctt    91620
atcaatgcga cggcagaacg tatgatgccg gcacaaaaat aaaaattcct aaatctgctg   91680
tagtatatgc tcattctggt ctagtagatt gtactggaca aaatataatc ggatatttgc   91740
atcgggctgt taaaccggct aaccaactga aattgatgga agatgcttta gttatttacc   91800
gtattacccg tgctcctgac cgtcgtgtat tttatattga tacagggaat atgccttcac   91860
gaaaggctgc gcaacacatg caaaatatca tgaacacgat gaaaaaccgt gttgtatatg   91920
atgcatctac aggtaaaatt aaaaatcagc aacacaatat gtccatgacg gaagattatt   91980
ggttgcaacg tcgtgacgga aaagcagtaa cagaaattga tactcttccg ggtatgtcag   92040
gaatgagtga tatggatgac gttcgttggt tcagaaacgc tctttatatg gctttacgag   92100
```

```
ttccattatc tcgtattcct aacgaccaac aaggcggagt tcaattcgat gctggcacat   92160
ctatcactag agacgaatta agtttttacaa aatttatccg tgagcttcag cataaatttg   92220
aagaaatctt cttagaccct cttaaaacta atttaattt aaaaggcgta attactgaag   92280
atgagtggaa tgatgaaata aataatatta agatttcatt ccaccgcgat tcatatttct   92340
ccgagcttaa agacgctgaa atcatggaac gcagaatcaa tatgcttcag atggccgaac   92400
catttattgg taaatatatt tcgcatcgtt cagctatgaa agatattctt catatgagcg   92460
acgaggaaat tgaacaagag gctaagcaaa ttgaacaaga gtctaaagag gctcgttacc   92520
aagacccaga aaatcaagag gatttctaat ggaaagtcaa tttatttccg catgcttatc   92580
caacgacctc gttcaggcac gtaagctttt tgaaagcatc atgcttgaaa ggactacgga   92640
tttaattggc gaacgcaaag ttgaaattgc gcgttcgttt ttaattgaag gcgaagagcc   92700
aaaagacgaa gatgagtcag atgaaaaaga taaaaaagaa tctgacgacg ccgatgaagg   92760
cgatgacgaa gatgaggata actaatgttt cttatccctg aagaccatga attagtaatc   92820
gaaaatgtcg agactcttat tccagaagct cagggccgtt acgagtcatt atcaaaagcg   92880
ttaagcaaag acgatataaa tacaattgta gaaaacatga ttgaaaccga taccgattta   92940
gcaattgcac tcggttcaat taacgaagat atgcaaatta acgaatttat cgttaagcat   93000
gtttcaagta aaggcgaaat aactcgaact aaagaccgag ctactagagc tagaaacgca   93060
tttcaaacta caggattgtc taaagctaaa cgccgccaaa ttgctcgtaa ggcaaccaag   93120
tcaaaacgcg ctaatccgtc aggacaagct cgtggacttc gtaaacgtaa gaaagctatg   93180
aagcgccgca aagcgttagg attaagctaa tgaaaaaata tggtaaccac agaaaaattt   93240
gggaagcagt taatggtcct ataccattag atgaatttgg acgtagttac catatacatc   93300
atattgacgg aaatccagcg aacaatgaat tatcaaattt attatgctta agcccaaatg   93360 accatttttga attacacagg tctcaaggcg atttcggggc agcgttttta ttactgaata   93420
accatttatc tttatccgca gaagagcgct ctgatattat atctaaggca aattcaaata   93480
gatgaaaaaa ttattctgat gctgaacgca aaagcataat aaataaaaat agaaattcaa   93540
atatatttac ttggtcttct gaaaggcttc gaagagagac tggtgctaaa attagtgcat   93600
cacactcagc caggaccaaa gagcagaaag agcaagaatc aatattaaga tcttcttcta   93660
taaaatctgc ttggaaatct agttcatttg acgctcaaag agaacatatg tcaactaaag   93720
ttgtatgtcc tcattgcgga agggaaggac aaaaagctgc tatgagcaga taccattttg   93780
acaggtgcaa atatggaaga gcagttatta attgagaact ggggtttacc cggtgagata   93840
aaagaaggaa aacctctaat tgaatcagta gattcaaacg gagaaaaatt gcctcctggc   93900
ttgtatattg aaggaatatt cctccaagct gaagttgtga accgtaataa gcgtctttat   93960
ccaaaacgta tcttggaaaa agctgtcgct aattacatga agaacaggt tcagactaag   94020 caagcattag gagaattaaa ccatccacct cgcgctaatg ttgaccctat gcaagccgct   94080
ataattatag aagatatgtg gtggaaagga aacgacgtat acggacgagc tcgtattatt   94140
gaaggtgacc acggtcccgg agataaaatta gcagctaata tccgagcagg ttggattccg   94200
ggtgtttcaa gtcgtggact tggttctttg actgaaacta caaaaggtta taagattgtg   94260
aacgaaggtt ttaaacttac tgtaggcgtt gatgcagtat ggggaccttc cgctccagat   94320
gcttgggtga ctccgaaaca aatttcggaa ggcacacaag attcggcacc agctgccaag   94380
aaaagtgctg atgaagcatt taagactctc gcagagagtt taaaagcatt ataaataata   94440
```

```
atgtaactta acaacaggaa catcaaaatg ctgaaacaag aacttatcgc tgaatccggt    94500
gcgctggaaa tcgcggtaga actcgacagc gttttcgaat cagttgaact ttctccggaa    94560
gtaaaagcta acttcagcac tgtattcgaa gccgcagtta aaaaaggtgc cgctgacctg    94620
gcagaaaaac gtattaatgc tctggtagaa gcagcagaag aaaaagttaa agacgaaaaa    94680
gaaaaagccg aagaagaagc tgaaaagaaa atcacagaag ctgcttctaa attttttcgac   94740 catttggcca acaatggct gagcgaaaac cagattgctg ttgaccgtgg tattaaatct     94800
gagttgttcg aatctatgct ttctggaatg aaagaactct tcgttaaaca caacgttgta    94860
gtcccagaag aaagtgtcga cgttgtcgct gaaatggaag aagaactagc tgagcagaaa    94920
gaagaaactg cgcgtctgtt cgaagaagtt tcaatgcgtg atgcttatat caattatgta    94980
agtcgtaccg ttgctgttaa tgaagccgtt aaagacctga ctgaatctca gaaagaaaaa    95040
gttgaatctt taactgaagg tatggaatat tctgatgctt ttggttccaa acttgaagca    95100
atcgtagaaa tggttaaagg tagttttca gaaaatgcgg cagtaaatga aagcataaat     95160
actgttgata ctgaggcaac tggccttaat ttcgtaactg aagcggtcgc tgaaccgtct    95220
gatccggcag aaaagtagt agctccttca atggcagcat acttagctgg tgcaaaacgt     95280
ctctattaat ttaacaaggt tatacaacac atgaaaagaa ataaactcgt agaaaatgg     95340 cagccgctgc tggaaaacga gaactgccg gaaattgttg gtgctagtaa aaaagctctg     95400
attgccaaaa ttcttgaaaa ccaggaagca gattttaaag tatctccgga ataccgtgat    95460
gagaaaatcg ctcaagcttt cggttctttc ttgactgaag ctgaaattgg cggagaccac    95520
ggttacgatg ctcagaatat cgctgcaggt cagacttctg cgcagtaac tcagattggg      95580 ccggctgtta tgggtatggt ccgtcgtgct atccctaacc tgattgcttt tgatatctgt    95640
ggcgttcagc caatgaacag ccctaccggt caggttttcg ctcttcgtgc tgtatacggt    95700
tctgacccgc tggctgataa agcaaaagaa gctttccatc cgatgtattc tccggacgca    95760
atgcattctg gtcaaggtgc cgctgagaaa ttcgctaaat tgaccgctgg cgttgctatc    95820
actgaaggcg atatcgttgt tcatgatttt gctgaaacag gtcgcgctta tctgcaggct    95880
gtagttgctg taactccaga tgctggcgct actgacccgg ctaaactcga cgctgctgta    95940
gttgctctga tggaagctgg tcagctggct gaaatcgctg aaggcatggc tacctctatc    96000
gctgaacttc aggaaggatt taacggttcc cagaataact cttggaatga atgggtttc     96060 cgtatcgata aacaagttat cgaagctaaa tctcgccaac tgaaagctgc atattccatc    96120
gaattggcac aggacctccg tgctgttcac ggtatggatg ctgacgctga actgagtggt    96180
attttggcta ctgaaatcat gctggaaatt aaccgtgaag ttgtagattg gattaacttc    96240
tctgcacagg ttggtaaatc tggtatgacc cagactgttg gttctaaagc tggtgtattt    96300
gaccttcagg accctatcga tatccgcggt gctcgttggg ctggtgaaag ctttaaagct    96360
cttctgttcc agattgacaa agaagctgca gaaattgcac gtcagactgg ccgtggtgct    96420
ggtaacttca tcatcgcttc ccgcaacgta gttaacgttc tggctgctgt tgatacttcc    96480
gtatctcctg ctgctcaggg tctgggtcgt ggttttgaaa ctgataccac taaagcagta    96540
ttcgctggtg ttcttggcgg taaatatcgc gtctatattg accagtatgc tcgtcaggac    96600
tacttcacca tcggttataa aggcgctaac gaaatggatg ctggtattta ctacgctcct    96660
tacgttgctc ttactccgct tcgtggttcc gatccgaaga acttccagcc ggtcatgggg    96720
ttcaaaactc gttacggtat cggtattaac ccgttcgctg attctgctgc acagcaacct    96780
aaaggccgta tcgtttccgg tatgccttct ctggttaact ctgttggtaa gaacgcttac    96840
```

```
tttagacgag tttacgtcaa aggaatttaa gatttaacct taattaaggg aaccttcggg   96900
ttcccttttt tcgtttttga tgtaaaacaa tattataaat aaaatatatc acaaaaggaa   96960
agcgcaatgg caaagattaa cgaattactg cgcgagtcaa ctacaacttc tagcagctct   97020
ttagctcgtc ctaatttggt tgctttgacc cgtgctacca ctaaattaat ttacagcgat   97080
attatcgcag aacaacgtac caatcaacct gtagcggctc tttatggagt aaaatatcta   97140
actccagata atgagtttag ttttcaaact ggtgctactt atggcggaca aatcagtgaa   97200
aaagaccgtg aaactattcc agaattaact agtaaaactc aaacacttgc agttggtgat   97260
tatttaaat atcaaaatgt cgtgtataaa gctttacaag ctaatccgtt ggcatctaca    97320
agcgcaacag atttatcaga cgcactgcaa gaaggattaa tttctcttac ttgccgttta   97380
gttccagatc tgctaatac tgaaaaattt gaagatactg atgttgaaat tagtagtgct    97440
gtatttgaag taaataaatg gaatgctcct gttaaaactc gtaaattgaa aacctcgttg   97500
actgtcgaac ttgcgcagga tatggagtca aacgggttcg attctccggc attttttagaa 97560
gatttattgg ctacagttat ggctgatgaa attaataaag atgttcttca gtcactgatt   97620
acggtgtcta gcggtacaa agttacaggc gtttctgata atggtattgt agacttgagt   97680
tacgcaaatg ccccggaagc ttcacgcaaa ctgtatgaaa tcgtgtgtga aatgaattca   97740
gaaattcaga aaacaacttc ttattcgggt acttacgtag tagcttcttc tagagcagcc   97800
gcattgctgg caggttcagg ctggttaaaa catcgtccag aagatgatga atggttgcct   97860
tctaccgcgt atggatatct gttaaatggg cttcctgtat tctgcgatgt aaatagtcct   97920
ctggattatg ttacagtagg cgttaaagaa aactacggtg gaaaagaagt agttggttct   97980
atttttttacg ctccatacac agaaggatta gacctagatg acccggacca tatcggtgca  98040
tataaggtaa ttgttgaccc agatagtttg caaccatcaa tttcattgat gatacgttat   98100
gctttgtctg ctaacccgta tacagtagct aaagatgaga aagaagctcg catcatagat   98160
gctactgaca tggataaaat ggctggacaa agtgatatgt catatttggt tggggttaaa   98220
ctgcctaaaa taatttatga ggcgccttaa tgcaaaaaat agataattta attagagaat   98280
ctactgtctc atcggccaac tcgcttggcc gtcctaattt attgtcatat acaaaagcta   98340
caaataagcg tattttcaaa tctctcgttg ctgaacagaa aactaatcag ccgattgctg   98400
cgttatatgg aatacgtgtt cttaatccag ttgataaaat gacatattta ggcggcgcta   98460
cttatgctgg tcaaattggt ttgtctgaac gtgaatcatt acctttagct tctactccat   98520
cccaatcttt taataaaggt gagatgtttt tatttgaaga tgttgttttt aaagcgttag   98580
aagataatcc attcgctgga acagctgaga ctgatatgag agaagttatt tcagaagcta   98640
tcgctgctgg acatatcaga atggtatctg acgccgctaa cacaaacaag tttgaaaatg   98700
gtcacccaga aattgccgaa gctggatttc gtattgataa atggcaaacc gaagttaaat   98760
cccgtaaatt gaaaacctca ataactgttg agttagcaca ggatttagag tctaatggtt   98820
ttgacgctcc aaattttatc gaagatgttt tagcagtaca aatggcggaa gaaattaata   98880
aagatgttct tcagtcattg attacagtgt ccagccggtt taaagtacaa ggtatatcgg   98940
aaaaaggtgt tttaaattta acggatccta aatacgataa tgctcaagac cgcgcgcgta   99000
ctctttatta ttatatgtgc gaaatgaatt ccgcagttca gagacaaaca tcatttttctg  99060
gtacatacgc agtagcttca tctcgatgtg ccgcgatttt agctgcatcc ggttgggttg   99120
aaaaatcaga agaccaagat gagttagcat atggtgtatt aaaaaatggt ttgccactct   99180
```

```
atgctgatgt aaacagccca tgtgattacg ttattgtcgg tgtaaatgct gatttaggtg   99240
aaggacagac ggttgcatca ctgtattatg ctccgtatgt tgaggggcta gatgatgttg   99300
atgaagaagg tgatacttct gttggtgagt tcaaagtaat tgttgaccca gatagtttac   99360
agcctactat tgctctttta gctcggtatg cattaactgc taatccatat acagtagcta   99420
aagatgagaa agaggcacga gttattgatg gtgctgacat ggataaaatg gctaatcaaa   99480
gccaattaag ttcttatctt ggcgttaagt taccaccgct tgagaaataa gaaaaaggg    99540 ccttcgggcc cttataaact aaatatatca aacttcggag catactgttc ttgtagctct   99600
tcgaaaactt tcttatcatt caaatttgta caaggtattc cgtgttgtct tgcaatacga   99660
gtagctatac gagttccacc ctgttcttcc ccatttctta ctggacacca ataataaacg   99720
cggtcaaccg gtgacataca atcttctccc aaaacttgca tcgcatttcg acagaacaat   99780
gtctttataa tatctcgttc agaatccagc cctggataag cttgcttagc tttgacgtaa   99840
ctctttatac gagattcatt acttaaatca gaccagcaaa ccacgccaat accggtgtgg   99900
caatgattaa acccatcata aggaataatc ctaagcgaaa gatgtctatc atatctgctc   99960
aaccaagctt cgtctgagcc tggagctcca ccagaataag agaaatgacc agcctccgaa  100020
aaggccaatc ccattaaact cattaagtca agatactttc ttggtgcttc tcttgacccg  100080
attaatgcta atcttaactt acgatttcta gccattttc tctgatagta ttactcacaa   100140
cagtctgaag ttctcgtttt acgaggtccg gattatcagc atgaacaata tcaacacctt  100200
ctcgtttagc ttcaataaag atatcctgta ttgtcagacc cataaccta ccgaagtctt   100260 tagctttaac ttcgccaata tgactaatca cgttagatac acggttccac gtagagtatt  100320
cacagaggtt cgccagaacg gtcgagtcgt tactagttaa tacagcttta ggtttaattg  100380
gcttatcaga tttttttctc tcagtgaatc tggagttctt agatttaatt gcaatgcggg  100440
tgccattatt aaagaaatca ggataaactg gttttagtac gtaaccttca gcaacattat  100500
catctgtcac taatgggtca aatacacaca aattgacttc tttcaaatca tcttttgctg  100560
cttcgttata agctttgatt acagatgtaa aattatttgg taattgaata agttcatcaa  100620
aagaaccaca tccaataaat ggagccattt taaatccgaa ttcgttacag aacgaagtca  100680
tcatcatatc gtccatataa agaacattac cattttgagt atttactaga atgtcaaata  100740
cataaaagtc tttttcacca taatcaactt cttttctgaat tccttgaccc gcgaactcac  100800
caaaaatttg ataagaactt actgaaccaa gttcattcgc attcatgcat cgttgaatag  100860
ttttaataga ctcgtcataa ttcttcaata taatttcgtg gccatagaat gattcactag  100920
gaagaatggg accactgcgc ttgcacgcag aaactgagtc tttggatacg atgattgaga  100980
aattagtgcc atgaattttt tcacgagcta cccacaaacc gccatcttta ccttcaaacc  101040
gaattttaga aataaattta ttgttgtagt ggttttcaag agaggagtac ttcttaaaca  101100 tttttttcacc attataaata gattaaatag agaacttcta ttcttttccg gcagagtgta  101160
atggttacta gatattatcc ttgaaaccat tatacaccat aaattcttaa agcatttttac  101220 cacgtaatca taatatacgt gccggaaatt tggcattggt tccagtatgc cgtaaatcct  101280 tcatcttta accatgacat gatatttcct ttgaaattag tttctttttgg gtagaaaacc  101340 agttgagtct tcccattttt ggcagcatta ttaattgatt cttcaattag ttcttttgc    101400 ttaacaaatc cttcattgtt ataagaatct gctaagttac ggtattttc tgataataac   101460 atttagacct cgcttggaat aatacgaata tcgatgaaac taaaatcttt tgattgtcgt  101520
aattcaatct gatttttatc accaacttca ataaccacta tttcatttaa ttcgatttca  101580
```

```
gcgatattaa aagcaaatcg gtttttaatt atgttataaa gtatcacaag ataatgttca  101640
ttgtaaaacg aactactatc tccaaaagaa tacgataatt ttttcataaa atctttgatt  101700
gaacaccatt tgttcacacc aagcgatgct ggagcaaaca aattttcata cagcatataa  101760
tcaatgatgt cagtaacaac tagttccgag tctatcagca cttgagttaa gttttcata   101820 ctattcctct cattttatta acaagtttct tacgacgaat attaacatca atatttgata  101880
agtgtttacg ataaacaatc ttctctttgt ttttcgcttt atctcttgcg gcctcaactt  101940
tagtaaacat taaagccgcg tcaaaagcac ttattccacc tataatttta gcaatatctt  102000
taaatgactt gccgttttca tgcatcatgt gcactttaat ttctgttttc ataatcatct  102060
cttcgttgga attgaattca ttgtaatcat actttagaaa agcaaaaagg gccgcaaggg  102120
cccttcatgt tatggataaa taataccagc ttctaaagca gaacgatgca caatatatcc  102180
atttctagat tcctgaacat caacttctgg ataatcatta agcattttg ctaataccgc    102240 aagatgacaa taatatggtg tatcagcttc ggtagctgtt ttccaatctt taccttcttc  102300
agtgagcttc tggatggcat ccataaccca ccagccaacc caaatataag ctgaatgacg  102360
ttgtggaaga ggatgaacat aaatcagtgg gcattcttcc ggaacaacag gttctgctgc  102420
ttcaacagta acagacacat taccggtttt aactgaatct gtaaatccag attgtgacac  102480
agtaacttca caagcatatg tcttcaagcc ttcagtagat tcagtacta ctcttgtggc    102540 ttctgtcgag ttgtcatccc atttatacgc aagagtagca ccaggaatag cagggtttat  102600
agaagctgtc aaattgaacg gaacatcaac tgttgcagta gacgggctcg aaatgtcaac  102660
agtgaactca gggaacgtat tattttcaac agtaataact accgcgtctg gcgttatagt  102720
ttgattgtta taatccgttg cagaaacggt aattaaacaa gtcaaagaaa caggtcccgc  102780
gacagtagca gtacgagtaa tatctttagt agtttcacca gtagaccaca aataatcaaa  102840
tgttgcacca cttggggcac cttcaacatt tgcagaggct ttatattcct gtccaacttt  102900
aaccgttgga gtagaagttg ataatgtacc ggttgcagtc atagttttat tattgactgt  102960
aatggtagtt tgagcttctg cggtttcagg ttctccttcg gctggggttg tggttgccac  103020
aaccttaact actttcgaac ccgccggact agccgcgatg taatccatgg tagcaataac  103080
agaactctgt ggaaccccat caacggtcca tacaaaagat tcggtacctg cagcagccgc  103140
gccggctcca gtagcagtaa atttagtcgt tgctcctatg acagctgtag gcgttaaagg  103200
ggcaattgtt acggtaaatg ccatatttcc tccaaggagc ttttgctcct tttattttg   103260 tttagtataa gcgcacaaaa gatgaatttc ttgtttcgcg gataagaata aaaccgtcgc  103320
gttgaatata ataaatcaaa cttagaagag tttgatgcgc ggtagcatgt ggaaaagaca  103380
atggtctttc tttccagtca ggattttcag aaatccattg ataaatccac caaggtaaag  103440
tataataacc tggattttta cccatcagtt gaaaatgagg attaaatgat tcggggagag  103500
aaaagctttt attttcaaca accgcagtat catcaataat cttcattatt tcatcagcag  103560
aggcagtttc tggaatacga actgcatctt ctggaatttc tttggttttc gccacttcta  103620
aaacagtaat ggtttcttcg gctggagagt caataataag ctctttgact tctactttat  103680
cttcgggttg aaccaaatct ttttgttctt ctttatcgtc gtcaattaag tcagaaattg  103740
aaataccatc attatcttct ggaagaggag catcagcgag cttttcaaat tcagcttcta  103800
aatccaaaag catattttcg aatgacttag ttttcttcaa tttaatacca aattgagatg  103860
cgtactcatc gagcttatct ttagcttctt tcttttcaag tacacggatt tcttctatat  103920
```

```
aattcatgtc tagcatagtg ttgcctcttt agttatataa atatacttgt atttataaca   103980
cggagatgtg aagttggaaa attgcaagta tcattatgtt tatgaaataa ccaataatat   104040
taatggtaaa aagtatatag gaaaacactc aaccaacaat ttagatgatg gatacgtggg   104100
ttcgggtgtt tttataaaaa aggccatcaa taagtatgga ttagaaaatt tcactaaaat   104160
aattataaag aaatttgata catccaaaga agcttttgag tttgaagccg agatggtaac   104220
agaagatgtt gttaaaaacc gaatgtatta caatgcgaaa ccgggtggtt atggcggaat   104280
ttatatgaca gaagagatta aaagaagat gaaagagtca tctagaaaaa gatatctcaa   104340
ttcgcctggc acaacattgg gaactacgtg ttatacaaat ggaaagaaaa atagattttt   104400
aaaacctggc gataaaatac cagatggatt ttatattggt caagttattc caaataaaaa   104460
atgccgaaag gggtgcgccg ttaaaccaac tacaactgga acattttggg ttaataacgg   104520
aacaataaat aaacttatgc aaccgtcatc tgaaatccca gttggctttg ttaaaggtcg   104580
cttgatgaag cgtggtatta atggtgaatt cataaagggt taattgtgga tataaaagtt   104640
cattttaaag actttagtca tgtttatata gaatgtgaag aatccattct attcgaacta   104700
aaagactatt tttcattttt tgctgatggg tataaattta acccaaagtt tcgttatgga   104760
aactggtcag gtaaaattta tttattagac cataaccgtc ttttaccttt cggtttagtt   104820
ggtcaaatta aaaagttttg tgataacttt ggttacaaat tttggattga cccaaaaatt   104880
tttgaaaaag aagacttgtc ccgtaatgac tttgatgaat ggttagggaa gctccagata   104940
tactctggga acaccaaaat tgaaccgcat tggtatcaaa aggatgctgt atatgaaggg   105000
atagtgaacc gcaggcgtat tctaaattta cccacttctg ctggtaaatc tttaattcag   105060
tgtcttcttt ctcgttatta tgttgaaaaa tatgaaggaa aaattttaat catcgtccca   105120
acaattgcgt tagtagacca gatgattaat gattttgcg attaccgctt atttggtaaa   105180
cagcacatgc ttggtattcg atcgggtaca aggcgcgact cggatgctat gatttatgtc   105240
gcaacctggc agactgcaat aaagcaacca aaagagtggt tttctcaatt tggtttgatg   105300
atgaacgacg agtgctttga tggcgacaca ttaatcaaaa caccaaatgg tgatgttaaa   105360
attaaagaca tcaagcctgg tgataagatt tattcttata atgaagatac aaaagaagta   105420
tttgaagatg aggtagttaa acttcataaa aacttaacta agtcatcatc tgaaaaaatg   105480
tatgaactcg aaatggacga cggtactatc ataaaagtaa ccggtaacca taaattttta   105540
acaaacagag gctgggtcag agccgatgaa ctcactgaaa atgacgacat agtagaatgg   105600
aaataaaaat attacgcggc ccaagcggcc gcattctaac taagtctatg gtcaaaaacg   105660
gtacaataaa tgctttaaaa gccatgtaca cgtggtgtat agataaacct agtgctttgg   105720
tgtactgtta tgaaaataat tctattcaac ctaattgtaa attctgtggc gaagggttaa   105780
attcaccgat taatagctat tgcaatccaa gatgtcaaat gaaacacctt ggcggatttc   105840
ctaaagactg taatgttgga aagacccccgt ggaataaagg tcttaaagat aattctagac   105900
attgcagtat agtaaatccg gaaaaatggg aagcagccaa gcataaaata tccaaagcta   105960
attccggaga aaataacgga atgtatggtt gggataatga agaccagcga cggcgtcaaa   106020
gcgaaactat aaaggctaaa atactttcag gcgaatttac tcctaatacc aataacagaa   106080
gaacttcatt tgatgttgtg tatgatggaa aaaattacag aagcagctgg gaagccgcgt   106140
acgcttccat aaacaaaact gctgtacatg agagaatccg tgttccttat attggaaacg   106200
atttaaagaa acacatttat atttcagatt ttttaaatcc ggaaacaaac gaaatcgtgg   106260
aaatccgtcc ggcgtctcta tacgatgaca atcatccaaa aattgtggct attaaaaagt   106320
```

```
attgtgattc caatggatat aaatatactc atattgatat agagtatttc tacgcgaacc   106380
gtcatttgat agattacgat ggtttaggtg atgacacatc caggaaaatt acaaatgcga   106440
ttaaaaagta taaagaaat  aaaaaaacct gacgttgtat acaacttgca tgttaaaaca   106500
aatcacaact attttgcgaa tggtgcatta gcacataact gccacttagc taccggtaaa   106560
tcaatttcaa ctattgtttc tgggctgaat aattgcatgt tcaaattcgg tctttctggt   106620
tctctgaaag atggtagagc taatatcatg cagtatgttg gaatgttcgg tgaaattttt   106680
aaaccagttt caacatccaa attaatggaa gacggtcaag taacagaact taaaattaat   106740
tctatcttct tgcgttaccc ggatgaagcc acgttaaga  tgaaaggtaa aacatatcaa   106800
gaagaagtta aagctgtcac tggatttaaa agaagaaata aatgggttgc tgctcttgcc   106860
aaacgattgg ctgataaagg cgaaaatgct tttgttatgt ttaaatttac tgcacatggt   106920
aaagagcttt atcagatgat taaagacctt ggacatgaaa aagtttatta tgtttcaggc   106980
gaagtgtcaa cagaaactcg taatgctctc aaagaaatgg cagaaaacgg taaggaatt   107040
attattgtag cttcttacgg agtattctct accggtattt ctgttaagaa tcttcatcac   107100
attattttg  ctcatggtgt aaaatctaaa attactgtat tgcaatcaat tggccgagtt   107160
ctacgtaaac atgcgtcaaa aagcttagct acagtttggg atttaattga tgatttaggt   107220
gttaaaccaa agtcagctaa cacaaagaaa aaatatgttc atattaatta tttgttaaag   107280
catggtttag agcgtattca gcggtatgct gatgaaaaat ttaattacac tatgaaaact   107340
atcgatcttt gaggaaacta tggaatttaa acaatttata cgtgaagcaa gcatcggttc   107400
atttatgaat aaaatcgctc aatgccagac attagctgga ttagatgaac tggaagctta   107460
ttacaagaaa agaattaaaa caactgaaat caatgacact gatgatatct ctattcgaga   107520
cgctttggcg ggcaaaagaa tggattttga gtcagatgat gagtctgaag ttgaagaaga   107580
tttctaatac aaaaaagccc cgaccacaag gaagggcaa  aaccaacaag ttggctatca   107640
acactagact aaattagcaa ttgagtttcg tttaaatgct cttctgtatt ttcagatacc   107700
ggcaattcaa cgacataatt ataacacggc ccaggatgaa caggacctt  atctgtgtga   107760
acaaccaatg ccgaatcgat cggttgctta caaacagcgc agatttcaga cattgtttgt   107820
ctcctttagt taattacata tctatttata cagttattta cccgcctcaa actgtctcat   107880
ctcaataaca tgcttaattc caaaacctct ggatttaata gcatccattg ctcctgagca   107940
aaattcaagc aaaattcccc agtattgtaa actagtgtca attttaagaa cttcagaatc   108000
agctcccaaa actgttttca tttcagactt ttcgtaacgg tccatgctaa aatcatctcc   108060
atcaccacgt cccgtgtagt agtccaattt ctttttaaga gctgattttt tctgtgcttc   108120
aatacgaagc atttctttac gaattgatga atgcttattt aaccattttc catacaaaac   108180
tggattatta gcagcttcgt attgtaattt agttgagtct aagattaaat cttgtttcaa   108240
ctcttcttgt aaatcctcga gtttcaattc attacctctt tcttgttcat tgtaatctt   108300
gttgttattg attgaaagga actaagacca ttataaccat taatcactga aagcgtatca   108360
tctattactt gaagcaagtt gtagtttaat ctgctcgata tcatccggat tatcaacaac   108420
gctgaattga acttccacta taagcgtata atcatcataa actggagtga cattaactgc   108480
taaatatcta atcctcggct cgtatgctcg tatagaagat tctatatttc gttgaacagt   108540
gtcagcagtc aatggcgtca tattttcaaa taattggtcc gtaagcgagc aaccaaaatt   108600
tgggtcaaaa ggcctgcttc cttttctggt tgttataata cctaaaagag agttttaat   108660
```

```
tgcccgaagc ccgcgtgagc gcgctacgtc tttatcccag tccatttaa attctgggtc    108720 aatatctgaa tacaaatttt ttatatcagc cattatatta acttaaagaa ttctttaagc    108780 cccttatga tatgaacatg attttctccg cattcactgc atttaaccgg aactgcgagt    108840
tgtactgtgg gttttagcag gagatttta atattaatga tatcgtcttc tgttatagca    108900
gaatataaat cttctatttc tctgctgttt aaatcttcaa taccgatagt ttcgccatta    108960
acgtgaatgg tttgaataca cgacgatatc atagaagcaa tgttctcatc ctcgaaaaga    109020
tttggatatc tgagttttat tttaaaatgt ctcaggttat accagagctc ctctggttca    109080
tcgatacatg cgaatgtaaa gttaatcggc acttgtgttt catgtccgca ggaacacacc    109140
catgtattct ggtgattaac ctcacctaaa ctgtgagacc acaaatttac taacaataat    109200
tcagattctt gcttgttcaa atttttagca tttgtacagt ttttaatcaa atctaatacg    109260
ttttgcttta catgaccatt tgtttagct atgattagat ttttatattc ttctagtgta    109320
aaagccctgc actcgatggt cttttcaccg attaggactt caaaattata gtcatagttc    109380
atgatttact cctcttatta ctttatttat aaatattaat aaaggagacc acaatggcta    109440
atatcatacg atgtgtgctt cctgatggtg ttcaccgttt caaaccgttt acagtcgcag    109500
attatcgaga ttttctgctt gttagaaacg atttactgaa caagtcatcg gacgagcaaa    109560
ctaatatact aaatgaactt ttaaatgatt attttcccga atttcccgaa acttggagac    109620
ctcatatttt tcttaaagtt tttaccgggt caataggaaa aacaaaaata ccaattgcgt    109680
tttcatgccc ggtttgcgaa aagaagaaac aaacattatt tgatttgcat ttgaatgatt    109740
taaaatctcc ggaagtagaa gttgctggta ttaaaattta tttaattttt cctgataaat    109800
tttatgaaga taaagcccaa caaattaatg ataatataaa gtctgtttta taacggaa      109860 cagaaatttt atgggaagat ttatcagaag acgataagtt acaagttatc gacgctatag    109920
atattgacac attagaaaaa ataataagtc aaatgacacc aatgagttta actcttaaaa    109980
tgaaatgctg taaaactacc actataaaat atgaagattt tttaaatata ttttgtcttc    110040
tattaaatcc agatgaagtt tttagttttt atcagattaa ccatatgctg gtaaagaacc    110100
aatacgatat gaacagcata atgaatatga tacctgtaga acgaagcata gctctttctt    110160
tggtagagaa ggataatagc aaatgataac acaaattcca ggttttccca atttaagtat    110220
aaaactttat caagattacg attcttggca aaccaaccga tacgtcgagc ttgctgctac    110280
cgtaataact ttaacaatgc gcgacggtct atatggtaga aatgaaggtg tattgcaatt    110340
cttcgattca aagaatttac acactttaat ggacggcaga caaataatac aaatatccgt    110400
agctaattca aatacaaaga aagtgcaaaa cagaatttat ggatgtaaac actatagcgt    110460
atctgttgat tccaaaggag ataatatttt agctataaat ttaggactga tacatgaaat    110520
agaagaccta aaatttagca gatgcttttt taatgatgct ggtgaatcac ttaaagaaat    110580
gatcggtgtc atatatgaag ataaacccttt aatagctcct gctatcaaca caatcaacac    110640
atacgttcct cgggttccgt ggactagcaa tataacaact tataagcagt acgtccgaga    110700
tataggttta gctgtagata atgaccaatt tgttttgta tgggaagaca tttatggttt    110760
aaacatgatg gactataaca ctatggtaaa tcaagagacc acaaaagttg tagttggtga    110820
acctaggaca ataggacaat tgttaatga gcttgagtat aatttagctt atgattttga    110880
gtggctaact aaagccaact ctcatgtacg agaccctatt ttaacgcta ctatatattc    110940 acactcattt atggataatg aaattccaag aatagtaact ggagatgta gcaatagtat    111000 ttttgtttct aggtctggtg cgtattcgga gatgacatac aggaacggat atgaagaagc    111060
```

```
agttcgtatc caaactatgg cgcaatatga tggttatgct acctgtaaaa tggttggaga    111120
ttttgaaatg actccaggcg ataaaataaa tttcttcgat acaaagagac agttcagagc    111180
tgatttttat atcgatgaag tcattcatga agtttccaat aatcaaagta taactactct    111240
gtatatgttt actaattctc gtagaataga gaatgttgaa ccaattaagg tgaaaaatga    111300
acttaaacct gatacttcca attaagaaaa taaaatgcaa taataaagaa atatctattc    111360
ctaagctcgg tttaaaacat catcatttaa taaaagaagt gagagaccta tcagaaaata    111420
tggggatttt gttggattca atccacccag gcctcactgc agcagaatcc gacttagtgt    111480
gtcttcattt attagaattc aacggtaaat taaagtctac tgtaacaaag gacggtttta    111540
cttacaatat aaatgacgtt tatatatgcc aacggttaga atttcaatat caaggaatta    111600
cattttattt tcgttctcct gagaggtacg aagttttttac cacagtagat aaaatgctgt    111660
cttcttgttt tattaaaact aatttatccg acgaggcacc tgatttcctt agaatgccag    111720
catttgtttc aaaatgggca gatgatataa caaacatgat agcaattcct ggtccacatg    111780
aacctatcaa aggaacctct aaaatattag ggctatttga atgaaaaccg aaaacatgac    111840
atcctttaga cgccgcaaag ttattgctga ttctaaagga gaaagagatg cagctgcggc    111900
tgcatcaaat caagttgaat cattagattc tatagggtac aaattagact cagttcaatc    111960
tgctacggag cttacatctg aagtaattga acagaaatcc aatgatatta tatccgctgt    112020
gaatgacact acagctggtg ttgaattaac agccgaattt gctgagaata cttcaaagac    112080
ggtaagagaa ttaacagatg taacatctgc gataagcgac aaaatatcta aattgacgga    112140
tatgcttgag cagaaaatac aggcagttca acaaaaattt gttgatagct caaaggttac    112200
cgatgatact cttaaagtca ttggagacag cattcctgag cccgttgaaa gtaatttacc    112260
tgcaatcccg gaaaaaatat tcgataaacc tgaagaaaat aattctccgg atgctgattt    112320 cttttccaact ttaccaagta aagccgaaga agttgataac aaaaaagact ccgataaaaa    112380
aattcttgac actgaaaatt tgttaaaaga tttggtcggg actacaaaga ctgggttcaa    112440
agcaacagtt tcaataacag ataagatatc aaatatgtta ttcaaatata ctgtgtccgc    112500
tttagctgaa tcggcaaaat tagctggaac tattttttgct attgtacttg gtatagattt    112560
gcttagagcc cattttaaat attggagcga taaattcagc agcaactttg acgaattcag    112620
tcaatccgcc ggagaatggg gtagtttatt gcaatctgtt ctgggctctt tacaagaaat    112680
taaaaaattc tgggaaaata atgactggtc cgggttagct gtggcaatag ttaaaggtct    112740
tgctgatgtt ctttataatt taagcgaatt aatgtctttta ggcatttcaa aaatatccgc    112800
cgctatttta agcgctcttg gatttgataa tgctgctcta tcaattaaag gtgctgctct    112860
tgaaggattt caagcaagaa caggaaatga gctgaatgaa gaagaccaag atacattagc    112920
tcgttatcaa actcgccgaa ttcaagaagg gccggatgct tttgataaat tttccgaata    112980
taagactaga gcttttgatt ttataacagg acgagataat aaaaacacca caacaacgga    113040
acaagaacgg gaagctgaag ttaagaagtt aaaatctctt ccagaagaag aattaaacga    113100
gattaataaa aagagcaata acgctagagc cgctttagtt agatttgaaa aatatatggg    113160
tgatgttgac cctgaaaatg cgactaatat tgaatctctg gataaagctt acaataatgt    113220
taaatctctt gttaatgatt ctgaactgaa taaagcccca gctattaaaa aggaattaga    113280
agtacgttta caaaagctg aagctagata tcagaaaatt aaaactgagt ctaagcctga    113340
acctgctgcc ccatcagcct ctgaagacgt gcagaaagtt caaaacatcg aaaaggcaga    113400
```

```
acaagctaaa aaatcagatg ctaatcagag cagttcatct agcgttgtta atgcccaagt 113460
taataacgta aataatagta gaacaattca aactattaat cctgttactg ctacacctgc 113520
tccgggtgta tttaaagcaa cgggcgtaaa ctaaggaaaa attatgattg ttaaagagct 113580
taaagatacg gctaaagaac tatggaataa aggcgaaaaa atttctgctg gtcaaagttc 113640
tcaatcatct aaaattaaaa gcactgtaac tgtacaatac ccgtctgagc gttcagctgg 113700
taacgatgtt acaggcaact tgagagttca cgatttatat aaaaacggtc ttttatttac 113760
cgcatacgat atgaattcta gaacctctgg tgatatgaga acatgcgtc tgggagaact 113820 cagacgtact tcacaagata tagtcaaatc cgtgaccggt aaaaatacta acaggttga 113880 taaaatacct gttgctaata ttcttttgcc taggtctaaa tccgacgttg attcgacttc 113940
gcataaattt aatgacgttg ctgattcttt aatttcaaga ggcgggggaa ctgctacggg 114000
agttttaagt aatgttgcgt caactgctgt atttggtgcg ttggagtctg taactcaagg 114060
actaatggct gataataatg agcagatata caatacggct agaagcatgt atgctggcgc 114120
tgataaccgc acaaaagtat tcacttggga cttaactccg cgttctgttc atgacccttat 114180 agctattgtt gaaatatacg aatattttaa ttattattct tatggtgaaa ctggtaattc 114240
aacttttgca aaagaagtta aatctacttt agatgaatgg tataaatcca cttttttaga 114300
tactttaaca cctaccggtg ctcctcaaaa cgatacagta tttgagaaaa taacttcatt 114360
tttaagtaac gttattgttg taagtaaccc taccgtgtgg tatgtaagaa actttggtaa 114420
tacttctaaa tttgatggta aaactgatat ttttggaccg tgccagatac aaagcatacg 114480
atttgataaa actcctaacg gagttttcaa tggtctggct gttgcaccaa acttaccgag 114540
tacttttact ttagaaataa caatgcgtga atacttaca ctcaataggt cgtcaatata 114600
ttcggaaggt ttttaatgta tactttagat gaatttaaaa atcaggcagc taatatagac 114660
ttccaaagaa caaatatgtt tagctgcgtc tttgcgacta ctccttctgc gaaatcccag 114720
cagttattgg accaatttgg agggatgcta tttaataatc ttccactgaa taatgactgg 114780
cttgggttaa cgcaaggaga atttactcag ggcttaacaa atataataac ttctggtaca 114840
agagatttaa ctagaaaatc tggcgtatcc aaatatctca ttggagctat gagtaaccga 114900
gttgttcaat cttttattagg cgaatttgaa gtaggaacat acctgattga ttttttcaat 114960
atggtttatc ctcaatcggg cttaatgatt tattctgtta aaataccaga gaatagattg 115020
tcacatgaaa tggacttcat gcacaattct cctaatataa aataactgg cagagattta 115080 gaaccgttaa cagtgtcatt cagaatggac ccagaagctt caaattatag ggctatgcag 115140
gattgggtta atgctgttca agacccggta acagggctta gagcacttcc aactgatgtt 115200
gaagctgata tacaagtcaa tttacacgct cgtaatggaa tacctcacac tgttattatg 115260
ttcactgggt gcataccaat tagttgtgga gcccccgaat tgacatatga gggagataat 115320
cagattgctg tttttgatgt aacatttgct tatagagtga tgcaggcagg cgccgttggt 115380
cgccaggcgg cgatagattg gttagaagat aaaactgtcg attcaataga taagataaat 115440
cccgatttat ctctaaacgg aagtttaagc agactttcga gattaggagg agctggcggg 115500
ggtatttcta atattgtaaa tagagtattc taaaaaaggg gaccaacgcg gtcccttttt 115560
ttagttaacg aaatacaaca aatcctacta cattagatat ttgattgtcc tcagcgataa 115620
tactaattgc acacggaact tcaccaacta aattacccga caatacgcca gaaatatagt 115680
tatcagcttg tccttctttt accccaaatc tcggtaaagg gtgtaattga aaattttgt 115740 cagttccata caattcttga agcagttcat atgctgcttc attaaattca cgcgaatcag 115800
```

```
gtttagcatt ttcaattaca atttcagtgc ttgcaatacg taaaatagat ttcataatat   115860
gttcctcatg ttgatttagt ataattataa cacatccttc catggatgta aacggtcaat   115920
cgacaaaacg atttggtgta tcgtcgaggt ctataaacga agctaaaaga gataaaacac   115980
tggtctcttc agatattttc gcggatttga caaaattacc aaaatcaatc aatccagcgc   116040
ccaaactccc tcgttctgta tcatctgaat actctataac ttcaccagtt tccattaaat   116100
ggtccccgtc ataaacaaca gtacattcag aaagttgttc tgatgtcatg atttcagctt   116160
gaatgaattt ttgattgctg tattccattc cgtcattata tgaagcatct gtgattttgt   116220
taatttgaac catcgtacca cgaggtaaaa tgatttccat ttcactagtc atgttactta   116280
aatcacctgg ataaatcaca ttaactttat gagcgccgtc aatagcccaa ccaacattaa   116340
ctttaatacg ctcttgttta actgggtcca ttttagactc ataatcgtct aatttaacgt   116400
cttcaatgcc accgtcaata ttcaatacat tcctagtagc gtcagacgta aatgcgacac   116460
cctgattacc tttccacccg ccaaaaataa tcggagctaa agaagttgat acataattcc   116520
taaaatagaa tactctgttt ttaaccaaag cttcatatat cggtttgcga attgtttgag   116580
aacgccaaat tgtgattcct tctggtagtc tatcgcctct taaaaagct ttatctaaac    116640 tagaaatcgc cttttttgact tcttttctg ttaatgtatc atagttgtcg atagtgtatc   116700
gaccgagtaa catattattg atatcagaat acgcagaacc aacatattct tttatgccct   116760
gacgctcttc tttagtatat tgctttggag tgcggtacat agtaatatca cgaatattac   116820
gagatactgt tttagcataa ccttgtaata gctctttat aagcttaact ctttgcatgt    116880
tccatgcgcg ttcagcatgt tcttgctttt ctaaagcaga cataccataa ggagctgatt   116940
ttatttgagc ctcaatgaaa ttatgcttat tttcttctaa tctgtcaagc atagtctgca   117000
caaatgcttg catactttg acagaagtta aattatcatc gccaattcgc tttaaaagct    117060
ccttttgaac atttttttct tctctttcaa aatccgtaaa tgtcttacct acgattttgg   117120
aaacatgata gacaatttca cctgatgcag taagagctga tacagccttt gaagcttttg   117180
agcttatagc atttaaaatc tctttggatt ctggaattat tttcgccgta gcaggtttac   117240
taaattcagc ggcggtagct tcatagcgtt caaaatctgg gccttcaaaa cgttcagttt   117300
ccaaagactg tgacatcgcg acctggcgac gagaaatttt agctcgagaa attacgcttt   117360
gaactgaacg agtgtcattt tcctttgcaa tagatgaagc aattgccgtg ttttggaaa   117420 cttgattgcc ggttttaaca tcaacgtaaa cttcgcctac agcagtatca accttcttga   117480
actcatccgt tgatatctct gggacccctg aacggttga gaggtcaata ttttacgat    117540 gaataagaat atatgcgtac ttcttatcat aatcccagag ttctttgagt ataacgtatt   117600
tacctccagt gcggctacgg actaatcggt ccatgataat ctggagttga cgggcttgtc   117660
cgccaatttt agatttagtg atacggaaca acactgcatc aattttatat tgacgcatag   117720
atgaataaac aatattgaat acggtagaaa tagttccgat tgggtctgga cccaagtttt   117780
tcattttaac caaagaacct ttttcgctca agataacat aactacgtgc gccatcttat    117840
cgccaggctt aatattttta ttagtatcgc cgcctgacgt ataagtacac atacgaaaag   117900
ccggcgtcgt accttggtca atttcgccaa tagcaaaaat ctgtggtatt ttcgtttttg   117960
gataaagatt tgtaaccgga aggtccaact tatcttcatc aaaaacttca tttaattcta   118020
acataaacag tcctctatag tttattatat ttatagcga aaaagccccc gaagggctta    118080
atacattttt gttacttgtc gccagatttt aattcccgga gcttcttcaa atgatactac   118140
```

```
atcttcaaaa tacttatcgg ctatatccca actattaaat tcgagctggt ttgttgtgat    118200
agctacatta ccattgtctg atagaacagt aacttctaat aaaatatcgt aactcataat    118260
ccagtaacct catggaaatc accccagata tctgcaaacg tattagcaac atctttatca    118320
cgccgcatct ttattgcaat aggaagaaac agtttaacat aatcagttcg gccttctgcc    118380
gccaaccaac cattacattc actttccaat acgcttccga tatattcttc ttggttttcc    118440
caaatgcgtg tacggtcaag ttcgtgagcg tcttttccgg gcttgtcttt taagcctgaa    118500
ccggctttaa ctttaattaa cccgcattcc gattcaagat aaaaaccacc agcttttcct    118560
ggatgtttac tatgcggata aattccaaca atacgaaggt caacagtaat tacttcttta    118620
aatttatatt ggttttttga acgagcattc tcccaaaaac caccaatatt cttaagaata    118680
atcccttcga gtcctttatc aacatatttg cgataaacga ctttagcttc gtcaagattg    118740
tggacgatat ggttctcaat gagaatcatc tgagagtagt cttgaaccat tagttccagc    118800
gctcggaaac gaacatcata cgcaaaacca ggttcttttc catcggaata tactacatcc    118860
aatggaacat aatcccacac ttgaaacttc atacctgcag cttctttggc tgagatagtt    118920
cctttcagag atttgttggc tagcccgttt gatgcagttc gagattcgtt ttcttctgat    118980
ttactcaatt cagtcaaatc accgaacata tcctctaatg gtccagaagg ttctttcaca    119040
gcatgataaa ccaactcacc gtcaatcata accccgcccg gatgacgttc acgagcttct    119100
ttggtcatat caataagttg ctgttttaac aaatctaaac caagatattc attaccagca    119160
cgagacagaa ttttttacatc atctaattca tcaccacgaa cttcggcaaa cgccccttgcg    119220 ccatcagcct taagctgcgc aaatgcaggg aatttaatat tcttaagaat atcttttttcg    119280 ttataagatg aagcaagcat ttgtggttgt tctggaatta atccagccca aactttattt    119340
gcaatagaac gggatgcacc acaacgaagg tcacgaagaa gaacctttttt caatacttct    119400 gcatcagaga cattcaagtc tgcgatataa cttgctaatt caacaatagc agcgttacca    119460
gtaatttcac gagtggctaa gttatattca aggaaatcta aagcatcatc taaagttaac    119520
attccaaaac attgtgtacg ctcaccagcg ccaggccact tcttgatgta atattgaagt    119580
tttccgtcat aagtcattcg aaatacgcgc tttaaaactt cattatcttt attgcgacga    119640
atgattgctt cttttttcttt ggtagaacct atggctgcaa tttcattaat aatatctaaa    119700
atcatattca tcttctctgt ttataaggat acaactattt tatcatatcc agattaaagc    119760
ttttaaatat tcacgtcatg ccagcttttg acgtaattgc actctaattt aggttcatgg    119820
ttcctttcac cgcgaggcat gtaaaacacc ttcgcccgag aattatactg tttgaacacc    119880
gctgctgcgg aatcagtatg tttgcccagg tcatcaacgt aacaaacgac acgctcacca    119940
tatttttcca ttacctgggt taatagagca tccttagatg cattataatc acatactaat    120000
atttctttaa atgctcccgg aaaaagcgca tttaaattaa actggcgatt tagatgagca    120060
tcaactgagt tacctaacgc agtaaccgca acgaaatcgt aagttttctt taattcgtta    120120
acaactttca atgcatcttc ataaactgat agataccgta taaaatctga gttgttatat    120180
tttaacaaaa gtttggttgc gaattcttct gaacaattaa aaagaacccc aggagcaata    120240 aattttttcat caaccatcat ttcaagaata tgatttaatg gaagattata tttctgggca    120300
aaatatggta aaccgctttg ccacttaacc aaaattccat caacgtcagt aacaattact    120360
ggcttttctt gttccaaaat catacaattt ctcttaacat tgtaatagga gaaagttctt    120420
gttccatgtg cacagaccga tttccgtcaa cccaatcaat ttcatatgca gctaaaacac    120480
cgtacttagc aataggttta atcacatagc agatagttcc aggaatgcca gatgatttaa    120540
```

```
gttgtactgt ctgaagttct ttgtattttg ctttcatact ttttcagcct taaccaaaat  120600
aacatcactc catatgccaa acggagggag agcttcctta actttgtgga attctgttgt  120660
tttatcttcc cagaaccata gttttatttc tctagttact tggaaagaat ccatcgcccg  120720
acctgacggt gaaacatcaa ttacatcaaa tgttaacttg taagttggat aaagacgctt  120780
aattaactta gtcaataatt tcataataca accacccatg acggaatttc aaagaaatcg  120840
ggagcatcaa tttcatactc aaccgaatga ttacgcacac gtacttcaat tacatcaatc  120900
attgggcaat taatcatacg ttcaaatttg gcagctacag atttagcaac agatacaatc  120960
attttcaatt cctcaagtgt tgggcccgaa ggccctttaa ttaaaattca atttcgttag  121020
caacaacatc ccacagtgct tcaagttgtt cttcagtagc tcttttacca atagcccgcc  121080
gtagataaag cttgaccaaa agagcccgat tagttttcca agaaggatga gtacttaaat  121140
cgcgccggaa tatttcatca tgaaaaccaa cctttatttc tgaaccattg aactgaacat  121200
ctaaagttgg accattttca aaactgatga aaacgtaatt atcttcccag tacatatcaa  121260
tctgtgctac tgtaccgttg ttatgttccc acaataaagt ggtagaaata tcccaaccgt  121320
tgttttgaac gtatttacgt ctgaagttag tgaagtccat gttattctcc gttgtatctg  121380
tttgtttatt gagtttatac tataacacat acaacggagg atgtaaacgg ttagacaaaa  121440
cttattttga cattttctct agcttctaac ttaagctctg tgataaaaac atgataatta  121500
tcacttgttg acatgcataa ttcttctgca attttcttgg cttttttctaa agtaaagagg  121560 ttcttttcgt tttctctaaa aacgactgca cttccgcatt caagagagcg aacaaccatg  121620
aatgtttcag gtccttcagt ctcagattta aactcaattt ttccttgctt cacttcatca  121680
aaatcaaaca gattccaacc gagccagtct tggccgcaat ctgcgccatt ataacgcctg  121740
tccaagaatt ctacttcagt gatatacttc ccaccgacag atacttgagt agctttaagc  121800
caatcatttc caaacaagca tttgattttg gtgtcaaatg agtctaaatc gccaccccat  121860
ttatcagtca tacggaatac atcaccaact tcaaagcatg ttttcataat ttcctcatta  121920
aatttaaact aagacagtat tggttattga gtttatacta taacacactt ttctgttaat  121980
gtaaacggca gactttagaa ataaaaaagg gactccttcg ggagtcccta acttatgctt  122040
tatgctttct tacgcggatt accaaacgca gcgtcgtgag caagaacttt acgagcacga  122100
gatgctagct ggtcagccaa tggattgata cgagagttag acccacgctt gtagccagcg  122160
cgtttagagg taccaacaac ttctttact gcagttttg ctttagcttg tttagccatt  122220
ttcaatcttc catattggag aaatacaatg aactggtctt attgacactg ccagttctca  122280
agccctcaaa gggtacttag gttttggat atttaacgac aggataacca taaacctcgt  122340
caacattcaa gaggcgcacc gtaaaacatt tccggcagc ttctcgtttt tagctcacac  122400
taaggcagtg aatctccaac gagttacttc aaagtaacta caaaatgccg aactgcttta  122460
cgagctgaac tgcataagcc tttagcgaat tttaattcgt cttttaaaag aagagcatca  122520
cgaaaatcag cttgtgctgg attaagatgt ttaaaccctt tcagtacttc aagagcttca  122580
gccaatacat caattgatgc accgtaattt tcatgacctg cattccaggc agtgcgttgc  122640
agagaaagag cgtgttcaag ttgtttgttc atttaaaaag cctcaaatga ggtgaataaa  122700
aggaaggcgg tataaggagt ttaagccctg cgccttccac catgtaatca gaaagattac  122760
aataatattt atatcactta taaacgcacg ctaacgattt ataatgacaa gtaacaaatt  122820
tttgtttaat ttctttaggt tgcttaatgc ctaacgcaac taatggatga gttacattgc  122880
```

```
gaatattacc aacaggcaac ggagttaaat caccaatttc tacgaagcca gcaggtacat   122940
cagcaccaat tgaatatact tcacacattt caggaagttg gccctgaatt tctttaccta   123000
agaaaatacc cgaatctgaa attttttcat caccagattg tgctggttct gataccaaaa   123060
taacaaattc gcctagagct ttaataggaa gttccattct tacagtttac cttgcttgtt   123120
aacatgaatt aataataaca tgaatttctt aaagcaaatt actgagtaat caactgaact   123180
aaatgttcag cctttacacc attaacagaa attagtttat caaaactaaa ggcgcgccag   123240
ccttcacttt ctgtgtcata aactggaagc atatcaacag cttcttttcg tttaacttga   123300
gattctttga ctaattcaaa atcactagga agaatatctc ggtcacgagt gcaacgcatt   123360
gaacgaatgg ttccgtctgc ttttttcaaaa accacctgag attcgccatt actcaacaca   123420
gcttttagag tttcacgaag ttgtactttt tgctcggttg taagtttcat tttattaacc   123480
tatgatagtt ttaattttat gtgcgccacg aacctttaat gcttcatgaa gttcttgaca   123540
acgtttaagc cgctcttcaa ctttggcttt atcatcgata gatacataat cagtttgata   123600
aagtactttc catttagaaa agaagttttt cttatattct actgagtatc caatattaat   123660
tttagcgtaa gaactcaatc cagttgtttg tactaatcga gttttcattc ttcaattccg   123720
cagtattcgt taatatatg ccagttcaat ttaccgaggc ttttcttggg aacattgaac   123780
acctctatac cagcagcccg taagatatta tcccagccag gttcatttt atcgtaagtc   123840 tcacaataaa ctaatgtttt aattccagat tgagcaatag cttttgcaca gtctggacat   123900
ggagaaagag ttacatacat tgtagctcct tcaattgatg aaccattacg agcggcgaac   123960
aaaatagcat ttaattctgc gtgaatttca ttcacttttg accaagcgct atgagccgct   124020
ctatgtttgc tagataaacc aaccctcgtt ggcttccatt catcttgacg taggcccgac   124080 cattttctg tgattaacca gccttggtca tctgcatggt cgcaacagtt aactcctcct   124140
gccggagaac cattatacac ggtagaaata atgcggccat ttttctcaat aactgctcct   124200
actttccaag agcaacattt cgattcttga gaaactaagt aagcaatttg gagcactgtt   124260
gaagctttca ttattttatc accaaataag ttgaacgatg tgttttaaca agacttattt   124320
cactaaacag ttttttcaact gaaagtactg tcccgataat tatataacat ccgtctttaa   124380
agcgttcttt cttatctaat aacacatcgc ctgcaaatct tttacctact tcaatttctt   124440
cagtaaccca aggaacatct ccgagcagca cagcatcgta tgttgacggg tctattgaat   124500
taaagcaccg gtcaaaatgc aaaagagttt ttatttcttg gacgccgtct tcagtaaatt   124560
ctttgtcttc agacaaccaa ggacgacaag gacgatattc agtttcacga attcttctaa   124620
tagcttcaac tagtgtaatc ataaatttcc taaaatattt gtcatggtaa ctgaaccatc   124680
acgatttaac tttaacccgg tgtgttgaga tttaaatcct tgctcaactg aaataataac   124740
accattagtt aacgggtcat ttcgcatagt aactgaacct ccaggaattt tgttagcaac   124800
ctgctgcgca aattttttag caagttctgt aaattcagtt cgactaaatg ttttatctga   124860
tgtcattatt cccacccata cactattttg aaactaataa aatcttcatt agaactatta   124920
aaatcatcat tatcgcatgg ataaacaatg aagtcaaacg tataagaata tgagtcgtat   124980
gaagttatga tactatactt tatatctttc catagaacac caaaaatcga cttgatatca   125040
gcatccatac gtaagtacag tgcattactt gggccttggt taatataatt atccatcacg   125100
taagaaataa tttctttagc aatgccagta tatgacagac tactatttgc tcttactttc   125160
attagtgcac cgtatgtacg ttgacttaa ctacgaattg agttacaact tctccaatag   125220
gattaaactc aacatgatac tcgcccttat agcgagaatt taaatctgtt cgaatttggg   125280
```

```
caagcttatt gataagcgct ggtgtcatac tcatacctac gcattgctgt aaaagcttgt   125340
atgcttcttc ttcaacttca tgatgtttgt tatacattat attcttccaa atattctagc   125400
acaatttcaa cggatttaaa aatcccgcca ccaatgagtt cttcattgtc atagtccatt   125460
atgtctaaac caatagttcc atcgtttaaa caatatgcac aaaacagata ttcttgtttc   125520
ttttcaattt ctgtaattaa atcaaaaatc tctttaagat tattcataag tcgtaggttt   125580
tccatggtag agggatttta gttttcttaa cagttaactc ataccggga tttaattttc   125640 tcaacctaag acattcatcc catgctttaa tttcactgga aaatgaataa aacataccat   125700
ctacagtaac aatacgtttt tcattattca tattaacaat agcccagatt tcatgatgag   125760
ttgccattaa aaatctccaa agttaacttg ccagcattcg acgccaatac gtcgccacat   125820
ttctaccact tgagaccggt catcaacggc aagaactaca ttatacttat cagcaatatg   125880
ggtccaaaag atttcttctt taactacatc atctttgcga aatcaccctt gtgcccgctg   125940
aaaatggtct tctggaacac agatatgatt atcccataac caatgaagag tatgaatacg   126000
atactttaac ggttcatctt tagttccaga ttctctacca gatacagtta tgatttata   126060 tcctttatct gaaagcattt taagaaaatt aacaaccatt tccttaggag tatcttcccg   126120 gagttttct aagtcaaaag gagaacgatg actgttatct gcaagtgttc cgtcaaggtc   126180
aaagataact gcctttggtt tagacaaatc cggaacgtac attttctcaa cttccatcaa   126240
ctgatagaaa tgacgcagaa tatcgattgg aacagccttt tcaccacgat actgattacg   126300
cttaagaagt tcagtccatg gtacgctaaa tttcttgaac tcaatcacat actgcccctt   126360
gaaacgaagt tcccactttt ctgtggtttt tgggttcaag ttcgtgtctg caataatgac   126420
acctttggta tgctccaaat taagtaaaga ctccgccgcg gacatctgag ctgtagtcac   126480 agcttttcg cgctgcttag agtatttgta atcattccgc gcatttagac caaacaattt   126540
ctcacggaaa tcatctcggc ttagaatata ccaacccggg ttctttgata caaactcatt   126600
tgcccaggtg cttttacctg aaccggggca accaacagtc ataataatct ttttcatttt   126660
tcacctaaga attgttcaag agcttcgatt ttattatcca aagggccgaa gcccttattt   126720
tgtaaaaagt tttactgtat aatacacggt tacacaaata attaaaacaa ctaatgggtc   126780
catcatttac accgctcttc atttaagtct ttacgataat aacatatcgt agcattagca   126840
tcttttacgt atctgcttac atcatttaac caaattctca tttcttgaga ttcagcaaat   126900
ggcattccaa cccaggcttc tccgtcgata actttaactt cccacttccc attccatact   126960
gatataggtt cgggccatga tggatggatt aatggtttag ggacagcctc tggcttgcta   127020 gcacaccta ttagtaaagc catagatact atcagtaaca tgttccgaat catctagttg   127080
attcctgtaa atctctggca aatgaattaa aactctcgtt gatttgtttt tcgacgagtc   127140
ttggctttgc agccaccacg ttgcttttct tcgcgtcttt acgcattttc gcattagaag   127200
tttccgtgat taatctattt gaactacgtt tctcatctaa aattttata ttttaaaat    127260 cttctttgag ttggtcaata gatttggcct gctcatctgc aacttctttt actgcatgca   127320
aatcttcttt taacccttct acccgctgtg aaaggtaaaa aatagaacct gcaacaacaa   127380
ttccagctat tgccagcgtt tttatactta tttgcataat ttgacaatta cctctacaat   127440
atcgtcttga gataatccgt tccataagac gtgatttgga gcgtctgatt gtgacacttt   127500
aaatccttga atttcatctg ccatttctga cgaattcata tacggattat gaatacctaa   127560
gcgatgctta ccataaattg ggtcaactgt tatatagcat ttacaatcat tgataagcac   127620
```

```
gttaggttga gtgatattaa taatcacttc tgctccgtat ttcgtaagct ggttttcaag   127680 aaaattttc  atttcttcaa cagcttcagg catcgcttct tggcgagcct ctgtaacttt   127740
attgttgtac tcttttgct  ttttgcgctt tttctgatcc gtggcgaatg cctttctgag   127800
gtcagttaag tatccaaccc gccgggaacc tttgaatacc gagataccgt cgtgatgagt   127860
accatacttt tctactaaag cttcgttagt gataagttgt aagttcattg ttaatctccg   127920
tttagttggt gtaagaacat agtatcataa ctaaacggag atgtaaacgg tcttattcgt   127980
attcttttgg aatgaacgtt ttgtagttct tcatgaacag ctcgtttacc ttcttgatag   128040
ttgtgtcgta gtccatgcta tcattgaaca tcagcatcaa aattgtaaac aagaacggta   128100
aacgttcagc atcagccagt ctctttgcct cgcctgcgta tgttttacgg tctaaaccac   128160 gaagttttg  atacgacgta gagataaacg acaatgaacg gcgcagataa tcaagataaa   128220
cttcttcgaa cttattaatt ttctttaaag aataagcatc gttagaaaaa agtcctttga   128280
ggtcatcaga agcgttattc acaataactt caaatagtct atcattttt  gtgatagagt   128340 ccttagtatg atgtaaagct gtgtaccaat cagtctttaa cttaaatcga agaccattgt   128400
ccatcacaaa aacataacct tcaatcccctt ccattgcttt aatatcggat acaaaatctc   128460
cttccggaat tcatacgac  tctaccaaat actgacgaag aacagggtct ttagcgattt   128520
cgttgtatgg aacataagct ccagtatcat tttcacggat attcaaaaga ataaggtctt   128580
ttttctgata agcgagaaca atacgatttt caggagatac gtattcaaag ttagctgtaa   128640
aaccatcacg agctagttca agaagtctcc acaacaacgc ttcatgagtg atgctagtaa   128700
gcatagcaga agacaaataa gcttgttcag atttaagcga agactttgat ttaaagcgaa   128760
gaatattgcc atccaaatag cttgacacca agaaccatc  ttctttcttc atcatatgaa   128820
ccgcgttaga aagatcgagg ttcattgtaa acggagtttc atttaaatta agaattttt   128880 ccattggtct agaagcaatt cttactggta ctccgtcaat catttcaaac ataattcctc   128940
gacactctaa agcatctgga agcaaccaat ctgaatatga agcatagtta taactaaaaa   129000
ttctgtactt tagcccagac ggagaaatat catcacgata aaagaaccgt gattcgtccg   129060
tatcattaca taaattcatc aaattgtcga atagctcttt catggtttag ccttgtgttg   129120
agtgttccat ggaggattaa atcttttaat aaacataggt tcttcaagag acatcgtctc   129180
taccgacatt gtaccaagtt catttgtcat gcttaagtta aagcattgac gagcccagaa   129240
ttcaactttt ttaccttcca ttaaagcttc taaaatcttt gctgattta  cggaatctga   129300 agtctggtct tttctgttta tagcagtacg ataataattt atacgcttac gaagattttt   129360 tgttttcca  atataaacaa gttcatcatc aacagcaatt gcataaacta cattcttctt   129420 attgggacc  tctatagttt taatagaggc atcttctagt aattcaagct cagcgtattt   129480
tataaatgaa aattcattag caatatcttt catattaaaa aaggggccga agcccttac   129540 cttaaaaata tttttgaaa  ccaataatta tattgtcgtc aacgtcgttg tcgatttgag   129600
ctactaagta acttgaaatt tcaacttcct gcggagcaga ttgtaccgca tctgagttta   129660
agtattcacg aatccatgga attggatgac gagtaggagc atcgactatt gggcatggaa   129720
gaccgcaact acgcatacga gaaactgtca aatagtcaac aaaatcatgc agaattttta   129780
cattcagacc tggcaacccg ccatctttga acaagtgaat agcccattct ttttcttggc   129840
ggttgatttc catgaagata tcaactgctt cttgttcgca ttcacgagta atctgaaccc   129900
attcgtcccc atctgcgcct tgttgaagct gacgaataat atattgagta cccttaagat   129960
gcaactgttc atcacgagcg atgaacttca taatcttgga gttaccttcc attatttcca   130020
```

```
tgttcttgtg gaaattaaat gtaccgtacg ttcgattgag ctcgctagtt ctcaacccgt   130080
tctcttatga actgctgcat attactatgc agtccagact atatcacaat cccaaaggga   130140
ttctccccat ttcgagtcgc ttgaccctac gtccgaagac tagtcgttga accttgcttt   130200
gcaattgtcg ccgtgccaac gtttatatga tgacggtgat aaatccttct tatcacagtg   130260
tggacaattc aattgaattc tatttggatt gaatttacat cgttcgttgt gttttagata   130320
aaatcccgga cctttacctt tatgcccgca gaaatcacat acaatttctt tttgggccgg   130380
atgggttccg ttattaacca tttctaatgt ttttatcgat gttcttttct tatgttcttc   130440
tgataagaaa tgatgattgc catcatttac tcttttttgat tgagttttttg attgcatttt   130500 accaccgcaa acacatgaa tgccttcctt tatagctttg gcattacggt ctttaacttt   130560
tttaatatgc ccgacttgtt gaaaattatg tatcccaat gcaactcgat ttaaattaga   130620
cttacgttgt atttcaccgc ttaaaaggtg aaatgtaccg ttttctattt tagttttaat   130680
agaggcaatg ttttttagctc gcacttcagg aatattaaaa acttgtattt ttcgcgattt   130740
agctgctttt gaagcaagtt ctgaaatttc ttctgcagaa tatttcattc gtaactttat   130800
cgcatgacaa gcttgataat cttttttgagc taaatgtaaa tcataatgtt cctgtataga   130860
aaggcacatt aaattatcta aatcattatt ttcacggttc ccgtctttat gatgaatttc   130920
ataagttcta ccattttcat cttttggtat agggccgttt tcttttatcc aaattttctct   130980 ataattcaat tgtgcatcct cttaaaagta taaccatatt tataatatta tactaattaa   131040
aggtgcaagc aaaaccttgg ctgctagttt tcctataaag gactttccag caattaaagg   131100
agttttcgat aagcgttacc acttaaaggc gcattttacg caaaagatac ataaaaacga   131160
attgcttcaa gaccattgat gacatgcaaa cacaaataaa gtgctttcat taagtcacgt   131220
ttagtttctt taacttggtc ttttgcgtct cgaataagtt cttcatcatg ctcagtggct   131280
tcataaaact ctaaatcagc tttagaattt tcccagtaac gagttttacg aataacatca   131340
tcatagtaac ggccaattga ttcagctcga gccataatag catcatctaa aacaatttca   131400
tcaaaaattt tggccgggtc cgcgaacagg ttacgcataa tgtgcgtgta agaacgagag   131460
tgaatcgttt cagagaaagt ccaagtctgg ttccaagtat ctaatgacgg gtcagaaatc   131520
aaagcagaaa gaactgcagc aggagcccgt ccttgaatac tgtctaaaag agactgatat   131580
ttcaagttgt taataaaaat attttttttga tgctctggga gtttatcaaa ttgagctctg   131640
tcagtcatca agttaacttc ttctgggcgc cagaaaaatg agagctgctt ttcaatcagt   131700
tcttcaaatg tacggtgacg ctgaatatca taccgtgcta aaccaagacc gcttccgaaa   131760
aacatcggtt cattcaaaac attaactggt tgtgtattaa aaactgtact catttattca   131820
cctttgctct tcctcttatc catccttcag gaatagtttc agaggattca attaatttat   131880
tcttaaaccc gtcgtttata caaattttac cacgggctcc tttataattt cgtggtttta   131940
ttttatcaaa attaggagta agcgaatacg accatctgaa tccgtaagca tactggaaat   132000
ggccttcagc gcaatatttg atattagaac cgttcccatt aactgattta gcagcttcgg   132060
atatagaagg aaatgtctct atgaaattac cgtctaaatc aaatttgtgt atagttacag   132120
aaacttcttc tgcccttta attaatggta atttaatctt ttctaaagaa tctttagagt   132180 gcttttttgct aagcattccc ttggggtgtg ggttattagc taaatattct ttcatatatt   132240
tagaggattc ttcggaaaat ctctctcggt gccaagcata taatctatta ttaattctat   132300
ttccggattt atcggtgcac attaaagtga tagcacataa taaaccgtat gttttatgaa   132360
```

```
ttttataaag caactgatgc gcaataaagt gttctcttgc gctcaatgcc actaagttat   132420
ctttatcatc tgaaccaccc atgcatcggg gaatgatgtg gtgattttcg gtatagccga   132480
tgaaaggaga ggcttttcgc ctctccatta agctatcata tattctttga tagttcatta   132540
taatttacaa gctgcacagt catctgcttt tggttgctca acttcatagt catctgtgcc   132600
agaaccatct ctagtgttat gataatagag acttttccg ccaaaatacc agaagtaaag    132660
caggtcatca agcatcacac tcattggtac tttacctttt tcataattct gagggtcata   132720
gtaagtatta gcagaagcgc tttgacacaa gaacttggtc atgatagcaa cttgagttag   132780
gtaaggtttg ttaccttgtt tagccaattt ccatgcataa tcataaaggt ctatgttgtg   132840
ctcaatattg ggcacgactt gattaaagga accctctttt gactctttaa cagagactgg   132900
tccacgcgga ggttcgatgc cgtttgtact gttagaaact tgggaagatg actcacacgg   132960
cataagtgca gataaggtgc tattacggat gccgtggcta accaggtctt cccgcaagct   133020
ctcccagtca cacacataat tgggcgctgc gatttggtca atctttttat tgtaccagtc   133080
gataggtaat tcgcctctag accaacgagt ttctgaataa tattcgcaag gtccttttc    133140 tttggcgagt ttaattgagg ctttaatgag tgcatattgt aatctctcaa ataattcatg   133200
agttaaatca tttgcatctg catatgatgc aaaattatca gccaaccaag cagcgtagtt   133260
tgtgacacct acacctaatg cccggcgctt cttagctttc aatgcttctt ttacaggata   133320
accttgatag tccaataaat tatctaaagc acgaacttga acttctgcaa gttcttcaat   133380
cttgtcttgg tcctgccagt caaaattacc caacacaaat gcagctaatg tgcacaacgc   133440
aatttcaggg tcatcactac caacgtcttt ggtcggtaaa gcaatttcta aacaaagatt   133500
gctctgttta attggcgatg tttcacgaat gaacggagta taacggttca tattatcagt   133560
gaacgctgga tacactcgag ccgtgccaga acgttctgtc atgaacaatt caaacaattc   133620
aagagctttg atgcgtttct tgcgaataat tggattttt tctagttctt catacaattc    133680
acggaattta tcttcatccc ggaaataaga atcgaacaat tcgccattag ccacatctgg   133740
gctgaacagt gtgatgtacc cattttacc gagacgttcc atcatcaaat cattgatttg     133800
cagaccgtaa tctagatgac gaatgcggtt ttcatctaca cctttgttgt tctttaatac   133860
caacaggttt tcaacctcaa gatgccacat tggataataa agagtagctg caccaccacg   133920
tacaccgcct tgagaacaag atttactgc agtctgaaaa tgtttccaga aaggaattac     133980
gccagtatgt tttacttcgc cattaccaat ttttgagcct tcagctcgaa tcataccggc   134040
gttgatgccg ataccagctc gcttgctgat atacttaata atactgttac ttgccgcatt   134100
aatagaattc agtgaatcgc cagcttcaat aactacacaa gaactaaact gacgagtagg   134160
agtacgagcc cctgccataa tcggtgtagg caatgaaatc tggcgagtag atacagcatc   134220
ataaaaacga ataatatgag ccagacgatt ttctggttct tcttggtgta gtgccatacc   134280
aattagcatg aatgcaaatt gaggtgtctc gtaaattta ccagttgaac ggtctttaac     134340
cagatatttt tctttgagct gcatcgcccc agcataagtt aaatcaaaat cacgttcgtg   134400
tttgattttt gattccaaga aagtgatttc ttcagctgaa tacttggaga gtaattctga   134460
atcatattta ccctcattaa cacaataaga aatgtggtcg ataaaagacg gcggttcgaa   134520
ttgtccgtac acttctttac gtaatgcgaa catagccagg ttagaagcaa catattgata   134580
atccggttct tcttttgaaa tggagtttgc agctacttta atagcagctt gttgaatatc   134640
cttggtgcta attccgtctt ggatatggct tttaatacgc tcatataatt catatgggtc   134700
aattgaagta ccttcagcgg cccatactaa aatctttgga agtttggatg gaataaattc   134760
```

```
ctgtttaatt cccgatgatt ttactacttg cattttatat ccttagttat cagataatttt   134820 attttatcat caaagacttt tagcttatcg tttcctcaaa gactaaaatg gcagcccgaa    134880
ggctgcctgt agtgttatat ttattattta agcttctttt actacaacaa ctttaaccgg    134940
gcttcggttc atgtcaatac tcagaaatat tgattggata atataaaaat atccattaat    135000
cattatttgg ccgccttctt tcaattcacg accaatatca ctttcagttt cggcaaatac    135060
tttatcaccg tgctctgatg taaatttaat aagcataata ttcctataga aacagattca    135120
acgaaataat tataataaga aaaatgataa gcgcaatagt tagtttgttc atagcagtca    135180
tactgccagt atcatttaca aatctagtaa tcattcacaa gccatcagtg ctgcttcgag    135240
cacttcaatt aagtttcgaa cttggtctag aggtaactca aaacctaagc cagaatagtt    135300
gattttcaga caaactctat cacagtaatt cgggtaaact acagcccgaa tttcttcttg    135360
atatttgtct gtcacatggt ctatgataac ctgatgaaac atatcaccag gttcattcat    135420
atctttacgt ttaatcatac agccattttt cctttgattg tagggtggct ctcgtaaccg    135480
tcaagaacaa aatccgccgg ggtcatatga gtgcaaaccc aatacaactg catttcggtg    135540
tcccagtctt caaaaccttc aggaaaatta attttcagtt cacagagttc ttttggcttt    135600
cgacggagaa cttctttaca ctgttcaacg tggttcaaat atatgtgagt attaccacca    135660
gtgaacacca gatgtccagg ttttaaccca gtcattttag ctacaatatg aatcaaagca    135720
gcataagatg caatgttaaa tggtaaacca aggaagacat caacgcttcg ttgggaccac    135780
attaaatcta aaaacccatt acgcacgtta aattggaacg catagtgaca cggtggaagc    135840
gccatcttag agagctctag agggttccag gctgtcacaa tctgcctccg gtctgccggc    135900 atttcttttta ttctatcaat gactaacttc aattggtcca cgcccatgaa atcacgccat    135960
tgtttaccat aaaccggtcc tagttcaccg tcagtataac ccatcgaaac agcttgattt    136020
tcataattat catcccagac ggttttccct tctgttcgag aaccatgttg aatttcacgg    136080
aggtcatcta catttgttga gccagataag aaccacaaca attcagcaat gcacgctttc    136140
cacgcgagtt tctttgttgt tacagctgga aatccttcct gtaaatcaaa acgaagctga    136200
gtgccaaata cagcaattgt tcccgtgccc gtacggtcat cagtctcata gccttcatca    136260
aaaatgtgtt gaattagttc ttgatattgt tcattgtttt tccaacttta aagagaattt    136320
cggcgccttt cttttcaaaa cggccttgca tccaaaggag accattttca actttcatat    136380
aaccaagatt aatatagtcc aacatctgac gattactgaa aaacgcttta aatgttccat    136440
ggttagaacg tacatatata ccattagtgc acgcagagtg gatattctcc aacggcgccc    136500
taacctcata aaacccatga ggaatagtaa catatttctc tggatttcgt ttaaactggt    136560
caattgtagg ggccattcca tcgataacca aagcccagtc cttttgcttc tcttcaacaa    136620
ttaaatctaa tttagcagtc aaaatgtttc ctctgttaat gggtcgaaaa atattacatt    136680
accggatttt ctaaaccgtc caaccattga acagcaaatt ccattaaagc gagtttgccc    136740
tacgcttact gattgaaata tagttttcat ttcacgacac aattcaagac gaccaataac    136800
cccatcaagc aaacaatgag aaccattcca tgaagaaatt gagtcaatat caaattcaag    136860
aagataaatt ccatgaggaa tgttgaaacg ctgccatttc ttttgcactt catctttttc    136920
caataaagtg attttgtata ttttattcat cacgccctct cataaacatc ttctgaaata    136980
ttagtaagtt cgtcaatatt ataccaatga gtctcaacaa gttccatatc ttcactgata    137040
ttccatataa aatctgccga gagtttaata tcagaattta cacgatgttt tttgcgaata    137100
```

```
gttgtgcata taattttatc tgcgtaaatt ctcgaatgct caataatatg tgcaccgcca   137160
ataacagaat aattggcatc atcgcgttga ataaaacaat tatacccaaa atcatgccca   137220
gaaacttgaa ctttattacc ttctaaaaat tgttgaaact gtgtttcatt gatatagagc   137280
tcagcggttt gtcctgattt agttttgca taaggacgag aaaatcttg tactacaata   137340 tgagaacgtc catgaagttt tcctcttaag ctcataaatg tttttgcacc cataataaga   137400
acagtatctt tagttctgga agcaaaattt tgcatgtctt gcttgatatg tccccatgga   137460
agaccagtgt ttaacccaaa cgcaaattca tttttattgt cgacagtttt agtagggcaa   137520
tacgcaaaaa ttaactgaat cattataata cctcaacata agcgatgtca gatggctcga   137580
tataattggt tttgcattga cctttataat tattaatgca aaaataaaac tgcgatttgg   137640
cattgctcca aaccaaattg accttatgca aatcacctttt tatagtttca actaaaaaca   137700
cgctatcaaa atatgcttta tttgagcaaa tatcttcaat atttaaatct tgaaaaattt   137760
ccattaaatt tatagttttc atcatccttg cctcattta caattaggac aaattccacc   137820
tgcgaacaaa agtccgccgc cgcaaatatt acactcccag tcggttaaaa ttttcatctt   137880
aagttcctaa tacgttcacg gatgatattc aaaaactgcc gtgtcatttc aatgttagct   137940
tctcgccata agaagttgct attcatagca ttatattcag cagtcacatg gtcgtttaac   138000
tcacataacg cgtgtagttt gccatgtttt actgcatcag aaattgcttt atcaaactct   138060
tcttttgaca ttgtaatttg cattatttgt ttgaacccctt tttagaggct aaaaccatgg   138120
tacgaagcat tctaaggcct ttatcaacag cttcagcaat ttcgcccgcc acgttctcat   138180
tgaatagacc gagagttcct gatttgatat cttccattaa aatgtagttt atgtcatttt   138240
cagttaaaga aatttctggg ccaattccac ctgaaaaatt aatcttacag aatacattct   138300
gtccacgttg ttcttggtag cgaatattaa tgtgtgtcac accaggaaca tggtcaaact   138360
gacaacgaac attaacttca ggagcagcag aacaccagat atcagccatt ataattcttc   138420
cttagcttct ttaaatgatt ttttgaaatc ttcaacgtat tcgataggaa tccagaaccc   138480
agaaccataa ccgtcttcat agcatgggca catatcgcaa aactgttgcc aatgaatagt   138540
tttaccttct acagtgaagg gagcttccat ttcgcataaa gactcttcaa caagttcaat   138600
catcgctgga ttttttgtcat aaatgcagaa attccaaaca cctttaactg tggaatcttt   138660
aatgctttca cgttgtaatt tcattttatt atcctcattt gttttgatag ggttatagta   138720
tcataaccat aacccgttgt aaacggtcat ttgaaagttt tttgtaaaag ttcaatgatt   138780
tcgtctacgt tttgtttgt aacaacacaa tgaattttag ttacaccgtc agtatcttta   138840
cattcgtcat caagaactgg ttcttcatat tcgcgaaagc aatagaactc attatcgtaa   138900
agttcaaaat aacaatcacc tagaccatcg tcgcaaaagc actcaccatt agcgcagaca   138960
atttcagtta caaaatattg gttgtcaaat aattctatag atttttacttc aaaccaaccg   139020 ccatttcgt ggataatatc taccatttca gcattattca aagggcttaa gccaataaaa   139080
tcattaataa gctctgggac tagttcgtat tttttgccta ttttcatttt gatttcctca   139140
attattagtt attgaatgtt aaaagttgct ttaatcaatg caatggcttc agcggcgttg   139200
ctttgattaa cctgcatgtg aatggtttgg gtgtcgacca caggagaatc atctacttcc   139260
aagaagtatt tgaattcata ttcagcgagt tcaaaatagt cttcaccttt ctcgcacatg   139320
gaagtaagga tggacccgtc tttcatttca accttttcaa caaagcactc accaccatac   139380
atttgcatgt caagaacttt aaaactatct ccgcactctg ccatccgctt aaccataagc   139440
gcgttatcat ctgggcagtc agcgatgaaa cgttttttag ccgccgggtt taatacgtaa   139500
```

```
attttaccga ttttcatttt gatttcctca gttattcttt aattaaaccc atataaaaca    139560
ttttatcttc gggttccata ccttcgcagt actcaatttc cataaaacga ttaatagctt    139620
ttaaaggacc attaatgaca acatttatgt tccatgattt ggaattctgt gaattagcga    139680
tacgaagttc tgggtatcga ttacgaataa cttcttcaat gtattcaaaa tctacaacat    139740
caatatcaac actagccatt ttattttcct catttgtttt gatagggtta tagtatcata    139800
accataaccc attgtaaaca attaattgat atcactcata tacatttcga tatcttcata    139860
ttcgcaaatt tccaaatact cgcggatatc ttcaacttca ccaatgattt caactaaagg    139920
ccatccgcca gcgggtccac gttctgctat aacgttaaac tccaatttac caggaagaat    139980
ttccatgaac cgagtgcaat catcaaattc taaatcaata atcattccgc cttcatcttt    140040
gataatttca catactaagt caagttctaa acgtgccatg atattttcct tcatttgttt    140100
tgataaggta atagtaacgc agtttaaagc tgatgtaaac agttaattgc aaatttctgc    140160
atcaacttta ctcttcaca acttaattca ttgcctagaa aaatcataga caatagtcat    140220
ttgcactctc aataacatcg tatgaggtta taccataact ataacctcat aatgtagtat    140280
acgtcttatt gttccataaa ttcatctagc aaccaatcaa tgtcttccca ttgattatct    140340
tcaagccatt tgcggatatt ttttcagac ccgcgaagat aaatcactgg ccatccgccg    140400
ccggtgcctt cttcgattat aaggtcaaaa tcaagaccat ggtcaacatc ataaaaacgg    140460
cttccatcct caaaaattaa atcagttgca attccatgct cattgcggtg aacttcagct    140520
acaatatcaa gttctaaacg tgccattttc aatttcctca tttgttttga tgaaataata    140580
gtatcacagt ttttggagga tgtaaacggt tagctccaga aacaacaaag gagcccgtag    140640 gctccttta ttattaaaga ccgttcaaaa tgtcgtccag gtcatcatcg tcagatgaac    140700
taacatctga agtagaattg ttagttgtag aaccagatga gaaagcttcc atatctttat    140760
caaaagcgtc caggtcatca gctactttat cagcctgtcg ttcagctttt gctgcggcac    140820
cgcccatagc agcagttccc ataactttct caaatttctt ttggttgtcg tcaaaagatt    140880
taaatttatc tttagaggtc atttcagtta aatcaaccat ctggtcattg agagatttct    140940
gaacagattc atcgtcaata tttgggattt cagattggcc caagaattc gattcgtcgt    141000 agttactaaa accggatact ttcttaactt tcagtacaaa gtttgcacct tcataaggac    141060
aagttacatc aactggagtt tcacccatat cagtatcaac tgcaatcatt gcgttgattt    141120
tgtcccaaat tttcttacca aaacgatatt tgaaaacttt accttcattt tccggagaag    141180
ccgggtcttt aatgaccagg atatttgccc agtaagaagt tttgcgtttc agtagtttgt    141240
attcttcgtt atttgtgttg tagctatcat tcttggaaag atattgacaa accggacaag    141300
aatcgtaatc accatgagta gatgtgcagt tttcaatgta ccactgatta ttttcttaa    141360 agccgtggtt aatcagaaga gcaaacggag cagcttcttc attttggaa ggcagaaaac    141420 gaatcaccgc ttgaccatta cctgcgttgt cgagcttaag tttccattca cctttatctg    141480
aatcttggaa accacctttg ttaccagaca gagcagccag ttgagcttga agttgagcgg    141540
gatttttacg tttaaacata ttatttacct tattaatatt tacagttttt tacagtttt    141600 acgaacagtt gttttgcttc taatgcatcg acatcaagaa ttttcttgta tgcgttgagc    141660
ttagttgaat aatttgacca aactaaattg tccgttgcct ggtcatgatt atttataata    141720
tccaaaaatg aatcaagaat tataaaagtt tcgaagaaa taatactact ttgaagtagt    141780
ttaaacacat atgatgtgtt gattttgtta ttatatacaa atatttcgtt tagcgtttta    141840
```

```
acttcaactt ttttgctgaa gtaatagata tttctgacgt cttcttcaaa ggtgctttta  141900
atcattttca atttgccgat atattctcta taaaatacaa gagcatcggc atcactgata  141960
tctccaatcc aagcatcttg atttgcaaca agattgctca tgaagattat tgcaagctct  142020
ttaagcttgt acttttctga tagttttca aagaaatatt tatcgcggcg cttctgatac  142080
gccttatcag aaacccgcat acgccagttg tattttatta catcatatct gccagcgaaa  142140
tgatttttta acatcaagta caacaaatat actgatttgc cattgatgta tctattacca  142200
tcaggcggca tgcggatttt aatcataaca gaaattctaa cgtattagtt ttttcaccac  142260
gagagacact aggtcttagc atatgctcat cgatagcttc tgacctaatt ttttcaataa  142320
taccggatgg tataaattta gagtacattg tttctgggat ggaattttct tccatccaca  142380
tagtagtagc ttctaaatac cctaatccgt tttcttcaac taaagcttca ataataaatc  142440
cgttttgttg cttatctagc aactcattta atttatcatt ttttctta gtagatggaa  142500 ccggaattgt ttcgtcattt agtgaaaata gagtcataaa tttcaaccac tttatctttt  142560
tcttcttcaa actgttcacg agtatcttta tgatacattg ccaataattg attaaaagct  142620
ttcgaatcga cgcctaaatc atctttggca gctgctttca aatcagcgat tagtactcga  142680
taaccagaaa ttttcagaag atggtcagaa gcttctttaa ttttcttacg gaggtcttca  142740
ccatgaatag cttcatcaaa ttctacagca actttctttt ctttggccat tttaaaactc  142800
attaatgtga ttagttaatt tagcaagacc cgacttcaca aagtaagaat aaatcttacc  142860
gcgaggaggt gttttgtata attcataata ttctataatc ggtttagcaa tttcttctgg  142920
aatataacta aaatcgataa gaactctatt ttcaagataa cgattatatt cggcttctgt  142980
taaaagcgat ttcattcctt ctggaccagc atctaaacac tgttcaagga gcttagttga  143040
aaacgaagga gttcgctcac cgtcaatttt agtgtaccaa taatcagaac gtactttaac  143100
tgatgcgatg ttatctttgc ggtcgccttt taacacttta gttaaacatt caagttcagc  143160
gtcaccggtt ttgcatacaa caaatttctt ttgcatcggg gaccactgtt taacattagg  143220
atatcgatga agttgtttaa agtcaccgtc agaagaaaca atcataattt tatgtcccttttca  143280 caaggaaaga taaggaacaa gaataccaat atggtcatca gcctcgtatt tgtcaatatt  143340
catgacggta taaggcatat atttctggaa ttcatcaata attgtgcgaa ttccagtaaa  143400
atatccttcc caatcccaag tgctttcttc acgaccttgt ttacggttct ttttataata  143460
atatgcaata tcacgacgcc agtaacctga tttagcgtta tctgcgcaaa tgataacttt  143520
ttcatatcct tgtttgcgga attgtaggac attcttttg agtgtactta acacaagatg  143580
tcgcatcata gatggctgaa ttttctcttt atcagagaat gtgtttaacg ctgctgctaa  143640
agcaatttgt gataaatcca ctaaaacaat accttctttt gtttggtctt cttcgccaaa  143700
cagacaatct agatttgaca ttgaataatc tcattcagta gttaacgtaa ctattataaa  143760
tacattctat aatagcaaat aggagcaatc atggccgaat taaaacgtaa gttcagagct  143820
caagaaggtc tggacgctgc gggtgagaaa gtcatcaacg ttgccaaggc ggatcgcacg  143880
gtcatgtccg atggcgttaa cgttgaatac cttatccaag aaaacacatt acaacaatat  143940
gatagtactc gcggttatcc agcacatttt gctgtcattt atgataatcg tatttgggtg  144000
tctaatagag aaattgctga accagcaggc gattttactg agctttactg gaattctgta  144060
cgcactgatg caaaatggaa aacagtgtca tctggaacaa caaatttaaa atcaggtgat  144120
tttatttcag ctgacactgc cggaagaaca gatatgaaat tcattcttcc tagcaatccg  144180
caagatggcg ataccatttt tattaaagat attggtggtc agccaggata tgcttctctt  144240
```

```
actgtcgatg catctattca atccatagta tggatgggtt ctcaaataag aaccgctcaa   144300
atgacgcatc catactcaca aatggttttc gttttcagta atcgtttgtg caactttat    144360
ataagtgata acgaatcaag agccacttat ataactccag ctagtattca tgaagcgcaa   144420
gcaggcgaaa atctagttag aagatttact tctggagcag aagttttat  tactcttcct   144480
aaacatgcta acaacggtga tataatttcc gtagttgatt tagattctct taacccgttg   144540
tttcatacta cattaaaaac ttatgaccaa aatactagta taggccaagt tggaactcat   144600
gagatgcagt tccgtacttc cggagatgga tttgtagtat ttgattcagc tgataattta   144660
tggagagtat gggacggtga tttacgtacc cgcttgcgta ttgtaactga agatactgac   144720
gttagaccaa attctcatat catggttttt ggggctaaca atgacgaaat aaagacagtt   144780
aatctaaact tgcccgaatc tccagctatt ggagacacag taaaaatttc tcttaactat   144840
atgagaaaag ggcaaacagt taatataaac gctactggaa ctgacacaat agcttcaaat   144900
attgaacttt tgcaatttcc aaaacgctct gattatccgc ctggagctac ttgggttcaa   144960
agcagtactt taacgttcaa tggtgatgaa tcttatgttc aatttttaga tttatcttac   145020
atagaagatg aaaactctca atattgggta gttgcagata atactccgac cgttgaaaga   145080
gtcgattcga ctaatgatga gacccgagct cgtttaggtg ttattgcttt ggcaacccaa   145140
gagcaagcta ataagataa  agaagataat ccagaaaaag aattagcgat tactccagaa   145200
actttggcta accgtattgc tactaaaatc cgccgcggta ttgctcgttt agctactcaa   145260
gctgaattag aagttaaaac tggcgggggct ttattagatg atgtgattgt tactccgaaa   145320
gttctgaatg accgtaccgc tttagaagac cgtcaaggcc tcgctgaatt agcaactcaa   145380
tcagaaacta acgatggtgt tgatgattct agaattgtaa ctccgaaaaa gttacataac   145440
cgcaaagctt cagaaatatt aaccggtatt ttggcgttag ttaaaactgg aatttcaact   145500
cttgcaggtg tagatagaga tacaaaagga agtaacgtat atgactatac tgataatgaa   145560
aaagctgtaa ctccagcttc tttatttgaa aacaaagcta catatacatc acaaggtggt   145620
tcatacttag ctacagaaac cgaagttatt cagggcactc cacatgaccc taaagtgcct   145680
acagtagtaa ctccagtcga attgcataag aaaactgcta ctgaaacacg tattggtttt   145740
agtgaaattg ctacgcaaaa cgaagtcaat actgggacag atgatttccg ttatgttact   145800
cctaagaaat taaatggccg taatgctacg gaagatttaa ctggtatttc gcgagtcgcg   145860
acagacgctg aattcgctgc tggggagcta gataatgtta tttctactcc taaaaagatt   145920
aagaattact tttcttctcc tgaccgtaaa tctgttgtta ctgaatctgg attagttgaa   145980
tcaggtaact cctgggacca ttataacctt gatattcaaa aagcatctga gacgcaacgc   146040
ggcacattac aattagccac acaagttctc actgacgctg gggttgatga cacgactgct   146100
gtaactccga aaaagttaca agctaaaaag acatctgaaa cttctgaagg cattattcag   146160
atagcgactc agtcagaaac aacaagtggt actgtaggaa ataaagctgt tcctccgaag   146220
catctaaaat atgctatcca agaacaacct gattgggaag cttctcctct tcgtagaggt   146280
ccagttaaat taacagaagg cgctttaacg tttgttggtg ataaagaatt tggttctggt   146340
gtcaaatttg acactacaac tggtctttat attaatgata atgataagtt aaatgccgga   146400
aattatttca aatctggata tgctatatct ccctttgaaa tgaacaagac tcttcaaaac   146460
tttttgccaa taaacgcaac tgctgttaat tcgcataagt tagataatct tgattcaact   146520
cagttcatca gaagagatat tgaccaaacg gtcgaaggtt cgttaacgtt aacgcaacaa   146580
```

```
acgaacacta gtgctcctct agtatcctct agtactgcga agtttgttag tatgttggtt  146640
actacagaag ctactatcgg ggacgctacg ggtcactctg tgattaattt ggacgctaaa  146700
accaataaat gggttattga tggacaagct aattctcagt atttagattt tactgccgga  146760
actacagatg ttcttaagct caaacgagat ggagacgtta acgtagccca acatattcg  146820
gctggtaata gagtagatgc ttcaaaaggc tttagcgtcg aaggtggtat aatggttatt  146880
aatcctaccg ccaacaatat tcaaattggt tcacaatcta aagctactaa tatccaaaca  146940
acagacgccg gaaacttgaa agttactgat acatcaggct cttctgtgat attgaccact  147000
aaaaacgctg ttactatcgt aggtaataac ttcgttaata aagctggcga ttcaatgtct  147060
ggccgtttag atatttctgc tgcaatgagt tcagtaatta ctgaagctaa agcgataggt  147120
cctcttacta acgaaactgt gggtaattgg tcagcagaaa tcataactga agatatctac  147180
aaaacattgc ctggatttat ggttccaatt tattctgacg atggcggtgg taaagtaatt  147240
ataggttatg tagattatga cccggctgat gcatcaaaac gcggtgtaag agctccgggt  147300
gtattatctc agattggaac gagtaaaaag gaattcacat atcaaatatg gaaccctcgt  147360
ccagctacag cttatacaga tgctaaatct tctctttgga ttagaaccta tgacccagtt  147420
aaaggtgcat tcaatgaatg gggaagagtt tacactactg aagctcctgt tacgtctgct  147480
gaaattggtg ccgtttctac agctggttct tcatttaata acttaacaat cagagactgg  147540
ttacagattg gtaatgttcg cattacgcct aatcctgata cccaatctgt tgattttact  147600
tggatacctt aatggaaaaa atgatggcga gttttggtaa cggatatacc aaaactcaag  147660
ttatttctga aaataattcc atcaaataca aaatttcatt tgctgcgggg tcggtttttt  147720
cgaccccttc ttctgcttat tttacctttc aggataatcc aataggtaac cagcaagatg  147780
gtgctggtat aaatatcaga gttttttaatc cagcattgaa tactgtatct gctaagaaaa  147840
cattttatt gacacccaat gataatgacc caggcaatag agcattcatt gaatatttgt  147900
caacatttac tcaagataat actaacttgt taatattcac cacatcaggt gatattaaaa  147960
cgagcaattt agtagagaat aaatttaagt ccatttattc aactatgtgg ccaaataaat  148020
ggatgacatc tcggtattca tgtacttatt gcggtttatt ttcaataaaa aataataaaa  148080
ttattgccga aaacgtaaca tattctgatg gagttcttcg ggacgaagac atcagacctg  148140
ctttagaatt cgtttatgat aaagctgatg atattggagc taccgggttt tcttatagag  148200
ctgttgaaga ttttgaagaa tacactagtt ccgcagcaac aataaaaaga tatccagttg  148260
attctgcttc gggcgtagaa attagctcaa ttggaatatc tcctggcgat attctgttct  148320
ggtcatttga attttttgcat ggagataata ttccgccgga agttccaggg acaaataata  148380
ataaaataag aatagaaata agatggttaa attcatctgg agggtggatt aaatcagtta  148440
atgttgactc taaccacgca aatgctggaa aatggataca gcacgaacaa actgttgaag  148500
tccctgctga cgctgcccgg atagttattc ttgcttctaa aactactcca actgatacgg  148560
tcggtactgg aggtgttcgt agtatgattt taactgaaac ttcgcgagct actgaggcat  148620
taacttctcc atctgcgata tcagttaatg gtattcgttt gaatactata gtttcaggag  148680
ataacccgac gctgcttatt ttacctgcta acgaagttga ttcaactggc aaaccattac  148740
caggtgaaga tgtttcagga ataatttaca gttctgattg gagagagttt gagaaaaata  148800
tttaagggcc gaaaggcccct tttctttgt aaaataacaa ataaatatga atatacttaa  148860
gaggacttca tatggccgat ttaaaagcaa atagtacagt aggcggagct ccgatatggc  148920
ataaaggaaa ttttcctttg tctccggtag gtgatacgct actttataag actttcaaag  148980
```

-continued

```
tctatacaga attcgataaa cctcaagcag tagataacga ttttgtttct aaagccgctg    149040
gaggagaata tttaaaaaac gttaatttta aagaaggctt atcatttagc gacaaagatg    149100
gagcttctgt ttttattggt gttcctaaaa atactacagc aacagctact tataccgcat    149160
caataaaatt aaccggacaa ttcgctttag aaactcctga taataaacca tttatcatat    149220
ttgacccaaa cgagtcattt agccctgatg tatatcgctt aactgttatg ggtgatatgc    149280
tttctcgtca aatttatgat gaatccggaa gagttttttc tcctgggaat actccgtcaa    149340
aagcgcaagt tgggttagat ttagtcgata cgctaagca agttcaactt gaaaaatctg      149400
gtgttcaaac aatgaccggg gttttggctg ctccaaactt tataagtacc aatccggcaa    149460
cggcagataa tcatgtagct cgttttgacc agattgtaat aaaagactca attcaagatt    149520
ttggatatta tagttaagag gacatatggc tactataaaa caaatacaat ttaaaagaac    149580
taaagtagca ggctctcgtc ctactgccgc tcaactcgct gaaggcgaac ttgctattaa    149640
cttaaaagac cgcactattt tcacgaaaga cgatttgaac caaatcattg atttaggttt    149700
tgcaaaaggc ggtgaagtat caggagatat cacgcagatt ggtaattata cccaaactgg    149760
gaactataat ttaaccggcg atgctactat atcaggcaaa actactacaa gcacactgga    149820
tgttgggtct gtttcagatc taagacagac aaactttaga ccagtattaa gcacaacaac    149880
tggttctaat tttattatat caaactctgg cggcttgatt aaaccaatta ctttgacggt    149940
agaaggcaca gctacaagtt caaacactat tctgcgccat tcagttgata ctactgtagc    150000
agcttctgga tttatcgatt caattaatgt ttctttaaat ccgacggacg gcgctcttgt    150060
tacagctctc aatggtactg tgaatatcgg tagttccctt aaaactccta aactttcagt    150120
ttctggcgcg gaaactgctt tgggagatta tagtatttca atcggtgata atgatacagg    150180
atttaaatgg aattctgatg gtgtattcag cttagttact gacagtaatt caatttatac    150240
atactctcgt gataggacat attctaaccg tccaacaaat ttccggtata cgtctgactt    150300
tgatgctacg acacctgctt tagctccgcc aggcacatgg ttagcttcag ttgaaactgc    150360
aatagacggt aacgcttacg gcgatggaat gagctatctc ggttataaag ataccgcagg    150420
ttatagttttt tatttccgcg gcggcggcac ttttaacgta gcttctaaag gtggatttaa    150480
tgtagacaca gctgcggctt ttgccaaaac ggttgatgta tctgatattc taacatgcag    150540
ctctattatt aaagctaaag gcccaggtca agttgatgtt actagtgctg gtaatatcgc    150600
acttggtgga actattcaat gggtgccttc gtatatgagc ggaagcccaa atagagcacg    150660
agatacaata gctacagcag cttggggcga tgccgaccaa cgaattaacg tattagaaac    150720
atctgacccg catggttggt ggtattatat acagcgcgca ggttctggaa gttcttctcc    150780
tacgggaata gaagggcgag tcaatggctc ttggcaggca tctgatttaa tttctgataa    150840
tactctaaga gtagctggag cttttcacttg tactagaaga aactccgcag gatggggtga    150900
taacgctgga tggtatgctg gagcaacacc agtagtagct aaccaaggaa acgttcaaga    150960
aatggacccc ggtgtaggcg gtttttatcc tggatttgct caatataact ataatggcac    151020
tggatggaac caagcatttg ttctgggggtt actaggccaa ggtgttcaga gatggcgtcg    151080
tggtgtatta gctcttagag gcgatggccc tgttgatgct ggacaacaaa ttgctcgttg    151140
gtatttagt caagaagacg gaagtttgga atcagaaggt ccgcttaaag ctcctagtgt    151200
tcaagctgga caaataacat ctttttggtgt aaacgttaca aacgcgttag gcagtgcgtc    151260
tatagctatt ggcgataacg ataccggatt gcgctggggc ggcgatggta tcgttcaaat    151320
```

```
tgtagctaat aacgctatcg taggcggatg gaattcaaca gatattttta ctgaagctgg  151380
taaacatata acatccaatg gaaatttaaa tcaatgggc ggaggcgcaa tttattgtag  151440
agaccttaat gttagttccg acagaagaat aagaaagac ataaaagcat ttgaaaatcc  151500
cgtagatatt ttaagcacta taggcggtta tacttatctt attgaaaaag gatttaatga  151560
agatggaagt caggcttacg aagagtccgc tggattaatt gctcaagaag tagaagctgt  151620
tcttcctcgt ttagttaaaa tatccaatga tggaacaaaa gatgttaaaa gacttaatta  151680
taatggtata acagctttaa atactgctgc tataaatgta catactaaag aaattaatga  151740
gctcaaaaag caattaaaag agcttaaaga cattgttaag ttttttaacta aataagagcc  151800 tacgggctct ttaggagata ttatggcagt tcaaggacct tgggtaggtt cgtcttatgt  151860
cgctgaaaca ggtcaaaact gggcctcatt agcggcgaat gaattaagag taacggagag  151920
gcccttttgg atttcctcat ttatagggcg ctctaaagaa gaaatttggg aatggactgg  151980
agaaaatcac agtttcaaca aagattggtt aataggcgaa cttcgcaata gaggtggtac  152040
tcctgtagta attaatataa gagctcatca agtgtcttat actccaggcg caccttttatt  152100 tgaatttccc ggagaccttc caaatgcata tattacactt aacatttatg cagatatata  152160
tggaagaggt ggtactggtg gagttgctta tttaggcgga aaccccggcg gagactgtat  152220
tcataattgg attggaaaca gacttagaat aaacaaccaa ggctggattt gtggtggcgg  152280
aggcggcggc ggtggctttc gtgttggaca tactgaagct ggtggtggtg gcggacgacc  152340
tttgggagcg ggcggagttt caagcttaaa tctaaacgga gacaatgcta ctttgggtgc  152400
tcccgggcga ggatatcaac ttggaaacga ttatgcaggt aacggcggcg atgtcggtaa  152460
tcctggttca gctagttcag ccgaaatggg cggtggagcg gctggacgag ctgttgtagg  152520
aacctcacct caatggataa atgttggtaa tattgctggt tcttggttat aaatatctct  152580
aaggagataa tatggcttca aaaatttcgt taccaataac ggatataatt tttggagtgt  152640
gggacagagt ttttaaagat aatgcatccg ggagggtttt agtctcccgg ttgttgttg  152700 taattatttt ctttgtactt ggattagttt ggtcaaaaag cgatgcaata ctaaccactt  152760
acagagattc gtcttacgat gcgtacgcga aaattataca acaagaacgc gaatcacgct  152820
ttgaaacaac tgctctggaa cagcttcaaa tagttcacat atccagcgga gcagatttca  152880
ctgctgtgta ttcgtttaga cctaaaaatt taaattattt tgttgattta atagcgtatg  152940
agggtagatt accttcaacc gtttcggaaa aaagtcttga cggtttcccg gttgataaaa  153000
ctactaatga atattctaca catttaggag gaagagtttt taaatcatca caagaatttg  153060
cttttctacc gtcaaagaaa aaaacaactg aattaaaata catgttcagt tgtccttact  153120
tcaatttaga taatatatat gccggaactg tttctatgta ctggtacgac ggagctccaa  153180
gtgtaagccc ggaacgactt gaatcgatat gtggccaagc cgctcgtaca ttaggaaggt  153240
cacgttagaa attacttatt ggtatgcatc gtcagatgac gatagatatc ttcaaatcct  153300
tcgttgaatt cttcaacaag cattccttc tcttctgcag ttaaatcaga attatttttt  153360
ctaaagctac tctgatttaa ctgcttccaa ttttttatcag cactcatcgt ttcattgata  153420
aaagcaataa agttatctcg tttatcaaca atatcatcgc gaccaaattt aattaacaaa  153480
gacgcaatag taacaacttc acgagcaact tcaaacttag tcatcttata tccttagta  153540 tttaatttt aaatcaataa acggtataga agtatagtat caaaattta ttggtattgt  153600 aaacggttga gtgaactaat ttaaaacttc ccaacgaacc atcagatgct caggttgagt  153660
tatgtactca tttccagaat tgttcactcg aatggcgtag cggcctcctt gcattgcagc  153720
```

```
tgatatatac cattcggctc ctactggacg aaccctacgt cccatccaat gacagatttc   153780
catggcctcg tgaaaagagt aatcttcttt gtccattgcc aaattaatca tcatgctttc   153840
aatgtaacgc tgaatttcta cagtttggtt gctcataatt ttcccttcaa ttctttagat   153900
aaaatattat caaaataaat cacggcagct tcaagaatgt ttggattctg ataagtagaa   153960
aatttgaaat tgcatccaga ataagaccct cccatgtact tcacatgaac accgtacttt   154020
ttatagacct tttcttctgc cctctcaatt tcgtcaggaa aatcacttcc aaactttcca   154080
aatttaatta cttcagaagt gtgtaaataa ctgtgctctg tgacaatatt tttatgcttg   154140
aaagtcattt gactgtcctt tgtgtttttg tttgcgtttg gagtcattaa tggatttctt   154200
tttattttta tgaaatccac ctttgttaaa atcattttttt gccactgggt tattcaacta   154260
attttcctct tgcgttttta agctgcttaa cttgatgagc aaatgctgc agtgaatat    154320 tttcatcttg gttaagattt cgtctaatta attcaacaaa ccactcatat tttggtcttt   154380
ttgataattc agccctaagt ttagcatttt cttgttcagc tatggtagct ctctgcctat   154440
aatccattta aaattccttt gataattatt tgaaccacat tttaattctc atccataggg   154500
atttctgaac agctttgttt accccgtaag aacgaattac tggctgactt tcttgaagtt   154560
ctttataatc agctttataa acttcgcaag cagcgggaac aaatgaacta attgctgcca   154620
taaaatttgt acgttcacct aaaggattta ctgaactatc gcgaacaatc aaatattttc   154680
cagctttaac cttcacgata gttccaagat atgcaccatg ataccaaata tcccaacctt   154740
ctgaagtagg ttctacacaa cgctgaagtt cattcataat tgcaaaacgg ttcataatac   154800
ttcctagact ttaacaacgt gttcaataaa taacccatgt ttatttttcgc cttgagtgcc   154860 ttgtataaag attctcactg cgtttggaat atctctagca aatatttcaa cccaatatgt   154920
accaccacca atctcgtaag tgattttata tttgttcata attcctcaca gtgtgtcaac   154980
agagttgatg atagtttcaa tattttcttg agtacgaacg atatctaaat aaacattacc   155040
atttttagaa tgtttggcaa tcataccaag gtcttcaaag tgcttaactt gctcttcagt   155100
cattttataa cccgaaatac ggaagttacc tttattgcta acctcgaaac tgcgaatacc   155160
aaatgtgcgt ttttcaagga ccgcgataaa gttactacga taaacatcaa gttttttgat   155220
tttgaaaagt tcttctttag ttccaagaag ctccatcata aaatctttat ctgcttccat   155280
atcacccgta atcgggcgag ctttacgagt attgcgtttt tctagaagtt caggagcatt   155340
ttcctgtgca taaagtaccg ccgcgtttga gatgatgtcc tgtgcttcac ccgtgattac   155400
tagaccatca ccagattttt caattaatcc tttcttaatc aaaacaccaa tattactgtt   155460
gactgaagat gcagtcattt tatcttctaa ctgttcacga agttcagctg aagtgatgaa   155520
atcttgtttt gcaactttaa ctaaaatcga tgcagttttt tcattcagaa catcattaga   155580
agctttgatg atataagtta cttttgacat tttgtttctc cgataatcta tttgtttgtt   155640
gataaagtaa tagtaacaca gtttaaagcg atgtaaacg gttgaagtaa aaattttaa    155700 agttaaccag aacggttgag agtaacgcag aagaaaggat gattaattat atggaccggg   155760
ctctagaatt tactagagcc gcatagagtt acagcaaaat ggagagaagt gcaagaagaa   155820
gggctaaacc gcctaaaact acgacgattg acaacagccc ggctactaag accgggcttg   155880
cataccaaag aaaaaccgcc agcgaaatta tcagagctac tcgcatagct cctccaaatc   155940
cttcatgaac tcaacttccg gagtggtatc tttccagtac tgatactctt tcttgagctc   156000
tttggcagcc tctacgagtt ttttggcttc atctgacgtt atgtgataaa tgttcatacc   156060
```

```
aaccaatttta tcaatatgag ccttgaacaa ttcagttttt tctagttctg ttacaagctg    156120
cttacgagtt tttccttgaa taacaatttc acccgaaatt acttgtttaa tgaattgagc    156180
tttagctact gccaagttca actgagacaa aacgtcttca cgcttaaact caattcgttt    156240
ttcaacaaaa gtcttacgga cttcaacaaa atgtttaatg agttcagacg ctttttgaaa    156300
cttgtcgttt aacttgccat tttcgtcaat gacaacaatg aactgcgaaa gttttttcaat   156360
taatttgaaa tctcgcatta cagcgtcatg ccgtttatct tcgtctgccg gtaacccata    156420
atctttcttg aattttactt taaagccaaa cccagatttt gaacagtcat ccgtataagt    156480
aataaaacct ttgtcttcta acgggtcgag tacttttca atataagtat cacggtcaaa     156540
tttatacgga atttcactga tatacatctg tgtagctgaa gtgaatttat aaacaccgtg    156600
taattcaact ccaccgtcat cagtcggaac aattttacca ttgaattttg gaaattcaac    156660
ttctggctct ttatcaagct ttccctgtaa agcgagttta gtgcattcta caactgattt    156720
aaaactgtgc ggaagaatat tagttgcgta cccggtagca ataccgcgaa caccatttaa    156780
taatacggta ggaataaccg gaagataaaa agctggcggt gtatgttctt cgtctttgtg    156840
ttttggagca atctctaagt ctttataaac tttacggaaa ttgtcagaaa tacggcaaaa    156900
gatgtaacga gacgcagcag cttttttgtac taaacgcgaa ccaaagttac cttgtccgtc   156960
caataaaggg aaattgttat tccacgtatt agccatcagt gccccggcat cttgtgcaga    157020
gccttcaccg tgatgatacc ctaaatcagc tactccgcca gcgactgatg caagcttatg    157080
aaatttttct ttattacctt tgctgaggtc taatgctcga cgaataacaa aacgctgtac    157140
tggtttaaat ccatcaatca tatttggaat tgcacgattt tctactgtgt agattgcgaa    157200
ttctttagct tcagtatcaa taatactttg taaacttctt tcatttaatt gcatatgatt    157260
tccaattacc aaatgtatga actgacgtca attataacac gtgtaaagaa aagcgtcatc    157320
tgtagtgcta taaaatataa gcttgcgaga attattccaa atatcgctaa acaaatcgcg    157380
gcgattgtca aaattctcat ttaattatac cactataaga gaataaccgc tccagcgaca    157440
gagcagctat tccgaaacac atagcgccaa gaactcttga cggagggggt aacccctccc    157500
aaaataaacat cccagaaact atgaataacg gtatcattat aataaacacg gtcgcccata   157560
tagttttaat tgcattattc atattatttc ctagataatt taaaattgtt taaatgcggt    157620
aatgactaaa actagaccaa gagtcaattg agcaacaaac tgagccacga atgaagactc    157680
tcgtgtcact gcagtgtaaa ttgctaaacc aaaccacacc gcggcgatta ataatgtcaa    157740
catttcaaat cctcttaata tttctgcaga ataaatttaa aattatcatt taacatgcga    157800
ttcatttctt cgaggttctg aaatgcatct tcgtgtttac gagtgaaagc taaagacaat    157860
tgtcctttac catgacctgt cgtaagaggt ttcatttttt cagctggaac gaataccacg    157920
ctatacacct ggtgattatt gctcaaagta cgaccaagtt gagagcgtcc ttgtcgaaat    157980
tgcgataaag tattagaaaa cccggtttta gaacgttgac gaccaacgta actacgagat    158040
accgcaaatc cagcgatatt cataataaag taaaaacctg ggcgagatag ttcttcttcc    158100
attggaatac cacccaccca atttgcgttt ttaatcacgc caattacagt tgcgccagct    158160
tttgacaaag tttcgataga caaaaatgta cgacgggtca tattgatatc ctcaagttaa    158220
gtaatttatt atcctataat atcacaaatt ttaattaatg taaacggtta tgatagtttc    158280
catagcaaca agctaaaaca aacgcaaatc aacgggatac ataatatcca aattaagcac    158340
caagctttac tgctcatgat tacctcttag taattagtca tgttatgttt tgatgaggta    158400
atagtaacac atccttccat ggatgtaaac ggctgataat caaatcatta ggtaccaacc    158460
```

-continued

```
ttcatactta cttctttga caatttcttt agtgtcttct gggtccccaa cgaacactgg   158520
ggtaaactcg aagcctccag ttaaattctc tacgacatct aatataatta tacagtctgc   158580
aacttgatga ttcaggaatg gccctagatt aaccccataa ccatagggaa agttaccaga   158640
gtatcccgta gtaactgaaa tccacttaga ctctgattga tgtgttttta cttcaatgcg   158700
gagaccacag tatcttggat gcgcaagtac atcccatgcg aaggtgtaag ggtcatcatg   158760
attttcttga ccatgcatta cataaccatt aacccattct gcgacggcct tttcagctaa   158820
ttgcgctatc atgcaccttt taaccgcggc ctctttatct tggcctgggt cttttgacat   158880
cgtgtaattt acggtgtctt ttattttaac tctatcttct ggagttaaat cattcttccc   158940
gcggataaat gtcggcagtt tcttcagtct caacaacccc ggattgttct tgttcatttt   159000
gctcacctgt ataaacgtct tttacccgaa gaataccaca ataaattcgg tcatcaaaat   159060
ttaaactttc tttgtttgag agagcaaatt gtatgtgttc tttaccaata aaaacatcat   159120
cgcaagtcag tacaccatca acattagggt caatcaccaa atccaaagca tacacatttt   159180
gagctttgtg attgccgtgc aatcgtgatt cattaatttt cgaatcagaa acgttaatcc   159240
aattaatcat aatcatctct taaagaaaaa gggaccgaag tcccttagaa ttaaattagc   159300
gatgcgacgg tattagaacg tgcaccattt gctagttaca tcttcaatta cttggtattt   159360
acatgtacgc atttagcat cgccgtaatc aaccgggata gatactacat ctcgcggatg   159420
aactttaact gaaacgatac ggtcactaga accacggaaa tagctaatat aactcttaga   159480
gcaaacatgc aatccagctg aacatgtacg ttcgtcatct tcatcaacct ggttacgagc   159540
catttctaca gtaaccccag gggagttatc aaaagtgcgg ctatggcaat cttttgtagtt  159600
ttcagtaaca actttccaag cgataaaatg gccgtcatca gtgatttcaa tatcgttcgc   159660
aaccaagaaa tcaaacagac gagctacagc tttgcgactt gggttttcca tcaaattttc   159720
aaggaaaggc atatagaatt cgaagttctc gccctgttcc atggatttca ggatacgctc   159780
tgtgagacct gatttaattt cgatgtcttt atagaacaga cggccttcgt caattttaac   159840
attacctta acgtaagagg tcaaaccttt ttcagcgtta acgatttcca atgcgccttc   159900
aatatcacca tcaatcaggc gctgcagagc aatttaaaa ccgggtagtt tatcatctgc   159960
cggataagtt ttgtgagtgc tcaaatcggt aattgagata aatttattag aagcgttcca   160020
gatatattct ggcgcagcaa ccggagtttc aactgcttca atttcttcta ctttagtttc   160080
ttgagccatt tctttaacta cgcggcggat agtatctact gaacagttga agtgcttagc   160140
aatccagtct cgtttgtagc ctgaatcaac ataatcaacg atagacaatt tctgagaacg   160200
agtaaacatt tgtacggcca t                                             160221
```

<210> SEQ ID NO 2
<211> LENGTH: 3822
<212> TYPE: DNA
<213> ORGANISM: Unknown
<220> FEATURE:
<223> OTHER INFORMATION: Salmonella bacteriophage S16

<400> SEQUENCE: 2

```
atggccgaat taaaacgtaa gttcagagct caagaaggtc tggacgctgc gggtgagaaa        60
gtcatcaacg ttgccaaggc ggatcgcacg gtcatgtccg atggcgttaa cgttgaatac       120
cttatccaag aaaacacatt acaacaatat gatagtactc gcggttatcc agcacatttt       180
gctgtcattt atgataatcg tatttgggtg tctaatagag aaattgctga accagcaggc       240
```

-continued

```
gattttactg agctttactg gaattctgta cgcactgatg caaaatggaa aacagtgtca    300
tctggaacaa caaatttaaa atcaggtgat tttatttcag ctgacactgc cggaagaaca    360
gatatgaaat tcattcttcc tagcaatccg caagatggcg ataccatttt tattaaagat    420
attggtggtc agccaggata tgcttctctt actgtcgatg catctattca atccatagta    480
tggatgggtt ctcaaataag aaccgctcaa atgacgcatc catactcaca aatggttttc    540
gttttcagta tcgtttgtg gcaactttat ataagtgata cgaatcaag agccacttat      600 ataactccag ctagtattca tgaagcgcaa gcaggcgaaa atctagttag aagatttact    660
tctggagcag aagtttttat tactcttcct aaacatgcta acaacggtga tataatttcc    720
gtagttgatt tagattctct taacccgttg tttcatacta cattaaaaac ttatgaccaa    780
aatactagta taggccaagt tggaactcat gagatgcagt tccgtacttc cggagatgga    840
tttgtagtat ttgattcagc tgataattta tggagagtat gggacggtga tttacgtacc    900
cgcttgcgta ttgtaactga agatactgac gttagaccaa attctcatat catggttttt    960
ggggctaaca atgacgaaat aaagacagtt aatctaaact tgcccgaatc tccagctatt   1020
ggagacacag taaaaattc tcttaactat atgagaaaag ggcaaacagt taatataaac    1080
gctactggaa ctgacacaat agcttcaaat attgaacttt tgcaatttcc aaaacgctct   1140
gattatccgc ctggagctac ttgggttcaa agcagtactt taacgttcaa tggtgatgaa   1200
tcttatgttc caattttaga tttatcttac atagaagatg aaaactctca atattgggta   1260
gttgcagata atactccgac cgttgaaaga gtcgattcga ctaatgatga ccccgagct    1320 cgtttaggtg ttattgcttt ggcaacccaa gagcaagcta aaagataa agaagataat     1380 ccagaaaaag aattagcgat tactccagaa actttggcta accgtattgc tactaaaatc   1440
cgccgcggta ttgctcgttt agctactcaa gctgaattag aagttaaaac tggcggggct   1500
ttattagatg atgtgattgt tactccgaaa gttctgaatg accgtaccgc tttagaagac   1560
cgtcaaggcc tcgctgaatt agcaactcaa tcagaaacta cgatggtgt tgatgattct    1620 agaattgtaa ctccgaaaaa gttacataac cgcaaagctt cagaaatatt aaccggtatt   1680
ttggcgttag ttaaaactgg aatttcaact cttgcaggtg tagatagaga tacaaaagga   1740
agtaacgtat atgactatac tgataatgaa aaagctgtaa ctccagcttc tttatttgaa   1800
aacaaagcta catatacatc acaaggtggt tcatacttag ctacagaaac cgaagttatt   1860
cagggcactc cacatgaccc taaagtgcct acagtagtaa ctccagtcga attgcataag   1920
aaaactgcta ctgaaacacg tattggtttt agtgaaattg ctacgcaaaa cgaagtcaat   1980
actgggacag atgatttccg ttatgttact cctaagaaat aaatggccg taatgctacg    2040 gaagatttaa ctggtatttc gcgagtcgcg acagacgctg aattcgctgc tggggagcta   2100
gataatgtta tttctactcc taaaaagatt aagaattact tttcttctcc tgaccgtaaa   2160
tctgttgtta ctgaatctgg attagttgaa tcaggtaact cctgggacca ttataacctt    2220
gatattcaaa aagcatctga gacgcaacgc ggcacattac aattagccac acaagttctc   2280
actgacgctg gggttgatga cacgactgct gtaactccga aaagttaca agctaaaaag   2340 acatctgaaa cttctgaagg cattattcag atagcgactc agtcagaaac aacagtggt    2400 actgtaggaa ataaagctgt tcctccgaag catctaaaat atgctatcca agaacaacct   2460
gattgggaag cttctcctct tcgtagaggt ccagttaaat taacagaagg cgctttaacg   2520
tttgttggtg ataaagaatt tggttctggt gtcaaatttg acactacaac tggtctttat   2580
attaatgata atgataagtt aaatgccgga aattatttca aatctggata tgctatatct   2640
```

-continued

```
ccctttgaaa tgaacaagac tcttcaaaac tttttgccaa taaacgcaac tgctgttaat    2700
tcgcataagt tagataatct tgattcaact cagttcatca gaagagatat tgaccaaacg    2760
gtcgaaggtt cgttaacgtt aacgcaacaa acgaacacta gtgctcctct agtatcctct    2820
agtactgcga agtttgttag tatgttggtt actacagaag ctactatcgg ggacgctacg    2880
ggtcactctg tgattaattt ggacgctaaa accataaaat gggttattga tggacaagct    2940
aattctcagt atttagattt tactgccgga actacagatg ttcttaagct caaacgagat    3000
ggagacgtta acgtagccca aacattatcg gctggtaata gagtagatgc ttcaaaaggc    3060
tttagcgtcg aaggtggtat aatggttatt aatcctaccg ccaacaatat tcaaattggt    3120
tcacaatcta agctactaa tatccaaaca acagacgccg gaaacttgaa agttactgat     3180
acatcaggct cttctgtgat attgaccact aaaaacgctg ttactatcgt aggtaataac    3240
ttcgttaata aagctggcga ttcaatgtct ggccgtttag atatttctgc tgcaatgagt    3300
tcagtaatta ctgaagctaa agcgataggt cctcttacta acgaaactgt gggtaattgg    3360
tcagcagaaa tcataactga agatatctac aaaacattgc ctggatttat ggttccaatt    3420
tattctgacg atggcggtgg taaagtaatt ataggttatg tagattatga cccggctgat    3480
gcatcaaaac gcggtgtaag agctccgggt gtattatctc agattggaac gagtaaaaag    3540
gaattcacat atcaaatatg gaaccctcgt ccagctacag cttatacaga tgctaaatct    3600
tctctttgga ttagaaccta tgacccagtt aaaggtgcat tcaatgaatg gggaagagtt    3660
tacactactg aagctcctgt tacgtctgct gaaattggtg ccgtttctac agctggttct    3720
tcatttaata acttaacaat cagagactgg ttacagattg gtaatgttcg cattacgcct    3780
aatcctgata cccaatctgt tgattttact tggatacctt aa                       3822
```

<210> SEQ ID NO 3
<211> LENGTH: 1273
<212> TYPE: PRT
<213> ORGANISM: Unknown
<220> FEATURE:
<223> OTHER INFORMATION: Salmonella bacteriophage S16

<400> SEQUENCE: 3

```
Met Ala Glu Leu Lys Arg Lys Phe Arg Ala Gln Glu Gly Leu Asp Ala
1               5                   10                  15

Ala Gly Glu Lys Val Ile Asn Val Ala Lys Ala Asp Arg Thr Val Met
                20                  25                  30

Ser Asp Gly Val Asn Val Glu Tyr Leu Ile Gln Glu Asn Thr Leu Gln
            35                  40                  45

Gln Tyr Asp Ser Thr Arg Gly Tyr Pro Ala His Phe Ala Val Ile Tyr
        50                  55                  60

Asp Asn Arg Ile Trp Val Ser Asn Arg Glu Ile Ala Glu Pro Ala Gly
65                  70                  75                  80

Asp Phe Thr Glu Leu Tyr Trp Asn Ser Val Arg Thr Asp Ala Lys Trp
                85                  90                  95

Lys Thr Val Ser Ser Gly Thr Thr Asn Leu Lys Ser Gly Asp Phe Ile
                100                 105                 110

Ser Ala Asp Thr Ala Gly Arg Thr Asp Met Lys Phe Ile Leu Pro Ser
            115                 120                 125

Asn Pro Gln Asp Gly Asp Thr Ile Phe Ile Lys Asp Ile Gly Gly Gln
        130                 135                 140

Pro Gly Tyr Ala Ser Leu Thr Val Asp Ala Ser Ile Gln Ser Ile Val
```

-continued

```
            145                 150                 155                 160
Trp Met Gly Ser Gln Ile Arg Thr Ala Gln Met Thr His Pro Tyr Ser
                    165                 170                 175
Gln Met Val Phe Val Phe Ser Asn Arg Leu Trp Gln Leu Tyr Ile Ser
                    180                 185                 190
Asp Asn Glu Ser Arg Ala Thr Tyr Ile Thr Pro Ala Ser Ile His Glu
                    195                 200                 205
Ala Gln Ala Gly Glu Asn Leu Val Arg Arg Phe Thr Ser Gly Ala Glu
                    210                 215                 220
Val Phe Ile Thr Leu Pro Lys His Ala Asn Asn Gly Asp Ile Ile Ser
225                 230                 235                 240
Val Val Asp Leu Asp Ser Leu Asn Pro Leu Phe His Thr Thr Leu Lys
                    245                 250                 255
Thr Tyr Asp Gln Asn Thr Ser Ile Gly Gln Val Gly Thr His Glu Met
                    260                 265                 270
Gln Phe Arg Thr Ser Gly Asp Gly Phe Val Val Phe Asp Ser Ala Asp
                    275                 280                 285
Asn Leu Trp Arg Val Trp Asp Gly Asp Leu Arg Thr Arg Leu Arg Ile
                    290                 295                 300
Val Thr Glu Asp Thr Asp Val Arg Pro Asn Ser His Ile Met Val Phe
305                 310                 315                 320
Gly Ala Asn Asn Asp Glu Ile Lys Thr Val Asn Leu Asn Leu Pro Glu
                    325                 330                 335
Ser Pro Ala Ile Gly Asp Thr Val Lys Ile Ser Leu Asn Tyr Met Arg
                    340                 345                 350
Lys Gly Gln Thr Val Asn Ile Asn Ala Thr Gly Thr Asp Thr Ile Ala
                    355                 360                 365
Ser Asn Ile Glu Leu Leu Gln Phe Pro Lys Arg Ser Asp Tyr Pro Pro
                    370                 375                 380
Gly Ala Thr Trp Val Gln Ser Ser Thr Leu Thr Phe Asn Gly Asp Glu
385                 390                 395                 400
Ser Tyr Val Pro Ile Leu Asp Leu Ser Tyr Ile Glu Asp Glu Asn Ser
                    405                 410                 415
Gln Tyr Trp Val Val Ala Asp Asn Thr Pro Thr Val Glu Arg Val Asp
                    420                 425                 430
Ser Thr Asn Asp Glu Thr Arg Ala Arg Leu Gly Val Ile Ala Leu Ala
                    435                 440                 445
Thr Gln Glu Gln Ala Asn Lys Asp Lys Glu Asp Asn Pro Glu Lys Glu
                    450                 455                 460
Leu Ala Ile Thr Pro Glu Thr Leu Ala Asn Arg Ile Ala Thr Lys Ile
465                 470                 475                 480
Arg Arg Gly Ile Ala Arg Leu Ala Thr Gln Ala Glu Leu Glu Val Lys
                    485                 490                 495
Thr Gly Gly Ala Leu Leu Asp Asp Val Ile Val Thr Pro Lys Val Leu
                    500                 505                 510
Asn Asp Arg Thr Ala Leu Glu Asp Arg Gln Gly Leu Ala Glu Leu Ala
                    515                 520                 525
Thr Gln Ser Glu Thr Asn Asp Gly Val Asp Asp Ser Arg Ile Val Thr
                    530                 535                 540
Pro Lys Lys Leu His Asn Arg Lys Ala Ser Glu Ile Leu Thr Gly Ile
545                 550                 555                 560
Leu Ala Leu Val Lys Thr Gly Ile Ser Thr Leu Ala Gly Val Asp Arg
                    565                 570                 575
```

```
Asp Thr Lys Gly Ser Asn Val Tyr Asp Tyr Thr Asp Asn Glu Lys Ala
            580                 585                 590

Val Thr Pro Ala Ser Leu Phe Glu Asn Lys Ala Thr Tyr Thr Ser Gln
        595                 600                 605

Gly Gly Ser Tyr Leu Ala Thr Glu Thr Glu Val Ile Gln Gly Thr Pro
    610                 615                 620

His Asp Pro Lys Val Pro Thr Val Val Thr Pro Val Glu Leu His Lys
625                 630                 635                 640

Lys Thr Ala Thr Glu Thr Arg Ile Gly Phe Ser Glu Ile Ala Thr Gln
                645                 650                 655

Asn Glu Val Asn Thr Gly Thr Asp Asp Phe Arg Tyr Val Thr Pro Lys
            660                 665                 670

Lys Leu Asn Gly Arg Asn Ala Thr Glu Asp Leu Thr Gly Ile Ser Arg
        675                 680                 685

Val Ala Thr Asp Ala Glu Phe Ala Ala Gly Glu Leu Asp Asn Val Ile
    690                 695                 700

Ser Thr Pro Lys Lys Ile Lys Asn Tyr Phe Ser Ser Pro Asp Arg Lys
705                 710                 715                 720

Ser Val Val Thr Glu Ser Gly Leu Val Glu Ser Gly Asn Ser Trp Asp
                725                 730                 735

His Tyr Asn Leu Asp Ile Gln Lys Ala Ser Glu Thr Gln Arg Gly Thr
            740                 745                 750

Leu Gln Leu Ala Thr Gln Val Leu Thr Asp Ala Gly Val Asp Asp Thr
        755                 760                 765

Thr Ala Val Thr Pro Lys Lys Leu Gln Ala Lys Lys Thr Ser Glu Thr
    770                 775                 780

Ser Glu Gly Ile Ile Gln Ile Ala Thr Gln Ser Glu Thr Thr Ser Gly
785                 790                 795                 800

Thr Val Gly Asn Lys Ala Val Pro Pro Lys His Leu Lys Tyr Ala Ile
                805                 810                 815

Gln Glu Gln Pro Asp Trp Glu Ala Ser Pro Leu Arg Arg Gly Pro Val
            820                 825                 830

Lys Leu Thr Glu Gly Ala Leu Thr Phe Val Gly Asp Lys Glu Phe Gly
        835                 840                 845

Ser Gly Val Lys Phe Asp Thr Thr Thr Gly Leu Tyr Ile Asn Asp Asn
850                 855                 860

Asp Lys Leu Asn Ala Gly Asn Tyr Phe Lys Ser Gly Tyr Ala Ile Ser
865                 870                 875                 880

Pro Phe Glu Met Asn Lys Thr Leu Gln Asn Phe Leu Pro Ile Asn Ala
                885                 890                 895

Thr Ala Val Asn Ser His Lys Leu Asp Asn Leu Asp Ser Thr Gln Phe
            900                 905                 910

Ile Arg Arg Asp Ile Asp Gln Thr Val Glu Gly Ser Leu Thr Leu Thr
        915                 920                 925

Gln Gln Thr Asn Thr Ser Ala Pro Leu Val Ser Ser Thr Ala Lys
    930                 935                 940

Phe Val Ser Met Leu Val Thr Glu Ala Thr Ile Gly Asp Ala Thr
945                 950                 955                 960

Gly His Ser Val Ile Asn Leu Asp Ala Lys Thr Asn Lys Trp Val Ile
                965                 970                 975

Asp Gly Gln Ala Asn Ser Gln Tyr Leu Asp Phe Thr Ala Gly Thr Thr
            980                 985                 990
```

-continued

Asp Val Leu Lys Leu Lys Arg Asp Gly Asp Val Asn Val Ala Gln Thr
       995                1000                1005

Leu Ser Ala Gly Asn Arg Val Asp Ala Ser Lys Gly Phe Ser Val
   1010                1015                1020

Glu Gly Gly Ile Met Val Ile Asn Pro Thr Ala Asn Asn Ile Gln
   1025                1030                1035

Ile Gly Ser Gln Ser Lys Ala Thr Asn Ile Gln Thr Thr Asp Ala
   1040                1045                1050

Gly Asn Leu Lys Val Thr Asp Thr Ser Gly Ser Ser Val Ile Leu
   1055                1060                1065

Thr Thr Lys Asn Ala Val Thr Ile Val Gly Asn Asn Phe Val Asn
   1070                1075                1080

Lys Ala Gly Asp Ser Met Ser Gly Arg Leu Asp Ile Ser Ala Ala
   1085                1090                1095

Met Ser Ser Val Ile Thr Glu Ala Lys Ala Ile Gly Pro Leu Thr
   1100                1105                1110

Asn Glu Thr Val Gly Asn Trp Ser Ala Glu Ile Ile Thr Glu Asp
   1115                1120                1125

Ile Tyr Lys Thr Leu Pro Gly Phe Met Val Pro Ile Tyr Ser Asp
   1130                1135                1140

Asp Gly Gly Gly Lys Val Ile Ile Gly Tyr Val Asp Tyr Asp Pro
   1145                1150                1155

Ala Asp Ala Ser Lys Arg Gly Val Arg Ala Pro Gly Val Leu Ser
   1160                1165                1170

Gln Ile Gly Thr Ser Lys Lys Glu Phe Thr Tyr Gln Ile Trp Asn
   1175                1180                1185

Pro Arg Pro Ala Thr Ala Tyr Thr Asp Ala Lys Ser Ser Leu Trp
   1190                1195                1200

Ile Arg Thr Tyr Asp Pro Val Lys Gly Ala Phe Asn Glu Trp Gly
   1205                1210                1215

Arg Val Tyr Thr Thr Glu Ala Pro Val Thr Ser Ala Glu Ile Gly
   1220                1225                1230

Ala Val Ser Thr Ala Gly Ser Ser Phe Asn Asn Leu Thr Ile Arg
   1235                1240                1245

Asp Trp Leu Gln Ile Gly Asn Val Arg Ile Thr Pro Asn Pro Asp
   1250                1255                1260

Thr Gln Ser Val Asp Phe Thr Trp Ile Pro
   1265                1270

<210> SEQ ID NO 4
<211> LENGTH: 1182
<212> TYPE: DNA
<213> ORGANISM: Unknown
<220> FEATURE:
<223> OTHER INFORMATION: Salmonella bacteriophage S16

<400> SEQUENCE: 4
atggcgagtt ttggtaacgg atataccaaa actcaagtta tttctgaaaa taattccatc      60
aaatacaaaa tttcatttgc tgcggggtcg gttttttcga cccccttcttc tgcttatttt    120 acctttcagg ataatccaat aggtaaccag caagatggtg ctggtataaa tatcagagtt    180
tttaatccag cattgaatac tgtatctgct aagaaaacat ttttattgac acccaatgat    240
aatgacccag gcaatagagc attcattgaa tatttgtcaa catttactca agataatact    300
aacttgttaa tattcaccac atcaggtgat attaaaacga gcaatttagt agagaataaa    360

```
tttaagtcca tttattcaac tatgtggcca aataaatgga tgacatctcg gtattcatgt      420
acttattgcg gtttattttc aataaaaaat aataaaatta ttgccgaaaa cgtaacatat      480
tctgatggag ttcttcggga cgaagacatc agacctgctt tagaattcgt ttatgataaa      540
gctgatgata ttggagctac cgggttttct tatagagctg ttgaagattt tgaagaatac      600
actagttccg cagcaacaat aaaaagatat ccagttgatt ctgcttcggg cgtagaaatt      660
agctcaattg gaatatctcc tggcgatatt ctgttctggt catttgaatt tttgcatgga      720
gataatattc cgccggaagt tccagggaca aataataata aataagaat agaaataaga       780 tggttaaatt catctggagg gtggattaaa tcagttaatg ttgactctaa ccacgcaaat      840
gctggaaaat ggatacagca cgaacaaact gttgaagtcc ctgctgacgc tgcccggata      900
gttattcttg cttctaaaac tactccaact gatacggtcg gtactggagg tgttcgtagt      960
atgattttaa ctgaaacttc gcgagctact gaggcattaa cttctccatc tgcgatatca     1020
gttaatggta ttcgtttgaa tactatagtt tcaggagata acccgacgct gcttattta      1080 cctgctaacg aagttgattc aactggcaaa ccattaccag gtgaagatgt ttcaggaata     1140
atttacagtt ctgattggag agagtttgag aaaaatattt aa                       1182
```

<210> SEQ ID NO 5
<211> LENGTH: 393
<212> TYPE: PRT
<213> ORGANISM: Unknown
<220> FEATURE:
<223> OTHER INFORMATION: Salmonella bacteriophage S16

<400> SEQUENCE: 5

```
Met Ala Ser Phe Gly Asn Gly Tyr Thr Lys Thr Gln Val Ile Ser Glu
1               5                   10                  15

Asn Asn Ser Ile Lys Tyr Lys Ile Ser Phe Ala Ala Gly Ser Val Phe
            20                  25                  30

Ser Thr Pro Ser Ser Ala Tyr Phe Thr Phe Gln Asp Asn Pro Ile Gly
        35                  40                  45

Asn Gln Gln Asp Gly Ala Gly Ile Asn Ile Arg Val Phe Asn Pro Ala
    50                  55                  60

Leu Asn Thr Val Ser Ala Lys Lys Thr Phe Leu Leu Thr Pro Asn Asp
65                  70                  75                  80

Asn Asp Pro Gly Asn Arg Ala Phe Ile Glu Tyr Leu Ser Thr Phe Thr
                85                  90                  95

Gln Asp Asn Thr Asn Leu Leu Ile Phe Thr Thr Ser Gly Asp Ile Lys
            100                 105                 110

Thr Ser Asn Leu Val Glu Asn Lys Phe Lys Ser Ile Tyr Ser Thr Met
        115                 120                 125

Trp Pro Asn Lys Trp Met Thr Ser Arg Tyr Ser Cys Thr Cys Gly
    130                 135                 140

Leu Phe Ser Ile Lys Asn Asn Lys Ile Ile Ala Glu Asn Val Thr Tyr
145                 150                 155                 160

Ser Asp Gly Val Leu Arg Asp Glu Asp Ile Arg Pro Ala Leu Glu Phe
                165                 170                 175

Val Tyr Asp Lys Ala Asp Asp Ile Gly Ala Thr Gly Phe Ser Tyr Arg
            180                 185                 190

Ala Val Glu Asp Phe Glu Glu Tyr Thr Ser Ser Ala Ala Thr Ile Lys
        195                 200                 205

Arg Tyr Pro Val Asp Ser Ala Ser Gly Val Glu Ile Ser Ser Ile Gly
    210                 215                 220
```

```
Ile Ser Pro Gly Asp Ile Leu Phe Trp Ser Phe Glu Phe Leu His Gly
225                 230                 235                 240

Asp Asn Ile Pro Pro Glu Val Pro Gly Thr Asn Asn Lys Ile Arg
            245                 250                 255

Ile Glu Ile Arg Trp Leu Asn Ser Ser Gly Gly Trp Ile Lys Ser Val
            260                 265                 270

Asn Val Asp Ser Asn His Ala Asn Ala Gly Lys Trp Ile Gln His Glu
            275                 280                 285

Gln Thr Val Glu Val Pro Ala Asp Ala Arg Ile Val Ile Leu Ala
        290                 295                 300

Ser Lys Thr Thr Pro Thr Asp Thr Val Gly Thr Gly Val Arg Ser
305                 310                 315                 320

Met Ile Leu Thr Glu Thr Ser Arg Ala Thr Glu Ala Leu Thr Ser Pro
                325                 330                 335

Ser Ala Ile Ser Val Asn Gly Ile Arg Leu Asn Thr Ile Val Ser Gly
                340                 345                 350

Asp Asn Pro Thr Leu Leu Ile Leu Pro Ala Asn Glu Val Asp Ser Thr
            355                 360                 365

Gly Lys Pro Leu Pro Gly Glu Asp Val Ser Gly Ile Ile Tyr Ser Ser
    370                 375                 380

Asp Trp Arg Glu Phe Glu Lys Asn Ile
385                 390

<210> SEQ ID NO 6
<211> LENGTH: 666
<212> TYPE: DNA
<213> ORGANISM: Unknown
<220> FEATURE:
<223> OTHER INFORMATION: Salmonella bacteriophage S16

<400> SEQUENCE: 6
atggccgatt taaaagcaaa tagtacagta ggcggagctc cgatatggca taaaggaaat      60
tttcctttgt ctccggtagg tgatacgcta ctttataaga ctttcaaagt ctatacagaa     120
ttcgataaac tcaagcagt  agataacgat tttgtttcta aagccgctgg aggagaatat     180
ttaaaaaacg ttaattttaa agaaggctta tcatttagcg acaaagatgg agcttctgtt     240
tttattggtg ttcctaaaaa tactacagca acagctactt ataccgcatc aataaaatta     300
accggacaat tcgctttaga aactcctgat aataaaccat ttatcatatt tgacccaaac     360
gagtcattta gccctgatgt atatcgctta actgttatgg gtgatatgct ttctcgtcaa     420
atttatgatg aatccggaag agttttttct cctgggaata ctccgtcaaa agcgcaagtt     480
gggttagatt tagtcgataa cgctaagcaa gttcaacttg aaaaatctgg tgttcaaaca     540
atgaccgggg ttttggctgc tccaaacttt ataagtacca atccggcaac ggcagataat     600
catgtagctc gttttgacca gattgtaata aaagactcaa ttcaagattt tggatattat     660
agttaa                                                                666

<210> SEQ ID NO 7
<211> LENGTH: 221
<212> TYPE: PRT
<213> ORGANISM: Unknown
<220> FEATURE:
<223> OTHER INFORMATION: Salmonella bacteriophage S16

<400> SEQUENCE: 7

Met Ala Asp Leu Lys Ala Asn Ser Thr Val Gly Gly Ala Pro Ile Trp
```

```
1               5                   10                  15
His Lys Gly Asn Phe Pro Leu Ser Pro Val Gly Asp Thr Leu Leu Tyr
            20                  25                  30

Lys Thr Phe Lys Val Tyr Thr Glu Phe Asp Lys Pro Gln Ala Val Asp
            35                  40                  45

Asn Asp Phe Val Ser Lys Ala Ala Gly Gly Glu Tyr Leu Lys Asn Val
50                      55                  60

Asn Phe Lys Glu Gly Leu Ser Phe Ser Asp Lys Asp Gly Ala Ser Val
65                      70                  75                  80

Phe Ile Gly Val Pro Lys Asn Thr Thr Ala Thr Ala Thr Tyr Thr Ala
            85                  90                  95

Ser Ile Lys Leu Thr Gly Gln Phe Ala Leu Glu Thr Pro Asp Asn Lys
            100                 105                 110

Pro Phe Ile Ile Phe Asp Pro Asn Glu Ser Phe Ser Pro Asp Val Tyr
            115                 120                 125

Arg Leu Thr Val Met Gly Asp Met Leu Ser Arg Gln Ile Tyr Asp Glu
130                     135                 140

Ser Gly Arg Val Phe Ser Pro Gly Asn Thr Pro Ser Lys Ala Gln Val
145                     150                 155                 160

Gly Leu Asp Leu Val Asp Asn Ala Lys Gln Val Leu Glu Lys Ser
            165                 170                 175

Gly Val Gln Thr Met Thr Gly Val Leu Ala Ala Pro Asn Phe Ile Ser
            180                 185                 190

Thr Asn Pro Ala Thr Ala Asp Asn His Val Ala Arg Phe Asp Gln Ile
            195                 200                 205

Val Ile Lys Asp Ser Ile Gln Asp Phe Gly Tyr Tyr Ser
            210                 215                 220

<210> SEQ ID NO 8
<211> LENGTH: 2250
<212> TYPE: DNA
<213> ORGANISM: Unknown
<220> FEATURE:
<223> OTHER INFORMATION: Salmonella bacteriophage S16

<400> SEQUENCE: 8
atggctacta taaaacaaat acaatttaaa agaactaaag tagcaggctc tcgtcctact      60
gccgctcaac tcgctgaagg cgaacttgct attaacttaa agaccgcac tattttcacg     120
aaagacgatt tgaaccaaat cattgattta ggttttgcaa aaggcggtga agtatcagga    180
gatatcacgc agattggtaa ttatacccaa actgggaact ataatttaac cggcgatgct    240
actatatcag gcaaaactac tacaagcaca ctggatgttg gtctgtttc agatctaaga     300
cagacaaact ttagaccagt attaagcaca acaactggtt ctaattttat tatatcaaac    360
tctggcggct tgattaaacc aattactttg acggtagaag gcacagctac aagttcaaac    420
actattctgc gccattcagt tgatactact gtagcagctt ctggatttat cgattcaatt    480
aatgtttctt taaatccgac ggacggcgct cttgttacag ctctcaatgg tactgtgaat    540
atcggtagtt cccttaaaac tcctaaaact tcagtttctg gcgcggaaac tgctttggga    600
gattatagta tttcaatcgg tgataatgat acaggattta atggaattc tgatggtgta     660
ttcagcttag ttactgacag taattcaatt tatacatact ctcgtgatag gacatattct    720
aaccgtccaa caatttccg gtatacgtct gactttgatg ctacgacacc tgctttagct    780
ccgccaggca catggttagc ttcagttgaa actgcaatag acggtaacgc ttacggcgat    840
```

-continued

```
ggaatgagct atctcggtta taaagatacc gcaggttata gttttatttt ccgcggcggc    900
ggcacttttta acgtagcttc taaaggtgga tttaatgtag acacagctgc ggcttttgcc    960
aaaacggttg atgtatctga tattctaaca tgcagctcta ttattaaagc taaaggccca   1020
ggtcaagttg atgttactag tgctggtaat atcgcacttg gtggaactat tcaatgggtg   1080
ccttcgtata tgagcggaag cccaaataga gcacgagata caatagctac agcagcttgg   1140
ggcgatgccg accaacgaat taacgtatta gaaacatctg acccgcatgg ttggtggtat   1200
tatatacagc gcgcaggttc tggaagttct tctcctacgg gaatagaagg gcgagtcaat   1260
ggctcttggc aggcatctga tttaatttct gataatactc taagagtagc tggagctttc   1320
acttgtacta aagaaactc cgcaggatgg ggtgataacg ctggatggta tgctggagca   1380
acaccagtag tagctaacca aggaaacgtt caagaaatgg accccggtgt aggcggtttt   1440
tatcctggat ttgctcaata taactataat ggcactggat ggaaccaagc atttgttctg   1500
gggttactag gccaaggtgt tcagagatgg cgtcgtggtg tattagctct tagaggcgat   1560
ggccctgttg atgctggaca acaaattgct cgttggtatt ttagtcaaga agacggaagt   1620
ttggaatcag aaggtccgct taaagctcct agtgttcaag ctggacaaat aacatctttt   1680
ggtgtaaacg ttacaaacgc gttaggcagt gcgtctatag ctattggcga taacgatacc   1740
ggattgcgct ggggcggcga tggtatcgtt caaattgtag ctaataacgc tatcgtaggc   1800
ggatggaatt caacagatat ttttactgaa gctggtaaac atataacatc caatggaaat   1860
ttaaatcaat ggggcggagg cgcaatttat tgtagagacc ttaatgttag ttccgacaga   1920
agaattaaga aagacataaa agcatttgaa atcccgtag atattttaag cactataggc   1980
ggttatactt atcttattga aaaggatttt aatgaagatg gaagtcaggc ttacgaagag   2040
tccgctggat taattgctca agaagtagaa gctgttcttc ctcgtttagt taaaatatcc   2100
aatgatggaa caaagatgt taaaagactt aattataatg gtataacagc tttaaatact   2160
gctgctataa atgtacatac taaagaaatt aatgagctca aaaagcaatt aaaagagctt   2220
aaagacattg ttaagttttt aactaaataa                                     2250
```

<210> SEQ ID NO 9
<211> LENGTH: 749
<212> TYPE: PRT
<213> ORGANISM: Unknown
<220> FEATURE:
<223> OTHER INFORMATION: Salmonella bacteriophage S16

<400> SEQUENCE: 9

```
Met Ala Thr Ile Lys Gln Ile Gln Phe Lys Arg Thr Lys Val Ala Gly
1               5                   10                  15

Ser Arg Pro Thr Ala Ala Gln Leu Ala Glu Gly Glu Leu Ala Ile Asn
            20                  25                  30

Leu Lys Asp Arg Thr Ile Phe Thr Lys Asp Asp Leu Asn Gln Ile Ile
        35                  40                  45

Asp Leu Gly Phe Ala Lys Gly Gly Glu Val Ser Gly Asp Ile Thr Gln
    50                  55                  60

Ile Gly Asn Tyr Thr Gln Thr Gly Asn Tyr Asn Leu Thr Gly Asp Ala
65                  70                  75                  80

Thr Ile Ser Gly Lys Thr Thr Thr Ser Thr Leu Asp Val Gly Ser Val
                85                  90                  95

Ser Asp Leu Arg Gln Thr Asn Phe Arg Pro Val Leu Ser Thr Thr Thr
            100                 105                 110
```

```
Gly Ser Asn Phe Ile Ile Ser Asn Ser Gly Leu Ile Lys Pro Ile
            115                 120                 125

Thr Leu Thr Val Glu Gly Thr Ala Thr Ser Ser Asn Thr Ile Leu Arg
    130                 135                 140

His Ser Val Asp Thr Thr Val Ala Ala Ser Gly Phe Ile Asp Ser Ile
145                 150                 155                 160

Asn Val Ser Leu Asn Pro Thr Asp Gly Ala Leu Val Thr Ala Leu Asn
                165                 170                 175

Gly Thr Val Asn Ile Gly Ser Ser Leu Lys Thr Pro Lys Leu Ser Val
            180                 185                 190

Ser Gly Ala Glu Thr Ala Leu Gly Asp Tyr Ser Ile Ser Ile Gly Asp
        195                 200                 205

Asn Asp Thr Gly Phe Lys Trp Asn Ser Asp Gly Val Phe Ser Leu Val
    210                 215                 220

Thr Asp Ser Asn Ser Ile Tyr Thr Tyr Ser Arg Asp Arg Thr Tyr Ser
225                 230                 235                 240

Asn Arg Pro Thr Asn Phe Arg Tyr Thr Ser Asp Phe Asp Ala Thr Thr
                245                 250                 255

Pro Ala Leu Ala Pro Pro Gly Thr Trp Leu Ala Ser Val Glu Thr Ala
            260                 265                 270

Ile Asp Gly Asn Ala Tyr Gly Asp Gly Met Ser Tyr Leu Gly Tyr Lys
        275                 280                 285

Asp Thr Ala Gly Tyr Ser Phe Tyr Phe Arg Gly Gly Thr Phe Asn
    290                 295                 300

Val Ala Ser Lys Gly Gly Phe Asn Val Asp Thr Ala Ala Ala Phe Ala
305                 310                 315                 320

Lys Thr Val Asp Val Ser Asp Ile Leu Thr Cys Ser Ser Ile Ile Lys
                325                 330                 335

Ala Lys Gly Pro Gly Gln Val Asp Val Thr Ser Ala Gly Asn Ile Ala
            340                 345                 350

Leu Gly Gly Thr Ile Gln Trp Val Pro Ser Tyr Met Ser Gly Ser Pro
        355                 360                 365

Asn Arg Ala Arg Asp Thr Ile Ala Thr Ala Ala Trp Gly Asp Ala Asp
    370                 375                 380

Gln Arg Ile Asn Val Leu Glu Thr Ser Asp Pro His Gly Trp Trp Tyr
385                 390                 395                 400

Tyr Ile Gln Arg Ala Gly Ser Gly Ser Ser Ser Pro Thr Gly Ile Glu
                405                 410                 415

Gly Arg Val Asn Gly Ser Trp Gln Ala Ser Asp Leu Ile Ser Asp Asn
            420                 425                 430

Thr Leu Arg Val Ala Gly Ala Phe Thr Cys Thr Arg Arg Asn Ser Ala
        435                 440                 445

Gly Trp Gly Asp Asn Ala Gly Trp Tyr Ala Gly Ala Thr Pro Val Val
    450                 455                 460

Ala Asn Gln Gly Asn Val Gln Glu Met Asp Pro Gly Val Gly Gly Phe
465                 470                 475                 480

Tyr Pro Gly Phe Ala Gln Tyr Asn Tyr Asn Gly Thr Gly Trp Asn Gln
                485                 490                 495

Ala Phe Val Leu Gly Leu Leu Gly Gln Gly Val Gln Arg Trp Arg Arg
            500                 505                 510

Gly Val Leu Ala Leu Arg Gly Asp Gly Pro Val Asp Ala Gly Gln Gln
        515                 520                 525

Ile Ala Arg Trp Tyr Phe Ser Gln Glu Asp Gly Ser Leu Glu Ser Glu
```

```
Gly Pro Leu Lys Ala Pro Ser Val Gln Ala Gly Gln Ile Thr Ser Phe
545                 550                 555                 560

Gly Val Asn Val Thr Asn Ala Leu Gly Ser Ala Ser Ile Ala Ile Gly
                565                 570                 575

Asp Asn Asp Thr Gly Leu Arg Trp Gly Gly Asp Gly Ile Val Gln Ile
            580                 585                 590

Val Ala Asn Asn Ala Ile Val Gly Gly Trp Asn Ser Thr Asp Ile Phe
        595                 600                 605

Thr Glu Ala Gly Lys His Ile Thr Ser Asn Gly Asn Leu Asn Gln Trp
    610                 615                 620

Gly Gly Gly Ala Ile Tyr Cys Arg Asp Leu Asn Val Ser Ser Asp Arg
625                 630                 635                 640

Arg Ile Lys Lys Asp Ile Lys Ala Phe Glu Asn Pro Val Asp Ile Leu
                645                 650                 655

Ser Thr Ile Gly Gly Tyr Thr Tyr Leu Ile Glu Lys Gly Phe Asn Glu
            660                 665                 670

Asp Gly Ser Gln Ala Tyr Glu Glu Ser Ala Gly Leu Ile Ala Gln Glu
        675                 680                 685

Val Glu Ala Val Leu Pro Arg Leu Val Lys Ile Ser Asn Asp Gly Thr
    690                 695                 700

Lys Asp Val Lys Arg Leu Asn Tyr Asn Gly Ile Thr Ala Leu Asn Thr
705                 710                 715                 720

Ala Ala Ile Asn Val His Thr Lys Glu Ile Asn Glu Leu Lys Lys Gln
                725                 730                 735

Leu Lys Glu Leu Lys Asp Ile Val Lys Phe Leu Thr Lys
            740                 745

<210> SEQ ID NO 10
<211> LENGTH: 750
<212> TYPE: DNA
<213> ORGANISM: Unknown
<220> FEATURE:
<223> OTHER INFORMATION: Salmonella bacteriophage S16

<400> SEQUENCE: 10
atggcagttc aaggaccttg ggtaggttcg tcttatgtcg ctgaaacagg tcaaaactgg      60
gcctcattag cggcgaatga attaagagta acggagaggc ccttttggat ttcctcattt     120
atagggcgct ctaaagaaga aatttgggaa tggactggag aaaatcacag tttcaacaaa     180
gattggttaa taggcgaact tcgcaataga ggtggtactc ctgtagtaat taatataaga     240
gctcatcaag tgtcttatac tccaggcgca cctttatttg aatttcccgg agaccttcca     300
aatgcatata ttcacttaa catttatgca gatatatatg gaagaggtgg tactggtgga     360
gttgcttatt taggcggaaa ccccggcgga gactgtattc ataattggat tggaaacaga     420
cttagaataa acaaccaagg ctggatttgt ggtggcggag gcggcggcgg tggctttcgt     480
gttggacata ctgaagctgg tggtggtggc ggacgacctt gggagcggg cggagtttca     540
agcttaaatc taaacggaga caatgctact ttgggtgctc ccgggcgagg atatcaactt     600
ggaaacgatt atgcaggtaa cggcggcgat gtcggtaatc ctggttcagc tagttcagcc     660
gaaatgggcg gtggagcggc tggacgagct gttgtaggaa cctcacctca atggataaat     720
gttggtaata ttgctggttc ttggttataa                                       750

<210> SEQ ID NO 11
```

<211> LENGTH: 249
<212> TYPE: PRT
<213> ORGANISM: Unknown
<220> FEATURE:
<223> OTHER INFORMATION: Salmonella bacteriophage S16

<400> SEQUENCE: 11

```
Met Ala Val Gln Gly Pro Trp Val Gly Ser Tyr Val Ala Glu Thr
1               5                   10                  15

Gly Gln Asn Trp Ala Ser Leu Ala Ala Asn Glu Leu Arg Val Thr Glu
            20                  25                  30

Arg Pro Phe Trp Ile Ser Ser Phe Ile Gly Arg Ser Lys Glu Glu Ile
        35                  40                  45

Trp Glu Trp Thr Gly Glu Asn His Ser Phe Asn Lys Asp Trp Leu Ile
50                  55                  60

Gly Glu Leu Arg Asn Arg Gly Gly Thr Pro Val Val Ile Asn Ile Arg
65                  70                  75                  80

Ala His Gln Val Ser Tyr Thr Pro Gly Ala Pro Leu Phe Glu Phe Pro
                85                  90                  95

Gly Asp Leu Pro Asn Ala Tyr Ile Thr Leu Asn Ile Tyr Ala Asp Ile
            100                 105                 110

Tyr Gly Arg Gly Gly Thr Gly Gly Val Ala Tyr Leu Gly Gly Asn Pro
        115                 120                 125

Gly Gly Asp Cys Ile His Asn Trp Ile Gly Asn Arg Leu Arg Ile Asn
130                 135                 140

Asn Gln Gly Trp Ile Cys Gly Gly Gly Gly Gly Gly Gly Phe Arg
145                 150                 155                 160

Val Gly His Thr Glu Ala Gly Gly Gly Gly Arg Pro Leu Gly Ala
                165                 170                 175

Gly Gly Val Ser Ser Leu Asn Leu Asn Gly Asp Asn Ala Thr Leu Gly
            180                 185                 190

Ala Pro Gly Arg Gly Tyr Gln Leu Gly Asn Asp Tyr Ala Gly Asn Gly
        195                 200                 205

Gly Asp Val Gly Asn Pro Gly Ser Ala Ser Ala Glu Met Gly Gly
    210                 215                 220

Gly Ala Ala Gly Arg Ala Val Val Gly Thr Ser Pro Gln Trp Ile Asn
225                 230                 235                 240

Val Gly Asn Ile Ala Gly Ser Trp Leu
                245
```

<210> SEQ ID NO 12
<211> LENGTH: 228
<212> TYPE: DNA
<213> ORGANISM: Unknown
<220> FEATURE:
<223> OTHER INFORMATION: Salmonella bacteriophage S16

<400> SEQUENCE: 12

```
atgactgata aaattaaaca gcttgaagct actgtaactg ttcttaaagc tcgtcttttt      60
gatttgaatg agcaatttgc tgaaactact aacacggttc agtcgctaag cgatttggta     120
agtaaaattg tagaaaaaat cggtctagaa gttgttgaag gccaagtgac ctttgaagct     180
attcttgaaa aaattgatga gttaaccgca acgccggatg atgaatga                  228
```

<210> SEQ ID NO 13
<211> LENGTH: 75
<212> TYPE: PRT
<213> ORGANISM: Unknown

<220> FEATURE:
<223> OTHER INFORMATION: Salmonella bacteriophage S16

<400> SEQUENCE: 13

```
Met Thr Asp Lys Ile Lys Gln Leu Glu Ala Thr Val Thr Val Leu Lys
1               5                   10                  15

Ala Arg Leu Phe Asp Leu Asn Glu Gln Phe Ala Glu Thr Thr Asn Thr
            20                  25                  30

Val Gln Ser Leu Ser Asp Leu Val Ser Lys Ile Val Glu Lys Ile Gly
        35                  40                  45

Leu Glu Val Val Glu Gly Gln Val Thr Phe Glu Ala Ile Leu Glu Lys
    50                  55                  60

Ile Asp Glu Leu Thr Ala Thr Pro Asp Asp Glu
65                  70                  75
```

<210> SEQ ID NO 14
<211> LENGTH: 501
<212> TYPE: DNA
<213> ORGANISM: Unknown
<220> FEATURE:
<223> OTHER INFORMATION: Salmonella bacteriophage S16

<400> SEQUENCE: 14

```
atgaacattt ttgacatgct tcgcatcgac gaaggcttaa aacttgaaat ttataaagat    60
actgaaggtt tttggaccgt cggtataggt catcttttga ctaaaaaccc taataaatcg   120
gtagctatta gcgagttgga ccgtcttgtt ggccgggcta catccggtaa aattactaaa   180
gcggaagctg aaaaaatttt taatacagac gttgaaaaag ctatttcagg aattcttttct  240
aattctgtat tacgccccgt atataattct tttattggtg atgaacctcg tctggctgct   300
ctgattaaca tggttttttca atgggtgta gctggtgtag cgggttttaa aaattctatg   360
gctttactaa aagctaaaga ttgggataga gctgctgtaa atttagctca atctaaatgg   420
tacagacaaa caactaatcg cgcccgccgc gttattaaaa cttttgaaac aggaacttgg   480
aaagcatatg aaaacttatg a                                             501
```

<210> SEQ ID NO 15
<211> LENGTH: 166
<212> TYPE: PRT
<213> ORGANISM: Unknown
<220> FEATURE:
<223> OTHER INFORMATION: Salmonella bacteriophage S16

<400> SEQUENCE: 15

```
Met Asn Ile Phe Asp Met Leu Arg Ile Asp Glu Gly Leu Lys Leu Glu
1               5                   10                  15

Ile Tyr Lys Asp Thr Glu Gly Phe Trp Thr Val Gly Ile Gly His Leu
            20                  25                  30

Leu Thr Lys Asn Pro Asn Lys Ser Val Ala Ile Ser Glu Leu Asp Arg
        35                  40                  45

Leu Val Gly Arg Ala Thr Ser Gly Lys Ile Thr Lys Ala Glu Ala Glu
    50                  55                  60

Lys Ile Phe Asn Thr Asp Val Glu Lys Ala Ile Ser Gly Ile Leu Ser
65                  70                  75                  80

Asn Ser Val Leu Arg Pro Val Tyr Asn Ser Phe Ile Gly Asp Glu Pro
                85                  90                  95

Arg Leu Ala Ala Leu Ile Asn Met Val Phe Gln Met Gly Val Ala Gly
                100                 105                 110
```

```
Val Ala Gly Phe Lys Asn Ser Met Ala Leu Leu Lys Ala Lys Asp Trp
            115                 120                 125

Asp Arg Ala Ala Val Asn Leu Ala Gln Ser Lys Trp Tyr Arg Gln Thr
        130                 135                 140

Thr Asn Arg Ala Arg Arg Val Ile Lys Thr Phe Glu Thr Gly Thr Trp
145                 150                 155                 160

Lys Ala Tyr Glu Asn Leu
                165
```

<210> SEQ ID NO 16
<211> LENGTH: 1137
<212> TYPE: DNA
<213> ORGANISM: Salmonella typhimurium

<400> SEQUENCE: 16

```
atgaaagtta aagtactgtc cctcctggta ccagctctgc tggtggcggg cgcagcgaat      60
gcggctgaaa tttataataa agacggcaac aaattagacc tgtttggtaa agttgatggc     120
ctgcactact tctctgacga caaaggcagc gatggcgacc agacctacat gcgtatcggc     180
ttcaaaggcg aaacgcaggt taacgatcag ctgaccggtt atggccagtg gaatatcag     240
attcagggca accagactga aggcagcaac gactcctgga cgcgtgtggc gtttgcgggt     300
ctgaaattcg ctgatgcagg ttccttcgat tatggtcgta actacggcgt aacctatgac     360
gtgacctcct ggaccgacgt tctgccggag ttcggcggcg acacctacgg cgctgacaac     420
tttatgcagc agcgtggtaa cggctatgct acctaccgta acaccgactt cttcggcctg     480
gtggatggtc tggacttcgc gttacagtat cagggcaaaa acggcagcgt gagcggtgaa     540
aacaccaacg tcgcagcct gctgaaccag aacggcgacg ttacggcgg atcgctgact     600
tatgcaatcg cgaaggctt ctctgtcggt ggcgctatca ccacgtctaa acgtactgcc     660
gatcagaaca caccgctaa cgctcgcctg tatggtaacg gcgatcgcgc cacggtttac     720
accggcggcc tgaaatacga tgcgaacaac atctatctgg cagcgcagta ttctcagacc     780
tataacgcaa cccgttttgg tacctctaac ggtagcaacc cgtccacctc ttacggtttt     840
gccaacaaag cgcagaactt tgaagtggtt gctcagtacc agttcgactt tggtctgcgt     900
ccgtctgtgg cttacctgca gtctaaaggt aaggacatca gcaacggtta cggcgccagc     960
tatggcgacc aggacatcgt aaaatacgtt gatgtcggcg cgacttacta cttcaacaaa    1020
aacatgtcca cctatgttga ttacaaaatc aacctgctgg ataaaaacga ctttacccgc    1080
gatgcgggca tcaacaccga cgacatcgta gcgctgggtc tggtttacca gttctaa       1137
```

<210> SEQ ID NO 17
<211> LENGTH: 378
<212> TYPE: PRT
<213> ORGANISM: Salmonella typhimurium

<400> SEQUENCE: 17

```
Met Lys Val Lys Val Leu Ser Leu Leu Val Pro Ala Leu Leu Val Ala
1               5                   10                  15

Gly Ala Ala Asn Ala Ala Glu Ile Tyr Asn Lys Asp Gly Asn Lys Leu
            20                  25                  30

Asp Leu Phe Gly Lys Val Asp Gly Leu His Tyr Phe Ser Asp Asp Lys
        35                  40                  45

Gly Ser Asp Gly Asp Gln Thr Tyr Met Arg Ile Gly Phe Lys Gly Glu
    50                  55                  60

Thr Gln Val Asn Asp Gln Leu Thr Gly Tyr Gly Gln Trp Glu Tyr Gln
```

-continued

```
            65                  70                  75                  80
Ile Gln Gly Asn Gln Thr Glu Gly Ser Asn Asp Ser Trp Thr Arg Val
                85                  90                  95

Ala Phe Ala Gly Leu Lys Phe Ala Asp Ala Gly Ser Phe Asp Tyr Gly
               100                 105                 110

Arg Asn Tyr Gly Val Thr Tyr Asp Val Thr Ser Trp Thr Asp Val Leu
               115                 120                 125

Pro Glu Phe Gly Gly Asp Thr Tyr Gly Ala Asp Asn Phe Met Gln Gln
               130                 135                 140

Arg Gly Asn Gly Tyr Ala Thr Tyr Arg Asn Thr Asp Phe Phe Gly Leu
145                150                 155                 160

Val Asp Gly Leu Asp Phe Ala Leu Gln Tyr Gln Gly Lys Asn Gly Ser
               165                 170                 175

Val Ser Gly Glu Asn Thr Asn Gly Arg Ser Leu Leu Asn Gln Asn Gly
               180                 185                 190

Asp Gly Tyr Gly Gly Ser Leu Thr Tyr Ala Ile Gly Glu Gly Phe Ser
               195                 200                 205

Val Gly Gly Ala Ile Thr Thr Ser Lys Arg Thr Ala Asp Gln Asn Asn
      210                 215                 220

Thr Ala Asn Ala Arg Leu Tyr Gly Asn Gly Asp Arg Ala Thr Val Tyr
225                230                 235                 240

Thr Gly Gly Leu Lys Tyr Asp Ala Asn Asn Ile Tyr Leu Ala Ala Gln
               245                 250                 255

Tyr Ser Gln Thr Tyr Asn Ala Thr Arg Phe Gly Thr Ser Asn Gly Ser
               260                 265                 270

Asn Pro Ser Thr Ser Tyr Gly Phe Ala Asn Lys Ala Gln Asn Phe Glu
               275                 280                 285

Val Val Ala Gln Tyr Gln Phe Asp Phe Gly Leu Arg Pro Ser Val Ala
      290                 295                 300

Tyr Leu Gln Ser Lys Gly Lys Asp Ile Ser Asn Gly Tyr Gly Ala Ser
305                310                 315                 320

Tyr Gly Asp Gln Asp Ile Val Lys Tyr Val Asp Val Gly Ala Thr Tyr
               325                 330                 335

Tyr Phe Asn Lys Asn Met Ser Thr Tyr Val Asp Tyr Lys Ile Asn Leu
               340                 345                 350

Leu Asp Lys Asn Asp Phe Thr Arg Asp Ala Gly Ile Asn Thr Asp Asp
               355                 360                 365

Ile Val Ala Leu Gly Leu Val Tyr Gln Phe
      370                 375
```

BACTERIOPHAGE FOR BIOCONTROL OF *SALMONELLA* AND IN THE MANUFACTURING OR PROCESSING OF FOODS

CROSS REFERENCE TO RELATED APPLICATIONS

This application is a 35 U.S.C. § 371 national phase application of PCT/NL2013/050342, which was filed May 7, 2013, and claims the benefit of U.S. provisional patent application No. 61/643,420 filed May 7, 2012, and European patent application No. 12166986.5 filed May 7, 2012, all of which are incorporated herein by reference as if fully set forth.

The sequence listing filed with this application, titled "Sequence Listing," having a file size of 248,608 bytes, and created Nov. 6, 2014 is incorporated herein by reference as if fully set forth.

FIELD OF THE INVENTION

The invention relates to the field of microbiology, specifically to a bacteriophage, polypeptide and a corresponding polynucleotide, a nucleic acid molecule and/or vector and/or cell comprising such polynucleotide, a composition comprising said bacteriophage, polypeptide, polynucleotide, construct, vector and/or cell, preferably for preventing, treating or diagnosing contamination with and/or a condition in an individual related to *Salmonella*. The invention further relates to an antimicrobial composition for medical use, preferably for treating livestock, or for use as a food additive or as a disinfectant, or for detecting bacteria, preferably in a diagnostic application, wherein said antimicrobial composition comprises a bacteriophage, polypeptide, corresponding polynucleotide, construct and/or vector and/or cell comprising such polypeptide and/or composition according to the present invention.

BACKGROUND OF THE INVENTION

Members of *Salmonella enterica* are the causative agent of salmonellosis, one of the leading foodborne illnesses worldwide. *Salmonella enterica* is highly diverse, with more than 2'500 recognized serovars (Grimont and Weill, 2007). Many *Salmonella enterica* strains of various serovars contain antimicrobial resistance genes located on *Salmonella* genomic island 1 (SGI1). Due to the great number of different serovars and strains, biocontrol of *Salmonella enterica* is especially challenging.

There is thus a need for new antimicrobials with improved characteristics such as being specific for *Salmonella enterica* while targeting a broad host range within that species.

DESCRIPTION OF THE INVENTION

Bacteriophages, or phages for short, are viruses solely infecting prokaryotes. They are ubiquitously distributed in the environment and are the most abundant self-replicating entities on earth (estimated at $10^{32}$ (Rohwer and Edwards 2002; Brussow 2005)).

Provided here is a novel isolated bacteriophage named Phage S16 belonging to the order Caudovirales. Phage S16 has a contractile tail, which is the defining morphological feature of the Myoviridae family Phage S16 is the first strictly virulent, non-toxic broad host range T-even like bacteriophage solely infecting *Salmonella* bacteria ever described. Phage S16 lacks any kind of virulence factors as is the case for other T-even phages described in the literature. Phage S16 is a new member of the genus of T4-like viruses, belonging to the T-even type of subgroup and is the first fully characterized member of the T4-like phages limited to infecting *Salmonella*. Phage S16 has been deposited under the conditions of the Budapest Treaty at the CBS Fungal Biodiversity Centre at the Uppsalalaan 8, 3584 CT Utrecht, The Netherlands, on Sep. 6, 2011 (deposit number CBS 130493).

The T-even type of bacteriophages are known in the art to be characterized by a strictly lytic (virulent) life style, degradation of the host chromosome, and broad host ranges against the target species.

The inventors surprisingly found that the host range of this novel S16 bacteriophage was found to be even broader than the only broad host range bacteriophage known to date specific for and infecting most serovars within the genus *Salmonella*, Felix O1. The inventors found that 25 of the 32 *Salmonella* strains and 13 of the 14 LPS mutants of S. Tm LT2 tested were infected by Phage S16. The genome sequence of Phage S16 has been determined and annotated (Table 6).

The DNA modification system of Phage S16 renders its genome immune to many common restriction systems, giving it a further advantage over Felix O1. A phage's receptor binding protein and receptor on the host cell are its key characteristics. For Phage S16, these have been identified as the distal subunit of the long tail fibre comprising a single protein gp38 protein (SEQ ID NO: 11, encoded by SEQ ID NO: 10) located at the tip of a protein gp37 (SEQ ID NO: 9, encoded by SEQ ID NO: 8) trimer; and outer membrane protein C (OmpC, SEQ ID NO: 17, encoded by SEQ ID NO: 16), respectively. This distal subunit of the long tail fibre, being the minimal structure required for binding OmpC, comprises a single gp38 protein located at the tip of a gp37 protein trimer. The receptor binding characteristics are akin to those of phage T4, while the receptor binding protein itself is structurally more closely related to that of phage T2, where tail fibre and chaperone protein gp38 is also attached to gp37 in the mature tail fibre, enabling Phage S16, in contrast to Felix O1 which requires the terminal N-acetylglucosamine residue of the outer lipopolysaccharide (LPS) core for infection (Lindberg, 1967; Lindberg and Holme, 1969), to also infect deep rough strains. Deep rough strains are known in the art to be strains carrying a relatively common deep rough mutation resulting in a deficient lipopolysaccharide. Phage S16 has been found not to infect any strains not belonging to the genus *Salmonella*. The inventors have found that none of the 6 *E. coli* strains or 25 apathogenic isolates were sensitive to Phage S16. Phage S16 infects all *Salmonella* species and subspecies but none of the 28 tested *Escherichia* (including *E. coli* O157:H7; National Center for Enterobacteria (NEN7), further designation: N06-1382), *Cronobacter* (43 strains), *Enterobacter* (4 strains), *Citrobacter* (1 strain), *Klebsiella* (1 strain), *Vibrio* (1 strain), *Campylobacter* (1 strain) and *Pseudomonas* (3 strains) strains tested. No previous reports exist that show any T4-like phage infecting any *Salmonella* strain. Although other barriers may exist for successful infection with release of progeny phage, recognition and binding are essential for infection of a bacterial cell. The specificity of the phage-tail fibers for the receptor molecules and the low percentage identity between *Salmonella* ompC and *E. coli* ompC (the highest percentage identity of *Salmonella* ompC and *E. coli* ompC is <81%) may explain why none of the *E. coli* specific T4-like phages has ever been reported to infect *Salmonella* strains. The inventors found that the long tail fibres of Phage S16 specifically recognize *Salmonella* OmpC. Although Phage S16 shows no significant adsorption to an *E. coli* K12 wild type strain Phage S16 adsorption, can be transferred to this strain by substitution of ompC with the *Salmonella* homologue.

These findings suggest that Phage S16 is uniquely suited for combating *Salmonella*.

In a first aspect, the present invention provides a bacteriophage, preferably an isolated bacteriophage, belonging to the morphotype group of the Myoviridae, comprising at least one feature selected from the group consisting of:
the genome of the bacteriophage is at least 100 kbp,
the genome of the bacteriophage comprises at least one polynucleotide encoding a polypeptide with an amino acid sequence having at least 50% sequence identity with an amino acid sequence selected from the group consisting of SEQ ID NO: 3, 5, 7, 9 and 11,
the bacteriophage receptor is *Salmonella* outer membrane protein C (OmpC),
the bacteriophage can infect and lyse at least one *Salmonella* species.

Preferably, a bacteriophage according to the invention comprises at least 2, 3 and more preferably 4 of the above features.

A morphotype group is defined herein as a family of different subfamilies and genera.

Preferably a bacteriophage according to the present invention has a genome of preferably at least 100, 110, 120, 130, 140, 150, 155, 156, 157, 158, 159 or 160 kbp in size. More preferably, a bacteriophage according to the present invention has a genome of about 160 kbp, most preferably, the genome is 160,221 bp. Preferably, a bacteriophage according to the present invention has a genome comprising at least one polynucleotide encoding a polypeptide with an amino acid sequence having preferably at least 50, 55, 60, 65, 70, 75, 80, 81, 82, 83, 84, 85, 86, 87, 88, 89, 90, 91, 92, 93, 94, 95, 96, 97, 98, 99 or 100% sequence identity with one, preferably two, more preferably three and most preferably four different amino acid sequences selected from the group consisting of SEQ ID NO: 3, 5, 7, 9 and 11.

Preferably, the bacteriophage according to the present invention binds to *Salmonella* outer membrane protein C (OmpC). Binding of the bacteriophage of the present invention to OmpC can be assessed by any suitable binding assay known by a person skilled in the art. Preferably, binding or adsorption of a bacteriophage according to the present invention to a bacterial cell is tested via a pull down assay described more elaborately in Example 1. In brief, overnight cultures of a bacterial strain to be tested (1 mL, $OD_{600}$=1.0±0.05) are incubated with phage solution (10 µL, $10^9$ PFU/mL) or Luria-Bertani broth (LB, preferably comprising 10 g/L Soy peptone, 5 g/L yeast extract, 10 g/L NaCl and pH 7.5) as a control, incubated (10 min, RT) and centrifuged (20,000 g). Plaque Forming Units (PFU) in the supernatant are determined in triplicate and adsorption is calculated as the decrease in PFU in the supernatant. A bacteriophage of the present invention is said to bind to OmpC if a statistically relevant decrease, of preferably at least 10, 20, 30, 40, 45, 46, 47, 48, 49, 50, 60, 70, 80, 90, 95, 99 or 100% in adsorption is found using the pull down assay as defined herein using cells from ompC deletion mutant *Salmonella* strain, such as *Salmonella* Typhimurium DT7155 ΔompC, as compared to a cells of a wild type *Salmonella* strain, preferably *Salmonella* Typhimurium DT7155 wt.

Further preferred is a bacteriophage according to the present invention having a broad host range, preferably being able to infect and lyse at least 70, 80, 85, 90, 95 or 100% of all strains of *Salmonella* belonging to the group consisting of *Salmonella* Infantis, Kentucky, Newport, Stanley, Hadar, Virchow, *Typhimurium*, Enteritidis, Agona, Anatum, Senftenberg, Montevideo, Muenster, Javiana, Heidelberg, Derby, Wien, Porci, Braederup, Panama, Panama, Newington, Livingston, Bredeney, Dublin, Cholerasuis, Give, Amherstiana, Salmone, Tennessee, Blockley, Indiana and Java. Within the context of the present invention, a broad host range is meant at least 70% of the different strains identified herein are infected by a bacteriophage of the present invention.

Even more preferred is a bacteriophage according to the present invention wherein said bacteriophage is able to infect and lyse at least 70, 75, 80, 85, 90, 95 or 100% of *S. enterica*, strains. Preferably, a bacteriophage according to the present invention is able to infect and lyse *Salmonella* Re-LPS mutant (deep rough) strains, where only the inner core 2-keto-deoxy-d-octanoate (KDO) residues are present. This enables a bacteriophage according to the present invention, in contrast to Felix O1 which requires the terminal N-acetylglucosamine residue of the outer LPS core for infection (Lindberg, 1967; Lindberg and Holme, 1969), to also infect deep rough strains. Preferable, a bacteriophage according to the present invention is able to infect and lyse *Salmonella* LPS synthesis knock-out strains. Infection and lysis of a given bacterial strain with a bacteriophage according to the present invention can be quantitatively tested by any suitable assay known by the person skilled in the art. In a preferred assay, infection and subsequent lysis is tested by spot-on-the-lawn method described in detail in Example 1. In brief, Dry LB agar plates are flooded with 4 mL of log-phase culture of a bacterial strain to be tested, excess culture is removed and the agar plates are dried for 30 minutes (30° C.). 3 µL of phage dilutions $10^{-2}$ to $10^{-7}$ of production batches with a titer of $10^{11}$ PFU/ml in Sodium-Magnesium Buffer (comprising 5.8 g/L NaCl, 8 mM $MgSO_4$, 50 mM Tris-Cl, pH 7.4) are spotted onto plates and incubated overnight at 30° C. Within the context of the present invention, a bacteriophage is said to infect a strain if a single plaque can be observed in any one of the spots.

Preferably, the genome of a bacteriophage according to the present invention is resistant to at least 10, 15, 20, 25, 26, 27, 28, 29 30, 31 or 32 of the following restriction enzymes: Eco521 (EagI), DpnI, HhaI, Eco1051 (SanBI), HincII (HindII), KpnI, MluI, MpH1 1031 (NsiI), MspI (HpaII), NheI, SacI, SalI, OliI (AleI) Van91I (PflMI), PaeI (SphI), Eco881 (AvaI), MssI (PmeI), PvuII, PagI (BspHI), BseJI (BsaBI), Bsp68I (NruI), TaqI, EcoRI, EcoRV (Eco321), HindIII, PauI (BssHII), FspBI (BfaI) NdeI, MboI (all previous manufactured by Fermentas GmbH), Ssp1 (manufactured by GE Healthcare), PacI, SwaI (SmiI), XcmI, CaiI (last four manufactured by New England Biolabs). Restriction resistance can be tested using any suitable assay known by the person skilled in the art. Such an assay is described in detail in Example 1. In brief, purified phage DNA is incubated with a restriction enzyme at a concentration, temperature and for a time according to the manufacturer's instructions after which RFLP patterns can be analysed electrophoretically.

Preferably a bacteriophage of the present invention is none of the T4 like phages selected from the group consisting of J598, JS10, CC31 and F387/08.

For bacteriophages to be safely used in biocontrol of foodborne pathogens such as *Salmonella*, they need to be strictly virulent (avoiding lysogeny) and there must be no known virulence factors, toxins or antibiotic resistance genes encoded in the phage genome, and generalized transduction, the transfer of host DNA by phage particles, must be excluded (Hagens and Loessner, 2010). Preferably, a bacteriophage according to the present invention is strictly virulent (avoiding lysogeny) comprising no virulence factors or known toxins encoded in its genome. The absence of virulence factors or known toxins can be assessed by methods well known by the person skilled in the art. In one embodiment, the absence of virulence factors or known toxins is assessed by whole genome sequencing and screening for known virulence factors or toxins. Preferably, undesired virulence factors or toxins include any type of toxin, antibiotic resistance gene, hemolysin, strong antigenic protein and/or inflammation factor.

Preferably a bacteriophage according to the present invention does not demonstrate transduction activity, i.e. does not show any transfer of host DNA to other host cells. Transduction activity can be assessed by assays well known by the person skilled in the art. Such an assay is described in detail in Example 1. In brief, two mutant *Salmonella* strains are provided, the first strain resistant to a first antibiotic and the second strain resistant to a second antibiotic. The first strain is infected with a lysate prepared from the second strain that has been infected with a bacteriophage according to the present invention. Transduction activity is analysed by testing said first strain on its ability to grow colonies on plates containing both the first and second antibiotic. Within the context of the present invention, a bacteriophage is said to show no transduction activity if no colony growth occurs in this assay.

Transduction frequency is known to be increased by mutations in rIIA, rIIB, stp and ac (Young et al., 1982). It is preferred that the bacteriophage according to the present invention features functional ndd, denB, rIIA and rIIB genes. Within the context of the present invention, functionality can be assured through a transduction assay.

Preferably, a bacteriophage according to the present invention has a genome that has at least 50, 55, 60, 65, 70, 75, 80, 81, 82, 83, 84, 85, 86, 87, 88, 89, 90, 91, 92, 93, 94, 95, 96, 97, 98, 99 or 100% sequence identity with the genome of Phage S16, deposited at the CBS Fungal Biodiversity Centre under number CBS130493 and represented herein by SEQ ID NO: 1.

A bacteriophage according to the invention may be a mutant, chimeric and/or recombinant bacteriophage. The person skilled in the art may construct a bacteriophage starting from S16 by placing mutations in the genome and/or deleting and/or inserting coding sequences or parts thereof into the genome using methods known in the art.

Most preferably, a bacteriophage according to the present invention is Phage S16.

In a second aspect, the present invention provides a polypeptide, preferably an isolated polypeptide, comprising an amino acid sequence encoded by a gene of a bacteriophage according to the first aspect of the present invention, a polypeptide variant, or a chimeric polypeptide construct. Preferably, a polypeptide of the present invention is obtainable from a bacteriophage according to the first aspect of the present invention. Preferably said polypeptide is a long tail fibre polypeptide and has an amino acid sequence having at least 50, 55, 60, 65, 70, 75, 80, 81, 82, 83, 84, 85, 86, 87, 88, 89, 90, 91, 92, 93, 94, 95, 96, 97, 98, 99 or 100% sequence identity with an amino acid sequence selected from the group consisting of SEQ ID NO: 3, 5, 7, 9 and 11. In the mature S16 phage, gp34-38 identified herein by SEQ ID NO: 3, 5, 7, 9 and 11 encoded by SEQ ID NO: 2, 4, 6, 8 and 10, respectively, are required to form the complete long tail fibre structure. More preferably, said polypeptide has an amino acid sequence having at least 50, 55, 60, 65, 70, 75, 80, 81, 82, 83, 84, 85, 86, 87, 88, 89, 90, 91, 92, 93, 94, 95, 96, 97, 98, 99 or 100% sequence identity with SEQ ID NO: 9, encoded by SEQ ID NO: 8, being a gp37 polypeptide, a distal polypeptide subunit of the long tail fibre (LTF). Preferably, said polypeptide has a length of at least 500, 600 or 700 amino acids, and/or a length of at most 1000, 900, 800, or 750 amino acids. Most preferably, said polypeptide has a length of 749 amino acids. Also preferred is a polypeptide variant and/or a polypeptide construct comprising a long tail fibre polypeptide as defined herein.

A gp37 polypeptide of the present invention can be produced synthetically or recombinant. A recombinant production method for a gp37 polypeptide is described more elaborately in Bartual et al., 2010 and in Example 1. In short, said production requires the co-expression of the chaperone polypeptides gp57A and gp38. Preferably, a gp38 of the present invention polypeptide has at least 50, 55, 60, 65, 70, 75, 80, 81, 82, 83, 84, 85, 86, 87, 88, 89, 90, 91, 92, 93, 94, 95, 96, 97, 98, 99 or 100% sequence identity with SEQ ID NO: 11, encoded by SEQ ID NO: 10, and a length of at least 50, 100 or 150 amino acids and/or a length of at most 400, 300 or 250 amino acids. Most preferably, said polypeptide has a length of 249 amino acids. Preferably, a gp57A of the present invention has at least 50, 55, 60, 65, 70, 75, 80, 81, 82, 83, 84, 85, 86, 87, 88, 89, 90, 91, 92, 93, 94, 95, 96, 97, 98, 99 or 100% sequence identity with SEQ ID NO: 13, encoded by SEQ ID NO: 12, and a length of at least 40, 50, 60 or 70 amino acids and/or a length of at most 100, 90, 80 or 78 amino acids. Most preferably, said polypeptide has a length of 75 amino acids. The expressed polypeptide according to the present invention can be purified using any suitable method known by a person skilled in the art, such as by gravity flow immobilized metal affinity chromatography (IMAC) using low-density Ni-NTA beads (Chemie Brunschwig AG, Basel, Switzerland).

Preferably, a distal subunit of the long tail fibre according to the present invention binds to outer membrane protein OmpC as established by a suitable binding assay well known by a person skilled in the art. In a preferred assay, binding of distal subunit of the long tail fibre according to the present invention is established as described in detail in Example 1. In brief, a gp37 fluorescent tagged polypeptide trimer bound to gp38 according to the present invention is produced as described above wherein polynucleotides encoding gp37 (SEQ ID NO: 8 encoding SEQ ID NO: 9) and gp38 (SEQ ID NO: 10 encoding SEQ ID NO: 11), respectively, of the present invention are cloned in a pHGFP Amp$^r$ vector for transfection in an expression system (Loessner et al., 2002). 0.5 mL of a log-phase culture of the bacterial strain to be tested are pelleted and resuspended in 200 µl SM buffer (5.8 g/L NaCl, 8 mM MgSO$_4$, 50 mM Tris, pH 7.4). Fluorescent gp37/gp38 complexes, wherein a complex consists of a trimer of GFP labelled gp37 and single gp38 attached to the it, are centrifuged to remove aggregates (30 min, 31,000 g, 4° C.) and approximately 1 µg of fluorescent gp37/gp38 complexes is added to the bacterial cells. After 10 minutes incubation at room temperature, the cells are washed in SM buffer. A *Zeiss axioplan* micropsope at 100 fold magnification is used for fluorescence microscopy (excitation: BP 450-490 nm, FT 510 nm, emission LP 520 nm, Carl Zeiss AG, Germany) can be used to evaluate binding of fluorescent gp37/gp38 complex. Within the context of the present invention, gp37/gp38 complex is said to bind OmpC if a no observable binding can be detected as evaluated by detecting the fluorescence signal if HGFP_gp37/gp38 binding is assessed on a ompC *Salmonella* deletion mutant, preferably S. Tm DT7155 ΔompC, as compared to a wild type *Salmonella* strain, preferably S. Tm DT7155 wt. Another preferred binding assay for assessing OmpC binding by gp37/gp38 complex is a pull down assay as defined herein above. Within the context of the present invention, a complex of the present invention is said to bind to OmpC if an decrease of at least 15, 20, 25, 26, 27, 28, 29 or 30% of adsorption is detected in a pull down assay as defined herein above using a bacterial strain expressing OmpC, preferably wild type *Salmonella* strain, even more preferably *Salmonella typhymurium* DT7155 wt, pre-incubated with the fluorescent gp37/gp38 complex polypeptide as defined herein as compared to a bacterial strain per-incubation of said cells with green fluorescent protein (GFP). In a preferred embodiment, said bacterial strain expressing OmpC, preferably wild type *Salmonella* strain, even more preferably *Salmonella typhymurium* DT7155 wt, has been pre-incubated with 20 μg fluorescent gp37/gp38 complex as defined herein for 10 minutes before a bacteriophage of the present invention was added.

Another preferred polypeptide according to the present invention is an endolysin obtainable from a bacteriophage according to the first aspect of the present invention. Also preferred is a polypeptide variant and/or a polypeptide construct comprising an endolysin as defined herein.

Preferably, said endolysin polypeptide according to the present invention has an amino acid sequence having at least 50, 55, 60, 65, 70, 75, 80, 81, 82, 83, 84, 85, 86, 87, 88, 89, 90, 91, 92, 93, 94, 95, 96, 97, 98, 99 or 100% sequence identity with SEQ ID NO: 15, encoded by SEQ ID NO: 14, and a length of at least 50, 75 or 100 amino acids and/or at most 300, 250, 200 or 170 amino acids. Most preferably, said endolysin polypeptide has a length of 166 amino acids. Preferably said endolysin polypeptide according to the present invention has lytic activity. Lytic activity can be assessed by any suitable method known by the person skilled in the art. In an embodiment, lytic activity can be assessed spectrophotometrically by measuring a decrease in turbidity of substrate cell suspensions. Turbidity is assessed by measuring optical density at a wavelength of 600 nm, typically a culture is turbid when it exhibits an optical density of at least 0.3 OD at a wavelength of 600 nm. Preferably, lytic activity can be assessed spectrophotometrically measuring a decrease in turbidity of a *Salmonella* suspension, wherein turbidity is quantified by measuring $OD_{600}$ spectrophotometrically (Libra S22, Biochrom). More preferably, 200 nM of an endolysin polypeptide according to the present invention is incubated together with a *Salmonella* suspension having an initial $OD_{600}$ of 1±0.05, as assessed spectrophotometrically (Libra S22, Biochrom), in PBS buffer pH 7.4, 120 mM sodium chloride for 30 min at 37° C. The decrease in turbidity is calculated by subtracting the $OD_{600}$ after 30 min of incubation from the $OD_{600}$ before 30 min of incubation. Within the context of the present invention a polypeptide of the present invention is said to have lytic activity when using this assay a drop in turbidity of at least 10, 20, 30, 40, 50 or 60% is detected. Preferably, a drop of at least 70% is detected.

An embodiment of the present invention encompasses a variant polypeptide. A variant polypeptide may be a non-naturally occurring form of the polypeptide. A polypeptide variant may differ in some engineered way from the polypeptide isolated from its native source. A polypeptide variant may be made by site-directed mutagenesis starting from the nucleotide sequence encoding a polypeptide as defined herein and indicated by SEQ ID NO: 2, 4, 6, 8, 10, 12 and/or 14. Preferably, a polypeptide variant contains mutations that do not alter the biological function of the encoded polypeptide. According to a preferred embodiment, a polypeptide variant exhibits OmpC binding and/or a lytic activity which is the same or enhanced as compared to OmpC binding and/or a lytic activity of SEQ ID NO: 3, 5, 7, 9, 11, 13 and/or 15, respectively, as measured in an assay as earlier identified herein.

The present invention further provides a chimeric polypeptide encoded by naturally occurring or retrofitted polynucleotide contructs as later defined herein. Preferably, said chimeric polypeptide comprises at least one of the polypeptides as defined earlier herein and further comprising at least one additional functional domain. A functional domain within the present invention may be any domain showing signalling, catalytic, chaperone and/or binding activity.

In a preferred embodiment, the present invention relates to a chimeric polypeptide comprising an endolysin as defined herein, covalently linked to a hydrophobic pentapetpide on its C-terminus, preferably said hydrophobic pentopeptide is Phe-Phe-Val-Ala-Pro, resulting in increased bactericidal action of the endolysin especially towards gram negative bacteria as reported by Ibrahim et al., 1994 (JBC 1994 Vol. 269, p. 5053-5063).

In a third aspect, the present invention provides a polynucleotide, preferably an isolated polynucleotide, encoding a polypeptide, a polypeptide variant or a chimeric polypeptide according to the second aspect of the present invention. A polynucleotide according to the present invention preferably has at least 50, 60, 70, 80, 81, 82, 83, 84, 85, 86, 87, 88, 89, 90, 91, 92, 93, 94, 95, 96, 97, 98, 99 or 100% sequence identity with any of the sequences of SEQ ID NO: 2, 4, 6, 8, 10, 12 or 14. A polynucleotide according to the invention can have the minimum sequence identity with the corresponding sequences of SEQ ID NO's 2, 4, 6, 8, 10, 12 or 14, or alternatively hybridise under stringent conditions with these given sequences. Stringent hybridisation conditions are those as understood in the art, e.g. hybridisation in 6×SSC (20×SSC per 1000 ml:175.3 g NaCl, 107.1 g sodium citrate.5H 20, pH 7.0), 0.1% SDS, 0.05% sodium pyrophosphate, 5*Denhardt's solution and 20 μg/ml denatured herring sperm DNA at 56° C. for 18-24 hrs followed by two 30 min. washes in 5×SSC, 0.1% SDS at 56° C. and two 30 min. washes in 2×SSC, 0.1% SSC at 56° C. Preferably a polynucleotide of the present invention has a length of at least 40, 50, 60, 70, 75, 100, 150, 200, 300, 400, 500, 600 or 700 amino acids and/or at most 1500, 1400, 1300, 1000, 900, 800, 750, 400, 300, 250, 170, or 100 amino acids.

A polypeptide or polynucleotide, according to the present invention, may be derived from one of the polypeptides or polynucleotides presented herein by substituting, inserting, deleting, or adding 1, 2, 3, 4, 5, 6, 7, 8, 9, 10, 12, 14, 16, 18, 20 or more nucleotides or amino acids, respectively. A polypeptide according to the present invention may be derived from one of the polypeptides as identified herein by adding an additional N- or C-terminal amino acids or chemical moieties to increase stability, solubility and activity.

A polynucleotide according to the present invention may be a variant of a polynucleotide having a nucleotide sequence of SEQ ID NO: 2, 4, 6, 8, 10, 12 or 14. A polynucleotide variant preferably is comprised of at least 20, 30, 40, 50, 60, 70, 80, 90, 100, 150, 200, 300, 400 or 500 bp. Polynucleotide variants may be used for preparing a polypeptide variant as defined earlier herein. A polynucleotide variant according to the present invention may be a fragment of any of the polynucleotides as defined here above. A polynucleotide variant may also be a polynucleotide having a sequence that differs from SEQ ID NO: 2, 4, 6, 8, 10, 12 or 14 by virtue of the degeneracy of the genetic code. A polynucleotide variant may also be an allelic variant of a polynucleotide having a sequence of SEQ ID NO: 2, 4, 6, 8, 10, 12 or 14. An allelic variant denotes any of two or more alternative forms of a gene occupying the same chromosome locus. A preferred polynucleotide variant according to the present invention has a nucleotide sequence which contains silent mutation(s). Alternatively or in combination, a polynucleotide variant may also be obtained by introduction of nucleotide substitutions, which do not give rise to another amino acid sequence of the polypeptide encoded by the polynucleotide, but which corresponds to the codon usage of the host organism intended for production of the polypeptide of the present invention. According to a preferred embodiment, a polynucleotide variant according to the present invention encodes a polypeptide still exhibiting its biological function. More preferably, a polynucleotide variant according to the present invention encodes a polypeptide exhibiting OmpC binding activity or endolysin activity. Even more preferably, a polynucleotide variant according to the present invention encodes a polypeptide with enhanced OmpC binding activity or an endolysin activity as defined earlier herein. Enhanced activity is defined herein as having at least 110, 120, 130, 140, 150, 200, 300, 400 or 500% or more of the activity as compared to activity of the polypeptide of the present invention. Polynucleotides according to the present invention encoding a polypeptide exhibiting OmpC binding activity or endolysin activity may be produced synthetically or recombinantly by any suitable method known by the person skilled in the art. All these variants can be obtained using techniques known to the skilled person, such as screening of a library by hybridisation (e.g. using Southern blotting procedures) under low to medium to high hybridisation conditions with a polynucleotide having the nucleotide sequence of SEQ ID NO: 2, 4, 6, 8, 10, 12 or 14 or a variant thereof which can be used to design a probe. Low to medium to high stringency conditions means prehybridization and hybridization at 42° C. in 5×SSPE, 0.3% SDS, 200 pg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

In a fourth aspect, the present invention further provides a nucleic acid construct comprising polynucleotides according to the third aspect of the present invention encoding a polypeptide according to the second aspect of the present invention and/or a functional domain at any possible location within the construct. A functional domain within the present invention may be any domain showing signalling, catalytic, chaperone and/or binding activity. In a preferred embodiment said functional domain is a binding domain for ease of purification, also named a Protein Purification Tag. Such a Protein Purification Tag of the present invention can be, but is not limited to chitin binding protein (CBP), maltose binding protein (MBP), glutathione-S-transferase (GST), poly(His) tag, V5-tag, c-myc-tag, or HA-tag. Said nucleic acid construct comprising heterologous nucleotide sequences being defined herein as a "retrofitted construct".

In a fifth aspect, the present invention provides an expression vector comprising a polynucleotide according to the third aspect of the present invention or nucleic acid construct according to the fourth aspect of the present invention. Preferably, an expression vector comprises a polynucleotide according to third aspect of the present invention or a nucleic acid construct according to the fourth aspect of the present invention, which is operably linked to one or more control sequences, which direct the production or expression of the encoded polypeptide in a cell, a subject, or a cell-free expression system.

An expression vector may be seen as a recombinant expression vector. This vector can be a plasmid, a cosmid, a bacteriophage or a virus which is transformed by introducing a polynucleotide according to the present invention. Such transformation vectors allowing the host organism to be transformed are well known to those skilled in the art and widely described in the literature.

A further subject of the present invention is a process for the transformation of host organisms, by introducing a least one polynucleotide according to the present invention, which transformation may be carried out by any suitable known means which have been widely described in the specialist literature and in particular in the references cited in the present application, more particularly by the vector according to the present invention.

In a sixth aspect, the present invention provides a cell, which comprises a polynucleotide according to the third aspect of the present invention, a nucleic acid construct according to the fourth aspect of the present invention or an expression vector according to the fifth aspect of the present invention. A cell may be any microbial, prokaryotic or eukaryotic cell, which is suitable for expression of the polypeptide of the present invention. In a preferred embodiment, said cell is an *E. coli*. In an even more preferred embodiment, said cell is *E. coli* XL1blue MRF'.

In a preferred embodiment, the present invention provides a cell for propagation and/or production of a bacteriophage of the present invention. A bacteriophage of the present invention can be propagated and/or produced and optionally purified by any suitable method known by a person skilled in the art. Preferably, a bacteriophage of the present invention is propagated and purified by the double agar overlay method as described elaborately in Gratia, 1936 and in Example 1. In brief, 4 mL LC soft agar (7.5 g/L NaCl, 5 g/L Yeast Extract, 10 g/L tryptone, 1% glucose, 2 mM MgSO4, 10 mM $CaCl_2$) is mixed with 100 μl of bacterial overnight culture, preferably *Salmonella* Enteritidis isolate number 13, and 10 μl of bacteriophage dilution of a bacteriophage of the present invention and poured onto LB bottom agar plates (6 g/L agar). Plates are incubated overnight at 30° C. semiconfluent plates are scraped with 5 mL of SM buffer (5.8 g/L NaCl, 8 mM $MgSO_4$, 50 mM Tris, pH 7.4) for 5 h at room temperature, SM buffer is collected from the plates and phage is PEG precipitated overnight at 0° C. (8% PEG 8000 (Fluka) in 0.5 M NaCl). After centrifugation (15 min, 10,000 g, 4° C.) the pellet is resuspended in 5 mL SM buffer and twice CsCl gradient purified (stepped gradient) to yield highly pure bacteriophage particles (Sambrook and Russel 2001).

In a seventh aspect, the present invention provides a composition comprising a bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention, preferably said composition comprises a bacteriophage according to the first aspect of the present invention and/or endolysin according to the second aspect of the present invention present invention, most preferably said composition comprises a bacteriophage according to the first aspect of the present invention. Preferably, a composition according to the present invention is an antimicrobial, preferably a food preservative or a disinfectant. Preferably said antimicrobial is for killing a bacterium, preferably a bacterium of the genus *Salmonella*, more preferably a bacterium of the species *Salmonella enterica*. Preferably, the composition according to the present invention exhibits a broad host range *Salmonella* infection property, being strictly virulent, not showing transduction properties, having OmpC binding activity and/or lytic activity as defined herein.

A composition according to the present invention may comprise a mixture of different bacteriophages, and/or polypeptides, and/or polynucleotides, and/or nucleic acid constructs and/or vectors and/or cells according to the present invention.

A composition as defined herein may further comprise one or more additional active ingredients, preferably in a concentration known to be effective. Active preferably being defined herein as showing OmpC and/or LPS binding and/or lytic activity as earlier defined herein or aiding and/or enhancing any of such activities. Within the present invention active ingredients also include ingredients known in the art to show lytic activity towards one or more other prokaryotes than *Salmonella*, preferably pathogenic prokaryotes, even more preferably pathogenic bacteria, even more preferably bacterial foodborne pathogens, such as, but not limited to *Campylobacter jejuni, Clostridium perfringens, Escherichia coli, Bacillus cereus, Listeria monocytogenes, Shigella, Staphylococcus aureus, Staphylococcal enteritis, Streptococcus, Vibrio cholera, Vibrio parahaemolyticus, Vibrio vulnificus, Yersinia enterocolitica* and *Yersinia pseudotuberculosis*. Preferably said active ingredient is present in a concentration known in the art to result in a significantly reduced number of foodborne pathogens that would otherwise be present. Preferably, said one or more additional active ingredients are selected from the group consisting of a further bacteriophage, a bacteriostatic agent, a bactericidal agent, an antibiotic, a surfactant and/or an enzyme. An antibiotic of the present can be any antibiotic known in the art including antibiotics and chemotherapeutic agents, and including but not limited to vancomycin, nisin, danofloxacin and neomycin. An enzyme useful in a composition of the present invention includes but is not limited to enzymes that aid in breaking up biofims (e.g. biofilms found in food processing equipment) such as but not limited to polysaccharide depolymerise enzymes and protease. A surfactant useful in a composition of the present invention helps to wet the surface so that bacteriophages are properly distributed over the various surfaces, and to solubilise and remove dirt so that the *Salmonella* are accessible to the bacteriophage. Suitable surfactants include but are not limited to polysorbate (tween) 80, 20 and 81 and Dobanols (Shell Chemical Co.®).

An antimicrobial disinfectant composition of the present invention may further comprise surface disinfectants known in the art such as but not limited to benzoic acid and PBT, preferably disinfectants with which a bacteriophage of the present invention is compatible.

A further bacteriophage in a composition according to the present invention can be any phage known in literature, other than the bacteriophage of the present invention. Preferably, such a further bacteriophage includes, but is not limited to, a tailed phage of the order of Caurdovirales, consisting of Myoviridae, Siphoviridae and Podoviridae. Most preferably, said further bacteriophage is the broad host range phage Felix O1. Felix O1 and a bacteriophage of the present invention show largely overlapping but a nonetheless complementary host range. In conjunction with the well-studied broad host range *Salmonella* phage Felix O1 an almost complete host-range can be achieved making a combination of Felix O1 with a bacteriophage of the present invention uniquely useful for combating *Salmonella*-bacteria in the various applications, which are non-limitedly listed herein.

Furthermore, as the phage Felix O1 and a bacteriophage of the present invention have different receptors on *Salmonella* cells (Lipopolysaccharide or LPS and OmpC, respectively), a mutation leading to resistance to one of the two phages would still leave the cells susceptible to the other phage.

A composition according to the present invention may further comprise an excipient, preferably a pharmaceutically acceptable excipient. A composition according to the present invention further comprising a pharmaceutically acceptable excipient is herein referred to as a pharmaceutical composition according to the present invention and preferably is for use as a medicine or as a medicament. Excipients which can be used as a vehicle for the delivery of a bacteriophage according to the first aspect of the present invention, a polypeptide according to the second aspect of the present invention, polynucleotide according to the third aspect of the present invention, a nucleic acid construct according to the fourth aspect of the present invention, vector according to the fifth aspect of the present invention and/or cell according to the sixth aspect of the present invention of the present invention will be apparent to those skilled in the art. Preferably a pharmaceutical composition of the present invention is used in the treatment, prevention or delay of a *Salmonella* related condition in an individual.

A composition of the present invention may be in the liquid, solid or semi-liquid or semi-solid form.

In an eighth aspect, the present invention provides for a bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention, and/or a composition according to the seventh aspect of the present invention for use as a medicament, preferably a medicament for the treatment, prevention or delay of a *Salmonella* related condition in an individual. Preferably, a composition according to the seventh aspect of the present invention is for use as a medicament. This medicament is preferably for treatment, prevention or delay of a *Salmonella* related condition in an individual. An individual is defined herein as any human or animal subject, including livestock. The present invention also relates to a pharmaceutical or medical composition. A pharmaceutical or medical composition is defined herein as any substance having medicinal properties, preferably having antimicrobial properties, more preferably having specific antimicrobial properties, even more preferably having the property of specifically lysing a *Salmonella* bacterium. Even more preferably, the present invention relates to a pharmaceutical or medical composition for the prevention of an infectious disease. Preferably, the present invention relates to a pharmaceutical or medical composition for the prevention of an infectious disease caused by a bacterium, preferably a bacterium of the genus *Salmonella*, more preferably a bacterium of the species *S. enterica*. Preferably, said infectious disease is Salmonellosis.

A pharmaceutical composition according to the present invention can be used to treat individuals, preferably mammals and including animals, and humans, infected or running the risk of being infected with *Salmonella*. Any suitable route of administration can be used to administer said composition including but not limited to: oral, aerosol or other device for delivery to the lungs, nasal spray, intravenous, intramuscular, intraperitoneal, intrathecal, vaginal, rectal, topical, lumbar puncture, and direct application to the brain and/or meninges. A pharmaceutical composition according to the present invention may be administered to an individual or a cell, tissue or organ of said individual in an effective dose once, twice, three times or more during at least one week, one month, six month, one year or more.

In one embodiment, a composition of the present invention is admixed to the feed of livestock, preferably to pre-slaughter livestock, to control *Salmonella* in said livestock. Preferably, livestock or meat derived from livestock fed the feed to which the composition of the present invention is admixed, has a decrease in amount of *Salmonella* bacteria present as compared to livestock or meat derived from livestock that has been fed with feed in which the composition of the present invention is absent.

In another embodiment, a composition of the present invention is used for intravenous (IV) administration of a subject as defined herein. For example, the free phage according to the first aspect of the present invention, endolysin according to the second aspect of the present invention and/or host bacteria containing the endolysin according to the sixth aspect of the present invention could be in lyophilized form and be dissolved just prior to administration by IV injection. An effective dose is defined herein as a dose that produces the desired effect being a decrease in amount of *Salmonella* bacteria present in an individual or in a cell of said individual as defined herein below and/or a treatment, prevention or delay of a *Salmonella* related condition in an individual as defined herein below. The dosage of administration for a bacteriophage is contemplated to be in the range 40 of about $10^3$ to about $10^{13}$ PFU/per kg/per day, and preferably about $10^{12}$ PFU/per kg/per day. The dosage of administration for an endolysin is contemplated to be in the range of about 2-2000 ng/per g/per day, and preferably about 20-200 ng/per g/per day. The bacteriophage, endolysin and/or host bacteria containing the endolysin are administered until successful elimination of the *Salmonella* bacteria is achieved or until the amount of *Salmonella monocytogenes* is substantially reduced.

A pharmaceutical composition according to the present invention is preferably said to be active, functional or therapeutically active or able to treat, prevent and/or delay a *Salmonella* related condition when it decreases the amount of a *Salmonella* bacteria present in an individual or in a cell of said individual or in a cell line or in a cell free in vitro system and preferably means that 99%, 90%, 80%, 70%, 60%, 50%, 40%, 30%, 20%, 10%, 5% or less of the initial amount of a *Salmonella* bacteria, is still detectable. Preferably no *Salmonella* bacterium is detectable. In this paragraph, the expression "amount of *Salmonella* bacteria" preferably means viable *Salmonella* bacteria. *Salmonella* bacteria may be detected using standard techniques known by the person skilled in the art such as immunohistochemical techniques using *Salmonella* specific antibodies such as immunomagnetic separation, agglutination and enzyme-linked immune assays, immunochromatography or fluorescence detection; growing assays of specific enrichments on selective media such as Xylose-Lysine-Desoxycholate (XLD); and/or DNA-techniques such as PCR or hybridization. Viable *Salmonella* bacteria may be detected using standard techniques known by the person skilled in the art such as microbiological bacterial culture techniques and/or real-time quantitative reverse transcription polymerase chain reaction to assay for bacterial mRNA.

The decrease in percentage of amount of a *Salmonella* bacteria is preferably assessed in a sample, or tissue or in a cell of an individual by comparison to the amount present in said sample or individual before treatment with said composition or polypeptide of the present invention. Alternatively, the comparison can be made with a sample, or tissue or cell of said individual which has not yet been treated with said pharmaceutical composition according to the present invention in case the treatment is local.

In a ninth aspect, the present invention provides the use of a bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention, and/or a composition according to the seventh aspect of the present invention, preferably as an antimicrobial agent, more preferably as a food preservative or disinfectant, preferably for controlling a bacterium, preferably by lysing said bacterium, preferably a bacterium of the genus *Salmonella*, more preferably a bacterium of the species *Salmonella enterica*. Preferably, a bacteriophage, endolysin and/or cell comprising said bacteriophage or endolysin or composition according to the present invention, is used to reduce the counts of *Salmonella* bacteria and/or to prevent their growth in the first place, in food products (including but not limited to the dairy industry) as well as in food processing plants in which the food products are being processed such as on processing equipment and other sites in food industry facilities, e.g. food storage container.

A bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention, and/or a composition according to the seventh aspect of the present invention for use as an antimicrobial agent is applied on or into food products, and/or into various physical sites within the food processing plants on or in food processing equipment, by a number of means including, but not limited to, admixing, spraying or directly applying said bacteriophage, polypeptide, polynucleotide, nucleic acid construct, vector, cell or composition In a further embodiment, a polypeptide according to the second aspect of the present invention can be isolated from a cell according to the sixth aspect of the present invention or a cell according to the sixth aspect of the present invention containing a polypeptide according to the second aspect of the present invention can be directly applied or administered without isolation of said polypeptide. For example, a cell which produces a polypeptide of the present invention could be administered to a subject (human or animal) or applied to a surface where the polypeptide of the present invention would be secreted into food, onto a surface or into the subject's gut. The polypeptide of the present invention can then bind and optionally lyse bacterial cells, preferably a bacterium of the genus *Salmonella*, more preferably a bacterium of the species *Salmonella enterica*, present in this environment. The applications as defined herein significantly reduce the numbers of *Salmonella* bacteria that would otherwise be present.

In one embodiment, a food preservatives or disinfectant of the present invention is used in combination with one or more additional active ingredients. Active preferably being defined herein as showing OmpC and/or LPS binding and/or lytic activity as earlier defined herein or aiding and/or enhancing any of such activities. Within the present invention active ingredients also include ingredients known in the art to show lytic activity towards one or more other prokaryotes than *Salmonella*, preferably pathogenic prokaryotes, even more preferably pathogenic bacteria, even more preferably bacterial foodborne pathogens, such as, but not limited to *Campylobacter jejuni, Clostridium perfringens, Escherichia coli, Bacillus cereus, Listeria monocytogenes, Shigella, Staphylococcus aureus, Staphylococcal enteritis, Streptococcus, Vibrio cholera, Vibrio parahaemolyticus, Vibrio vulnificus, Yersinia enterocolitica* and *Yersinia pseudotuberculosis*. Preferably said active ingredient is present in a concentration known in the art to result in a significantly reduced number of foodborne pathogens that would otherwise be present. Preferably, said one or more additional active ingredients are selected from the group consisting of a further bacteriophage, a bacteriostatic agent, a bactericidal agent, an antibiotic, a surfactant and/or an enzyme. An antibiotic of the present can be any antibiotic known in the art including antibiotics and chemotherapeutic agents, and including but not limited to vancomycin, nisin, danofloxacin and neomycin. An enzyme useful in a composition of the present invention includes but is not limited to enzymes that aid in breaking up biofims (e.g. biofilms found in food processing equipment) such as but not limited to polysaccharide depolymerise enzymes and protease. Surfactants useful in a composition of the present invention help to wet the surface so that a bacteriophages are properly distributed over the various surfaces, and to solubilise and remove dirt so that the *Salmonella* are accessible to the bacteriophage. Suitable surfactants include but are not limited to polysorbate (tween) 80, 20 and 81 and Dobanols (Shell Chemical Co.®).

A further bacteriophage in a composition according to the present invention can be any phage known in literature, other than the bacteriophage of the present invention. Preferably, such a further bacteriophage includes, but is not limited to, a tailed phage of the order of Caurdovirales, consisting of Myoviridae, Siphoviridae and Podoviridae. Most preferably, said further bacteriophage is the broad host range phage Felix O1. Felix O1 and a bacteriophage of the present invention show largely overlapping but a nonetheless complementary host range. In conjunction with the well-studied broad host range *Salmonella* phage Felix O1 an almost complete host-range can be achieved making a combination of Felix O1 with a bacteriophage of the present invention uniquely useful for combating *Salmonella*-bacteria in the various applications, which are non-limitedly listed herein.

Furthermore, as the phage Felix O1 and a bacteriophage of the present invention have different receptors on *Salmonella* cells (Lipopolysaccharide or LPS and OmpC, respectively), a mutation leading to resistance to one of the two phages would still leave the cells susceptible to the other phage.

In yet another embodiment, the present invention relates to the use of a bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention and/or composition according to the seventh aspect of the present invention for detecting bacteria, more preferably for detecting bacteria of the genus *Salmonella*, more preferably a bacterium of the species *Salmonella enterica*. Preferably, said bacteriophage, polypeptide, polynucleotide, nucleic acid construct, a vector, cell and/or composition is used in a diagnostic application. Possibly said bacteriophage, polypeptide, polynucleotide, nucleic acid construct, a vector, cell and/or composition is used together with other detection agents.

In a tenth aspect, the present invention relates to the use of a bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention, and/or a composition according to the seventh aspect of the present invention for the manufacture of a medicament, preferably a medicament for the treatment, prevention or delay of a *Salmonella* related condition in an individual according to the eighth aspect of the present invention.

In an eleventh aspect, the present invention provides a method for treatment, prevention or delay of a *Salmonella* related condition in an individual, comprising administering a bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention, and/or a composition according to the seventh aspect of the present invention.

Preferably, the present invention provides for method of treatment, prevention or delay of an infectious disease. More preferably, the present invention relates to a method of treatment, prevention or delay of an infectious disease caused by a bacterium, preferably a bacterium of the genus *Salmonella*, more preferably a bacterium of the species *S. enterica*. Also preferred is a method of treatment, prevention or delay of *Salmonella* related condition in an individual. An individual is defined herein as any human or animal subject, including livestock. Preferably, said infectious disease is Salmonellosis.

Any suitable route of administration can be used in a method of treatment, prevention or delay of the present invention including but not limited to: oral, aerosol or other device for delivery to the lungs, nasal spray, intravenous, intramuscular, intraperitoneal, intrathecal, vaginal, rectal, topical, lumbar puncture, and direct application to the brain and/or meninges. Said method of treatment, prevention or delay according to the present invention may include the administration of a bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention, and/or a composition according to the seventh aspect of the present invention to an individual as defined herein or a cell, tissue or organ of said individual in an effective dose once, twice, three times or more during at least one week, one month, six month, one year or more.

In one embodiment, a method of treatment, prevention or delay of the present invention encompasses the admixing of a bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention, and/or a composition according to the seventh aspect of the present invention to the feed of livestock, preferably to pre-slaughter livestock, to control Salmonella in said livestock. Preferably, livestock or meat derived from livestock fed the feed to which the composition of the present invention is admixed, has a decrease in amount of Salmonella bacteria present as compared to livestock or meat derived from livestock that has been fed with feed in which the composition of the present invention is absent.

In another embodiment, a method of treatment, prevention or delay of the present invention encompasses the intravenous (IV) administration of a subject as defined herein. For example, the free phage according to the first aspect of the present invention, endolysin according to the second aspect of the present invention and/or host bacteria containing the endolysin according to the sixth aspect of the present invention could be in lyophilized form and be dissolved just prior to administration by IV injection. An effective dose is defined herein as a dose that produces the desired effect being a decrease in amount of Salmonella bacteria present in an individual or in a cell of said individual as defined herein below and/or a treatment, prevention or delay of a Salmonella related condition in an individual as defined herein below. The dosage of administration for a bacteriophage is contemplated to be in the range of about $10^3$ to about $10^{13}$ PFU/per kg/per day, and preferably about $10^{12}$ PFU/per kg/per day. The dosage of administration for an endolysin is contemplated to be in the range of about 2-2000 ng/per g/per day, and preferably about 20-200 ng/per g/per day. The bacteriophage, endolysin and/or host bacteria containing the endolysin are administered until successful elimination of the Salmonella bacteria is achieved or until the amount of Salmonella monocytogenes is substantially reduced.

A method or treatment, prevention or delay of the present invention is preferably said to be effective when it decreases the amount of a Salmonella bacteria present in an individual or in a cell of said individual or in a cell line or in a cell free in vitro system and preferably means that 99%, 90%, 80%, 70%, 60%, 50%, 40%, 30%, 20%, 10%, 5% or less of the initial amount of a Salmonella bacteria, is still detectable or would have been present in case the method of treatment, prevention or delay of the present invention would not have been provided. Preferably no Salmonella bacterium is detectable. In this paragraph, the expression "amount of Salmonella bacteria" preferably means viable Salmonella bacteria. Salmonella bacteria may be detected using standard techniques known by the person skilled in the art such as immunohistochemical techniques using Salmonella specific antibodies such as immunomagnetic separation, agglutination and enzyme-linked immune assays, immunochromatography or fluorescence detection; growing assays of specific enrichments on selective media such as Xylose-Lysine-Desoxycholate (XLD); and/or DNA-techniques such as PCR or hybridization. Viable Salmonella bacteria may be detected using standard techniques known by the person skilled in the art such as microbiological bacterial culture techniques and/or real-time quantitative reverse transcription polymerase chain reaction to assay for bacterial mRNA.

The decrease in percentage of amount of a Salmonella bacteria is preferably assessed in a sample, or tissue or in a cell of an individual by comparison to the amount present in said sample or individual before treatment with said composition or polypeptide of the present invention. Alternatively, the comparison can be made with a sample, or tissue or cell of said individual which has not yet been treated with said pharmaceutical composition according to the present invention in case the treatment is local.

In an twelfth aspect, the present invention relates to a method for controlling microbial contamination in a food- or feed product, on and/or in food- or feed processing equipment, on and/or in food- or feed containers comprising contacting a bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention, and/or a composition according to the seventh aspect of the present invention with the food- or feed product, the food- or feed processing equipment and/or the food- or feed containers.

Preferably said method is for controlling a bacterium of the genus Salmonella, more preferably a bacterium of the species Salmonella enterica. Preferably, said method of controlling includes the reduction of counts of Salmonella bacteria and/or the prevention of their growth in the first place, in food products (including but not limited to the dairy industry) as well as in food processing plants in which the food products are being processed such as on processing equipment and other sites in food industry facilities, e.g. food storage container. A method of the present invention encompasses the application of a bacteriophage according to the first aspect of the present invention, and/or a polypeptide according to the second aspect of the present invention, and/or a polynucleotide according to the third aspect of the present invention, and/or a nucleic acid construct according to the fourth aspect of the present invention and/or a vector according to the fifth aspect of the present invention and/or a cell according to the sixth aspect of the present invention, and/or a composition according to the seventh aspect of the present invention on or into food products, and/or into various physical sites within the food processing plants on or in food processing equipment, by a number of means including, but not limited to, admixing, spraying or directly applying said bacteriophage, polypeptide, polynucleotide, nucleic acid construct, vector, cell or composition.

In a further embodiment, a polypeptide according to the second aspect of the present invention can be isolated from a cell according to the sixth aspect of the present invention or a cell according to the sixth aspect of the present invention containing a polypeptide according to the second aspect of the present invention can be directly applied or administered without isolation of said polypeptide. For example, a cell which produces a polypeptide of the present invention could be administered to a subject (human or animal) or applied to a surface where the polypeptide of the present invention would be secreted into food, onto a surface or into the subject's gut. The polypeptide of the present invention can then bind and optionally lyse bacterial cells, preferably a bacterium of the genus *Salmonella*, more preferably a bacterium of the species *Salmonella enterica*, present in this environment. The applications as defined herein significantly reduce the numbers of *Salmonella* bacteria that would otherwise be present.

In a thirteenth aspect, the present invention relates to a method for the detection of the presence of *Salmonella*, comprising contacting a bacteriophage according to the first aspect of the present invention, a polypeptide according to the second aspect of the present invention, a polynucleotide according to the third aspect of the present invention, a nucleic acid construct according to the fourth aspect of the present invention, a vector according to the fifth aspect of the present invention, a cell according to the sixth aspect of the present invention and/or composition according to the seventh aspect of the present invention with a sample suspected to contain *Salmonella*. In a preferred embodiment, and detecting a change in the sample. The decrease in percentage of amount of a *Salmonella* bacteria is preferably assessed in a sample, or tissue or in a cell of an individual by comparison to the amount present in said sample or individual before treatment with said composition or polypeptide of the present invention. Alternatively, the comparison can be made with a sample, or tissue or cell of said individual which has not yet been treated with said pharmaceutical composition according to the present invention in case the treatment is local. Said sample can also be a sample of a food product or foodstuff, or a swab of a solid surface, preferably a solid surface where food products are processed or stored.

Preferably, a bacteriophage of the present invention is used to identify *Salmonella* bacteria present on (or within) foodstuffs, as well as those *Salmonella* bacteria present in the equipment or the general environment of the food processing plants in which the foodstuffs are being processed or on containers used for storage of foodstuffs and in animals infected with *Salmonella*. Any suitable method known by a person skilled in the art can be used for detection as meant herein. Preferably, a method is used in which recombinant DNA vector is prepared using bacteriophage of the present invention which is specific for *Salmonella*. The vector includes a genetic system comprising DNA which encodes the expression of one or more detectable proteins which are not a gene product of *Salmonella* bacteria. The DNA vector infects the bacteria of the genus *Salmonella* and transfers the genetic system to the bacteria. The detectable proteins are expressed by the bacteria and the detection of the detectable proteins indicates the presence of bacteria of the genus *Salmonella*.

For detection of the presence of bacteria of the genus *Salmonella*, marker genes are employed. These are genes which can be detected upon infection by the vector of a suitable host cell and subsequent culturing of the cells under conditions suitable for expression of the marker genes. It is preferred that the marker genes are those which do not occur in the bacteria of the genus *Salmonella*, and which are inserted into the vector, a bacteriophage of the present invention, using recombinant techniques. Such genes and their gene products are known in the art; they include bioluminescent proteins such as the lux gene which occurs in variants in various luminescent bacteria, for example of the genus *Vibrio*. The incorporation of the lux gene allows detection by luminescence measurement. An example of the lux gene is gene luxAB from *Vibrio harveyi*. Other suitable proteins include but are not limited to luciferase and fluorescent proteins such as green fluorescent protein.

The detection reaction can take place on as solid surface including but not limited to a test strip. In this embodiment, the vector containing the marker gene could be reversibly immobilized in or downstream from a sample application zone.

Alternatively, the vector could be incubated with the sample prior to application on the test strip. Anti-*Salmonella* antibodies would be irreversibly immobilized downstream from the vector and the sample application zone. If a sample is applied which contains *Salmonella*, the vector would infect the *Salmonella* and the detectable proteins would be expressed. As the sample moves down the test strip, the *Salmonella* would become immobilized by the anti-*Salmonella* antibodies. The marker proteins would then be detected in the immobilized *Salmonella*.

In a further aspect, the present invention provides a kit of parts, preferably for the detection of *Salmonella* comprising a bacteriophage, a polypeptide or a fragment thereof, a polynucleotide or a fragment thereof, a nucleic acid construct, a vector, a cell and/or a composition according to the present invention and further comprising at least one of a detection reagent, a labelling reagent, a control sample, control data, instructions for use, a hybridization- or amplification reagent and a container.

Definitions

"Sequence identity" is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. Within the present invention, sequence identity with a particular sequence preferably means sequence identity over the entire length of said particular polypeptide or polynucleotide sequence. The sequence information as provided herein should not be so narrowly construed as to require inclusion of erroneously identified bases. The skilled person is capable of identifying such erroneously identified bases and knows how to correct for such errors.

"Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A polynucleotide is represented by a nucleotide sequence. A polypeptide is represented by an amino acid sequence. A nucleic acid construct is defined as a polynucleotide which is isolated from a naturally occurring gene or which has been modified to contain segments of polynucleotides which are combined or juxtaposed in a manner which would not otherwise exist in nature. Optionally, a polynucleotide present in a nucleic acid construct is operably linked to one or more control sequences, which direct the production or expression of said peptide or polypeptide in a cell or in a subject.

As used herein the term "heterologous sequence" or "heterologous nucleic acid" is one that is not naturally found operably linked as neighbouring sequence of said first nucleotide sequence. As used herein, the term "heterologous" may mean "recombinant". "Recombinant" refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject.

"Operably linked" may also be used for defining a configuration in which a sequence is appropriately placed at a position relative to another sequence coding for a functional domain such that a chimeric polypeptide is encoded in a cell and/or in a subject.

Expression will be understood to include any step involved in the production of the peptide or polypeptide including, but not limited to, transcription, post-transcriptional modification, translation, post-translational modification and secretion.

Optionally, a promoter represented by a nucleotide sequence present in a nucleic acid construct is operably linked to another nucleotide sequence encoding a peptide or polypeptide as identified herein.

The term "transformation" refers to a permanent or transient genetic change induced in a cell following the incorporation of new DNA (i.e. DNA exogenous to the cell). When the cell is a bacterial cell, as is intended in the current invention, the term usually refers to an extrachromosomal, self-replicating vector which harbors a selectable antibiotic resistance.

An expression vector may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

The term "control sequences" is defined herein to include all components, which are necessary or advantageous for the expression of a polypeptide. Each control sequence may be native or foreign to the nucleic acid sequence encoding the polypeptide. Such control sequences include, but are not limited to, a leader, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and transcriptional and translational stop signals.

The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator, which is functional in the cell, may be used in the present invention.

The control sequence may also be a suitable leader sequence, a non-translated region of a mRNA which is important for translation by the host cell. The leader sequence is operably linked to the 5' terminus of the nucleic acid sequence encoding the polypeptide. Any leader sequence, which is functional in the cell, may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence, which is functional in the cell, may be used in the present invention.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

Sequence table

| SEQ ID NO | Name (GenBank accession number) | Organism |
|---|---|---|
| 1 | genome sequence (HQ331142) | Phage S16 |
| 2 | sequence encoding gp34 | Phage S16 |
| 3 | gp34; long tail fiber proximal subunit (AEO97169; gp166) | Phage S16 |
| 4 | sequence encoding gp35 | Phage S16 |
| 5 | gp35; hinge connector (AEO97170; gp167) | Phage S16 |
| 6 | sequence encoding gp36 | Phage S16 |
| 7 | gp36; hinge connector (AEO97171; gp168) | Phage S16 |
| 8 | sequence encoding gp37 | Phage S16 |
| 9 | gp37; long tail fiber distal subunit (AEO97172; gp169) | Phage S16 |
| 10 | sequence encoding gp38 | Phage S16 |
| 11 | gp38; chaperone for long tail fiber distal subunit (AEO97173; gp170) | Phage S16 |
| 12 | sequence encoding gp57A | Phage S16 |
| 13 | gp57A; chaperone for tail fiber formation (AEO97083; gp80) | Phage S16 |
| 14 | sequence encoding endolysin | Phage S16 |
| 15 | endolysin (AEO97074; gp72) | Phage S16 |
| 16 | sequence encoding OmpC | S. Typhimurium DT7155 |
| 17 | OmpC | S. Typhimurium DT7155 |

The Genbank accession number is given between brackets in column two; the Genbank accession number is followed by the consecutive number of the S16 gene product (be referred to Table 6). Further herein, the S16 coding sequences and gene products are referred to by the gp numbers of their T4 counterparts (e.g. S16 gp166 is referred to in the application as gp34).

A: Tail fibers are in the "stowed" position along the tail (arrow); B: The tail fibers are extended. Note the two-part structure of the fibers, consisting of the proximal and distal part, divided by the "knee" (arrow); C: Contracted tail and extended tail fibers. Note the tail tube (arrow) protruding from the contracted tail sheath, the distinctive morphological feature of Myoviridae. (TEM, 52.000 fold magnification, bars are 100 nm in length, 2% PWS; taken by Dr. Rudi Lurz, Max Planck Institute, Berlin, Germany).

Figure 2:
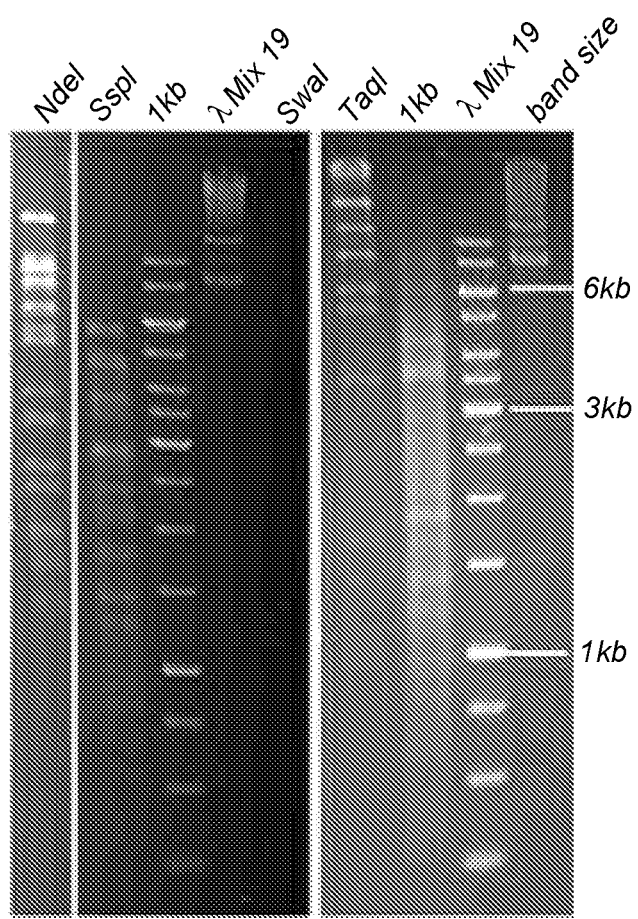

FIG. 2: Restriction Fragment length polymorphism (RFLP) analysis of S16 DNA. The genome is highly restriction resistant. Of the 34 enzymes tested, only SwaI, TaqI, NdeI and SspI are able to digest S16 genomic DNA.

Figure 3:
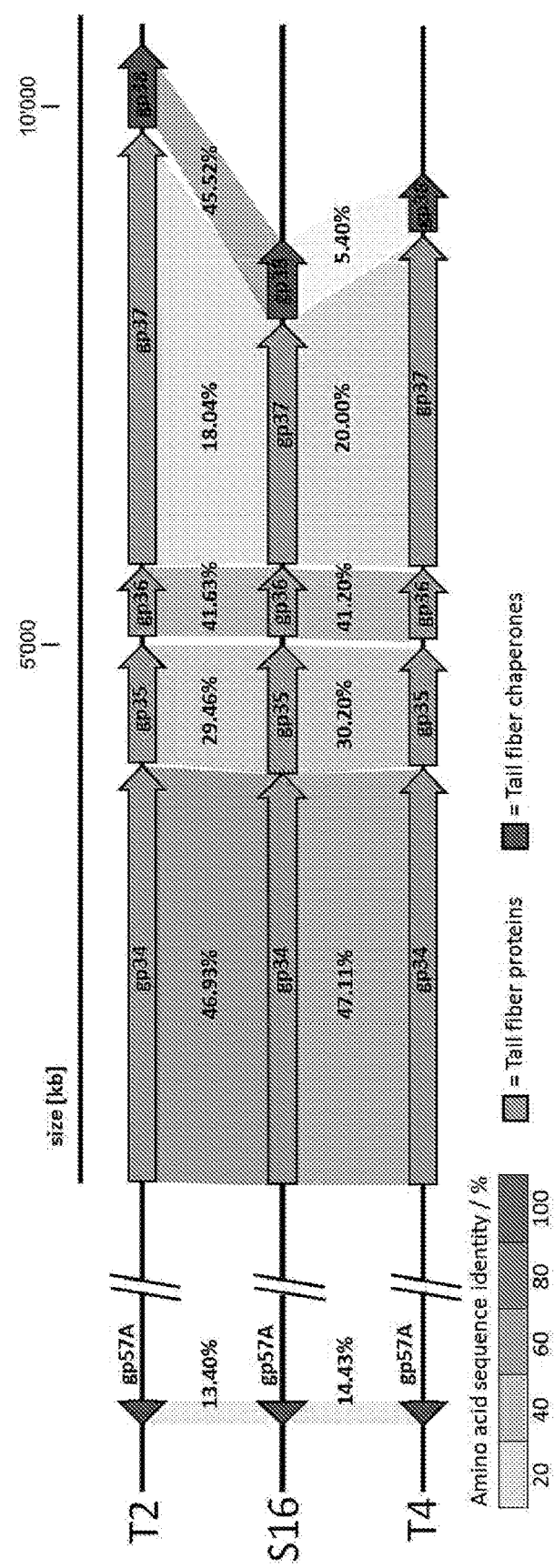

FIG. 3: Sequence comparisons between S16, T4 and T2.

Arrows represent annotated coding sequences. Shadings indicate % amino acid sequence identity between proteins.

Figure 4:
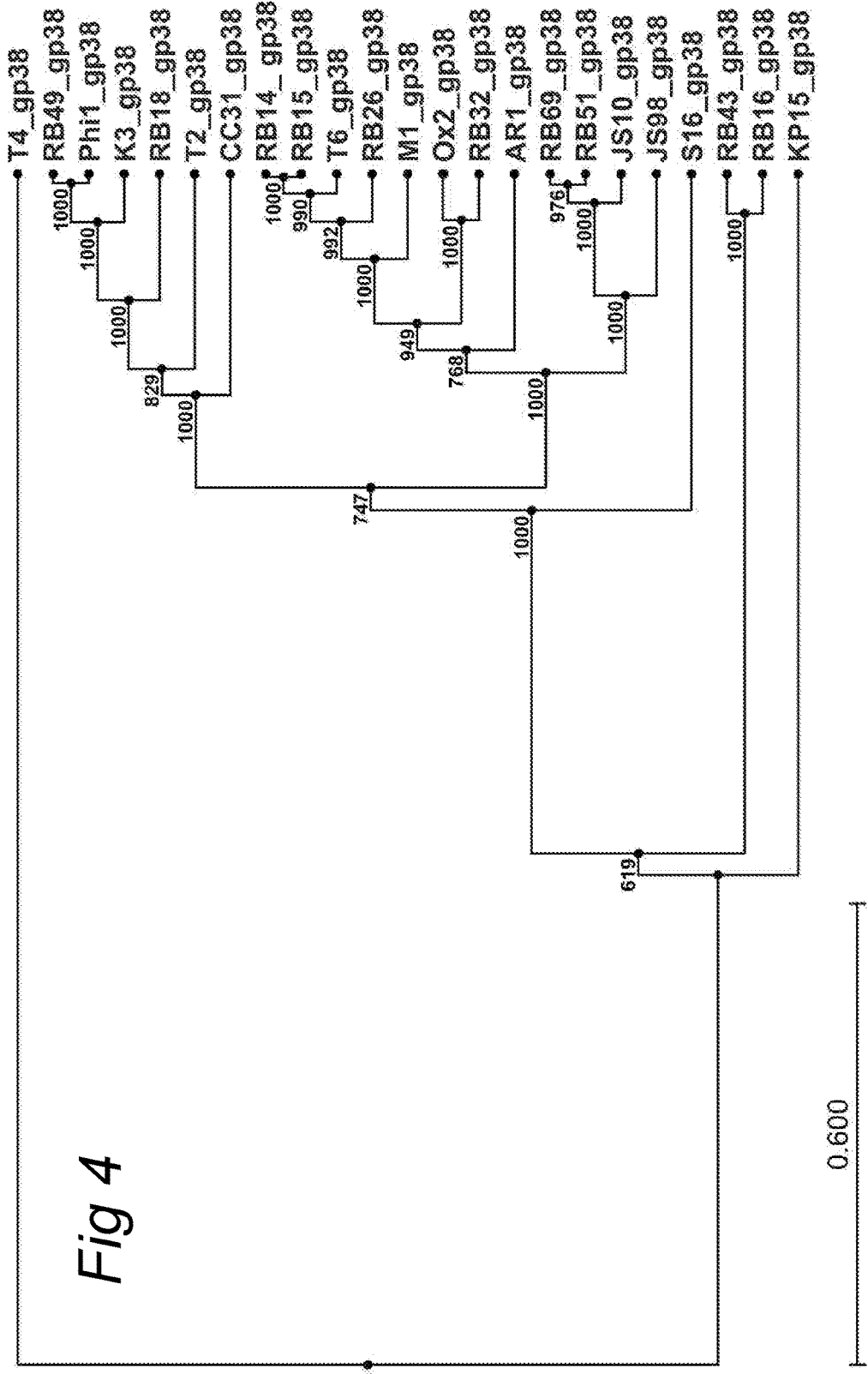

FIG. 4: Phylogenetic tree of gp38 adhesin proteins.

S16 gp38 is clearly placed with the T2-like phages but represents a separate branch (UPGMA algorithm, 1000 bootstrap replicates, CLC bio).

Figure 5:
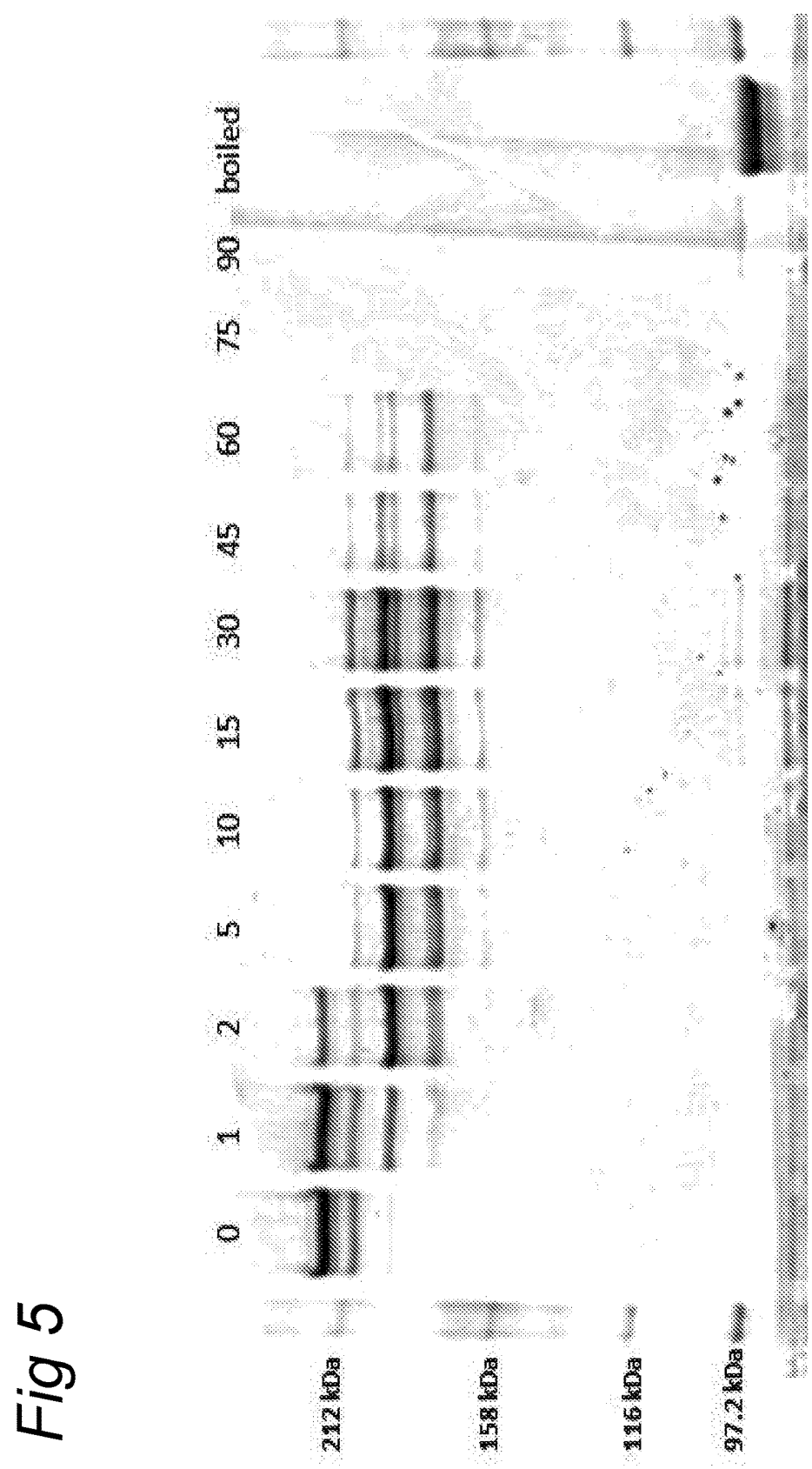

FIG. 5: Denaturation gradient SDS-PAGE of S16_gp37 at 65° C.

Numbers correspond to the incubation time in minutes at 65° C. The last sample was boiled 10 minutes before loading on the gel.

Figure 6:
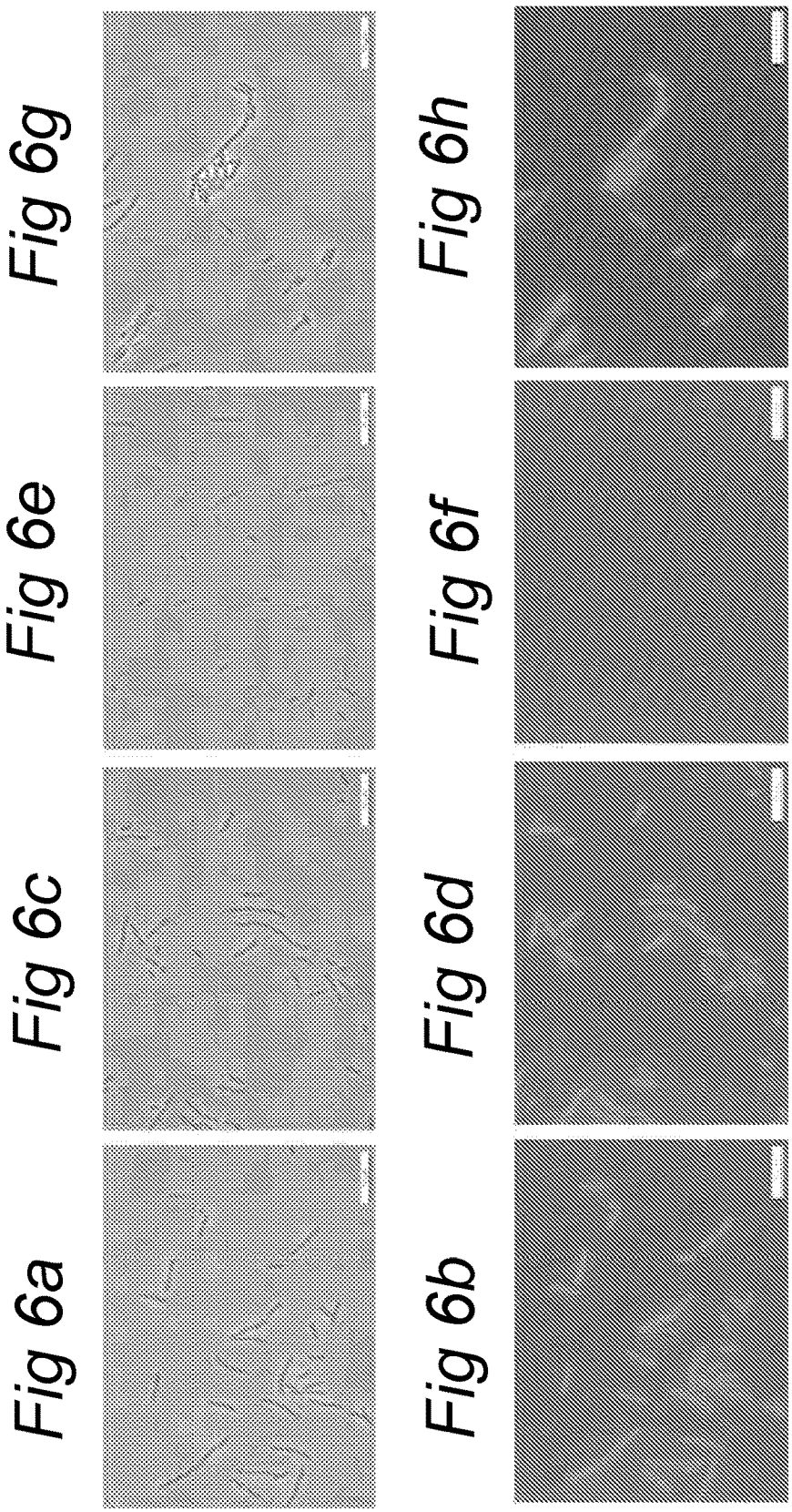

FIG. 6: Fluorescence microscopy pictures of HGFP_gp37 binding assays.

Phase contrast (A, C, E, and G) and fluorescence (B, D, F, and H) images of S. Tm. DT7155 wt (A, B), S. Tm.

DT7155 ΔompF (C, D), S. Tm. DT7155 ΔompC (E, F) and S. Tm. DT7155 ΔompC::ompC(DT) induced with 10 mM arabinose (G, H).

Figure 7:
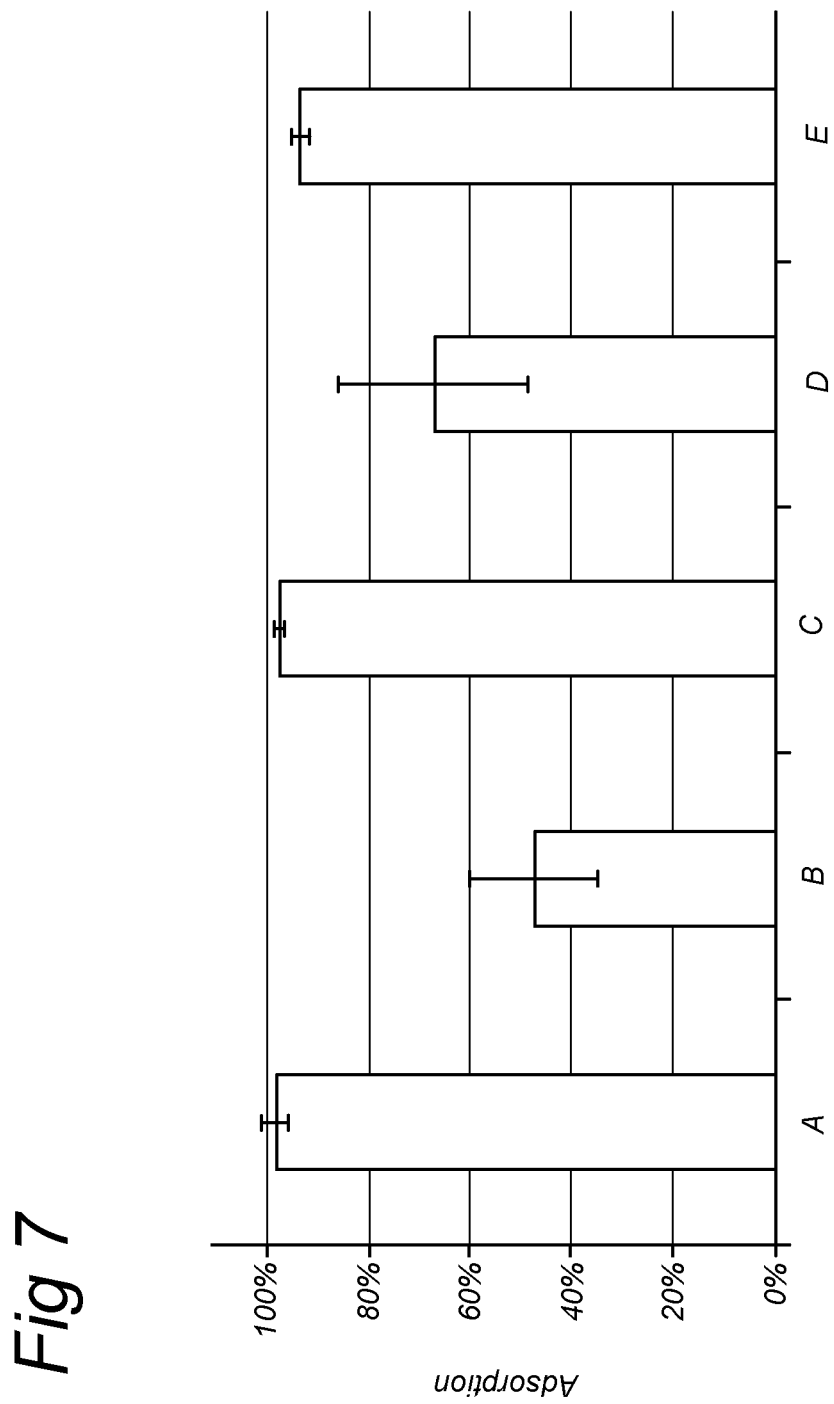

FIG. 7: Adsorption of S16 to S. Tm. DT7155.

Adsorption of S16 is significantly influenced by the presence or absence of outer membrane protein C (OmpC). A: S. Tm. DT7155 wt; B: S. Tm. DT7155 ΔompC; C: S. Tm. DT7155 ΔompC::ompC(DT) induced with 10 mM arabinose; D: S. Tm. DT7155 wt pre-incubated with GFP_gp37; E: S. Tm. DT7155 wt pre-incubated with GFP. (Values indicate averages of 3 experiments; error bars indicate corresponding standard deviations)

Figure 8:
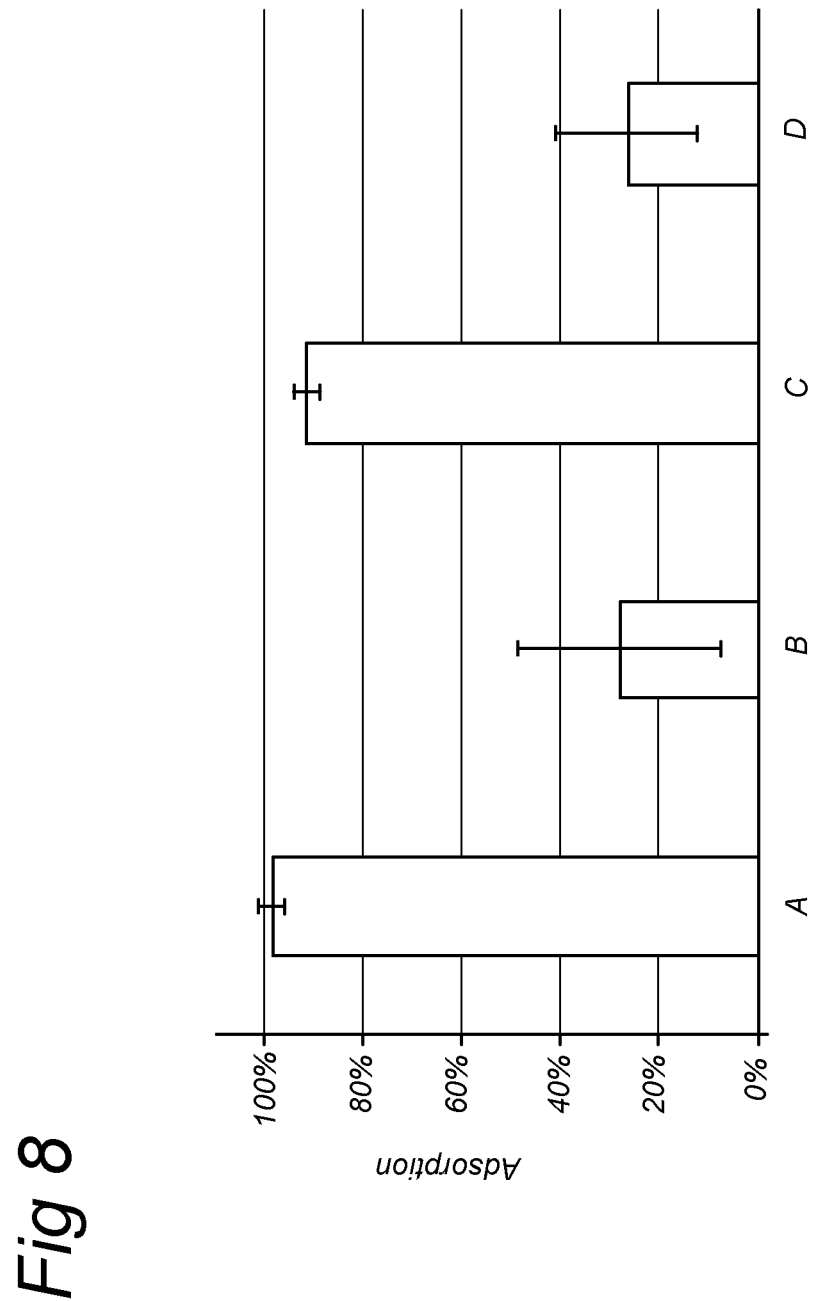

FIG. 8: Adsorption of S16 to E. coli K-12.

Expression of ompC(DT) in E. coli K-12 ΔompC, significantly increases adsorption of phage S16, while expression of ompC(K-12) does not. A: S. Tm. DT7155 wt; B: E. coli K-12 wt; C: E. coli K-12 ΔompC::ompC(DT) induced with 10 mM arabinose; D: E. coli K-12 ΔompC::ompC(DT) induced with 10 mM arabinose. (Values indicate averages of 3 experiments; error bars indicate corresponding standard deviations)

EXAMPLE 1

Materials and Methods
Strains and Plasmids:

An overview of the strains and plasmids used in this study is given in Table 1 and Table 2. Further strains used in host range analyses are listed and referenced in the Table 6. All bacteria were grown in LB media at 37° C. in test tubes in a shaker if not otherwise indicated. Concentrations of antibiotics used are as follows: Ampicillin (Amp, AppliChem GmbH, Darmstadt, Germany): 100 µg/ml; Chloramphenicol (Cm, Sigma-Aldrich, St. Louis, U.S.A.): 25 µg/ml; Kanamycin (Kan, Sigma-Aldrich): 200 m/ml for liquid cultures and 50 µg/ml for agar plates; Tetracycline (Tet, Sigma-Aldrich): 18 µg/ml.

Phage Propagation and Purification:

Bacteriophage was propagated by the double agar overlay method (Gratia, 1936). 4 ml LC soft agar (7.5 g/l NaCl, 5 g/l Yeas Extract, 10 g/l Tryptone, 1% glucose, 2 mM MgSO4, 10 mM CaCl2) was mixed with 100 µl of bacterial overnight culture and 10 µl of phage dilution and poured onto LB bottom agar plates (6 g/l agar). Plates were incubated overnight at 30° C. Semiconfluent plates were scraped with 5 ml of SM buffer (5.8 g/l NaCl, 8 mM MgSO4, 50 mM Tris, pH 7.4) for 5 h at room temperature. SM buffer was collected from the plates and phage was PEG precipitated overnight at 0° C. (8% PEG 8'000 Fluka; 0.5 M NaCl). After centrifugation (15 min., 10,000 g, 4° C.) phage was resuspended in 5 ml SM buffer and twice CsCl gradient purified (stepped gradient) to yield highly pure phage particles (Sambrook and Russel, 2001).

Phage DNA Preparation:

Two-fold CsCl gradient purified phage was dialysed against a 1000-fold excess of SM buffer. The solution was RNAse (10 µg/ml) and DNAse (20 µg/ml) treated for 20 min. at 37° C. After addition of 20 mM EDTA (pH 8) and proteinase K (50 µg/ml, Fermentas) for 1 h at 56° C., DNA was phenol/chloroform-extracted and ethanol-precipitated (Sambrook and Russel, 2001).

Restriction Fragment Length Polymorphism (RFLP) Analysis:

500 ng of purified phage DNA were digested with at least a 20-fold over-digest according to the maunfacturer's instructions. RFLP patterns were analyzed electrophoretically. Table 3 lists the restriction enzymes used.

One-Step Growth Curve:

All steps were carried out at 37° C. in LB media. Overnight cultures were diluted 1:100 in LB media and grown to an optical density of 0.5 at 600 nm (OD600). Phage was added at an MOI of 0.01, mixed and incubated for 5 min. After this adsorption step, the suspension was diluted 100-fold in pre-warmed media and plaque forming units (PFU) were subsequently determined every 5 minutes by standard soft agar overlays.

Transduction Assays:

Generalized transduction ability was tested using two different mutants of Salmonella Typhimurium DT7155: Δ1493::Cmr (Cm: chloramphenicol) and ΔPhoN::Kanr (Kan: kanamycin), which we constructed using site-directed mutagenesis as described below. Phage lysate was prepared on the Cmr strain and used to infect the Kanr strain. Cultures were tested for growth of colonies on plates containing both antibiotics.

Genome Sequencing, Assembly, Annotation and Comparison:

Genome sequencing of phage S16 was carried out by 454 pyrosequencing technology (FLX Titanium reagent, GATC biotech AG, Konstanz, Germany). Sequences were assembled into a single contig using GS De Novo assembler software (Newbler, Version 2.3, Roche AG, Switzerland). Further analyses were done using CLC Main Workbench (Version 6.0, CLC bio). Read lengths averaged 358 bp with 864 bp and 36 bp being the longest and shortest reads respectively. The average coverage of the genome is 84.38 reads (minimal=31, maximal=130). Loci with unclear consensus were PCR-amplified and confirmed by Sanger sequencing (GATC Biotech AG, Konstanz, Germany). Preliminary annotation of S16's genome was done using the "Genome Annotation Transfer Utility" (GATU; available at http://www.virology.ca/gatu) and the bacteriophage T4 complete genome (NC_000866) as reference (Tcherepanov et al., 2006). The annotation was manually refined. Putative tRNAs were annotated using tRNAscan-SE v.1.21 (available at http://lowelab.ucsc.edu/tRNAscan-SE/ (Lowe and Eddy 1997)). The annotated genome of S16 is available under GenBank accession number HQ331142.

Host Range Analysis:

Dry LB agar plates were flooded with 4 ml of log-phages cultures, excess culture removed and dried for 30 min. at 30° C. 3 µl of phage dilutions 10-2 to 10-7 of CsCl stocks>1012 PFU/ml were spotted onto plates and incubated overnight at 30° C. (spot-on-the-lawn method).

Site-Directed Mutagenesis Using PCR Products:

Insertion mutants in E. coli and Salmonella enterica subsp. enterica were created as previously described (Datsenko and Wanner, 2000). Homologous sequences were chosen such that the first 18 and last 36 nucleotides of the gene of interest remained unaltered. The rest of the gene was replaced by the resistance cassette (i.e. ΔompC::Kanr, or just ΔompC for short). Resistant colonies were screened for locus size. Positive clones were single colony purified and subsequently tested for Ampicillin sensitivity (loss of pKD46). Deletion mutants were complemented by supplying ompC of either S. Tm. DT7155 (ompC(DT)) or ompC of E. coli K-12 (ompC(K-12)) in trans on the vector pBAD18_Ampr inducible by arabinose ((Guzman et al., 1995), kindly provided by Dr. Thilo Fuchs, TU Munich).

Protein Expression and Purification:

The long tail fiber of phage S16 was cloned into the vector pHGFP Ampr (Loessner et al., 2002). This plasmid allows induction of transcription by IPTG (Isopropyl-ß-D-thiogalactopyranosid) and includes an N-terminal 6xHis tag (we abbreviate the 6×His-tag by a capital H; i.e. HGFP). The gp37 specific chaperone gp38 was cloned downstream of the long tail fiber gene in a bicistronic transcript (using AGGAGG as 13 RBS). Gp57A, a general trimerization chaperone, was placed on a second plasmid 14 (pBAD18_Cmr), under an arabinose inducible promotor. ((Guzman et al., 1995), kindly provided by Dr. Thilo Fuchs, TU Munich). The expression strain used was E. coli XL1 Blue MRF' (Stratagene AG, Basel, Switzerland). Protein expression was induced with 0.5 mM IPTG (Axon Lab, Baden-Dättwil, Switzerland) and carried out over night at 20° C. Purification was done by gravity flow immobilized metal affinity chromatography (IMAC) using low-density Ni-NTA beads (Chemie Brunschwig AG, Basel, Switzerland).

Statistical Analysis:

Data values were averaged and standard deviations calculated. P-values of student's t-test (one-tailed, two samples of unequal variance, significance level α=0.05) were determined (Excel 2010, Microsoft).

Binding Assays with GFP Fusion Proteins:

Binding assays were carried out using log-phase cultures. 0.5 ml were pelleted and resuspended in 200 μl SM buffer. Proteins were centrifuged to remove aggregates (30 min., 31,000 g, 4° C.) and approximately 1 μg protein was added to the cells. After 10 min. incubation at room temperature, the cells were washed in SM buffer. A Zeiss axioplan microscope at 100 fold magnification was used for fluorescence microscopy (excitation: BP 450-490 nm, FT 510 nm, emission: LP 520 nm, Carl Zeiss AG, Germany)

Pull Down Assays:

1 ml of overnight cultures was adjusted to OD600=1.0±0.05 and 10 μl of phage solution ($10^9$ pfu/ml) were added. Samples were incubated for 10 min. at room temperature and subsequently centrifuged (10 min., 20,000 g). Supernatant was removed and pfu determined in triplicate. Percentage of adsorption was determined relative to LB control. Inhibition of the pull down assay by HGFP_gp37 was determined with the following alterations: cells were pre-incubated with_20 μg of HGFP_gp37 for 10 min. before phage was added. Also, incubation with phage was reduced to three inversions of the test tubes, which did not decrease binding of the positive control.

Results

Phage S16 is a T4-Like Myovirus

Figure 1A:
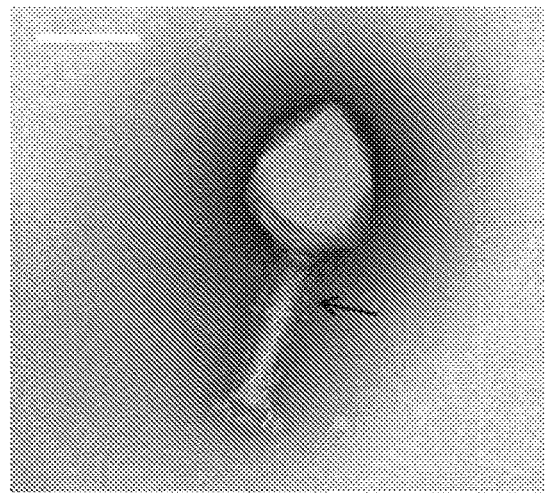
FIG. 1: Transmission electro micrographs of S16.
Figure 1B:
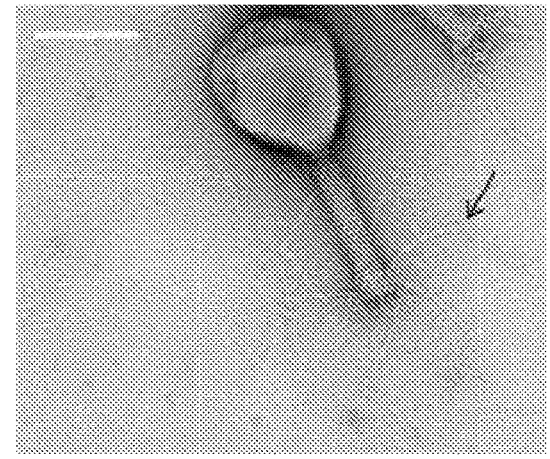
Figure 1C:
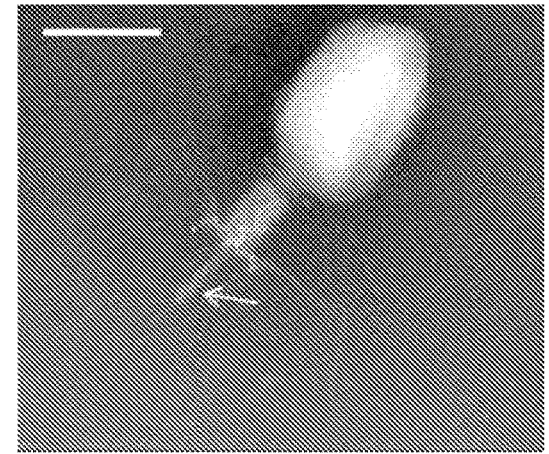

Phage S16 belongs to the order Caudovirales. Its contractile tail is the defining morphological feature of the Myoviridae family (FIG. 1). Further, S16 features a slightly elongated head which is 117.2±4.1 nm long and 91.5±2.8 nm wide (flat-flat) (n=10). Its tail length averages 120.2±2.8 nm (n=10). It is thus morphologically very similar to phage T4, whose head is 120 nm long and 85 nm wide with a tail 113 nm in length (Tetart et al., 2001; Calendar, 2006). S16 is can be placed within the A2 group of head morphology, which constitute approximately 3.2% of all known tailed phages (Ackermann 1998). S16's baseplate is depicted in FIG. 1 A, while the tail sheath disks are most clearly visible in FIG. 1B. The collar and tail sheath contraction can be seen in FIG. 1C. Whiskers (wac) which would hold the long tail fiber in their stored position could not be observed electron micrographs.

Phage S16 Specifically Infects Salmonella

Phage S16 infection was tested on Salmonella (32 strains and 14 LPS mutants of S. Tm LT2) and E. coli (6 strains plus 25 apathogenic isolates not in Table 4). S16 is able to lyse all but one of the clinical Salmonella isolates in when spotted. Single plaques were observed for 25 of the 32 isolates. E. coli were not found to be sensitive to this phage. LPS knock-out mutants of S. Tm. LT2 were all infected except one. Even Re-mutant strains, which completely lack any sugars after the inner core 2-keto-deoxy-d-octanoate (KDO) residues, were sensitive. The Rd2 mutant was not infected by S16. This result is quite inexplicable, since both longer and shorter LPS core types can be infected and the LPS mutant strains should be isogenic. Phage S16 has been proven to be very broadly and specifically active against Salmonella.

S16 Replicates Quickly

Growth parameters are an integral part of phage characterization. One step growth curves were carried out in triplicate as described above. Phage burst started after total incubation time of 20 minutes and was concluded at 30 to 35 min incubation. The average burst of three individual experiments was 37.2±1.3 particles per cell. The growth speed is thus comparable to other T-even phages (latency of 23 min. for both T2 and T4). The burst size, however, is lower than reported for related phages (T2: 135; T4: 150 (De Paepe and Taddei 29 2006)).

S16 does not Transduce Host DNA

Some phages are known to not only package their own DNA, but also that of their host organism. This process, called transduction, is a major source of horizontal gene transfer (Sternberg and Maurer, 1991). If a phage is ultimately intended for use as a biocontrol agent, transduction must be excluded (Hagens and Loessner, 2010). Phage P22 (HT mutant (Schmieger, 1972)) was used as a positive control. With this phage, colonies resistant to both Cm and Kan were readily observed. No colonies resistant to both antibiotics were observed with S16. It is therefore a non-transducing phage under the conditions tested.

Genome Sequencing and Assembly

The genome of S16 is 160.221 bp in length and features a G+C content of 36.9% while its host features a G+C content of 52.2%. It is also highly restriction resistant, with only 4 of the 34 restriction enzymes tested being able to digest S16 DNA (FIG. 2). A general overview of S16's genome and an alignment to T4 are given in FIG. 3. One hundred and eighty nine coding sequences (CDS) as well as 3 tRNA genes (Met, Gln and Arg with anticodons CAT, TTG and TCT respectively) were annotated. Due to S16's similarity to T4, we could assign functions to 61.38% of all CDS. The other 38.62% represent both hypothetical proteins only annotated in S16 and others that have close homologs in other T4-like phages but no assigned functions. CDS are on average 704 nucleotides in length, with 1.18 CDS per kb. The estimated coding capacity is 83%. The annotated start codon usage is: ATG (88.36%), TTG (4.76%), ATT (2.65%), GTG (2.12%), ATC and CTG with 1.06% each. S16 belongs to the T4-like viruses. The genus has recently been reviewed on the genome level and a set of core genes has been defined (Petrov et al., 2010). A comparison of core genome proteins between S16 and T4 is given in Table 5. Two of the 39 genes of the T4-like core genome are missing in S16. There is no full length gene for uvsW (a recombination DNA RNA helicase and DNA-dependent ATPase) in the S16 genome. Instead, two separate, shorter genes were found. These two proteins (named UvsW 1 and 2) are very similar to T4 UvsW residues 1 through 234 and 216 through 502 respectively. The crystal structure of T4 UvsW has previously been elucidated (Sickmier et al., 2004; Kerr et al., 2007). Secondary structure prediction of S16 UvsW 1 and 2 (using HHpred; http://toolkit.tuebingen.mpg.de/hhpred) was carried out. Both proteins have very strong similarities to T4

UvsW (domain 2oca_A; probability 100%, E-value 1.3*10-33 and probability: 99.97%, E-value: 2*10-30 for S16 UvsW 1 and 2 respectively). Thus, basically the entire T4 UvsW protein is encoded in the S16 genome, albeit in two separate genes. Whether these can fulfill the same function remains unknown. The second missing core gene is gp49 (endonuclease VII). Gp49 is an essential protein in T4 but has been found to be substituted by other endonucleases (with catalytic domains similar to I-TevII) in E. coli phage RB16 and Aeromonas phage 65 (Petrov, Nolan et al., 2006). S16 features I-TevIII, a homing endonuclease 269aa long and very similar to the I-TevIII of phage RB3 (88.52% identity, E-value: 0.00 (Robbins et al., 2007)). In T4, homing endonuclease I-TevIII is defunct. It is only 97 amino acids long with the N-terminal catalytic domain missing (Robbins et al., 2007). I-TevIII of S16 possibly compensates for the absence of gp49, as I-TevII does in the cases of E. coli phage RB16 and Aeromonas phage 65. As a further layer of destinction, the genus of T4-like phages was subdivided into genome types. According to those definitions, the presence of DNA modification genes (two glycosyltransferases and one dCMP hydroxymethylase) as well as the overall genome structure place S16 in the group of T-even type phages (Petrov, Ratnayaka et al., 2010). No bacterial virulence factors or toxin genes were found encoded in the genome of S16. The complete annotation can be found in the Table 6.

Identification and in Silico Analysis of Tail Fiber Genes

The long tail fibers (LTF) of T4-like phages mediate the initial, reversible recognition of the host cell surface. This interaction is more selective in nature than the binding of the short tail fibers which, in case of T4, bind to the inner LPS core common to all Enterobacteria. Gp34 through gp37 constitute the LTF from proximal to distal segments. Two chaperones are required for trimerization of the LTF. The general chaperone gp57A and the gp37-specific gp38 (FIG. 3 shows an alignment of S16, T2 and T4 LTF genes and their chaperones (Calendar 2006)). In T4, the C-terminal part of gp37 mediates binding to its receptor. The specificity appears to be determined by so-called His boxes (consensus sequence: GXHXH (Tetart et al., 1996)). No His boxes were found in S16 gp37. In T2 and T6, by contrast, binding is mediated by the gp38 chaperone itself. It acts as an adhesin, attaching to the C-terminal part of gp37 and mediating the binding to the cell surface (Riede et al., 1985). Glycine islands similar to those described for T2 gp38 could also be identified in S16. These islands are relatively conserved regions delimiting more diverse regions that likely determine receptor specificity of the adhesin (Tetart et al., 1996; Troj et al., 2011). Homology detection and secondary structure prediction (using HHpred; http://toolkit.tuebingen.mpg.de/hhpred) of S16 gp37 and gp38 show more similarities to the corresponding proteins of T2 than those of T4. Specifically, both S16 and T2 gp37 have a strong similarity in their C-terminus to an Endo-N-acetylneuraminidase domain of phage K1F (Probabilities: 99.49 and 99.35 and E-values: 2.6*10-14 and 4.9*10-13 respectively). Weak structural homologies identified indicate that gp38 of S16 and T2 cluster more closely together than gp38 of S16 and T4. Comparing gp38 of S16 to those of other sequenced T4-like phages in a phylogenetic tree clearly group S16 closer to T2 and T6 than T4 (FIG. 4). From these analyses the LTF of S16 is expected to have a structure closely related to that of T2, with gp38 bound to the C-terminal tip of gp37.

Purified Full-Length Long Tail Fiber (LTF) Protein was Obtained

Analogously to phage T4, two chaperones were found to be required for correct folding of LTF protein distal subunit (gp37) of S16: gp38 and gp57A (Bartual et al., 2010; Leiman et al., 2010). No soluble protein could be obtained without the co-expression of both (data not shown). The LTF of T4-like phages are active in a trimeric state (Cerritelli et al., 1996). Due to their mosaic structure indicating high frequency of horizontal gene transfer, it is assumed that all gp37 homologs of T4-like phages are trimers (Hashemolhosseini et al., 1996). The purified HGFP_gp37 was analyzed by heat denaturation gradient SDS-PAGE in order to illustrate the oligomeric structure of the protein (FIG. 5). A clearly visible, stepwise denaturation of higher molecular weight bands into lighter ones was observed, indicating an unraveling of higher order structures. The electrophoretic mobility of denatured S16 HGFP_gp37 was higher than expected from in silico predictions. The full length protein has a predicted molecular weight of 108.5 kDa, whereas the observed band ran just below 97 kDa (FIG. 5, last lane). It has previously been shown that gp37 of phage T2 undergoes proteolytic processing, resulting in the removal of its C-terminal 120 amino acids (Drexler et al., 1986). Such a C terminal proteolytic removal of the last 120 amino acids would result in a protein of 94.3 kDa, corresponding to the observed band size. The protein band was analyzed by means of MS/MS analysis (Functional Genomics Centre Zurich, FGCZ, Zurich, Switzerland).

There were no peptide hits to the C-terminal 201 amino acids of S16 gp37 except for one single 6aa peptide. Both chaperones were also detected by MS/MS (2 peptides for gp38 and 1 for gp57A). Based on these observations, combined with the structural predictions (see above), proteolytical processing of S16 gp37 C-terminus is likely to takes place.

S16 LTF Binds to Outer Membrane Protein C (OmpC)

By performing binding assays with the soluble, HGFP_gp37, the receptor of S16 LTF could be identified (FIG. 6). S. typhimurium DT7155 wt served as positive control (FIG. 6, A, B). Due to S16s similarity to T2 and T4 the receptor proteins of both these phages were knocked out to assess binding of HGFP_gp37. Removal of OmpF (the receptor of phage T2 (Hantke, 1978)) does not hinder cell decoration by HGFP_gp37 (FIG. 6, C, D). Deletion of OmpC (the receptor of phage T4 (Yu and Mizushima 1982)) on the other hand, prohibited such binding (FIG. 6 E, F). Attachment of HGFP_gp37 could be restored by providing ompC in trans on pBAD18 Ampr (FIG. 6 G, H). These results demonstrate that OmpC is necessary and sufficient for binding of the S16 LTF to S. typhimurium DT7155.

S16 Adsorbs to Cells with Salmonella

OmpC Pull-down assays were performed to prove that whole phage adsorption is also dependent on OmpC (FIG. 7). Although adsorption of S16 to S. typhimurium DT7155 $\Delta$ompC can still be observed, it is much lower than wild-type adsorption (47.46% as opposed to wild type: 98.43%, p-value: 0.0084). Complementation with ompC(DT) on pBAD18 Ampr restored near wild-type adsorption levels (97.50%). Furthermore, the addition of HGFP_gp37 could significantly reduce the adsorption ratio of S16 (67.25% compared to wild type: 98.43%, p-value: 0.0483), while HGFP alone did not (93.76% adsorption ratio). Even though resistant to phage infection, some adsorption of S16 to E. coli K-12 can be observed. It is, however, significantly lower than to S. typhimurium DT7155 (28.06% vs. 98.43%, p-value: 0.0127, FIG. 8). An E. coli K-12 $\Delta$ompC strain (CGSC4401) was constructed and complemented with either the ompC gene of K-12 (ompC(K-12)) or the ompC gene of *S. typhimurium* DT7155 (ompC(DT)). Deleting the indigenous ompC gene of strain K-12 and complementing with ompC(DT) significantly increased the adsorption ratio of S16 to 91.53% (p value: 0.0155, FIG. 8). The same experiment was carried out complementing with ompC(K-12). No increase in adsorption relative to *E. coli* K-12 wt was observed (26.44%, FIG. 8). This control rules out possible effects through different intracellular levels of OmpC. These findings demonstrate that not only LTF binding but also whole phage particle adsorption is dependent on OmpC. Further, phage S16 binds specifically to OmpC of *S. typhimurium* and not OmpC of *E. coli* K-12 wt.

Discussion

Phages are the natural enemies of bacteria. Their use for controlling bacterial pathogens is currently being evaluated by many researchers. Strains belonging to *Salmonella enterica* subspecies *enterica* are one of the leading causes of foodborne illness worldwide. This subspecies is very diverse, with more than 2'500 recognized serovars (Grimont and Weill, 2007), making the acquisition of phages with broad host ranges relatively difficult. In this work, a novel broad host range *Salmonella* Myovirus, S16, has been described. The genome sequence has been determined an annotated. S16 is a new member of the ever expanding genus of T4-like viruses, belonging to the T-even type subgroup. To our knowledge, S16 is the first fully characterized member of the T4-like phages limited to infecting *Salmonella* (Petrov et al., 2010). Its genome structure closely resembles that of phage T4 (FIG. 3). The host range of S16 is very broad within the genus *Salmonella*, while no *E. coli* isolates tested was susceptible. It can be argued that S16 is a more suitable phage for biocontrol than Felix O1 because of two main reasons. Firstly, Felix O1 requires the terminal N-acetylglucosamine residue of the outer LPS core for infection (Lindberg 1967; Lindberg and Holme 1969). It was demonstrated that S16 requires no more than the 2-keto-deoxy-d-octanoate (KDO) residues of the inner core (Re mutants), similar to T4. This enables S16, in contrast to Felix O1, to also infect deep rough strains. Of all the isogenic, sequential LPS core synthesis knock-out strains of *Salmonella Typhimurium* LT2 we tested, one strain was resistant. The LPS core of this Rd2 mutant only contains the 3 2-keto-deoxy-d-octanoate (KDO) residues and a single heptose. On basis of LPS structure alone, no explanation could be found why this strain should prove to be resistant. Other, unintended changes in this strain may have occurred, such as polar effects on LPS synthesis resulting in aberrant structures. Secondly, the DNA modification systems of S16 render its genome immune to many common restriction systems (FIG. 2), giving it a further advantage over Felix O1. Apart from specificity, there are several other criteria for phages to be used in biocontrol of foodborne pathogens. They need to be strictly virulent (avoiding lysogeny) and there must be no virulence factors or known allergens encoded in the phage genome. Generalized transduction, the transfer of host DNA by phage particles, must also be excluded (Hagens and Loessner, 2010). The first two points could be excluded by whole genome sequencing and annotation. The third was assessed by transduction experiments. No transduction of resistance cassettes was observed in our set-up with S16. Transduction could readily be observed in case of phage P22 (an HT mutant (Schmieger, 1972)). T4 itself is not known to transduce host DNA without several mutations (Wilson et al., 1979). Specifically, mutations in the gene for host nuclear disruption (ndd) plus endonuclease IV (denB) and possibly genes in the D1 region (between rIIB and denB) are all required to convert T4 to a generalized transducing phage. The frequency of transduction can be increased by mutations in rIIA, rIIB, stp and ac (Young et al., 1982). S16 features intact ndd, denB, rIIA and rIIB genes. Thus, the prerequisites for generalized transduction are not given for this phage. It does lack genes stp and ac, but the absence of these genes alone is not sufficient for conversion to a transducing phage. It can thus be concluded that S16 represents a prime candidate for biocontrol of *Salmonella* ssp. A phages receptor binding protein and receptor are one of its key characteristics. For S16, both have been identified. The distal subunit of the long tail fiber (LTF) of S16 has been identified. It is gene product gp37. Full-length, GFP tagged gp37 (HGFP_gp37) could be expressed and purified. The method for expression used was first described in (Bartual et al., 2010). The authors produced T4 LTF in large quantities by co-expression with the trimerization chaperones gp57A and gp38. In the same study, it was proposed that this method can be applied to other T4-like phages. In this present work it was demonstrated that this approach is indeed applicable to other phages as well. The native HGF-P_gp37 protein obtained was clearly shown to be an oligomer by heat denaturation SDS-PAGE (FIG. 5). Its functionality could be established in binding assays (FIG. 6) and by its ability to reduce phage adsorption (FIG. 7). By means of deletion mutants it was shown that the protein binds specifically to outer membrane protein C (OmpC) of *Salmonella*. *S. Typhimurium* DT7155 lacking OmpC could not be tagged and visualized by fluorescence microscopy and binding could be reconstituted by providing OmpC in trans (FIG. 6). Also, adsorption rates of phage particles to cells lacking OmpC were reduced and could be reconstituted by complementation with OmpC in trans (FIG. 7). Further, it was shown that whole phage binding requires *Salmonella enterica* ssp. *enterica* OmpC. Phage adsorption rates were greatly increased for *E. coli* K-12 ΔompC::ompC(DT) as compared to both wild-type *E. coli* K-12 and *E. coli* K-12 ΔompC::ompC(K-12) (FIG. 8). Thus OmpC of *S. typhimurium* DT7155 but not of *E. coli* K-12 was found to be found a receptor sufficient for adsorption of phage S16. There may be further surface structures to which the S16 LTF can bind, as is the case for T4 (OmpC or LPS in *E. coli* B) and T2 (OmpF or FadL) (Hantke, 1978; Yu and Mizushima, 1982; Trojet et al., 2011). Besides OmpC and OmpF, the following knock-outs were also tested: ompA, ompX btuB tonB and tsx. None of these mutant strains showed decreased susceptibility to S16 (data not shown). It has previously been shown that mutations in gp38 can change receptor specificity. The T2-like phage Ml, for example, uses OmpA as its receptor. However, its specificity can be changed to OmpC or OmpT. These changes are apparently mediated by amino acid substitutions of mainly Tyrosine, Tryptophane, Serine or Asparagine in the variable regions between glycine islands (Hashemolhosseini et al., 1994; Tetart et al., 1998; Trojet et al., 2011). With this flexibility, it is not surprising to find a T2-like gp38 sequence binding to OmpC instead of OmpF. Since gp38 does not act as the adhesin in case of T4, the phylogenetic tree of T-even gp38 proteins clearly separates T4 gp38 from the rest. Within the group of phages where gp38 does act as the adhesin, S16 defines a novel, separate branch (FIG. 4). Note that all other phages represented in the tree are *E. coli* phages. Further *Salmonella* T-even phages may be placed in this same branch as S16 and the formation of a new subgroup of T-even phages may be indicated. In this work the novel, broad host range *Salmonella* phage S16 has been fully characterized. It is the first member of the T4-like genus specific for *Salmonella*. Its host range is even greater than that of Felix O1. Due to its DNA modification systems and ability to infect rough strains, S16 is proposed to be a superior choice as a biocontrol agent.

TABLE 1

Strains used in this study

| Strain | Further designations | Source |
|---|---|---|
| *Salmonella Typhimurium* | DT7155 | Laboratory stock |
| *Escherichia coli* | XL1 Blue MRF', Tetr | Stratagene, Santa Clara, CA, U.S.A. |
| *Escherichia coli* K-12 wild type | CGSC4401 | Coli Genetic Stock Center, Yale University |

TABLE 2

Plasmids used in this study

| Plasmid | Features | Source/Reference |
|---|---|---|
| pBAD18 Amp$^r$ | Amp$^r$; Arabinose inducible transcription | (24) |
| pBAD18 Cm$^r$ | Cm$^r$; Arabinose inducible expression | (24) |
| pHGFP | Amp$^r$; IPTG inducible expression; 6xHis-tag (N-terminal) | (43) |
| pKD3 | Amp$^r$; Cm$^r$ cassette flanked by P1 and P2 | (17) |
| pKD4 | Amp$^r$; Kan$^r$ cassette flanked by P1 and P2 | (17) |
| pKD46 | Amp$^r$, red recombinase, temp, sensitive, permissive: 30° C. | (17) |

TABLE 3

Restriction enzymes used in this study Enzymes were manufactured by Fermentas GmbH (St. Leon-Rot, Germany), New England Biolabs (Ipswich, U.S.A.) or GE Healthcare (Little Chalfont, England)

| Name | Target sequence 5'...3' | # of sites | Methylation effects: Dam, Dcm, CpG, EcoKI, EcoBI | Manufacturer |
|---|---|---|---|---|
| Eco52I (EagI) | C^G G C C G | 2 | Blocked by CpG | Fermentas GmbH |
| DpnI | G m6A^T C | 38 | Cleaves only dam methylated DNA | Fermentas |
| HhaI | G C G^C | 230 | Blocked by CpG | Fermentas |
| Eco105I (SnaBI) | T A C^G T A | 23 | Blocked by CpG | Fermentas |
| HincII (HindII) | G T Y^R A C | 114 | Impaired by CpG; blocked by EcoKI, EcoBI | Fermentas |
| KpnI | G G T A C^C | 4 | Not affected | Fermentas |
| MluI | A^C G C G T | 10 | Blocked by CpG | Fermentas |
| MpH1103I (NsiI) | A T G C A^T | 45 | Not affected (EcoBI unknown) | Fermentas |
| MspI (HpaII) | C^C G G | 312 | Not affected | Fermentas |
| NheI | G^C T A G C | 3 | Impaired by CpG | Fermentas |
| SacI | G A G C T^C | 34 | Not affected | Fermentas |
| SalI | G^T C G A C | 8 | Blocked by CpG | Fermentas |
| OliI (AleI) | C A C N N^N N G T G | 11 | Impaired by CpG; blocked by EcoKI, EcoBI | Fermentas |
| Van91I (PflMI) | C C A N N N N^N T G G | 32 | Blocked by DcM | Fermentas |
| PacI | T T A A T^T A A | 9 | Not affected (EcoKI unknown) | New England Biolabs |
| PaeI (SphI) | G C A T G^C | 11 | Blocked by EcoBI | Fermentas |
| Eco88I (AvaI) | C^Y C G R G | 31 | Impaired by CpG | Fermentas |
| MssI (PmeI) | G T T T^A A A C | 12 | Blocked by EcoKI | Fermentas |
| PvuII | C A G^C T G | 40 | Not affected (EcoBI unknown) | Fermentas |
| PagI (BspHI) | T^C A T G A | 72 | Impaired by Dam and EcoBI | Fermentas |

TABLE 3-continued

Restriction enzymes used in this study Enzymes were manufactured by Fermentas GmbH (St. Leon-Rot, Germany), New England Biolabs (Ipswich, U.S.A.) or GE Healthcare (Little Chalfont, England)

| Name | Target sequence 5' . . . 3' | # of sites | Methylation effects: Dam, Dcm, CpG, EcoKI, EcoBI | Manufacturer |
| --- | --- | --- | --- | --- |
| BseJI (BsaBI) | G A T N N^N N A T C | 28 | Blocked by Dam (EcoBI unknown) | Fermentas |
| Bsp68I (NruI) | T C G^C G A | 30 | Blocked by CpG | Fermentas |
| SwaI (SmiI)* | A T T T^A A A T | 15 | Not affected | New England Biolabs |
| TaqI* | T^C G A | 337 | Blocked by Dam | Fermentas |
| EcoRI | G^A A T T C | 90 | Impaired by CpG | Fermentas |
| EcoRV (Eco32I) | G A T^A T C | 74 | Not affected (EcoBI unknown) | Fermentas |
| HindIII | A^A G C T T | 88 | Impaired by EcoBI | Fermentas |
| PauI (BssHII) | G^C G C G C | 10 | Blocked by CpG | Fermentas |
| XcmI | CCANNNNN^NNNNTGG | 34 | Not affected | New England Biolabs |
| ClaI | AT^CGAT | 35 | Blocked by Dam, CpG | New England Biolabs |
| FspBI (BfaI) | C^T A G | 234 | Not affected | Fermentas |
| NdeI* | C A^T A T G | 45 | Not affected | Fermentas |
| MboI | ^G A T C | 38 | Blocked by Dam, EcoBI | Fermentas |
| SspI* | A A T^A T T | 172 | Not affected | GE Healthcare |

TABLE 4

Host range analysis of phage S16

| Strain | Misc Info | further designations | Lysis in spots | single plaques | Source |
| --- | --- | --- | --- | --- | --- |
| S. Typhimurium | | DT7155 | ++ | + | 1 |
| E. coli | LPS Chemotype R1 | F470* | − | − | 2 |
| E. coli | LPS Chemotype R2 | F576* | − | − | 2 |
| E. coli | LPS Chemotype R3 | F653† | − | − | 2 |
| E. coli | LPS Chemotype R4 | F2513† | − | − | 2 |
| E. coli | LPS Chemotype B | BL21 (DE3) | − | − | 3 |
| E. coli | LPS Chemotype K-12 | CGSC4401 | − | − | 4 |
| S. Senftenberg | clinical isolate | | ++ | + | 5 |
| S. Enteritidis C | clinical isolate | | ++ | + | 5 |
| S. Virchow | clinical isolate | | + | + | 5 |
| S. Indiana | clinical isolate | | ++ | + | 5 |
| S. Enteritidis A | clinical isolate | | ++ | + | 5 |
| S. Enteritidis | clinical isolate | N2939-08 | + | − | 6 |
| S. Enteritidis | clinical isolate | N90-09 | + | − | 6 |
| S. Javiana | clinical isolate | N2427-08 | ++ | + | 6 |
| S. Montevideo | clinical isolate | N2888-08 | ++ | + | 6 |
| S. Montevideo | clinical isolate | N1689-08 | + | − | 6 |
| S. Newport | clinical isolate | N2932-08 | ++ | + | 6 |
| S. Newport | clinical isolate | N2889-08 | ++ | + | 6 |
| S. Senftenberg | clinical isolate | N1589-08 | + | + | 6 |
| S. Typhimurium | clinical isolate | N59-09 | + | − | 6 |
| S. Typhimurium | clinical isolate | N62-09 | ++ | − | 6 |
| S. Typhimurium | clinical isolate | N75-09 | + | − | 6 |
| S. Enteritidis | clinical isolate | N239-07 | ++ | + | 6 |
| S. Enteritidis | clinical isolate | N289-07 | − | − | 6 |
| S. Hadar | clinical isolate | N284-07 | ++ | + | 6 |

TABLE 4-continued

Host range analysis of phage S16

| Strain | Misc Info | further designations | Lysis in spots | single plaques | Source |
|---|---|---|---|---|---|
| S. Hadar | clinical isolate | WS 2691 | + | + | 1 |
| S. Typhimurium | | DT104 | ++ | + | 1 |
| S. Typhimurium LT2 | | ATCC 14028 | ++ | + | 7 |
| S. Choleraesuis | | SC-B67 | + | + | 8 |
| S. Gallinarum | | 287/91 | ++ | + | 9 |
| S. Enteritidis PT4 | sequenced | P125109 | ++ | + | 9 |
| S. e. subsp. Salamae | 30:l, z28:z6 | N09-2794 | ++ | + | 6 |
| S. e. subsp. arizonae | 56:z4, z23:— | N09-0860 | ++ | + | 6 |
| S. e. subsp. diarizonae | 61:c:z35 | N09-2338 | + | − | 6 |
| S. e. subsp. houtenae | 38:z4, z23:— | N09-2589 | ++ | + | 6 |
| S. bongori | 48:z35:— | N268-08 | + | + | 6 |
| S. e. subsp. enterica | O rough:i:— | N2592-08 | ++ | + | 6 |
| S. indica | 6.14.25:a:e, n, x | N2576-03 | ++ | + | 6 |
| S. Typhimurium LT2 | smooth | SL3770 | ++ | + | 10 |
| S. Typhimurium LT2 | smooth | SA1355 | ++ | + | 10 |
| S. Typhimurium LT2 | Ra LPS mutant | SA1627 | ++ | + | 10 |
| S. Typhimurium LT2 | Ra LPS mutant | SL3749 | ++ | + | 10 |
| S. Typhimurium LT2 | Rb1 LPS mutant | SL733 | ++ | + | 10 |
| S. Typhimurium LT2 | Rb2 LPS mutant | SL3750 | ++ | + | 10 |
| S. Typhimurium LT2 | Rb3 LPS mutant | SL3748 | ++ | + | 10 |
| S. Typhimurium LT2 | Rc LPS mutant | SL1306 | ++ | + | 10 |
| S. Typhimurium LT2 | Rd1 LPS mutant | SL3769 | ++ | + | 10 |
| S. Typhimurium LT2 | Rd2 LPS mutant | SL3789 | − | − | 10 |
| S. Typhimurium LT2 | Re LPS mutant | SL1102 | ++ | + | 10 |
| S. Typhimurium LT2 | Re LPS mutant | SA1377 | ++ | + | 10 |
| S. Typhimurium LT2 | Re LPS mutant | SL3600 | ++ | + | 10 |
| S. Typhimurium LT2 | RfaP LPS mutant | SH7770 | ++ | + | 10 |

(lysis in spots: ++: comparable to S. Typhimurium DT7155; +: greater than 2 log reduced lysis compared to S. Typhimurium DT7155; −: no lysis observed; single plaques: +: plaques observed; −: no plaques observed)
*(68),
†(49)

Sources
1: lab stock;
2: Prof. Dr. med. Helmut Brade (Research Center Borstel; Germany);
3: Novagen (Merck Biosciences);
4: Coli Genetic Stock Center (CGSC, Yale University, U.S.A.);
5: Prof. Horn/Prof. Frosch (University of Würzburg, Germany);
6: National Center for Enterobacteria (NENT);
7: Dr. Thilo Fuchs (Technical University of Munich, Germany);
8: Dr. Cheng-Hsun Chiu (Chang Gung Hospital, Taiwan);
9: Nicholas R. Thomson (Sanger Institute, UK);
10: Strains of the Salmonella Genetic Stock Centre (SGSC, University of Calgary, Canada) kindly provided by Dr. Uwe Mamat (Research Center Borstel; Germany).

TABLE 5

Comparison of T4-like core genome proteins of S16 and T4 on amino acid level. Core genome proteins chosen and arranged as defined in (Petrov et al., 2010)

| Functional group | T4Gene | S16 CDS | (Putative) function | aa S16 | aa T4 | % aa identity |
|---|---|---|---|---|---|---|
| DNA replication, repair and recombination | gp43 | gp28 | DNA polymerase | 897 | 898 | 80.11 |
| | gp45 | gp32 | trimeric sliding clamp | 228 | 228 | 80.35 |
| | gp44 | gp31 | sliding clamp loader | 321 | 319 | 77.33 |
| | gp62 | gp30 | complex | 187 | 187 | 73.40 |
| | gp41 | gp20 | helicase-primase complex with gp61 | 457 | 475 | 77.08 |
| | gp59 | gp162 | Helicase primase loader & gp43 regulator | 217 | 217 | 76.15 |
| | gp32 | gp161 | single-strand binding protein | 301 | 301 | 75.91 |
| | gp46 | gp35 | subunits of a recombination nuclease | 561 | 560 | 75.27 |
| | gp47 | gp36 | complex required for initiation of DNA replication | 340 | 339 | 72.43 |
| | uvsW | gp114/ gp115 | recombination DNA-RNA helicase, DNA-dependent ATPase; two smaller genes found in S16 | 326/ 314 | 587 | 34.63/ 39.73 |
| Auxiliary metabolism | nrdA | gp152 | subunits of an aerobic | 751 | 754 | 82.25 |
| | nrdB | gp147 | ribonucleotide reductase complex | 177 | 388 | 36.25 |
| Gene Expression | gp33 | gp163 | essential protein that mediates gp55-gp45-RNA polymerase interactions in late transcription | 104 | 112 | 64.04 |

TABLE 5-continued

Comparison of T4-like core genome proteins of S16 and T4 on amino acid level.
Core genome proteins chosen and arranged as defined in (Petrov et al., 2010)

| Functional group | T4Gene | S16 CDS | (Putative) function | aa S16 | aa T4 | % aa identity |
|---|---|---|---|---|---|---|
| | gp55 | gp40 | sigma factor for late transcription | 179 | 185 | 78.07 |
| | regA | gp29 | mRNA binding translational repressor; also involved in host nucleoid unfolding | 120 | 122 | 73.17 |
| Phage Morphogenesis | gp3 | gp81.1 | sheath terminator | 195 | 176 | 55.05 |
| | gp4 | gp83 | headcompletion protein | 149 | 150 | 68.21 |
| | gp5 | gp85 | baseplate lysozyme hub component | 577 | 575 | 74.39 |
| | gp6 | gp87 | baseplate wedge component | 646 | 660 | 76.85 |
| | gp8 | gp89 | baseplate wedge | 337 | 334 | 75.44 |
| | gp13 | gp95 | head completion protein | 309 | 309 | 75.48 |
| | gp14 | gp96 | head completion protein | 256 | 256 | 74.13 |
| | gp15 | gp97 | tail completion protein | 263 | 272 | 63.70 |
| | gp16 | gp98 | subunits of the | 165 | 164 | 75.60 |
| | gp17 | gp99 | terminase for DNA packaging | 612 | 610 | 82.38 |
| | gp18 | gp100 | tail sheath subunit | 658 | 659 | 76.82 |
| | gp19 | gp101 | tail tube subunit | 163 | 163 | 76.22 |
| | gp20 | gp102 | head portal vertex protein | 521 | 524 | 79.81 |
| | gp21 | gp105 | prohead core protein and protease | 213 | 212 | 7.48 |
| | gp22 | gp106 | prohead core protein | 273 | 269 | 9.61 |
| | gp23 | gp107 | precursor of major head protein | 519 | 521 | 83.94 |
| | gp25 | gp118 | base plate wedge subunit | 131 | 132 | 83.46 |
| | gp26 | gp119 | base plate hub subunit | 209 | 208 | 63.33 |
| | gp34 | gp166 | proximal tail fiber protein subunit | 1273 | 1289 | 47.41 |
| | gp35 | gp167 | tail fiber hinge protein | 393 | 372 | 30.64 |
| | gp36 | gp168 | small distal tail fiber protein subunit | 221 | 221 | 42.67 |
| | gp37 | gp169 | large distal tail fiber protein subunit | 749 | 1026 | 24.50 |
| | gp49 | — | endo VII; required for DNA packaging Not found in S16 | — | 157 | — |
| | gp53 | gp84 | baseplate wedge component | 191 | 196 | 69.04 |

TABLE 6

Annotation table of S16

| CDS | Product | Pos. | Size [nt] | Size [aa] | Start |
|---|---|---|---|---|---|
| 1 | rIIA | 10-2'124< | 2115 | 704 | ATG |
| 2 | rIIA.1 | 2225-2428< | 204 | 67 | ATG |
| 2.1 | Hypothetical protein | 2748-2903< | 156 | 51 | ATG |
| 2.2 | Gp60 DNA topoisomerase II large subunit C-terminal region | 2938 . . . 3273< | 336 | 111 | ATT |
| 3 | homing endonuclease | 3452-4261< | 810 | 269 | ATG |
| 4 | DNA topoisomerase II large subunit | 4258-5811< | 1554 | 517 | ATG |
| 5 | hypothetical protein | 5851-6216< | 366 | 121 | ATG |
| 5.1 | FmdB family putative regulatory protein | 6238 . . . 6417< | 180 | 59 | ATG |
| 6 | hypothetical protein | 6417-6851< | 435 | 144 | ATG |
| 6.1 | Cef modifier of suppressor tRNAs | 6851 . . . 7045< | 195 | 64 | ATG |
| 7 | hypothetical protein | 7108-7545< | 438 | 145 | ATG |
| 8 | DexA endonuclease | 7605-8300< | 696 | 231 | ATG |
| 9 | DNA helicase | 8531-9856< | 1329 | 442 | ATG |
| 9.1 | Dda.1 hypothetical protein | 9853-10149< | 297 | 98 | ATG |
| 10 | putative srd anti-sigma factor | 10149-10931< | 783 | 260 | ATG |
| 11 | modB ADP-rybosylase | 11019-11651< | 633 | 210 | ATG |
| 12 | modA.2 hypothetical protein | 11710-11904< | 195 | 64 | ATG |
| 13 | modA.3 hypothetical protein | 11904-12389< | 486 | 161 | ATG |
| 14 | postulated decoy of simga32 | 12404-12607< | 204 | 67 | ATG |
| 14.1 | hypothetical protein | 12604-12843< | 240 | 79 | ATG |
| 15 | soc small outer capsid protein | 12923-13168< | 246 | 81 | ATG |
| 15.1 | hypothetical protein | 13202-13354< | 153 | 50 | ATG |
| 16 | gp56 dCTP pyrophosphatase | 13354-13872< | 519 | 172 | ATG |
| 17 | gp61 DNA primase | 14119-15147< | 1029 | 342 | ATG |
| 18 | gp61.1 conserved hypothetical protein | 15186-15650< | 465 | 154 | ATG |
| 18.1 | hypothetical protein | 15669-15866< | 198 | 65 | ATG |
| 18.2 | hypothetical protein | 15879-16199< | 321 | 106 | ATT |
| 19 | hypothetical protein | 16230-16454< | 225 | 74 | TTG |
| 20 | gp41 DNA primase-helicase | 16451-17824< | 1374 | 457 | ATG |
| 21 | gp40 head vertex assembly chaperone | 17901-18260< | 360 | 119 | ATG |
| 22 | RecA-like recombinase protein | 18260-19423< | 1164 | 387 | ATG |
| 23 | b-gt beta glucosyl transferase | 19705-20781< | 1077 | 358 | ATG |
| 24 | beta-glucosyl-HMC-alpha-glucosyl-transferase | 20778-21614< | 837 | 278 | TTG |
| 25 | gp42 dCMP hydroxymethylase | 21605-22342< | 738 | 245 | ATG |

TABLE 6-continued

Annotation table of S16

| CDS | Product | Pos. | Size [nt] | Size [aa] | Start |
|---|---|---|---|---|---|
| 26 | Imm immunity to superinfection membrane protein | 22339-22587< | 249 | 82 | ATG |
| 27 | hypothetical protein | 22616-23104< | 489 | 162 | ATG |
| 28 | gp43 DNA polymerase | 23125-25181< | 2694 | 897 | ATG |
| 29 | RegA translational repressor protein | 25920-26282< | 363 | 120 | ATG |
| 30 | gp62 clamp loader subunit | 26285-26848< | 564 | 187 | ATG |
| 31 | gp44 clamp loader subunit | 26848-27813< | 966 | 321 | ATG |
| 32 | gp45 sliding clamp | 27882-28568< | 687 | 228 | ATG |
| 33 | RpbA RNA polymerase binding protein, function unknown | 28610-29002< | 393 | 130 | ATG |
| 34 | conserved hypothetical protein | 29019-29210< | 192 | 63 | ATG |
| 35 | gp46 endonuclease subunit | 29207-30892< | 1686 | 561 | ATG |
| 35.1 | gp46.1 hypothetical protein | 30889-31011< | 123 | 40 | ATG |
| 36 | gp47 endonuclease subunit | 31092-32114< | 1023 | 340 | ATG |
| 36.1 | hypothetical protein | 32169-32516< | 348 | 115 | TTG |
| 36.2 | a-gt.2 hypothetical protein | 32534-32677< | 144 | 47 | ATG |
| 37 | a-gt.3 conserved hypothetical protein | 32671-32883< | 213 | 70 | ATG |
| 38 | a-gt.4 hypothetical protein | 32864-33193< | 330 | 109 | ATG |
| 39 | a-gt.5 hypothetical protein | 33203-33430< | 228 | 75 | ATG |
| 40 | gp55 sigma factor for late transcription | 33414-33953< | 540 | 179 | ATG |
| 41 | hypothetical protein | 34023-34310< | 288 | 95 | ATG |
| 42 | hypothetical protein | 34399-34569< | 231 | 76 | ATG |
| 43 | hypothetical protein | 34562-34825< | 264 | 87 | ATG |
| 44 | hypothetical protein | 34562-34825< | 264 | 87 | ATG |
| 44.1 | Conserved hypothetical protein | 35271-35456< | 186 | 61 | ATG |
| 45 | NrdH thioredoxin | 35873-36184< | 312 | 103 | ATG |
| 45.1 | hypothetical protein | 36255-36353< | 99 | 32 | ATG |
| 46 | NrdG anaerobic ribonucleotide reductase | 36627-37118< | 492 | 163 | TTG |
| 47 | NrdD anaerobic ribonucleotide reductase | 37108-38931< | 1824 | 607 | ATG |
| 48 | conserved hypothetical protein | 38928-40013< | 1086 | 361 | ATG |
| 48.1 | hypothetical protein | 40594-40758< | 165 | 54 | ATG |
| 49 | conserved protein | 4078-40897< | 150 | 49 | ATG |
| 50 | gp49.2 hypothetical protein | 40882-41190< | 309 | 102 | ATG |
| 50.1 | hypothetical protein | 41190-41354< | 165 | 54 | ATG |
| 50.2 | hypothetical protein | 41535-41750< | 216 | 71 | ATG |
| 51 | NrdC thioredoxin | 41759-42022< | 264 | 87 | ATG |
| 52 | hypothetical protein | 42022-42528< | 507 | 168 | ATG |
| 52.1 | hypothetical protein | 42802-43029< | 228 | 75 | ATG |
| 52.2 | hypothetical protein | 43019-43249< | 231 | 76 | ATG |
| 53 | hypothetical protein | 44276-45058< | 783 | 260 | ATG |
| 53.1 | hypothetical protein | 45169-45300< | 132 | 43 | ATG |
| 54 | hypothetical protein | 45965-46315< | 351 | 116 | ATG |
| 54.1 | hypothetical protein | 46339-46611< | 273 | 90 | TTG |
| 55 | NrdC.10 conserved hypothetical protein | 46619-47596< | 978 | 325 | ATG |
| 55.1 | hypothetical protein | 47676-47924< | 249 | 82 | TTG |
| 55.2 | hypothetical protein | 48039-48293< | 255 | 84 | ATG |
| 56 | nrdC.11 hypothetical protein | 48297-49055< | 759 | 252 | ATG |
| 56.1 | nrdC.11 hypothetical protein | 49181-49282< | 102 | 33 | TTG |
| 57 | hypothetical protein | 49868-50293< | 426 | 141 | ATG |
| 58 | hypothetical protein | 50290-50751< | 462 | 153 | ATG |
| 59 | hypothetical protein | 50751-50999< | 249 | 82 | ATG |
| 60 | hypothetical protein | 51097-51411< | 315 | 54 | ATG |
| 60.1 | hypothetical protein | 51442-51606< | 165 | 104 | ATG |
| 61 | MobD.2 conserved hypothetical protein | 51603-51713< | 111 | 36 | ATG |
| 62 | hypothetical protein | 51766-52185< | 420 | 139 | ATG |
| 63 | rI.-1 hypothetical protein | 52289-52675< | 387 | 128 | ATG |
| 63.1 | rI lysis inhibition regulator | 52665-52994< | 330 | 109 | ATT |
| 64 | rI.1 conserved hypothetical protein | 52961-53173< | 213 | 70 | ATG |
| 65 | Tk thymidine kinase | 53221-53799< | 579 | 192 | ATG |
| 66 | Tk.1 conserved hypothetical protein | 53799-53987< | 189 | 62 | ATG |
| 66.1 | hypothetical protein | 53984-54157< | 174 | 57 | ATG |
| 67 | tk.4 hypothetical protein | 54365-54817< | 453 | 150 | ATG |
| 67.1 | hypothetical protein | 54814-55215< | 402 | 133 | TTG |
| 67.2 | Valyl tRNA synthetase modifier | 55212-55523< | 312 | 103 | ATC |
| 68 | s.8 conserved hypothetical protein | 55532-56080< | 549 | 182 | ATG |
| 69 | RegB site-specific RNA endonuclease | 56099-56566< | 468 | 155 | ATG |
| 69.1 | hypothetical protein | 56644-56874< | 231 | 76 | ATG |
| 70 | Vs.8 conserved hypothetical protein | 56902-57444< | 543 | 180 | ATG |
| 70.1 | hypothetical protein | 57622-57885< | 264 | 87 | ATG |
| 71 | Ip4 protein | 57969-58469< | 501 | 166 | TTG |
| 72 | e Lysozyme murein hydrolase | 58432-58932< | 501 | 166 | ATG |
| 72.1 | hypothetical protein | 59441-59656< | 216 | 71 | TTG |
| 73 | hypothetical protein | 59843-60394< | 552 | 183 | ATG |
| 74 | gp30.3 conserved hypothetical protein | 60416-60859< | 444 | 147 | ATG |
| 74.1 | hypothetical protein | 60892-60990< | 99 | 32 | CTG |

TABLE 6-continued

Annotation table of S16

| CDS | Product | Pos. | Size [nt] | Size [aa] | Start |
|---|---|---|---|---|---|
| 74.2 | hypothetical protein | 61042-61149< | 108 | 35 | ATG |
| 75 | hypothetical protein | 61377-61958< | 582 | 193 | CTG |
| 76 | Tma.2 conserved hypothetical protein | 62254-62541< | 288 | 95 | ATG |
| 77 | Tma.3 conserved hypothetical protein | 62541-62753< | 213 | 70 | ATG |
| 77.1 | Tma.4 conserved hypothetical predicted membrane protein | 62928-63113< | 186 | 61 | ATG |
| 77.2 | hypothetical protein | 63176-63409< | 234 | 77 | ATG |
| 78 | hypothetical protein | 63470-63781< | 312 | 103 | TTG |
| 79 | 57B hypothetical protein | 63760-64218< | 459 | 152 | ATG |
| 80 | gp57A chaperone for long tail fiber formation | 64215-64442< | 228 | 75 | ATG |
| 81 | gp1 deoxynucleoside monophosphate kinase | 64439-65164< | 726 | 241 | ATG |
| 81.1 | gp3 tail completion and sheath stabilizer protein | 65164 . . . 65751< | 588 | 195 | TTG |
| 82 | gp2 DNA end protector protein | 65838-66674< | 837 | 278 | ATG |
| 83 | gp4 head completion protein | 66674-67123< | 450 | 149 | ATG |
| 84 | gp53 baseplate wedge subunit | 67175-67750 | 576 | 191 | ATG |
| 85 | gp5 baseplate hub subunit and tail lysozyme | 67750-69483 | 1734 | 577 | ATG |
| 86 | gp5.1 hypothetical protein | 69513-70022 | 510 | 169 | ATG |
| 86.1 | gp5.4 conserved hypothetical protein | 70022-70315 | 294 | 97 | ATG |
| 87 | gp6 baseplate wedge subunit | 70315-72255 | 1941 | 646 | ATG |
| 88 | gp7 baseplate wedge subunit | 72252-75353 | 3102 | 1033 | ATG |
| 89 | Gp8 baseplate wedge subunit | 75346-76359 | 1014 | 337 | ATG |
| 90 | Gp9 baseplate wedge tail fiber connector | 76440-77312 | 873 | 290 | ATG |
| 91 | Gp10 baseplate wedge subunit and tail pin | 77309-79117 | 1809 | 602 | ATG |
| 92 | Gp11 baseplate wedge subunit and tail pin | 79117-79770 | 654 | 217 | ATG |
| 93 | gp12 short tail fiber | 79770-81194 | 1425 | 474 | ATG |
| 94 | Wac fibritin neck whiskers | 81205-82596 | 1392 | 463 | ATG |
| 95 | Gp13 neckprotein | 82628-83557 | 930 | 309 | ATG |
| 96 | Gp14 neck protein | 83574-84344 | 771 | 256 | ATG |
| 97 | Gp15 tail sheath stabilizer and completion protein | 84440-85991 | 792 | 263 | ATG |
| 98 | Gp16 small terminase protein | 85241-85738 | 498 | 165 | ATG |
| 99 | Gp17 large terminase protein | 85716-87554 | 1839 | 612 | ATG |
| 100 | Gp18 tail sheath protein | 87588-89564 | 1977 | 658 | ATG |
| 100.1 | hypothetical protein | 89900-90220 | 321 | 106 | TTG |
| 101 | Gp19 tail tube protein | 90344-90835 | 492 | 163 | ATG |
| 102 | Gp20 portal vertex protein | 90984-92549 | 1566 | 521 | ATG |
| 103 | Gp67 prohead core protein | 92549-92785 | 237 | 78 | ATG |
| 104 | Gp68 prohead core protein | 92785-93210 | 426 | 141 | ATG |
| 104.1 | I-TevIII | 93210-93815 | 606 | 201 | ATG |
| 105 | Gp21 prohead core scaffolding protein and protease | 93793-94434 | 642 | 213 | ATG |
| 106 | Gp22 prohead core protein | 94468-95289 | 822 | 273 | ATG |
| 107 | Gp23 major capsid protein | 95311-96870 | 1560 | 519 | ATG |
| 108 | Gp24 head vertex protein | 96967-98250 | 1284 | 427 | ATG |
| 109 | Gp24 head vertex protein | 98250-99530 | 1281 | 426 | ATG |
| 109.1 | hypothetical protein | 99552-100115< | 564 | 187 | ATG |
| 110 | RnIB RNA ligase 2 | 100094-101101< | 1008 | 335 | ATG |
| 110.1 | hypothetical protein | 101463-101819< | 357 | 118 | ATG |
| 111 | hoc head pute capsid protein | 102130-103224< | 1095 | 364 | ATG |
| 112 | Inh inhibitor of prohead protease gp21 | 103262-103936< | 675 | 224 | ATG |
| 113 | homing endonuclease | 103988-104623 | 636 | 211 | GTG |
| 114 | ATP-dependent DNA Helicase; uvsW | 104626-105606 | 981 | 326 | GTG |
| 115 | Helicase; uvsW | 106408-107352 | 945 | 314 | GTG |
| 115.1 | UvsW.1 hypothetical protein | 107360-107587 | 228 | 75 | ATG |
| 116 | UvsY.-2 hypothetical protein | 107649-107813< | 165 | 54 | ATG |
| 117 | UvsY recombination, repair and ssDNA binding protein | 107854-108267< | 414 | 137 | TTG |
| 118 | Gp25 baseplate wedge subunit | 108358-108753< | 396 | 131 | ATG |
| 119 | gp26 baseplate hub subunit | 108753-109382 | 630 | 209 | ATG |
| 119.1 | gp26 internal in-frame translation initiation | 108753-108992< | 240 | 79 | ATG |
| 120 | Gp51 baseplate hub assembly protein | 109434-110186 | 753 | 250 | ATG |
| 121 | Gp27 baseplate hub subunit | 110183-111325 | 1143 | 380 | ATG |
| 122 | gp28 baseplate hub distal subunit | 111297-111824 | 528 | 175 | ATG |
| 123 | gp29 base plate hub | 111821-113554 | 1734 | 577 | ATG |
| 124 | Gp48 baseplate subunit | 113564-114616 | 1053 | 350 | ATG |
| 125 | Gp54 baseplate subunit | 114161-115533 | 918 | 305 | ATG |
| 125.1 | alt.3 conserved hypothetical protein | 115565 . . . 115885 < | 321 | 106 | ATT |
| 126 | alt ADP-ribosyltransferase | 115916-118024< | 2109 | 702 | ATG |
| 127 | Gp30 DNA ligase | 118254-119705< | 1452 | 483 | ATG |
| 128 | gp30.2 conserved hypothetical protein | 119763-120383< | 621 | 206 | ATG |
| 128.1 | gp30.5 hypothetical protein | 120380-120577< | 198 | 65 | ATG |
| 129 | gp30.7 conserved hypotthetical protein | 121001-121360< | 360 | 119 | ATG |
| 130 | hypothetical protein | 121431-121907< | 477 | 158 | ATG |
| 131 | gp30.9 conserved hypotthetical protein | 122040-122219< | 180 | 59 | ATG |

TABLE 6-continued

Annotation table of S16

| CDS | Product | Pos. | Size [nt] | Size [aa] | Start |
|---|---|---|---|---|---|
| 132 | rIII lysis inhibition accessory protein, rapid lysis phenotype | 122424-122672< | 249 | 82 | ATG |
| 133 | gp31 head assembly cochaperone with GroEL | 122774-123097< | 324 | 107 | ATG |
| 134 | gp31.1 conserved hypothetical protein | 123159-123470< | 312 | 103 | ATG |
| 135 | gp31.2 hypothetical protein | 123475-123708< | 234 | 77 | ATG |
| 136 | deoxycytidylate deaminase | 123705-124271< | 567 | 188 | ATG |
| 137 | hypothetical protein | 124271-124642< | 372 | 123 | ATG |
| 137.1 | hypothetical protein | 124639-124866< | 228 | 75 | ATG |
| 138 | hypothetical protein | 125162-125377< | 216 | 71 | ATG |
| 139 | Cd.4 conserved hypothetical protein | 125370-125567< | 198 | 65 | ATG |
| 140 | Cd.5 hypothetcal protein | 125564-125767< | 204 | 67 | ATG |
| 141 | pseT polynucleotide kinase | 125767-126657< | 891 | 296 | ATG |
| 141.1 | hypothetical protein | 126665-126802< | 138 | 45 | ATG |
| 142 | PseT.2 conserved hypothetical protein | 126783-127073< | 291 | 96 | ATG |
| 143 | PseT.3 conserved hypothetical predicted membrane protein | 127070-127417< | 348 | 115 | ATG |
| 144 | Alc inhibitor of host transcription | 127408-127908< | 501 | 166 | ATO |
| 145 | rnlA RNA ligase A | 127973-129103< | 1131 | 376 | ATG |
| 146 | denA endonuclease II | 129100-129513< | 414 | 137 | AlG |
| 147 | NrdB aerobic NDP reductase small subumt | 129542-130075< | 534 | 177 | TTG |
| 148 | I-TevIII homing endonuclease (defective) | 130180-130497< | 318 | 105 | ATG |
| 149 | hypothetical protein (nrdB intron) | 130180-130989< | 810 | 269 | TTG |
| 150 | NrdB aerobic NDP reductase small subunit | 131136-131813< | 678 | 225 | ATG |
| 151 | ModB homing endonuclease | 131810-132538< | 729 | 242 | ATG |
| 152 | nrdA NDP reductase large subunit | 132538-134793< | 2256 | 751 | ATG |
| 152.1 | hypothetical protein | 134908-135096< | 189 | 62 | ATG |
| 152.2 | hypothetical protein | 135211-135438< | 228 | 75 | AlG |
| 153 | dTMP thymidylate synthase | 135435-136295< | 861 | 286 | ATG |
| 154 | hypothetical protein | 136292-136642< | 351 | 116 | TTG |
| 155 | hypothetical protein | 136639-136953< | 315 | 104 | GTG |
| 156 | Frd dihydrofolate reductase | 136950-137543< | 594 | 197 | ATG |
| 156.1 | hypothetical protein | 137543-137785< | 243 | 80 | ATG |
| 156.2 | hypothetical protein | 137782-137877< | 96 | 31 | ATG |
| 157 | hypothetical protein | 138083-138409< | 327 | 108 | ATG |
| 158 | Frd.1 conserved hypothetical protein | 138409-138684< | 276 | 91 | ATG |
| 159 | Frd.2 conserved hypothetical protein | 138747-139127< | 381 | 126 | ATG |
| 159.1 | Frd.2 conserved hypothetical protein | 139149-139523 | 375 | 124 | ATC |
| 160 | Frd.3 hypothetical protein | 139532-139759< | 228 | 75 | ATG |
| 160.1 | hypothetical protein | 139822-140142 | 321 | 106 | CTG |
| 161 | Gp32 single-stranded DNA binding protein | 140654-141559< | 906 | 301 | AlG |
| 162 | Gp59 loader of gp41 DNA helicase | 141573-142226< | 654 | 217 | ATG |
| 163 | gp33 late promotertranscription accessory protein | 142223-142537< | 315 | 104 | ATG |
| 164 | dsbA double-stanned DNA binding protein | 142515-142790< | 276 | 91 | ATG |
| 165 | RnaseH | 142792-143721< | 930 | 309 | ATG |
| 166 | gp34 long tail fiber proximal subunit | 143791-147612 | 3822 | 1273 | ATG |
| 167 | gp35 hinge connector | 147624-148805 | 1182 | 393 | ATG |
| 168 | gp36 hinge connector | 148872-149537 | 666 | 221 | ATG |
| 169 | gp37 long tail fiber distal subunit | 149546-151795 | 2250 | 749 | ATG |
| 170 | gp38 receptor recognition protein | 151823-152572 | 750 | 249 | ATG |
| 171 | t holin lysis mediator | 152592-153248 | 657 | 218 | ATG |
| 172 | AsiA anti-sigma 70 protein | 153252-153524< | 273 | 90 | ATG |
| 172.1 | hypothetical protein | 153616-153876< | 261 | 86 | ATG |
| 172.2 | hypothetical protein | 154132-154257< | 126 | 41 | TTG |
| 172.3 | hypothetical protein | 154250-154447< | 198 | 65 | ATG |
| 173 | hypothetical protein | 154466-154795< | 330 | 109 | AlLr |
| 173.1 | hypothetical protein | 154804-154959< | 156 | 51 | ATG |
| 174 | MotA activator of middle period transcription | 154966-55610< | 645 | 214 | ATG |
| 174.1 | hypothetical protein | 155789-155926< | 138 | 45 | ATG |
| 175 | Gp52 DNA topisomerase II medium subunit | 155917-157254< | 1338 | 445 | ATG |
| 175.1 | hypothetical protein | 157397-157582< | 186 | 61 | ATG |
| 175.2 | hypothetical protein | 157600-157743< | 144 | 47 | ATG |
| 176 | Ndd nucleoid disruption protein | 157755-158201< | 447 | 148 | ATG |
| 176.1 | hypothetical protein | 158268-158357< | 90 | 29 | ATG |
| 177 | DenB DNA endonuclease IV | 158440-158997< | 558 | 185 | ATG |
| 177.1 | hypothetical protein | 158930 . . . 159253< | 324 | 107 | ATT |
| 178 | rIIB protector from prophage-induced early lysis | 159313-160221< | 909 | 302 | ATG |

<indicates a reverse orientation.
Size [nt] includes the stop codon, while size [aa] does not.

REFERENCES

Ackermann, H. W., (1998) Tailed bacteriophages: the order caudovirales. *Adv Virus Res* 51: 135-201.

Bartual, S. G., C. Garcia-Doval, J. Alonso, G. Schoehn & M. J. van Raaij, (2010) Two-chaperone assisted soluble expression and purification of the bacteriophage T4 long tail fibre protein gp37. *Protein Expr Purif* 70: 116-121.

Brussow, H. K., E., (2005) Phage ecology. In: Bacteriophages: biology and application. Boca Raton, Fla.: CRC Press, pp. 129-163.

Calendar, R., (2006) *The Bacteriophages*. Oxford University Press.

Cerritelli, M. E., J. S. Wall, M. N. Simon, J. F. Conway & A. C. Steven, (1996) Stoichiometry and domainal organization of the long tail-fiber of bacteriophage T4: a hinged viral adhesin. *Journal of Molecular Biology* 260: 767-780.

Datsenko, K. A. & B. L. Wanner, (2000) One-step inactivation of chromosomal genes in *Escherichia coli* K-12 using PCR products. *Proc Natl Acad Sci USA* 97: 6640-6645.

Drexler, K., I. Riede & U. Henning, (1986) Morphogenesis of the long tail fibers of bacteriophage T2 involves proteolytic processing of the polypeptide (gene product 37) constituting the distal part of the fiber. *J Mol Biol* 191: 267-272.

Gratia, A., (1936) Des relations numeriques entre bactéries lysogenes et particules de bactériophage. *Annales de l'Institut Pasteur:* 57:652-676.

Grimont, P. A. D. & F.-X. Weill, (2007) Antigenic formulae of the *Salmonella* Serovars. *WHO Colllaborating Centre for Reference and Research on Salmonella (WHOCC-Salm)*.

Guzman, L. M., D. Belin, M. J. Carson & J. Beckwith, (1995) Tight regulation, modulation, and high-level expression by vectors containing the arabinose PBAD promoter. *J Bacteriol* 177: 4121-4130.

Hagens, S. & M. J. Loessner, (2010) Bacteriophage for biocontrol of foodborne pathogens: calculations and considerations. *Curr Pharm Biotechnol* 11: 58-68.

Hantke, K., (1978) Major outer membrane proteins of *E. coli* K12 serve as receptors for the phages T2 (protein Ia) and 434 (protein Ib). *Mol Gen Genet* 164: 131-135.

Hashemolhosseini, S., Z. Holmes, B. Mutschler & U. Henning, (1994) Alterations of Receptor Specificities of Coliphages of the T2 Family. *Journal of Molecular Biology* 240: 105-110.

Hashemolhosseini, S., Y. D. Stierhof, I. Hindennach & U. Henning, (1996) Characterization of the helper proteins for the assembly of tail fibers of coliphages T4 and lambda. *J Bacteriol* 178: 6258-6265.

Kerr, I. D., S. Sivakolundu, Z. Li, J. C. Buchsbaum, L. A. Knox, R. Kriwacki & S. W. White, (2007) Crystallographic and NMR analyses of UvsW and UvsW.1 from bacteriophage T4. *J Biol Chem* 282: 34392-34400.

Leiman, P. G., F. Arisaka, M. J. van Raaij, V. A. Kostyuchenko, A. A. Aksyuk, S. Kanamaru & M. G. Rossmann, (2010) Morphogenesis of the T4 tail and tail fibers. *Virol J* 7:355.

Lindberg, A. A., (1967) Studies of a receptor for felix O-1 phage in *Salmonella* minnesota. *J Gen Microbiol* 48: 225-233.

Lindberg, A. A. & T. Holme, (1969) Influence of O side chains on the attachment of the Felix O-1 bacteriophage to *Salmonella* bacteria. *J Bacteriol* 99: 513-519.

Loessner, M. J., K. Kramer, F. Ebel & S. Scherer, (2002) C-terminal domains of *Listeria monocytogenes* bacteriophage murein hydrolases determine specific recognition and high-affinity binding to bacterial cell wall carbohydrates. *Mol Microbiol* 44: 335-349.

Petrov, V. M., Ratnayaka, S., Nolan, J. M., Miller, E. S. and Karam, J. D. (2010) Genomes of the T4-related bacteriophages as windows on microbial genome evolution. *Virol J* 7: 292-311.

Riede, I., M. Degen & U. Henning, (1985) The receptor specificity of bacteriophages can be determined by a tail fiber modifying protein. *EMBO J* 4: 2343-2346.

Robbins, J. B., M. Stapleton, M. J. Stanger, D. Smith, J. T. Dansereau, V. Derbyshire & M. Belfort, (2007) Homing endonuclease I-TevIII: dimerization as a means to a double-strand break. *Nucleic Acids Res* 35: 1589-1600.

Rohwer, F. & R. Edwards, (2002) The Phage Proteomic Tree: a genome-based taxonomy for phage. *J Bacteriol* 184: 4529-4535.

Sambrook & Russel, (2001) *Molecular Cloning: A Laboratory Manual*. Cold Spring Harbor Laboratory Press.

Schmieger, H., (1972) Phage P22-mutants with increased or decreased transduction abilities. *Mol Gen Genet* 119: 75-88.

Sickmier, E. A., K. N. Kreuzer & S. W. White, (2004) The crystal structure of the UvsW helicase from bacteriophage T4. *Structure* 12: 583-592.

Sternberg, N. L. & R. Maurer, (1991) Bacteriophage-mediated generalized transduction in *Escherichia coli* and *Salmonella typhimurium*. *Methods Enzymol* 204: 18-43.

Tcherepanov, V., A. Ehlers & C. Upton, (2006) Genome Annotation Transfer Utility (GATU): rapid annotation of viral genomes using a closely related reference genome. *BMC Genomics* 7: 150.

Tetart, F., F. Repoila, C. Monod & H. M. Krisch, (1996) Bacteriophage T4 host range is expanded by duplications of a small domain of the tail fiber adhesin. *Journal of Molecular Biology* 258: 726-731.

Tetart, F., C. Desplats & H. M. Krisch, (1998) Genome plasticity in the distal tail fiber locus of the T-even bacteriophage: recombination between conserved motifs swaps adhesin specificity. *Journal of Molecular Biology* 282: 543-556.

Tetart, F., C. Desplats, M. Kutateladze, C. Monod, H. W. Ackermann & H. M. Krisch, (2001) Phylogeny of the major head and tail genes of the wide-ranging T4-type bacteriophages. *J Bacteriol* 183: 358-366.

Trojet, S. N., Caumont-Sarcos, A., Perrody, E., Comeau, A. M. and Krisch, H. M. (2011) The gp38 adhesins of the T4 superfamily: a complex modular determinant of the phage's host specificity. *Genome Biol Evol* 3:674-686.

Wilson, G. G., K. Y. Young, G. J. Edlin & W. Konigsberg, (1979) High-frequency generalised transduction by bacteriophage T4. *Nature* 280: 80-82.

Young, K. K., G. J. Edlin & G. G. Wilson, (1982) Genetic analysis of bacteriophage T4 transducing bacteriophages. *J Virol* 41: 345-347.

Yu, F. & S. Mizushima, (1982) Roles of lipopolysaccharide and outer membrane protein OmpC of *Escherichia coli* K-12 in the receptor function for bacteriophage T4. *JBacteriol* 151: 718-722.

What is claimed is:

1. A method for the treatment, prevention or delay of a *Salmonella* related condition in an individual, comprising administering a composition to the individual, the composition comprising an isolated bacteriophage, wherein the isolated bacteriophage is Phage S16, deposit number CBS130493.

2. A method for controlling microbial contamination in a food- or feed product, on and/or in food- or feed processing equipment, on and/or in food- or feed containers comprising contacting a composition with the food- or feed product, the food- or feed processing equipment and/or the food- or feed containers, the composition comprising an isolated bacteriophage, wherein the isolated bacteriophage is Phage S16, deposit number CBS130493.

3. The method according to claim 1, wherein the composition further comprises an additional active ingredient selected from the group consisting of: a further bacteriophage, a bacteriostatic agent, a bactericide agent, an antibiotic, a surfactant and an enzyme.

4. The method according to claim 1, wherein the composition further comprises a Felix O1 bacteriophage.

5. The method according to claim 2, wherein the composition further comprises an additional active ingredient selected from the group consisting of: a further bacteriophage, a bacteriostatic agent, a bactericide agent, an antibiotic, a surfactant and an enzyme.

6. The method according to claim 2, wherein the composition further comprises a Felix O1 bacteriophage.

7. The method according to claim 2, wherein the composition further comprises an additional active ingredient selected from the group consisting of: a further bacteriophage, a bacteriostatic agent, a bactericide agent, an antibiotic, a surfactant and an enzyme.

* * * * *